US008198061B2

(12) United States Patent
Weill et al.

(10) Patent No.: US 8,198,061 B2
(45) Date of Patent: Jun. 12, 2012

(54) ACETYLCHOLINESTERASE GENE RESPONSIBLE FOR INSECTICIDE RESISTANCE AND APPLICATIONS THEREOF

(75) Inventors: Mylène Weill, Montpellier (FR); Philippe Fort, Castelnau le Lez (FR); Michel Raymond, Montpellier (FR); Nicole Pasteur, Montpellier (FR)

(73) Assignees: Centre National de la Recherche Scientifique, Paris (FR); Universite de Montpellier 2, Montpellier (FR)

( * ) Notice: Subject to any disclaimer, the term of this patent is extended or adjusted under 35 U.S.C. 154(b) by 1300 days.

(21) Appl. No.: 10/518,072

(22) PCT Filed: Jun. 19, 2003

(86) PCT No.: PCT/FR03/01876
§ 371 (c)(1),
(2), (4) Date: Sep. 22, 2005

(87) PCT Pub. No.: WO04/000994
PCT Pub. Date: Dec. 31, 2003

(65) Prior Publication Data
US 2008/0256649 A1 Oct. 16, 2008

(30) Foreign Application Priority Data

Jun. 20, 2002 (FR) ..................................... 02 07622
Nov. 5, 2002 (FR) ..................................... 02 13799

(51) Int. Cl.
*C12N 9/18* (2006.01)
(52) U.S. Cl. ..................................................... 435/197
(58) Field of Classification Search ........................ None
See application file for complete search history.

(56) References Cited

PUBLICATIONS

Gao, J.R. et al. "Molecular cloning and characterization of a greenbug (*Schizaphis graminum*) cDNA encoding acetylcholinesterase possibly evolved from a duplicate gene lineage", Insect Biochemistry and Molecular Biology, vol. 32, No. 7, pp. 765-775 2002.
Fort, P.P. "*Aedes albopictus* partial achE1 gene for acetylcholinesterase", retrieved from EBI, Database accession No. AJ438598, XP002234930 2002.
Fort, P.P. "*Anopheles albimanus* partial achE1 gene for acetylcholinesterase", retrieved from EBI, Database accession No. AJ438608, XP002234938 2002.
Fort, P.P. "*Anopheles darlingi* partial achE1 gene for acetylcholinesterase", retrieved from EBI, Database accession No. AJ438599, XP002234931 2002.
Fort, P.P. "*Anopheles funestus* partial achE1 gene for acetylcholinesterase", retrieved from EBI, Database accession No. AJ438604, XP002234933 2002.
Fort, P.P. "*Anopheles arabiensis* partial achE1 gene for acetylcholinesterase", retrieved from EBI, Database accession No. AJ438603, XP002234934 2002.
Fort, P.P. "*Anopheles sundaicus* partial achE1 gene for acetylcholinesterase", retrieved from EBI, Database accession No. AJ438600, XP002234932 2002.
Fort, P.P. "*Anopheles pseudopunctipennis* partial achE1 gene for acetylcholinesterase", retrieved from EBI, Database accession No. AJ438605, XP002234936 2002.
Fort, P.P. "*Anopheles moucheti* partial achE1 gene for acetylcholinesterase", retrieved from EBI, Database accession No. AJ438602, XP002234937 2002.
Fort, P.P. "*Anopheles sacharovi* partial achE1 gene for acetylcholinesterase", retrieved from EBI, Database accession No. AJ438606, XP002234939 2002.
Fort, P.P. "*Anopheles stephensi* partial achE1 gene for acetylcholinesterase", retrieved from EBI, Database accession No. AJ438607, XP002234940 2002.
Fort, P.P. "*Anopheles minimus* partial achE1 gene for acetylcholinesterase" retrieved from EBI, Database accession No. AJ438601, XP002234935 2002.
Fort, P.P. "*Anopheles nili* partial achE1 gene for acetylcholinesterase" retrieved from EBI, Database accession No. AJ438609, XP002234941 2002.
Malcolm, C.A. et al. "A sex-linked Ace gene, not linked to insensitive acetylcholinesterase-mediated insecticide resistance in *Culex pipiens*", Insect Molecular Biology, vol. 7, No. 2, pp. 107-120, XP002234923 1998.
Bourguet, Denis et al. "Determination of Ace.1 Genotypes in Single Mosquitoes: Toward an Ecumenical Biochemical Test", Pesticide Biochemistry and Physiology, vol. 55, No. 2, pp. 122-128, XP002234924 1996.
Mutero, Annick et al. "Resistance-associated point mutations in insecticide-insensitive acetylcholinesterase", Proc. Natl. Acad. Sci., vol. 91, No. 13, pp. 5922-5926, XP002234925 1994.
Holt, R.A. et al. "17000687086124 A.Gam.ad.cDNA.blood1 *Anopheles gambiae* cDNA clone 19600449729584 5', mRNA sequence", retrieved from EBI, Database accession No. BM608195, XP002234942 2002.
Anthony, Nicola et al. "Cloning, sequencing and functional expression of an acetylcholinesterase gene from the yellow fever mosquito *Aedes aegypti*", FEBS Letters, vol. 368, pp. 461-465, XP002234926 1995.
Bourguet, Denis et al. "Analysis of Molecular Forms and Pharmacological Properties of Acetylcholinesterase in Several Mosquito Species", Neurochem. Int., vol. 31, No. 1, pp. 65-72, XP002234927 1997.
Bourguet, Denis et al. "Existence of Two Acetylcholinesterases in the Mosquito *Culex pipiens* (Diptera: Culicidae)", Journal of Neurochemistry, vol. 67, No. 5, pp. 2115-2123, XP008013364 1996.
Walsh, Sinead B. et al. "Identification and characterization of mutations in housefly (*Musca domestica*) acetylcholinesterase involved in insecticide resistance", Biochem. J., vol. 359, pp. 175-181, XP002234928 2001.

(Continued)

*Primary Examiner* — Nashaat Nashed
(74) *Attorney, Agent, or Firm* — Oblon, Spivak, McClelland, Maier & Neustadt, L.L.P.

(57) ABSTRACT

The invention relates to a novel acetylcholinesterase gene (ace-1) responsible for resistance to organophosphorus and/or carbamates in mosquitoes, which is non-homologous to the *D. melanogaster* acetylcholinesterase gene (ace-2), products of the ace-1 gene (cDNA, protein AchE1) and the applications thereof, particularly for the screening of novel insecticides and the genetic detection of resistance to organophosphorus and/or carbamates in mosquito populations.

8 Claims, 19 Drawing Sheets

PUBLICATIONS

Figure 1A:
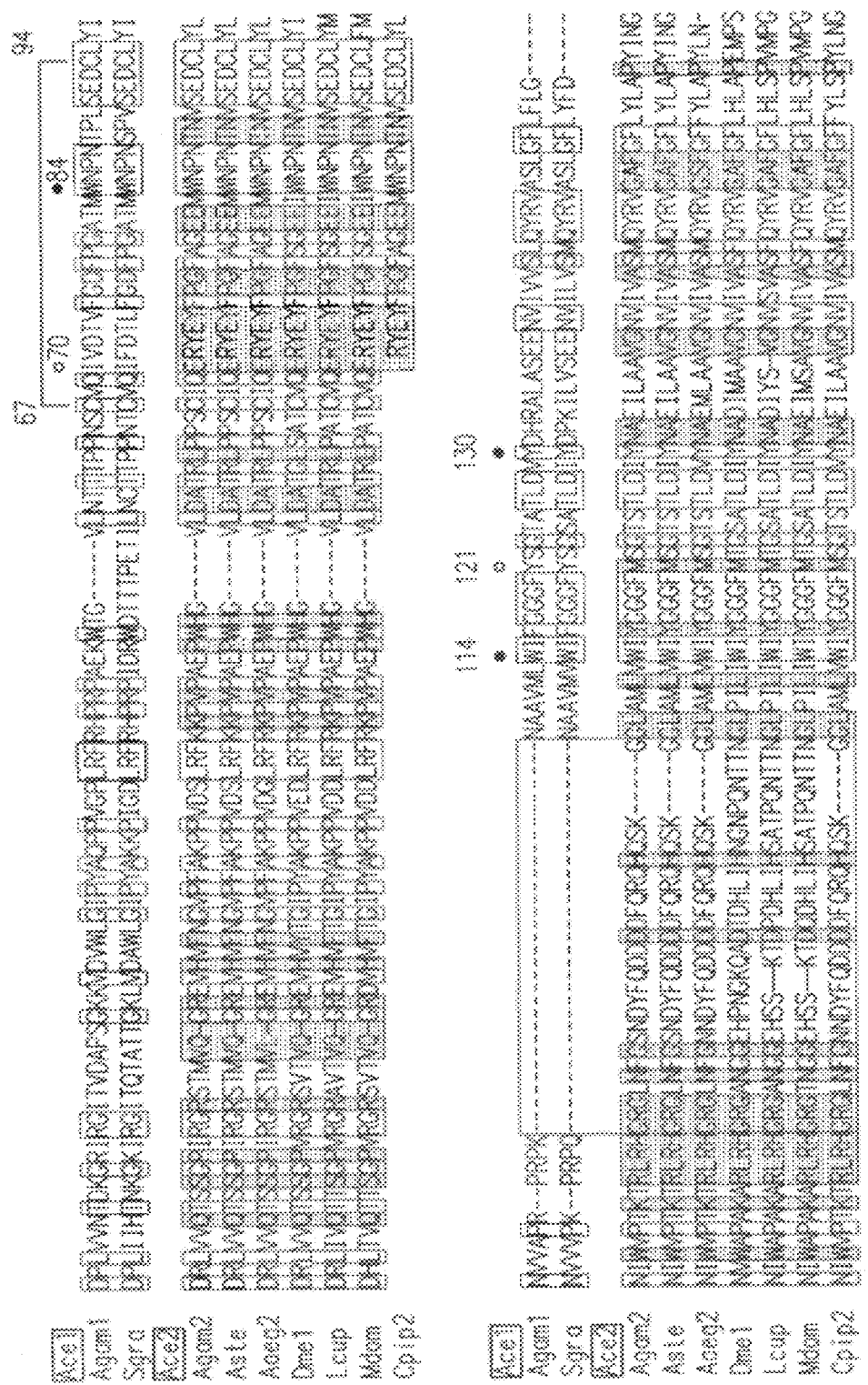

Bourguet, Denis et al. "Duplication of the Ace.1 Locus in *Culex pipiens* Mosquitoes from the Caribbean", Biochemical Genetics, vol. 34, No. 9-10, pp. 351-362, XP008015132 1996.

Weill, Mylene et al. "A novel acetylcholinesterase gene in mosquitoes codes for the insecticide target and is non-homologous to the ace gene in *Drosophila*", Proc. R. Soc. Lond. B, vol. 269, No. 1504, pp. 2007-2016, XP008015105 2002.

Weill, Mylene et al. "Comparative Genomics: Insecticide resistance in mosquito vectors", Nature, vol. 423, pp. 136-137, XP002269568 2003.

Li, Fei et al. "Two different genes encoding acetylcholinesterase existing in cotton aphid (*Aphis gossypii*)", Genome, vol. 45, No. 6, pp. 1134-1141, XP008013411 2002.

Fort, P.P. "*Anopheles gambiae* partial achE1 gene for acetylcholinesterase, exons 4-9", retrieved from EBI, Database accession No. AJ488492, XP002234943 2002.

Fort. P.P. "*Culex pipiens* partial achE1 gene for acetylcholinesterase, strain SLAB", retrieved from EBI, Database accession No. AJ428047, XP002234945 2002.

Fort, P.P. "*Aedes aegypti* partial achE1 gene for acetylcholinesterase", retrieved from EBI, Database accession No. AJ428049, XP002234946 2002.

Fort, P.P. "*Culex pipiens* partial achE1 gene for acetylcholinesterase", retrieved from EBI, Database accession No. AJ428048, XP002234947 2002.

Schumacher, Mark et al. "Primary structure of *Torpedo californica* acetylcholinesterase deduced from its cDNA sequence" Nature vol. 319, pp. 407-409, 1986.

Schumacher, Mark et al. "Multiple Messenger RNA Species Give Rise to the Structural Diversity in Acetylcholinesterase" The Journal of Biological Chemistry. vol. 263, No. 35, Issue of Dec. 15, pp. 18979-18987, 1988.

Gibney, Gretchen et al. "Biosynthesis of Torpedo Acetylcholinesterase in Mammalian Cells" The Journal of Biological Chemistry. vol. v265, No. 21, Issue Jul. 25, pp. 12576-12583, 1990.

Sussman, Joel L. "Atomic Structure of Acetylcholinesterase from *Torpedo californica*: A Prototypic acetylcholine-Binding Protein" Science, vol. 253, pp. 253-879, 1991.

Enyedy, Istvan J. "Molecular dynamics study of active-site interactions with tetracoordinate transiets in acetylcholinesterase and its mutants" Biochem. J. (2001) 353, 645-653.

```
        1                                                                    80
Ae alb  TEPDMPNSNR DALDKMMGDY HFTCNVNEFA QRYAEGNNV YMYLYTHRSK CNPWPRWTGV MKGDEINYVF GEPLNKPLGY
Ae aeg  TEPDMPNSNR DALDKMMGDY HFTCNVNEFA QRYAEGNNV YMYLYTHRSK CNPWPRWTGV MKGDEINYVF GEPLNKPLGY
An alb  TEPDMPNSNR DALDKMMGDY HFTCNVNEFA QRYAEGNNV YMYLYTHRSK CNPWPRWTGV MKGDEINYVF GEPLNKPLGY
An gam  TEPDMPNSNR DALDKMMGDY HFTCNVNEFA QRYAEGNNV YMYLYTHRSK CNPWPRWTGV MKGDEINYVF GEPLNKPLGY
An fun  TEPDMPNSNR DALDKMMGDY HFTCNVNEFA QRYAEGNNV YMYLYTHRSK CNPWPRWTGV MKGDEINYVF GEPLNKPLGY
An nil  TEPDMPNSNR DALDKMMGDY HFTCNVNEFA QRYAEGNNV YMYLYTHRSK CNPWPRWTGV MKGDEINYVF GEPLNKPLGY
An soc  TEPDMPNSNR DALDKMMGDY HFTCNVNEFA QRYAEGNNV YMYLYTHRSK CNPWPRWTGV MKGDEINYVF GEPLNKPLGY
An pse  TEPDMPNSNR DALDKMMGDY HFTCNVNEFA QRYAEGNNV YMYLYTHRSK CNPWPRWTGV MKGDEINYVF GEPLNKPLGY
Cx Pip  TEPDMPNSNR DALDKMMGDY HFTCNVNEFA QRYAEGNNV FMYLYTHRSK CNPWPRWTGV MKGDEINYVF GEPLNKPLGY 81        91
Ae alb  TIDEKDFSRK I
Ae aeg  TIDEKDFSRK I
An alb  TIDEKDFSRK I
An gam  TIDEKDFSRK I
An fun  TIDEKDFSRK I
An nil  TIDEKDFSRK I
An soc  TIDEKDFSRK I
An pse  TIDEKDFSRK I
Cx Pip  TIDEKDFSRK I
```

*Fig. 2A*

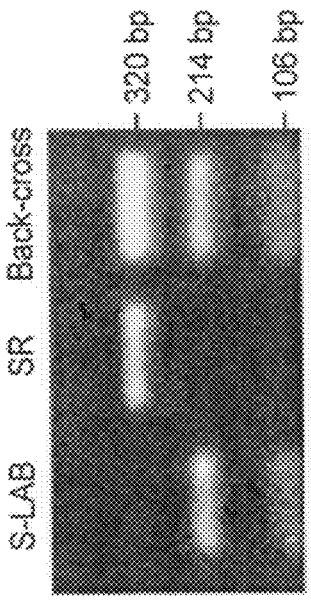

```
                  N  V  V  A  P  R  P  R  P  K  N  A  A  V  M  L  W  I  F  G  G   F  Y  S  G  T    720
KISUMU  TAACGTGGTGGCACCCCGACCCCGGCCCAAGAATGCGGCCGTCATGCTGTGGATCTTCGGCGGC TTCTACTCCGGCA
YAO     ------------------------G-----------------------------------------------------

A  T  L  D  V  Y  D  H  R  A  L  A  S  E  E  N  V  I  V  V  S  L  Q  Y  R  V    800
KISUMU  CCCCCACCCTGGACGTGTACGACCACCGGGCCCTTGCGTCCGAAGAAAACGTGATCGTGGTGTCCCTGCAGTACCGCGTG
YAO     --------------------------------------------------------------------------------

A  S  L  G  F  L  F  L  G  T  P  E  A  P  G  N  A  G  L  F  D  Q  N  L  A  L  R  880
KISUMU  GCCAGTCTGGGCTTCCTGTTTCTGGGCACCCCGGAAGCCCCCGGCAATGCGGGACTGTTCGATCAGAACTTGGCTCTGCG
YAO     --------------------------------------------------------------------------------

960
KISUMU  GTAGGTGTCTTTGCATGGTGAATGAGGGTATAGTATTCTAACGAGGTGCTCTTCTTCCCATCACTTCTTGGGAGTCAGC
YAO     -----------------G--T---TC--TA-T------------------------------------------------

W  V  R  D  N  I  H  R  F  G  G  D  P  S  R  V  T  L  F  G  E  S  A  G  A  V  S  1040
KISUMU  TGGGTGCGGGACAACATTCACCGGTTCGGTGGTGATCCGTCCCGTGTGACACTGTTCGGGGAGAGTGCCGGTGCCGTCTC
YAO     --------------------------------------------------------------------------------

V  S  L  H  L  L  S  A  L  S  R  D  L  F  Q  R  A  I  L  Q  S  G  S  P  T  A  P  1120
KISUMU  GGTGTCGCTGCATCTGCTGTCGGCGCTGTCGCGGGATCTGTTCCAGCGGGCCATCCTGCAGAGCGGCTCGCCGACGGCAC
YAO     -----------------T--------------------------------------------------------------
                                                        Amorce Ex3AGrev W  A  L  V  S  R  E  E  A  T  L  R                                             1200
KISUMU  CGTGGGCATTGGTATCGCGCGAGGAAGCCACGCTAAGGTACGTGCCAGCTGCTGCTTTCCCAAACCACCAACCCCGGAC
YAO     -----------------------------------------------------------------A--------------

A  L  R  L  A  E  A  V  G  C  P  H  1280
KISUMU  AGCTCACACAAACCCTCTTTTCCTTGGCTCTTTTCTCGGCTCCAGAGCACTGCGGTTGGCCGAGGCCGTCGGCTGCCCCAC
YAO     ----------------G---------------------------------------------------------------

E  P  S  K  L  S  D  A  V  E  C  L  R  G  K  D  P  H  V  L  V  N  N  E  W  G  T  1360
KISUMU  GAACCGAGCAAGCTGAGCGATGCGGTCGAGTGTCTGCGCGGCAAGGATCCCCACGTGCTGGTCAACAACGAGTGGGGCAC
YAO     --------------------------------------------------------------------------------
```

*Fig. 9B*

```
                                                                            1440
         L G I C E F P F V P V V D G A F L D E T P Q R S L A S
KISUMU GCTGGGCATTTGCGAGTTCCCGTTCGTGGCGGTGGTCGACGGTGCGTTCCTGGACGAGACGCCCCAGCGTTCGCTCGGCA
YAO    --------------------------------------------------------------------------------
                                                                            1520
         G R F K K T E I L T G S N T E E G Y Y F I I Y Y L T
KISUMU GGCGGGCGCTTCAAGAAGACGGAGATCCTCACGGGCAGCAACACGGAGGAGGGCTACTACTTCATCATCTACTACCTGACC
YAO    --------------------------------------------------------------------------------
                                                                            1600
         E L L R K E E G V T V T R E E F L Q A V R E L N P Y V
KISUMU GAGCTGCTGCGCAAGGAGGAGGGCGTGACCGTGACGCGCGAGGAGTTCCTGCAGGCGGTGCGCGAGCTCAACCCGTACGT
YAO    --------------------------------------------------------------------------------
                                                                            1680
         N G A A R Q A I V F E Y T D W T E P D N P N S N R D A
KISUMU GAACGGGGCGGCCCGGCAGGCGATCGTGTTCGAGTACACCGACTGGACCGAGCCGGACAACCCGAACAGCAACCGGGACG
YAO    --------------------------------------------------------------------------------
                                                                            1760
         L D K M V G D Y H F T C N V N E F A Q R Y A E E G N
KISUMU CGCTGGACAAGATGGTGGGCGACTATCACTTCACCTGCAACGTGAACGAGTTCGCGCAGCGGTACGCCGAGGAGGGCAAC
YAO    --------------------------------------------------------------------------------
                                                                            1840
         N V Y M Y L Y T H R S K G N P W P R W T G V M H G D E
KISUMU AACGTCTACATGTATCTGTACACGCACCGCAGCAAAGGCAACCCGTGGCCGCGGCTGGACGGGCGTGATGCACGGCGACGA
YAO    --------------------------------------------------------------------------------
                                                                            1920
         I N Y V F G E P L N P T L G Y T E D E K D F S R K I M
KISUMU GATCAACTACGTGTTCGGCGAACCGCTCAACCCCACGCTCGGCTACACCGAGGACGAGAAAGACTTTAGCCGGAAGATCA
YAO    --------------------------------------------------------------------------------
                                                                            2000
         R Y W S N F A K T G
KISUMU TGCGATACTGGTCTAACTTTGCCAAAACCGGGTAAGTGTGTGTGTGTGTGTGTGTCAAACACCAGACTGTCGATCGCTCT
YAO    -------------------------------------------------A-------C-A--A-----
                                                                            2080
                            N P N P N T A S S E F P E W P K H T
KISUMU AACGCC------TTCTCTCTTCAACAGCAATCCAAATCCCAACACGGCCAGCAGCGAATTCCCGACTGGCCCAAGCACA
YAO    ---A--AGCCGTC---------T---------------A-------
```

*Fig. 9C*

```
                                                                    2160
          A H G R H Y L E L G L N T S F V G R G P R L R Q C A
KISUMU CCGCCCACGGACGGCACTATCTGGAGCTGGGCCTCAACAGTCCTTCGTGGGTCGGGGGCCACGGTTGAGGCACTGTGCC
YAO    --------------------------------------------------------------------------------
                                                                    2240
         F W K K Y L P Q L V A A T S
KISUMU TTCTGGAAGAAGTACCTTCCCCAGCTAGTTGCAGCTACCTGTAACTCTCGT-GCAGGGCTTGAAATCCTCTCCCGCATCC
YAO    --------------------------------------A--T--T--A-GA---C--C---T--G---
                                                                    2320
                                                              N L P G
KISUMU TCAACAGGGTCCAGGTTGCAATAACAAATGTATCTCTCTCTCTCTCAGGTCTCTTTTCCCCAAAACAGGGAACCTACCAG
YAO    C--T--------A-A------------------------A-----
                                                                    2400
         P A P P S E P C E S S A F F Y R P D L I V L L V S L
KISUMU GGCCACCACCGCCCAGTGAACGGTGCCAAAGCAGCCCATTTTTTTACCGACCTGATCTGATCGTGCTGCTGGTGTCGCTG
YAO    --------------------------------------------------------------------------------
                                                                    2480
         L Y T A T V R F I Q *
KISUMU CTTACGGCGACGGTCAGATTCATACAATAATTACTACCCATCCATGCCTAGTTCTTTTAAGCTTTAAGATAGTGAGGA
YAO    -------------------------------------------G------------------------------

KISUMU ACAAATTTTTCCTAACCAATTTGCCAACGCCCTTTAGAGCAGAACGGAGGAGAGATAGGACT
YAO    --------------------------------------------------------------
```

*Fig. 9D*

Fig. 14

ACETYLCHOLINESTERASE GENE RESPONSIBLE FOR INSECTICIDE RESISTANCE AND APPLICATIONS THEREOF

The present invention relates to a novel acetylcholinesterase gene responsible for insecticide resistance, in particular in mosquitoes, to the products of this gene (cDNA, protein) and to the applications thereof, in particular for screening novel insecticides and for the genetic detection of resistance to organophosphorus compounds and/or to carbamates in mosquito populations.

Acetylcholinesterase (AChE, E.C. 3.1.1.7) is an essential enzyme which hydrolyzes acetylcholine in the synapses, thus terminating cholinergic transmissions at neuronal or neuromuscular junctions. The inhibition of AChE prevents the deactivation of the synaptic signal, thus resulting in a loss of control of cholinergic transmission. The biology of acetylcholinesterase has been greatly studied in invertebrates, and in particular insects, since this enzyme is the target for the main classes of pesticides used, organophosphorus compounds and carbamates. However, the massive use of pesticides over the past decades has caused resistant species to emerge. Among the mechanisms of resistance, the selection of mutations making AChE insensitive to insecticides has been observed in many cases (for a review, see Fournier et al., Comp. Biochem. Physiol., 1994, 108, 19-31).

In order to precisely determine the nature of the AChE that is a target for insecticides, and also the mutations responsible for the resistance to the latter, the genes encoding AChEs (ace genes) have been isolated in various arthropod (insect and arachnid) species.

The first ace gene was identified in drosophila (*Drosophila melanogaster*), by reverse genetics (Hall et al., EMBO J., 1986, 5, 2949-2954). The proof that this gene was involved in insecticide resistance was provided by the demonstration of amino acid substitutions in the AChE of resistant *drosophila*, conferring insensitivity to cholinergic insecticides (Mutéro et al., P.N.A.S., 1994, 91, 5922-5926). The studies in *D. melanogaster* therefore appear to indicate the presence of a single ace gene in insects, encoding the AChE that is a target for cholinergic insecticides.

However, with the exception of the ace gene of two other insects, *Musca domestics* (Williamson et al., 1992, in *Multidisciplinary approaches to cholinesterase functions*, Eds Schafferman A. & Velan B., Plenum Press, New-York, pp 83-86; Walsh et al., Biochem. J., 2001, 359, 175-181; Kozaki et al., Insect Biochem. Mol. Biol., 2001, 31, 991-997) and *Bactrocera oleae* (Vontas et al., Insect Molecular Biology, 2002, 11, 329-339), the study of the ace genes isolated from other insects or else from arachnids, by homology with that of *drosophila*, indicates that they are not involved in insecticide resistance.

In fact, no mutation in the amino acid sequence of AChE encoded by the ace gene of *Aphis gossypii*, of *Nephotettix cincticeps* and of *Boophilus microplus* is observed between resistant and sensitive individuals (Menozzi et al., doctoral thesis from the Paul Sabatier university, Toulouse, 2000; Tomita et al., Insect Biochem. Mol. Biol., 200, 30, 325-333; Baxter et al., Insect Biochem. Mol. Biol., 1998, 28, 581-589; Hernandez et al., J. Med. Entomol., 1999, 36, 764-770), and independent segregation is observed between the *Culex pipiens* and *C. tritaeniorynchus* ace gene and insecticide resistance (Malcolm et al., Insect. Mol. Biol., 1998, 7, 107-120; Mori et al., Insect Mol. Biol., 2001, 10, 197-203).

As regards the other ace genes isolated from other insects, their role in insecticide resistance has not been studied (*Lucilia cuprina*: Chen et al., Insect. Biochem. Mol. Biol., 2001, 31, 805-816; *Schizaphis graminum*: Gao et al., Insect. Biochem. Mol. Biol., 2001, 31, 1095-1104) or no insecticide-insensitive form of AChE has been described (*Aedes aegypti, Anopheles gambiae* and *Anopheles stephensi*: Anthony et al., FEBS letters, 1995, 368, 461-465; Malcolm et al., in *Molecular Insect Science*, Eds Hageborn et al., Plenum Press, New York, pp 57-65).

Two hypotheses have been put forward to explain the difference in insecticide resistance observed between *Drosophila melanogaster* or *Musca domestica* and the other insects or the arachnids which have been studied: the presence of a "modifier gene" responsible for post-transcriptional or post-translational modifications of AChE, resulting in AChE forms having different catalytic activities, and the presence of a second ace gene.

However, no study has made it possible to verify these hypotheses and, consequently, to determine the nature of the gene and that of the target (AChE) involved in insecticide resistance in insects other than *Drosophila melanogaster* and *Musca domestica* or else in arachnids:

The demonstration, in *C. pipiens*, of two AChE forms having distinct catalytic activities supports the two hypotheses, but the biochemical analysis of these AChEs has not made it possible to determine the nature of the AChE involved in insecticide resistance (Bourguet et al., J. Neurochemistry, 1996, 67, 2115-2123). In fact, the description of an AChE1 activity insensitive to propoxur in insect extracts by Bourguet et al. (Pesticide Biochemistry and Physiology, 1996, 55, 2, 122-128) provides no data on the effective existence of AChE1 in *Culex pipiens*, nor on the separation of AChE1 activity from AChE2 activity, in the context of two hypotheses mentioned above, in light of the subsequent article by the same authors (Bourguet D. et al., Neurochemistry Internat., 1997, 31, 1, 65-72), in which the existence of a second gene in many mosquitoes could not be demonstrated.

A second ace gene has been isolated in arachnids; however, this gene is not involved in insecticide resistance (Hernandez et al., Baxter et al., mentioned above).

It has not been possible to isolate a second ace gene in insects despite many attempts in various species (Menozzi et al., Tomita et al., Mori et al., mentioned above; Severson et al., J. Hered., 1997, 88, 520-524).

It emerges from the above that the nature of the gene and of the target (AChE) involved in the resistance to organophosphorus compounds and/or to carbamates has not been identified in most insects and in arachnids, in particular in those in which they have been investigated; mention may be made of those which are the most important in the human and animal health fields and agricultural field, such as pathogen vectors and pests, in particular many mosquitoes such as *Culex pipiens, Aedes aegypti, Anopheles gambiae, Anopheles albimanus* or *Anopheles stephensi*, and crop pests such as *Aphis gossypii, Nephotettix cincticeps* and *Leptinotarsa decemlineata*.

The inventors have identified a novel locus of the ace gene in the genome of *Anopheles gambiae* and of 15 different species of mosquitoes, and they have shown that this novel locus, which is not homologous to the locus previously described in *D. melanogaster*, is involved in insecticide resistance in mosquitoes.

The inventors have also shown that the insecticide resistance, at least in mosquitoes of the species *Culex pipiens* and *Anopheles gambiae*, is linked to a unique mutation in the acetylcholinesterase sequence encoded by this novel gene, located in the region of the catalytic site of the enzyme.

This novel gene represents a diagnostic tool for the genetic detection of insecticide (organophosphorus compound, carbamate) resistance in mosquito populations. The AChE encoded by this gene represents a target for the screening of novel molecules that are active on the populations of mosquitoes resistant to the insecticides currently used.

Consequently, a subject of the present invention is a protein, characterized in that it comprises a central catalytic region that has an amino acid sequence selected from the group consisting of the sequence SEQ ID NO. 1 and the sequences exhibiting at least 60% identity or 70% similarity with the sequence SEQ ID NO. 1, with the exclusion of the NCBI sequence AAK09373 corresponding to the *Schizaphis graminum* acetylcholinesterase (SEQ ID NO: 152).

The protein according to the invention represents a novel insect acetylcholinesterase, hereinafter referred to as AchE1, responsible for resistance to organophosphorus compounds and/or to carbamates, at least in mosquitoes, in particular in *C. pipiens*; the locus encoding said AchE1 is hereinafter referred to as ace-1; ace-2 represents the second ace locus, which is not involved in insecticide resistance in mosquitoes. The single ace gene present in *Drosophila melanogaster*, which is homologous to ace-2, is therefore also referred to as ace-2.

In accordance with the invention, said central catalytic region contains the catalytic domain of the AChE, and corresponds to that located between positions 70 and 593 of the sequence of *Anopheles gambiae* AChE1 (SEQ ID NO. 3,643 amino acids); it corresponds to that located, respectively, between positions 100 and 629 of the sequence of *Schizaphis graminum* AChE1 (NCBI AAK09373; SEQ ID NO: 152), 60 and 582 of the sequence of *Culex pipiens* AChE1 (SEQ ID NO. 7), 34 and 593 of the sequence of *Anopheles gambiae* AChE2 (FIG. 1, SEQ ID NO. 53), and 41 and 601 of the sequence of *Drosophila melanogaster* AChE2 (NCBI AAF54915). This central region, which contains the catalytic domain, is conserved in vertebrates and invertebrates, whereas the N- and C-terminal ends exhibit great variability between the various species.

In accordance with the invention, the identity of a sequence relative to a reference sequence (SEQ ID NO. 1) is assessed according to the percentage of amino acid residues which are identical, when the sequences corresponding to the catalytic region as defined above are aligned, so as to obtain the maximum correspondence between them.

A protein having an amino acid sequence having at least X % identity with the reference sequence SEQ ID NO. 1 is defined, in the present invention, as a protein which sequence corresponding to the central catalytic region as defined above can include up to 100-X alterations per 100 amino acids of the sequence SEQ ID NO. 1. For the purpose of the present invention, the term "alteration" includes consecutive or dispersed amino acid deletions, substitutions or insertions in the reference sequence. This definition applies, by analogy, to the nucleic acid molecules.

The similarity of a sequence relative to the reference sequence SEQ ID NO. 1 is assessed according to the percentage of amino acid residues which are identical or which differ by conservative substitutions, when the sequences corresponding to the central catalytic region as defined above are aligned so as to obtain the maximum correspondence between them. For the purpose of the present invention, the term "conservative substitution" is intended to mean the substitution of an amino acid with another which has similar chemical properties (size, charge or polarity), which generally does not modify the functional properties of the protein.

A protein having an amino acid sequence having at least X % similarity with the sequence SEQ ID NO. 1 is defined, in the present invention as a protein which sequence corresponding to the central catalytic region as defined above can include up to 100-X non-conservative alterations per 100 amino acids of the reference sequence. For the purpose of the present invention, the term "non-conservative alterations" includes consecutive or dispersed amino acid deletions, non-conservative substitutions or insertions in the sequence SEQ ID NO. 1.

The comparison of the AChE1 according to the invention with the insect AChEs available on the databases, by alignment of the sequences corresponding to the central region as defined above, using the BLAST program default parameters, inactivated filter) available on the worldwide web at ncbi.nlm.nih.gov/gorf/bl2.html shows that:

the insect AChE1 and AChE2 sequences exhibit 36-39% identity (53-57% similarity) with one another, the insect AChE1 sequences exhibit 65-97% identity (79-98% similarity) with one another, the insect AChE2 sequences exhibit 58-99% identity (73-99% similarity) with one another.

In addition, the phylogenetic analysis of the AChEs of the various animal species shows that the AChE1 protein sequences form a significant autonomous group (bootstrap 795/1000), and that the insect AChE1s form a significant distinct subgroup (bootstrap 856/1000).

The AChE1 according to the invention comprises units characteristic of AChEs (FIG. 1) located at the following positions, respectively, in the sequence SEQ ID NO. 3 and in the reference sequence from *Torpedo californica* (SWISSPROT P04058): a canonic unit of the FGESAG type around the serine at position 266 (200), which is characteristic of the AChE active site, a choline-binding site (tryptophan residue at position 151 (84)), three residues of the catalytic triad (serine, glutamic acid and histidine residues, respectively at positions 266 (200), 392 (327) and 506 (440)), six cysteine residues potentially involved in conserved disulfide bridges ($C_{134(67)}$-$C_{161(94)}$; $C_{320(254)}$-$C_{333(265)}$; $C_{468(402)}$-$C_{589(521)}$), aromatic residues bordering the active site gorge (10 residues) and a phenylalanine residue at position 355 (290) but not at position 353 (288), which distinguishes invertebrate AChEs from those of vertebrates. It also has a hydrophobic C-terminal peptide corresponding to a glycolipid addition signal, indicating post-translational cleavage of a C-terminal fragment and the addition of a glycolipid anchoring residue as in *Drosophila*; the cysteine residue in the C-terminal sequence preceding the potential site for cleavage of the hydrophobic peptide could be involved in an intermolecular disulfide bond linking the two catalytic subunits of the AChE dimer.

The AChE1 according to the invention differs from the AChE of *Drosophila* (AChE2) by the absence of a hydrophilic insertion of 31 amino acids between the residues located at positions 174 and 175 of the sequence SEQ ID NO. 3 (FIG. 1); this hydrophilic insertion could be characteristic of AChE2, at least in the Diptera.

The invention encompasses the insect AChE1s sensitive or resistant to organophosphorus compounds and/or to carbamates.

For the purpose of the present invention, the AChE1 sequences include both the primary sequences and the secondary sequences and the tertiary sequences of said AChE1s.

For the purpose of the present invention, the term "sensitive AChE" is intended to mean an AChE for which the acetylcholinesterase activity is inhibited in the presence of organophosphorus compounds or of carbamates.

For the purpose of the present invention, the term "resistant AChE" is intended to mean an AChE for which the activity is not inhibited by concentrations of organophosphorus compounds or of carbamates which inhibit 100% of the activity of the corresponding "sensitive AChE" derived from an individual of the same species; this "resistant AChE" differs from the preceding one by the presence of one or more mutations in its amino acid sequence (amino acid substitutions) which modify its sensitivity to acetylcholinesterase inhibitors; among these mutations, mention may be made of the following: F78S, I129V, G227A and F228Y, the amino acids being numbered with reference to the sequence of *Torpedo californica* AChE (SWISSPROT P04058).

The acetylcholinesterase activity and the catalytic parameters of the AChEs are measured by conventional enzymatic techniques such as those described in Bourguet et al., mentioned above.

The proteins according to the invention include any natural, synthetic, semi-synthetic or recombinant protein of any prokaryotic or eukaryotic organism, comprising or consisting of an amino acid sequence of an AChE1 protein as defined above. They include in particular the natural proteins isolated from any insect species, and also the recombinant proteins produced in a suitable expression system.

According to an advantageous embodiment of said AChE1, it corresponds to that of an insect which belongs to the order Diptera; preferably, said insect is chosen from the family Culicidae, from the genera *Culex, Aedes* and *Anopheles*.

According to an advantageous arrangement of this embodiment, said AChE1 consists of the sequences SEQ ID NO. 3, SEQ ID NO. 5 and SEQ ID NO. 126 of *Anopheles gambiae* and of sequence SEQ ID NO. 7 of *Culex pipiens* (S-LAB strain), that are sensitive to organophosphorus compounds and/or to carbamates.

According to another advantageous arrangement of this embodiment, said central catalytic region of the AChE1 corresponds to a sequence selected from the group consisting of the sequences SEQ ID NOs. 8 to 21 representing a fragment of approximately 91 amino acids (fragment K, FIG. 1), corresponding to that located between positions 445 and 535 of the sequence SEQ ID NO. 3.

According to another advantageous embodiment of the invention, said AChE1 is an acetylcholinesterase resistant to insecticides of the organophosphorus compound and carbamate class, that includes a mutation of the glycine located at position 119 to serine (mutation or substitution of G119S type), said position being indicated with reference to the sequence of *Torpedo californica* AChE (SWISSPROT P04058).

In fact, the inventors have shown that the residue at position 119 is close to the residues of the catalytic site (serine 200 and histidine 440) and that the replacement of the glycine of the AChE1 of sensitive mosquitoes with a serine, in the AChE1 of resistant mosquitoes, reduces the space of the catalytic site and prevents the insecticide from interacting with the catalytic serine (S200), due to the steric hindrance of the Van der Waals bonds of the side chain of the serine at position 119. The role of the G119S mutation in the insecticide resistance has been confirmed by analysis of the acetylcholinesterase activity of recombinant AChE1 proteins produced from the cDNA of *Culex pipiens* sensitive (S-LAB strain having an AChE1 that includes a glycine at position 119) or resistant (SR strain in which the AChE1 differs from the preceding one only by the presence of a serine at position 119) to insecticides; 90% of the activity of the AChE1 of the sensitive strain is inhibited in the presence of $10^{-3}$ M of propoxur, whereas the AChE1 of the resistant strain conserves 75% of its activity in the presence of 100-times higher concentrations of this insecticide ($10^{-1}$ M of propoxur).

According to an advantageous arrangement of this embodiment of said resistant AChE1, it corresponds to that of an insect (resistant to insecticides) which belongs to the order Diptera; preferably, said insect is chosen from the family Culicidae, from the genera *Culex, Aedes* and *Anopheles*.

Preferably, said resistant AChE1 has a sequence selected from the group consisting of:
the sequence SEQ ID NO. 57, corresponding to the complete sequence of the SR strain of *C. pipiens*, resistant to insecticides,
the sequence SEQ ID NO. 122, corresponding to the complete sequence of the AChE1 of the YAO strain of *An. gambiae* (isolated in Ivory Coast), resistant to insecticides, and
the sequences comprising a fragment of sequence SEQ ID NOs. 90, 93, 94, 95, 97 to 101, 113 and 116 representing a peptide fragment of approximately 150 amino acids encoded by the third coding exon of the ace-1 gene of a resistant insect as defined above, containing the substitution of G119S type, with reference to the sequence of *Torpedo californica* AChE (SWISSPROT P04058).

According to yet another advantageous embodiment of the invention, said AChE1 is an acetylcholinesterase sensitive to insecticides of the organophosphorus compound and carbamate class, comprising a sequence selected from the group consisting of SEQ ID NOs. 91, 92, 96, 102 to 112, 114, 115 and 117 to 119, representing a fragment of approximately 150 amino acids of the third coding exon of the ace-1 gene derived from an insect as defined above, sensitive to insecticides, said fragment including a glycine at position 119 with reference to the sequence of *Torpedo californica* AChE (SWISSPROT P04058).

A subject of the present invention is also a peptide, characterized in that it consists of a fragment of at least 7 amino acids of the AChE1 protein, as defined above; these fragments are particularly useful for producing antibodies that specifically recognize the AChE1 protein.

A subject of the present invention is also antibodies, characterized in that they are directed against the AChE1 protein or a fragment thereof, as defined above.

In accordance with the invention, said antibodies are either monoclonal antibodies or polyclonal antibodies.

These antibodies may be obtained by conventional methods, known in themselves, comprising in particular the immunization of an animal with a protein or a peptide in accordance with the invention, in order to make it produce antibodies directed against said protein or said peptide.

A subject of the present invention is also an isolated nucleic acid molecule, characterized in that it has a sequence selected from the group consisting of:
the sequences encoding an AChE1 protein as defined above (cDNA and genomic DNA fragment corresponding to the ace-1 gene),
the sequences complementary to the above sequences, which may be sense or antisense, and
the fragments of at least 8 bp, preferably of 15 bp to 500 bp, of the above sequences.

The invention encompasses the sequences of the alleles of the ace-1 gene derived from any insect, and also the sequences of the natural (sensitive or resistant alleles) or artificial mutants of the ace-1 gene encoding a sensitive or resistant AChE1 protein, as defined above.

According to an advantageous embodiment of the invention, said sequence encoding an AChE1 protein is selected from the group consisting of:

a) the sequences SEQ ID NO. 2, SEQ ID NO. 4, SEQ ID NO. 125, SEQ ID NO. 6, SEQ ID NO. 56 and SEQ ID NO. 121 which correspond to the cDNA of the AChE1 protein of amino acid sequence, respectively, SEQ ID NO. 3, SEQ ID NO. 5, SEQ ID NO. 126, SEQ ID NO. 7, SEQ ID NO. 57 and SEQ ID NO. 122, as defined above, b) the sequences SEQ ID NO. 22, SEQ ID NO. 23 and SEQ ID NO. 127 which correspond to the ace-1 gene of *Anopheles gambiae* encoding the AChE1s as defined above, which gene has an exon-intron organization comprising at least 9 exons (table I), and c) the sequences comprising the sequence SEQ ID NO. 120 which corresponds to the virtually complete sequence of the ace-1 gene of *Anopheles gambiae* encoding the resistant AChE1 of sequence SEQ ID NO. 122, as defined above.

TABLE I

Intron-exon organization of the ace-1 gene

| | 5' site | | 3' site | |
|---|---|---|---|---|
| | Position | Sequence | Position | Sequence |
| Intron1 | 301 | AGCAA/gtaat | 1255 | cgcag/CCATT |
| Intron2 | 1413 | CAATG/gtgag | 5338 | tgtag/CGCTC |
| Intron3 | 5696 | CGCAG/gtcgg | 7634 | ttcag/ACGCA |
| Intron4 | 7769 | CTCGG/gtaag | 7855 | ggcag/ACGCG |
| Intron5 | 8393 | CTACG/gtagg | 8472 | gtcag/CTGGG |
| Intron6 | 8670 | CTAAG/gtacg | 8756 | tccag/AGCAC |
| Intron7 | 9464 | ACCGG/gtaag | 9530 | tacag/CAATC |
| Intron8 | 9703 | TACCT/gtaag | 9810 | aacag/CGAAC |

In accordance with the present invention, the third coding exon of the ace-1 gene corresponds to that which is located between intron 4 and intron 5 in the sequence of *An. gambiae* (table I), i.e. between positions 7854 and 8393 of the sequence SEQ ID NO. 127.

According to another advantageous embodiment of the invention, said fragment is selected from the group consisting of the primers of sequence SEQ ID Nos. 39 to 50, 54, 55, 58, 59, 123, 124, 128 and 129 and the fragments of sequences SEQ ID Nos. 24 to 38 and 60 to 89.

The nucleic acid molecules according to the invention are obtained by conventional methods, known in themselves, according to standard protocols such as those described in *Current Protocols in Molecular Biology* (Frederick M. AUSUBEL, 2000, Wiley and son Inc, Library of Congress, USA). For example, they can be obtained by amplification of a nucleic acid sequence by PCR or RT-PCR, by screening genomic DNA libraries by hybridization with a homologous probe, or else by total or partial chemical synthesis.

The nucleic acid molecules as defined above can be used as probes or as primers for isolating the ace-1 gene of other species or alleles of this gene, in particular by screening a genomic DNA or cDNA library, and also for detecting/amplifying nucleic acid molecules (mRNA or genomic DNA) encoding an AChE1 protein as defined above.

These various nucleic acid molecules make it possible to demonstrate the ace-1 gene, allelic variants of this gene, or a functional alteration of this ace-1 gene (substantial change in insecticide sensitivity) resulting from a mutation (insertion, deletion or substitution) of one or more nucleotides in said gene.

A subject of the present invention is also a method for detecting insects carrying resistance to insecticides of the organophosphorus compound and carbamate class, characterized in that it comprises:

preparing a sample of nucleic acids from insects to be tested, and detecting, by any suitable means, the presence, in said nucleic acid sample, of a mutation in the ace-1 gene as defined above.

Said detection is carried out by conventional techniques which are known in themselves, for example: (i) by amplification of a region of said ace-1 gene liable to contain a mutation, and then detection of said mutation by sequencing, or by digestion with a suitable restriction enzyme, of the PCR product obtained, or else (ii) by hybridization with a labeled probe specific for a region of said ace-1 gene liable to contain a mutation, and then direct detection of the mismatches and/or digestion with a suitable restriction enzyme.

According to a first advantageous embodiment of said method, a fragment of approximately 320 bp (fragment K) is amplified by means of the primers SEQ ID NO. 39 and SEQ ID NO. 40. For example, in mosquitoes, a fragment of sequence SEQ ID NOs. 24 to 38 is obtained, which has mutations between insecticide-sensitive and insecticide-resistant mosquitoes. For example, in *C. pipiens* 3 substitutions are observed in the sequence of the resistant individuals, one of which introduces an EcoRI site. Analysis of the restriction profile after PCR amplification of the fragment K and digestion of the products obtained with EcoRI (RFLP analysis) makes it possible to rapidly detect the ace-1 genotype in a population of *C. pipiens*; the presence of a single fragment corresponds to the resistant homozygotes (RR), the presence of 2 fragments of approximately 106 bp and 214 bp corresponds to the sensitive homozygous individuals (SS) and the presence of 3 fragments of 106 bp, 214 bp and 320 bp corresponds to the resistant heterozygous individuals (RS).

According to a second advantageous embodiment of said method, the G119S mutation in the third coding exon of the ace-1 gene which is responsible for the resistance to insecticides of the organophosphorus compound and carbamate class in mosquitoes is detected according to one of the following alternatives, respectively in mosquitoes of the species *C. pipiens* and *An. gambiae*:

in mosquitoes of the species *Culex pipiens*, a 520 bp fragment of the third coding exon is amplified from the genomic DNA by PCR using the pair of primers Ex3dir and Ex3rev (SEQ ID NOs. 58 and 59); the PCR fragment is digested with Alu I and the digestion product is separated by agarose gel electrophoresis, and then the restriction profile thus obtained is analyzed: the presence of a 520 bp fragment corresponds to the sensitive homozygous SS individuals, the presence of two fragments (357 bp and 163 bp) corresponds to the resistant homozygous RR individuals and the presence of 3 fragments (520 bp, 357 bp and 163 bp) corresponds to the resistant heterozygous RS individuals, in mosquitoes of the species *Anopheles gambiae*, a 541 bp fragment of the third coding exon is amplified from the genomic DNA by PCR using the pair of primers Ex3AGdir and Ex3AGrev (SEQ ID NOs. 123 and 124); the PCR fragment is digested with Alu I and the digestion product is separated by agarose gel electrophoresis, and then the restriction profile thus obtained is analyzed: the presence of two fragments (403 bp and 138 bp)

corresponds to the sensitive homozygous SS individuals, the presence of 3 fragments (253 bp, 150 bp and 138 bp) corresponds to the resistant homozygous RR individuals and the presence of 4 fragments (403 bp, 253 bp, 150 bp and 138 bp) corresponds to the resistant heterozygous RS individuals; given that the 150 bp and 138 bp fragments co-migrate, the resistant homozygous and heterozygous individuals are detected, respectively, by the presence of 2 bands (253 bp and approximately 150 bp) and of 3 bands (403 bp, 253 bp and approximately 150 bp), in mosquitoes of the species *Culex pipiens, Anopheles gambiae* or *Anopheles albimanus*, a 194 bp fragment containing codon 119 of the third coding exon is amplified from the genomic DNA by PCR using the pair of primers Moustdir1 and Moustrev1 (SEQ ID NOs. 128 and 129); the PCR fragment is digested with Alu I and the digestion product is separated by agarose gel electrophoresis, and then the restriction profile thus obtained is analyzed: the presence of two fragments (74 bp and 120 bp) corresponds to the resistant homozygous RR individuals, the presence of a single fragment (no digestion) corresponds to the sensitive homozygous SS individuals and the presence of three fragments (194 bp, 74 bp and 120 bp) corresponds to the resistant heterozygous RS individuals.

A subject of the present invention is also a reagent for detecting insects carrying resistance to organophosphorus compounds and/or to carbamates, characterized in that it is selected from the group consisting of: the nucleic acid molecules and the fragments thereof as defined above (probes, primers) and the antibodies as defined above.

A subject of the present invention is also a recombinant vector, characterized in that it comprises an insert selected from the group consisting of the nucleic acid molecules encoding an AChE1 protein and the fragments thereof as defined above.

Preferably, said recombinant vector is an expression vector in which said nucleic acid molecule or one of its fragments are placed under the control of suitable regulatory elements for transcription and for translation.

These vectors are constructed and introduced into host cells by conventional recombinant DNA and genetic engineering methods which are known in themselves. Many vectors into which a nucleic acid molecule of interest may be inserted in order to introduce it into and to maintain it in a eukaryotic or prokaryotic host cell are known in themselves; the choice of a suitable vector depends on the use envisioned for this vector (for example, replication of the sequence of interest, expression of this sequence, maintenance of the sequence in extrachromosomal form or else integration into the host's chromosomal material), and also on the nature of the host cell. For example, viral vectors such as baculoviruses or nonviral vectors such as plasmids may be used. In order to express the AChE1, the ace-1 cDNA may be placed under the control of a constitutive promoter such as the actin 5C promoter, in a suitable vector, and said recombinant vector is introduced into insect cells such as drosophila cells (Schneider S2 cells).

A subject of the present invention is also prokaryotic or eukaryotic cells modified with a recombinant vector as defined above; preferably, these cells are insect cells.

The recombinant vectors and the modified cells as defined above are useful in particular for producing the AChE1 proteins and peptides according to the invention.

A subject of the present invention is also a transgenic invertebrate animal, characterized in that it contains cells modified with at least one nucleic acid molecule as defined above; preferably, said animal is an insect.

The transgenic animals and the modified cells as defined above are useful in particular for screening insecticidal substances and for biologically controlling pathogen vectors and insect pests.

A subject of the present invention is also a method for screening an insecticidal substance, characterized in that it comprises:

a) bringing the test substance into contact with an AChE1 protein selected from: an AChE1 protein isolated according to the invention, or an extract of modified cells or a biological sample from a transgenic animal containing said AChE1 protein, as defined above, in the presence of acetylcholine or of one of its derivatives, b) measuring, by any suitable means, the acetylcholinesterase activity of the mixture obtained in a), and c) selecting the substances capable of inhibiting said activity.

A subject of the present invention is also a method for screening an insecticidal substance, characterized in that it comprises:

bringing a transgenic animal as defined above into contact with the test substance, and measuring the animal's survival.

Advantageously, said screening methods use AChE1s resistant to organophosphorus compounds or to carbamates, or else cells or transgenic animals containing them.

A subject of the present invention is also a reagent for screening insecticidal substances, characterized in that it is selected from the group consisting of the AChE1 proteins, the recombinant vectors, the modified cells and the transgenic animals as defined above.

Insecticidal substances capable of inhibiting the acetylcholinesterase activity of the AChE1 proteins resistant to insecticides of the organophosphorus compound and carbamate class commonly used have applications: in animal and human health, for controlling pathogen vectors (for example *Aedes aegypti*, a vector of arboviroses such as dengue and yellow fever, *Culex pipiens*, a West-Nile virus vector, *Anopheles gambiae*, an African vector of the agent for malaria, etc.) and in the agricultural field, for controlling insect pests which devastate harvests (for example the Colorado potato beetle (*Leptinotarsa decemlineata*) which attacks potatoes, aphid pests such as *Aphis gossypii* and *Myzus persicae*, etc.).

A subject of the invention is also a detection and/or screening kit for carrying out the methods as defined above, characterized in that it includes at least one reagent as defined above.

A subject of the present invention is also a method for screening inhibitors of an AChE1 as defined above, characterized in that it comprises:

(a) identifying molecules (peptides or other chemical structures) having a significant probability of binding to said AChE1;

(b) isolating the potential inhibitors identified in step (a);

(c) bringing the substance isolated in step (b) into contact with an AChE1 as defined above, an extract of modified cells, a biological sample from a transgenic animal as defined above, or an extract of an insect sensitive or resistant to the above-mentioned insecticides, in the presence of acetylcholine or of one of its derivatives;

(d) measuring, by any suitable means, the acetylcholinesterase activity of the mixture obtained in (c); and (e) verifying that the molecules isolated in (b) inhibit the AChE1 activity.

The 3D structure of the torpedo fish acetylcholinesterase has made it possible to model the 3D structure of the C. pipiens AChE1. The G247S mutation [corresponding to a G119S substitution in the torpedo protein] results in a decrease in the space of the catalytic site due to the hindrance of the serine side chain.

Modeling of the structure of the C. pipiens or An. gambiae AChE1 thus makes it possible to screen AChE1 inhibitors by virtual screening ("Docking"). The method according to the invention comprises a computer simulation step (step (a)) aimed at identifying peptide or chemical structures having a significant probability of binding to a target protein. Various computer programs thus make it possible to simulate and to estimate the probabilities of interactions. Mention may in particular be made of the algorithms developed for the search for potential interactions described in Schneider et al. (Drug Discovery Today, 2002, 7, 1, 64-71). More precisely, the tools most commonly used up until now are FlexX (Tripos, St Louis, Mo., USA), DOCK (UCSF, San Francisco, Calif., USA) and GOLD (Cambridge Crystallographic Data Centre, Cambridge, United Kingdom).

It is thus possible to isolate potential inhibitors of the resistant form of AChE1 without biochemically having the protein, and then to directly test the inhibitory ability of each candidate on the AChE1 activity of an extract of sensitive or resistant insects (step (c) of the method). This approach can therefore be entirely free of the purification and/or of the production of target protein.

For the purpose of the present invention, the significance of a binding probability cannot be defined absolutely: it may depend on the type of amino acids involved in the interaction, and also on the programs used for the modeling. More precisely, the most commonly used methods select, for a given site of a target molecule, the compounds exhibiting the lowest binding energy. In general, the calculation of the energy takes into account the "hydrogen" bonds, the van der Waals, electrostatic and hydrophobic interactions, and also the entropy penalties. It is therefore a priori impossible to give a significant limit in absolute value beyond which a potential ligand will be accepted or rejected, since the energy will depend on the atoms involved in the bond. However, three selection criteria can be applied:

1. an arbitrary selection of the compounds with least binding energy. In general, the limit is fixed between 1% and 5% of the number of compounds tested.

2. an estimation of the binding affinity, according to the energy calculations. An acceptable value as a starting point could be between 1 and 300 micromolar. By way of example, onchidal, an AChE inhibitor, has an apparent affinity of 300 μM (Abramson et al., *Mol. Pharmacol.,* 1989, 36, 349).

3. a statistical selection of the compounds, estimating the probability of an identical or higher score for a compound being obtained randomly. In general, the compound is accepted when the estimated probability is ≦0.05.

Besides the above provisions, the invention also comprises other provisions which will emerge from the following description, which refers to examples of implementation of the ace-1 gene and of its products (cDNA, protein) according to the present invention and also to the table summarizing the sequences of the application and to the attached drawings in which:

FIG. 1 illustrates the amino acid sequence alignment for the AChE1 proteins of *Anopheles gambiae, Schizaphis graminum, An. stephensi, Aedes aegypti, Drosophila melanogaster, Lucilia cuprina, Musca domestica* and *Culex pipiens*. By convention, the amino acids are numbered with reference to the AChE sequence from the torpedo fish (*Torpedo californica*; SWISSPROT P04058). The N- and C-terminal sequences are not represented due to their variability. The amino acids that are conserved between AChE1 and AChE2 are indicated in gray. The amino acids specific for AChE2 are indicated in black. The 3 residues representing the catalytic triad ($S_{200}$, $E_{327}$ and $H_{440}$) have boxes drawn round them. The choline-binding site ($W_{84}$) is underlined. The circles represent the position of the 14 aromatic residues bordering the active site gorge in the *Torpedo* AChE, 10 of which are present in all the AChE1 s and AChE2s (solid circles), the others not being conserved (open circles). Three intramolecular disulfide bonds between cysteine residues are indicated. The horizontal arrow indicates the position of the fragment K (amplified by means of the primers PdirAGSG and PrevAGSG). The hypervariable region of AChE2, which is absent in AChE1, is enclosed in a box; the following sequence identifiers appear in FIG. 1: Agam1 (SEQ ID NO: 131), Sgra (SEQ ID NO: 132), Agam2 (SEQ ID NO: 133), Aste (SEQ ID NO: 134), Aaeg2 (SEQ ID NO: 135), Dmel (SEQ ID NO: 136), Lcup (SEQ ID NO: 137), Mdom (SEQ ID NO: 138), Cpip (SEQ ID NO: 139), Cpip1 (SEQ ID NO: 8) and Aeg1 (SEQ ID NO: 9).

FIG. 2 illustrates the genetic detection of mosquitoes resistant to organophosphorus compounds and/or to carbamates by PCR-RFLP:

FIG. 2A represents the comparison of the amino acid sequence of fragment K of various mosquito species: Cx Pip (*Culex pipiens*), Ae alb (*Aedes albopicus*), Ae aeg (*Aedes aegypti*), An alb (*Anopheles albimanus*), An gamb (*Anopheles gambiae*), An fun (*Anopheles funestus*), An nil (*Anopheles nili*), An sac (*Anopheles sacharovi*), An pse (*Anopheles pseudo-punctipennis*). The variant amino acids are shaded. The following sequences are identical: *An. darlingi* and *An. albimanus; An. sundaicus, An. gambiae* and *An. arbiensis; An. moucheti, An, funestus* and *An. minimus; An, stephensi* and *An. saccharovi*; the following sequence identifiers appear in FIG. 2A: Ae alb (SEQ ID NO: 10), Ae aeg (SEQ ID NO: 9), An alb (SEQ ID NO: 20), An gamb (SEQ ID NO: 140), An fun (SEQ ID NO: 16), An nil (SEQ ID NO: 21), An sac (SEQ ID NO: 18), An pse (SEQ ID NO: 17) and Cx Pip (SEQ ID NO: 81

FIG. 2B illustrates the comparison of the nucleotide sequences corresponding to fragment K of the sensitive (S-LAB) and resistant (SR) strains. The variant nucleotides are shaded (t→c at position 3; a→g at position 84: the EcoRI site (gaattc) located around this position, used for the PCR-RFLP analysis, is present only in the S-LAB strain; c→t at position 173). FIG. 2C illustrates the restriction profiles obtained after agarose gel electrophoresis of the products of digestion with EcoRI, of fragment K amplified by PCR. The sensitive homozygous S-LAB strain has a profile characterized by 2 bands (214 bp and 106 bp), the resistant homozygous strain has a profile characterized by a single band of 320 bp and the resistant mosquitoes derived from the back cross have a heterozygous profile characterized by 3 bands (320 bp, 214 bp and 106 bp); the following sequence identifiers appear in FIG. 2B: Acel-SLAB (SEQ ID NO: 24), Acel-SR (SEQ ID NO: 25);

FIG. 3 illustrates the phylogenetic tree for the AChE proteins. The phylogenetic analysis was carried out using 47 sequences of AChE proteins from 35 different species originating from the ESTHER database (available on the worldwide web at ensam.inra.fr/cgi-bin/ace/index). The sequences were aligned and a tree was constructed as described in example 1. Only the nodes corresponding to "bootstrap" values >50% (i.e. scores greater than 500) are indicated. The scale represents a divergence of 10%. Agam: *An. gambiae*;

Aeg: *Aedes aegypti*; Aste: *Anopheles stephensi*; Cp: *Culex pipiens*; Dmel: *Drosophila melanogaster*; Lcup: *Lucilia cuprina*; Mdom: *Musca domestics*; Ldec: *Leptinotarsa decemlineata*; Amel: *Apis mellifera*; Ncin: *Naphotettix cincticeps*; Sgra: *Schizaphis graminum*; Rapp: *Rhipicephalus appendiculatus*; Bmic: *Boophilus microplus*; Bdec: *Boophilus decoloratus*; Hsap: *Homo sapiens*; Btau: *Bos taurus*; Feat: *Felix tutus*; Ocun: *Oryctolagus cuniculus*; Rnor: *Rattus norvegicus*; Mmus: *Mus musculus*; Ggal: *Gallus gallus*; Drer: *Danio reno*; Eele: *Electrophorus electricus*; Tamr: *Torpedo marmorata*; Tcal: *Torpedo californica*; Bfas: *Bungarus fasciatus*; Mglu: *Myxine glutinosa*; Bflo: *Branchiostoma floridae*; Blan: *Branchiostoma lanceolatum*; Cint: *Ciona intestinalis*; Csav: *Ciona savignyi*; Cele: *Caenorhabditis elegans*; Cbrig: *Caenorhabditis briggsae*; Dviv: *Dictyocaulus viviparus*; Lopa: *Loligo opalescens*;

FIG. 4 illustrates the cladogram for the AChE1 and AChE2 proteins. The sequences of the AChE1 and AChE2 proteins were processed as in FIG. 1. The Bmic sequence was added as external sequence in order to define the origin of the tree. The boxes marked with an asterisk represent the proteins encoded by a gene which segregates with insecticide resistance. The open boxes represent the proteins encoded by a gene which does not segregate with insecticide resistance. The scale corresponds to a divergence of 10%;

FIG. 5 illustrates the comparison of the amino acid sequences of the AChE1 protein of *C. pipiens*, between an insecticide-sensitive strain (S-LAB) and an insecticide-resistant strain (SR). The single mutation glycine $_{247(119)} \rightarrow$ serine $_{247(119)}$ (indicated with shading) is responsible for the insecticide resistance in mosquitoes of the species *C. pipiens*; it corresponds to the substitution of the glycine located at position 247 of the sequence of *C. pipiens* AChE1 (or at position 119, with reference to the sequence of the torpedo fish AChE), with a serine; the following sequence identifiers appear in FIG. 5: SR (SEQ ID NO: 57) and S-LAB (SEQ ID NO: 7);

Figure 6A:
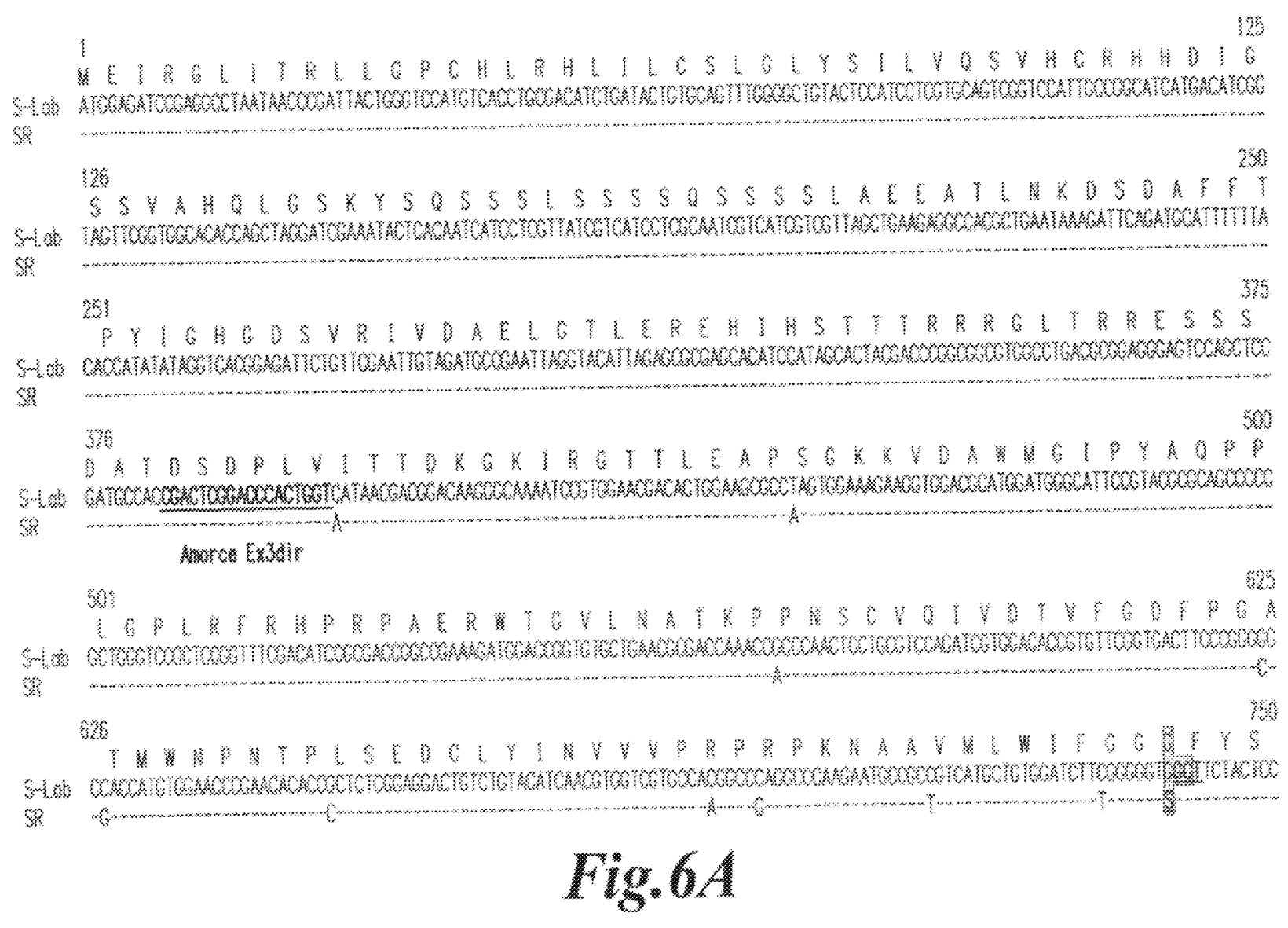
Figure 6B:
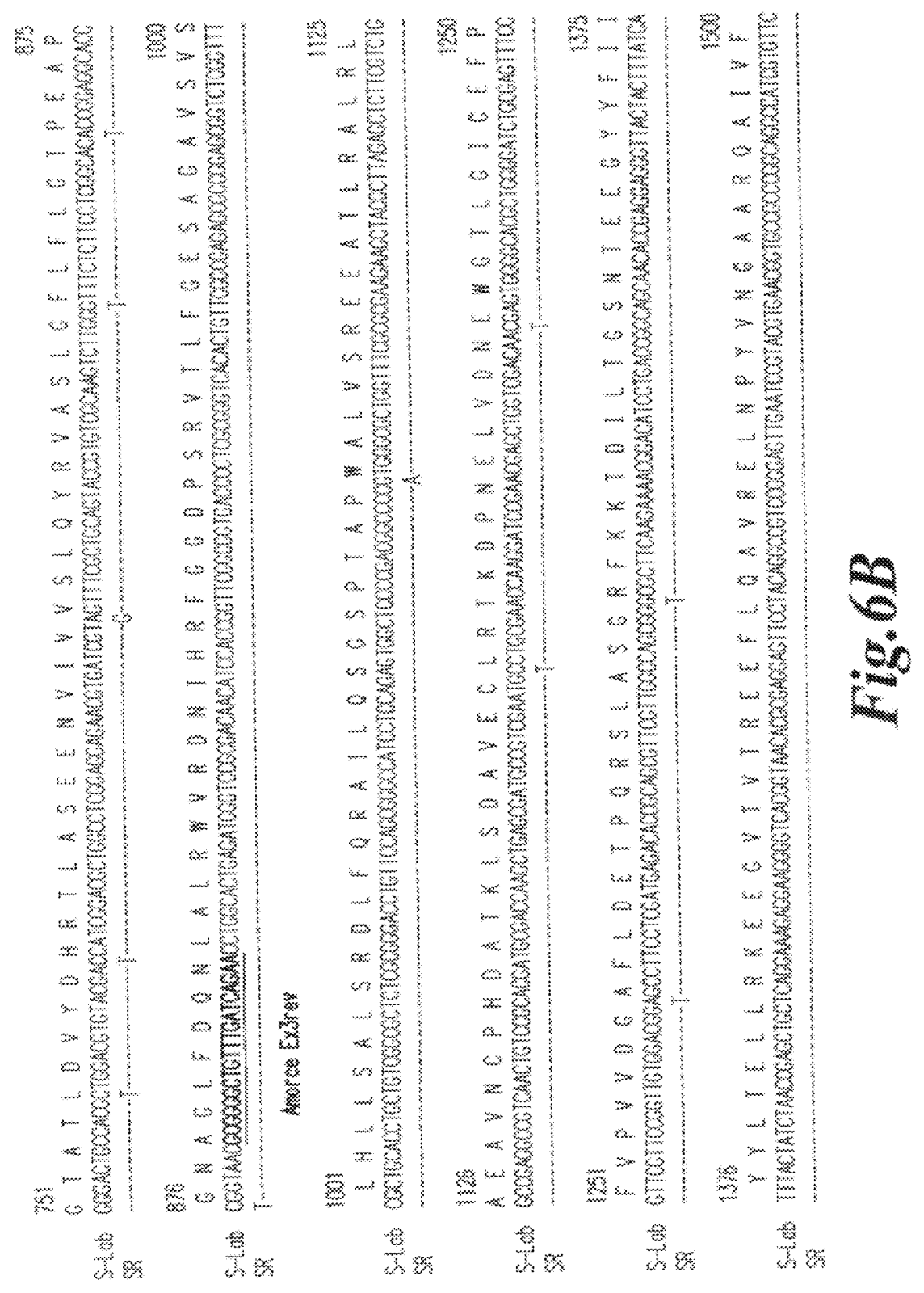

FIGS. 6A and 6B illustrate the comparison of the nucleotide sequences encoding the *C. pipiens* AChE1 protein, between an insecticide-sensitive strain (S-LAB) and an insecticide-resistant strain (SR); all the mutations are silent, with the exception of the mutation at position 739 (G→A), which results, firstly, in the substitution of the glycine codon (GGC) at position 247 of the sequence of the AChE1 protein of the sensitive strain (S-LAB) with a serine codon (AGC) responsible Thr insecticide resistance in the SR strain and, secondly, in the appearance of an Alu I site (AGCT) in the sequence of the resistant strain, that is useful for detecting the mutation, The mutation (G→A) at position 739 of the nucleotide sequence and the mutation glycine→serine at position 247 of the amino acid sequence are indicated with shading. The sequences of the primers used for detecting the mutation at position 739 (primer Ex3dir and Ex3rev), and also the Alu I site are indicated in bold and are underlined; the following sequence identifiers appear in FIGS. 6A and 6B: amino acid sequence 1 (on top) (SEQ ID NO: 7), S-lab (SEQ ID NO: 141), SR (SEQ ID NO: 56) and amino acid sequence 2 (on bottom) (SEQ ID NO: 57).

Figure 7:
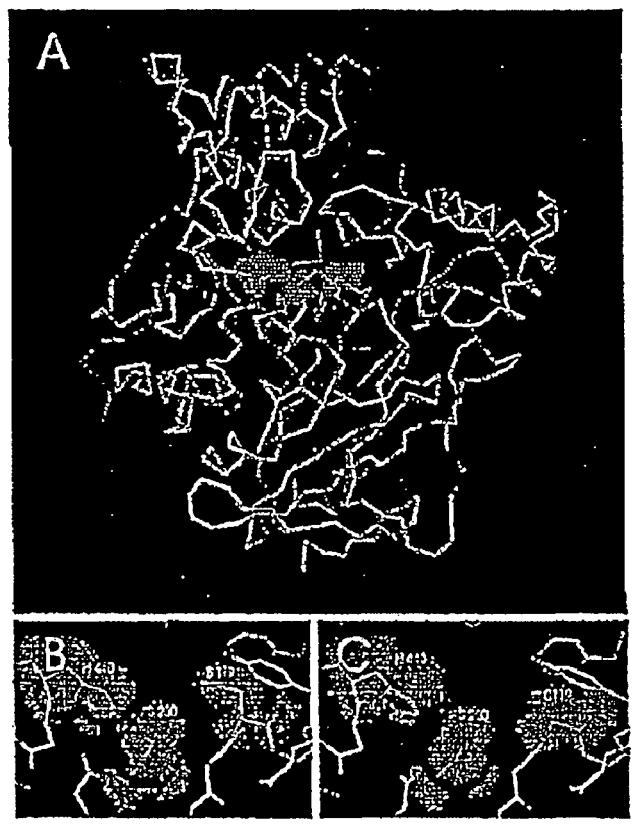
Figure 8:
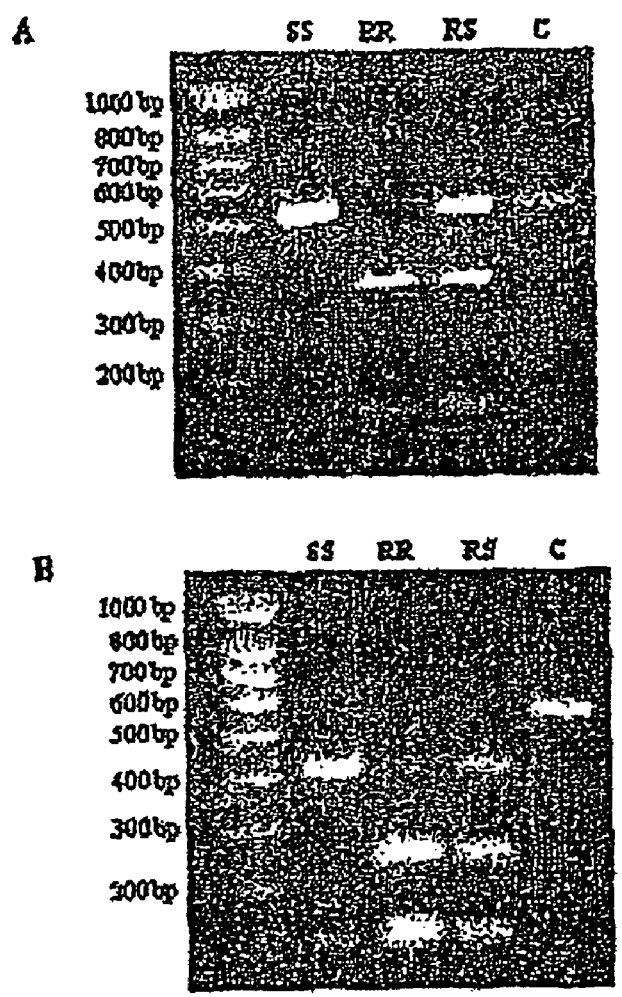
Figure 10:
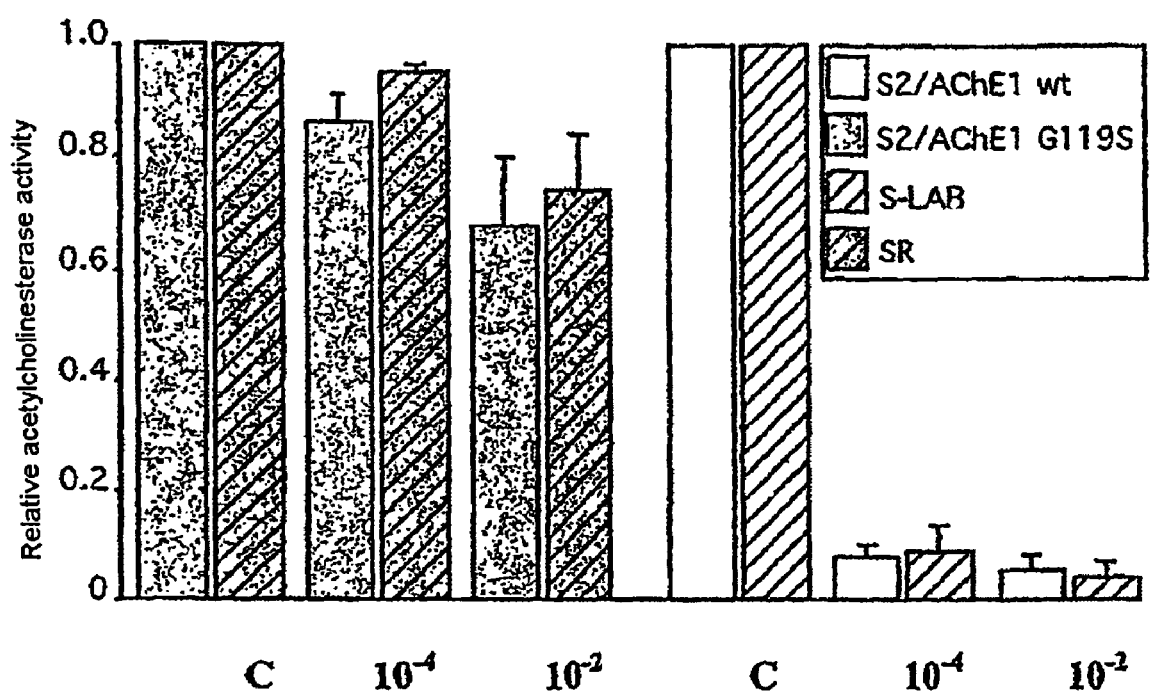
Figure 11:
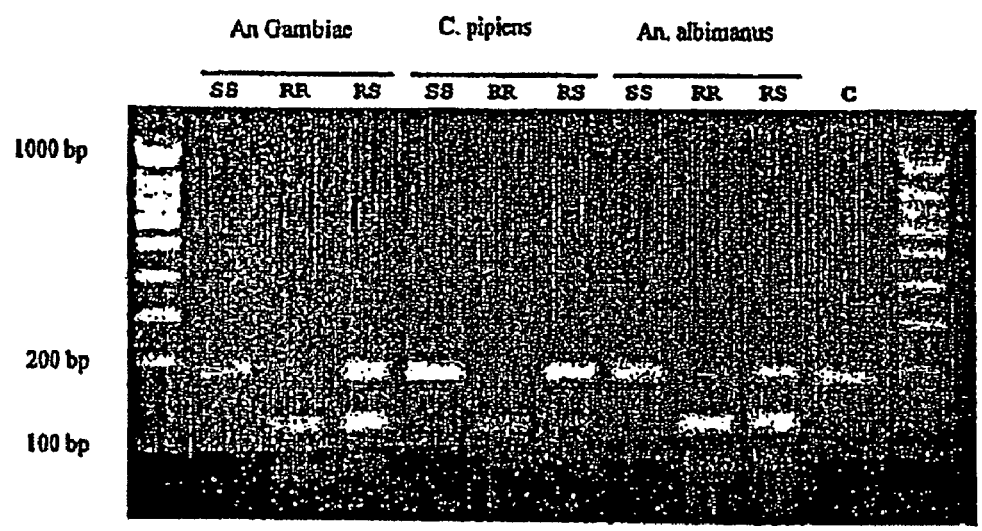
Figure 12:
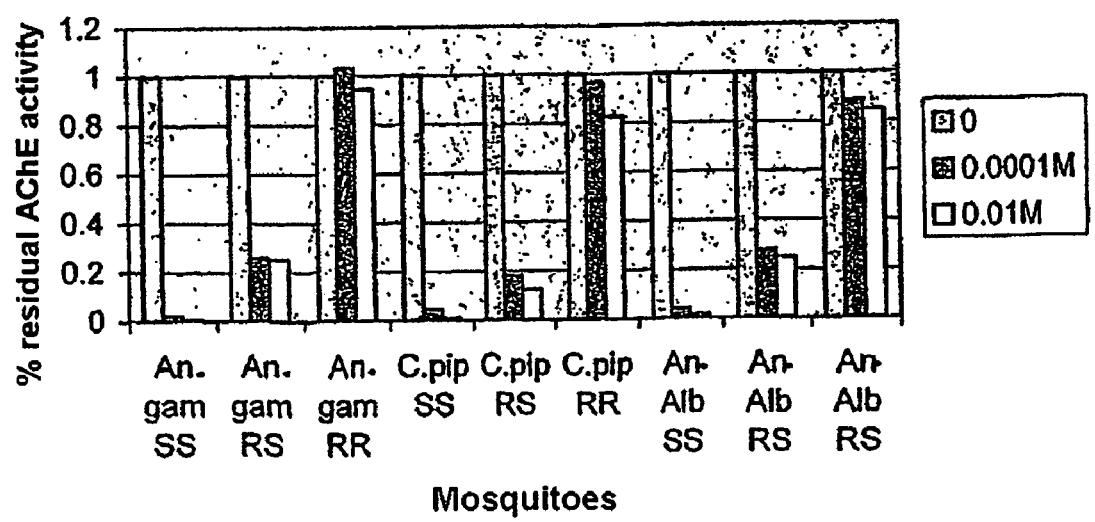
Figure 13:
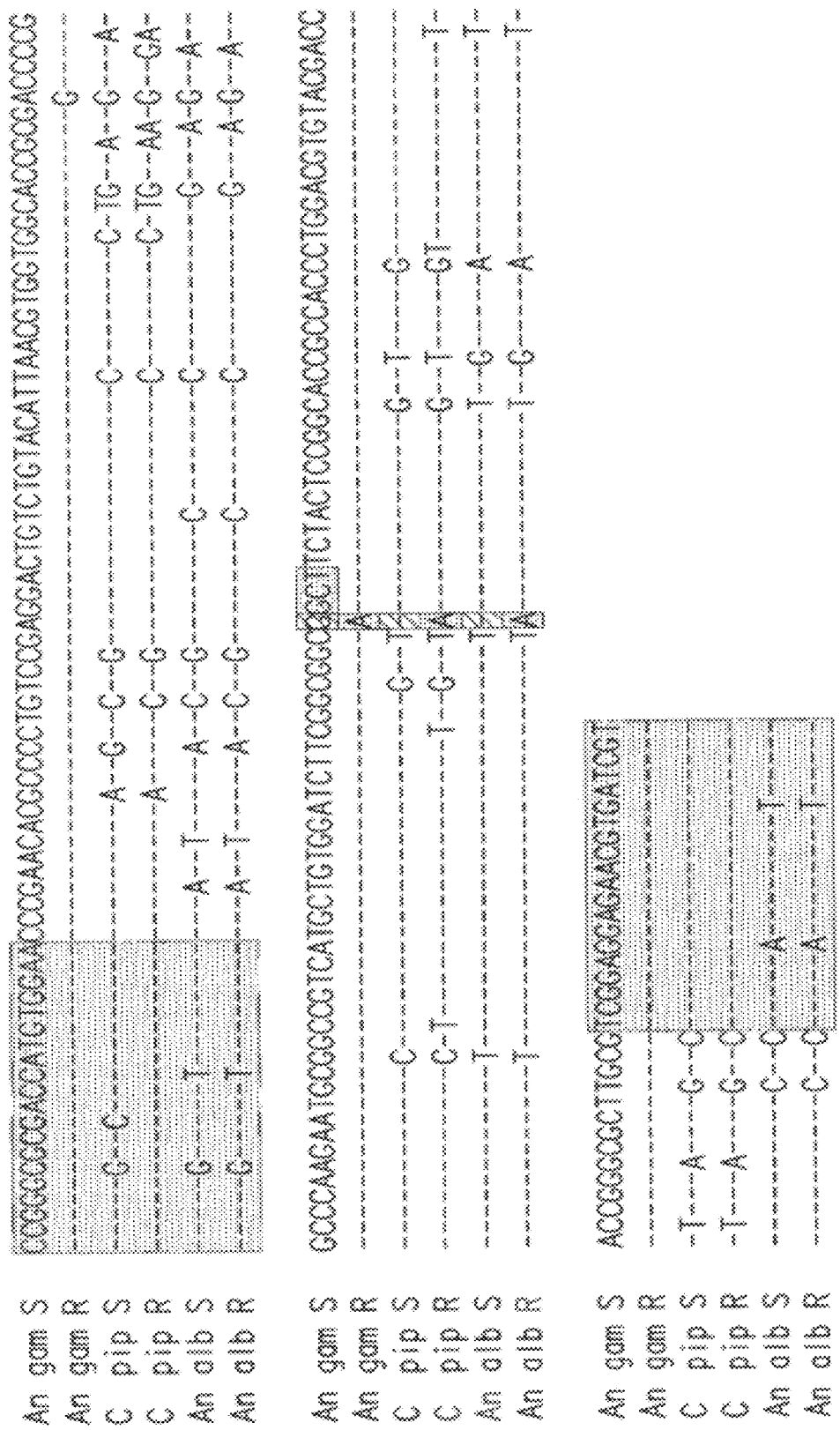

FIGS. 7 (A, B and C) illustrates the three-dimensional structure of the *C. pipiens* AChE1, obtained by molecular modeling from the structure of the torpedo fish AChE:

FIG. 7A illustrates (i) the overall structure of the two proteins and (ii) the steric hindrance of the Van der Waals bonds of the serine 200 and of the histidine 440 of the catalytic site of the enzyme, and also that of the amino acid in position 119 which is mutated in cases of resistance; the residue at position 119 is close to the residues $S_{200}$ and $H_{440}$ of the catalytic site;

FIGS. 7B and 7C illustrate the comparison of the steric hindrance of the Van der Waals bonds of the amino acid glycine (FIG. 7C) and serine (FIG. 7B) at position 119, of respectively the sensitive and resistant strain. The hindrance of the side chain of the serine at position 119 in the resistant strain decreases the space of the catalytic site, which probably prevents the insecticide from interacting with the catalytic serine ($S_{200}$);

FIG. 8 illustrates the detection by PCR-RFLP of the mutation glycine→serine in the third coding exon of the ace-1 gene, in mosquitoes of the species *C. pipiens*: 1 band (520 bp) is detected in the sensitive homozygous SS individuals, 2 bands (357 bp and 163 bp) are detected in the resistant homozygous RR individuals and 3 bands (520 bp, 357 bp and 163 bp) are detected in the resistant heterozygous RS individuals;

Figure 9A:
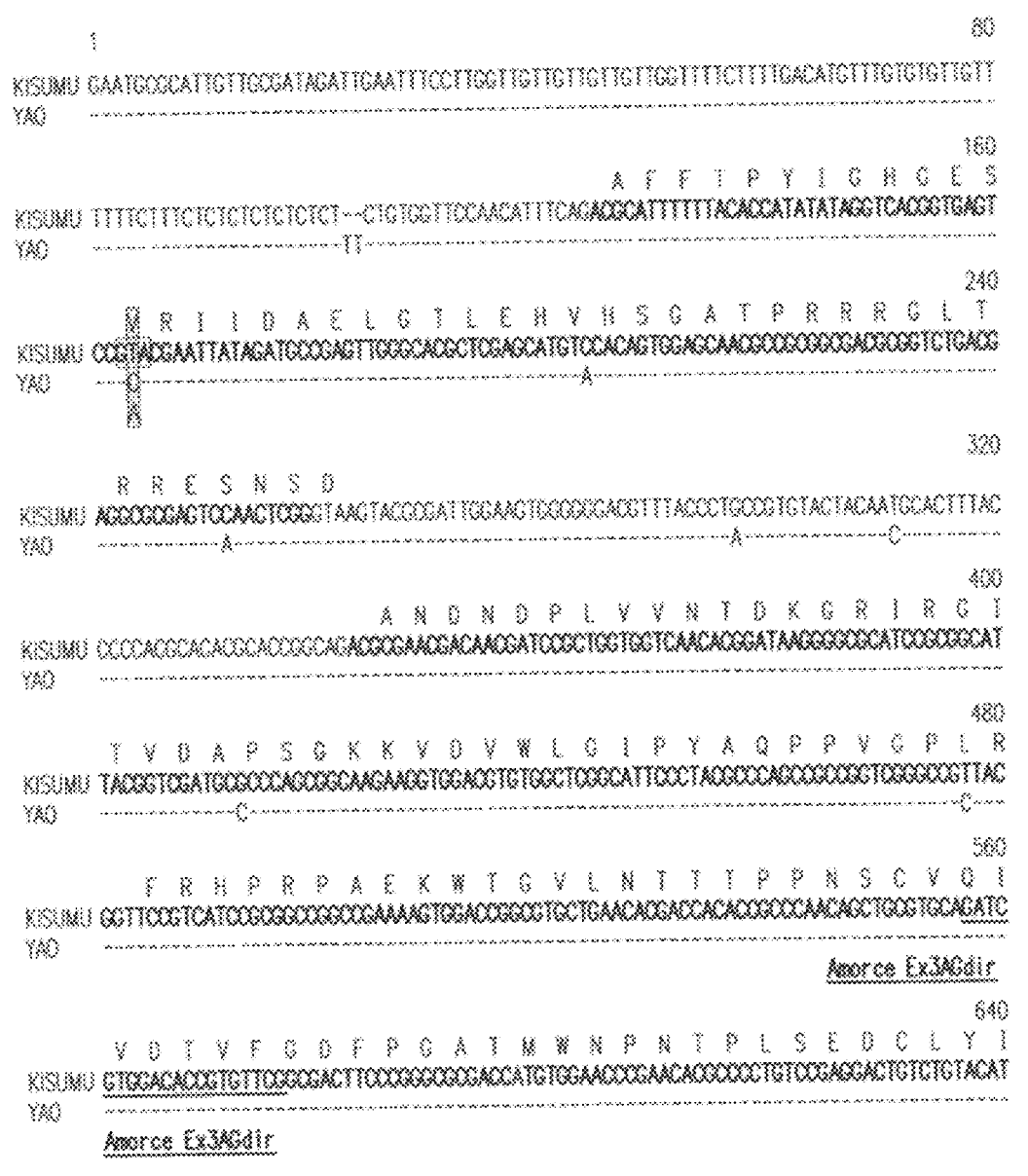

FIGS. 9A and 9B illustrate the comparison of the sequences of the *An. gambiae* ace-1 gene, between an insecticide-sensitive strain (KISUMU) and an insecticide-resistant strain (YAO); all the mutations are silent, with the exception of two mutations: the first corresponds to the replacement of the valine (CGT) at position 33 of the sequence of the AChE I of the sensitive strain (SEQ ID NO, 5) with an alanine (CGC) in the resistant strain, and the second is the same mutation, glycine (GGC)→serine (AGC) as that found in *Culex pipiens*. The mutation glycine (GGC)→serine (AGC) results in the appearance of a second Alu I site (ACCT) in the sequence of the third coding exon of the resistant strain, that is useful for detecting the mutation. The coding sequences of the ace-1 gene are indicated in bold and the mutations are indicated with shading. The sequences of the primers Ex3AGdir and Ex3Agrev used for detecting the mutation glycine (GGC)→serine (AGC), and also the Alu I sites of the third coding exon, are indicated in bold and are underlined; the following sequence identifiers appear in FIG. 9: amino acid sequence 1 of Kisumu (SEQ ID NO: 142), KISUMI (SEQ ID NO: 143), YAO (SEQ ID NO: 12) and amino acid sequence 2 (at bottom) (SEQ ID NO: 144);

FIG. 10 illustrates the quantification of the acetylcholinesterase activity of the recombinant *Culex pipiens* AChE1 proteins that are sensitive (S-LAB, white bars) and resistant (SR, shaded bars), produced in S2 insect cells, by comparison with that of ground material from *C. pipiens* strain S-LAB (hatched white bars) and strain SR (hatched shaded bars). The acetylcholinesterase activity of the cell extracts and of the ground materials from mosquitoes was measured in the absence (C) and in the presence of $10^{-4}$ M and $10^{-2}$ M of propoxur. The single mutation glycine$_{247(119)}$→serine$_{247(119)}$ renders the acetylcholinesterase insensitive to the insecticide;

FIG. 11 illustrates the detection by PCR-RFLP of the glycine→serine mutation in the third coding exon of the ace-1 gene, in mosquitoes of the species *Culex pipiens, Anopheles gambiae* and *Anopheles albimanus:* 1 band (194 bp) is detected in the sensitive homozygous SS individuals, 2 bands (74 bp and 120 bp) are detected in the resistant homozygous RR individuals and 3 bands (194 bp, 74 bp and 120 bp) are detected in the resistant heterozygous SS individuals;

FIG. 12 illustrates the quantification of the acetylcholinesterase activity of the AChE1 proteins of, respectively, *Culex pipiens, Anopheles gambiae* and *Anopheles albimanus* that are sensitive (SS, shaded bars) and resistant (RS, black bands and RR, white bands);

FIG. 13 represents the alignment of the nucleotide sequences of the 194 bp fragment from *Anopheles gambiae*, from *Culex pipiens* and from *Anopheles albimanus*, that are sensitive (S) or resistant (R). Light shaded background: sequences corresponding to the primers Moustdir1 and Moustrev1. Shaded background: Alu I site. Dark shaded background: guanine of the Gly codon of sensitive individuals; sequence identifiers appearing in FIG. 13 are: An gam S (SEQ ID NO: 145), An gam R (SEQ ID NO: 146), C pip S (SEQ ID NO: 147), C pip R (SEQ ID NO: 148), An alb S (SEQ ID NO: 149) and An alb R (SEQ ID NO: 150);

Figure 14:
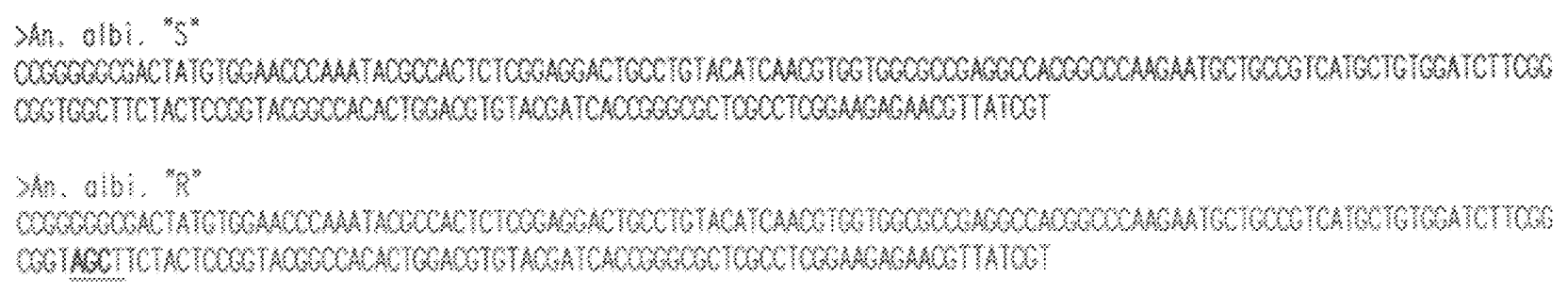

FIG. 14 represents the nucleotide sequences of the 194 bp fragment of sensitive (S) and resistant (R) *Anopheles albimanus*. The codon specifying Gly (GGC) and Ser (AGC) is in bold. The Alu I site is underlined. Sequence identifiers appearing in FIG. 14: An.albi."S" (SEQ ID NO: 149) and An.albi."R" SEQ ID NO: 150).

TABLE II

Sequence listing

| Identification number | Sequence |
|---|---|
| SEQ ID No.: 1 | Fragment of the central region of the *Anopheles gambiae* AChE1 protein (positions 70 to 593 of SEQ ID No. 3). |
| SEQ ID No.: 2 | *Anopheles gambiae* AChE1 cDNA |
| SEQ ID No.: 3 | *Anopheles gambiae* AChE1 protein |
| SEQ ID No.: 4 | *Anopheles gambiae* (strain KISUMU) AChE1 cDNA |
| SEQ ID No.: 5 | *Anopheles gambiae* (strain KISUMU) AChE1 protein |
| SEQ ID No.: 6 | *Culux pipiens* strain S-LAB AChE1 cDNA (complete sequence) |
| SEQ ID No.: 7 | *Culex pipiens* strain S-LAB AChE1 protein (complete sequence) |
| SEQ ID No.: 8 | Peptide fragment K AChE1 *Culex pipiens* |
| SEQ ID No.: 9 | Peptide fragment K AChE1 *Aedes aegypti* |
| SEQ ID No.: 10 | Peptide fragment K AChE1 *Aedes albopictus* |
| SEQ ID No.: 11 | Peptide fragment K peptide AChE1 *Anopheles darlingi* |
| SEQ ID No.: 12 | Peptide fragment K AChE1 *An. sundaicus* |
| SEQ ID No.: 13 | Peptide fragment K AChE1 *An. minimus* |
| SEQ ID No.: 14 | Peptide fragment K AChE1 *An. moucheti* |
| SEQ ID No.: 15 | Peptide fragment K AChE1 *An. arabiensis* |
| SEQ ID No.: 16 | Peptide fragment K AChE1 *An. funestus* |
| SEQ ID No.: 17 | Peptide fragment K AChE1 *An. pseudopunctipennis* |
| SEQ ID No.: 18 | Peptide fragment K AChE1 *An. sacharovi* |
| SEQ ID No.: 19 | Peptide fragment K AChE1 *An. stephensi* |
| SEQ ID No.: 20 | Peptide fragment K AChE1 *An. albimanus* |
| SEQ ID No.: 21 | Peptide fragment K AChE1 *An. nili* |
| SEQ ID No.: 22 | *An. gambiae* ace-1 gene |
| SEQ ID No.: 23 | *An. gambiae* KISUMU ace-1 gene |
| SEQ ID No.: 24 | Nucleotide fragment K AChE1 *C. pipiens* (strain S-LAB) |
| SEQ ID No.: 25 | Nucleotide fragment K AChE1 *C. pipiens* (strain SR) |
| SEQ ID No.: 26 | Nucleotide fragment K AChE1 *Aedes aegypti* |
| SEQ ID No.: 27 | Nucleotide fragment K AChE1 *Aedes albopictus* (AJ 438598) |
| SEQ ID No.: 28 | Nucleotide fragment K AChE1 *Anopheles darlingi* (AJ 438599) |
| SEQ ID No.: 29 | Nucleotide fragment K AChE1 *An. sundaicus* (AJ 438600) |
| SEQ ID No.: 30 | Nucleotide fragment K AChE1 *An. minimus* (AJ 438601) |
| SEQ ID No.: 31 | Nucleotide fragment K AChE1 *An. moucheti* (AJ 438602) |
| SEQ ID No.: 32 | Nucleotide fragment K AChE1 *An. arabiensis* (AJ 438603) |
| SEQ ID No.: 33 | Nucleotide fragment K AChE1 *An. funestus* (AJ 438604) |
| SEQ ID No.: 34 | Nucleotide fragment K AChE1 *An. pseudopunctipennis* (AJ 538605) |
| SEQ ID No.: 35 | Nucleotide fragment K AChE1 *An. sacharovi* (AJ 538606) |
| SEQ ID No.: 36 | Nucleotide fragment K AChE1 *An. stephensi* (AJ 538607) |
| SEQ ID No.: 37 | Nucleotide fragment K AChE1 *An. albimanus* (AJ 538608) |
| SEQ ID No.: 38 | Nucleotide fragment K AChE1 *An. nili* (AJ 538609) |
| SEQ ID No.: 39 | Primer PkdirAGSG |
| SEQ ID No.: 40 | Primer PkrevAGSG |
| SEQ ID No.: 41 | Primer PbdirAGSG |
| SEQ ID No.: 42 | Primer PbrevAGSG |
| SEQ ID No.: 43 | Primer culex-bdir1 |
| SEQ ID No.: 44 | Primer culex-krev1 |
| SEQ ID No.: 45 | Primer AG1-Adir |
| SEQ ID No.: 46 | Primer AG1-Arev |
| SEQ ID No.: 47 | Primer AG1-Bdir |
| SEQ ID No.: 48 | Primer AG1-Brev |
| SEQ ID No.: 49 | Primer AG1-Cdir |
| SEQ ID No.: 50 | Primer AG1-Crev |
| SEQ ID No.: 51 | *Ciona intestinalis* AChE1 protein |
| SEQ ID No.: 52 | *Ciona savignyi* AChE1 protein |
| SEQ ID No.: 53 | *Anopheles gambiae* AChE2 protein |
| SEQ ID No.: 54 | Primer culex-5'dir |
| SEQ ID No.: 55 | Primer culex-3'dir |
| SEQ ID No.: 56 | *C. pipiens* strain SR AChE1 cDNA (complete coding sequence) |
| SEQ ID No.: 57 | *C. pipiens* strain SR AChE1 protein (complete sequence) |
| SEQ ID No.: 58 | Primer Ex3dir |
| SEQ ID No.: 59 | Primer Ex3rev |
| SEQ ID No.: 60 | Nucleotide fragment of the third coding exon strain Espro-P*-R**** |
| SEQ ID No.: 61 | Nucleotide fragment of the third coding exon strain Pro-R-Q**-S |
| SEQ ID No.: 62 | Nucleotide fragment of the third coding exon strain S-LAB-Q-S***** |
| SEQ ID No.: 63 | Nucleotide fragment of the third coding exon strain Padova-P-R |
| SEQ ID No.: 64 | Nucleotide fragment of the third coding exon strain Praias-P-R |
| SEQ ID No.: 65 | Nucleotide fragment of the third coding exon strain Supercar-Q-R |
| SEQ ID No.: 66 | Nucleotide fragment of the third coding exon strain BrugesA-P-S |

TABLE II-continued

Sequence listing

| Identification number | Sequence |
|---|---|
| SEQ ID No.: 67 | Nucleotide fragment of the third coding exon strain BQ-Q-R |
| SEQ ID No.: 68 | Nucleotide fragment of the third coding exon strain DJI-Q-R |
| SEQ ID No.: 69 | Nucleotide fragment of the third coding exon strain Harare-Q-R |
| SEQ ID No.: 70 | Nucleotide fragment of the third coding exon strain Martinique-Q-R |
| SEQ ID No.: 71 | Nucleotide fragment of the third coding exon strain Barriol-P-R |
| SEQ ID No.: 72 | Nucleotide fragment of the third coding exon strain Bleuet-P-S |
| SEQ ID No.: 73 | Nucleotide fragment of the third coding exon strain BrugesB-P-S |
| SEQ ID No.: 74 | Nucleotide fragment of the third coding exon strain Heteren-P-S |
| SEQ ID No.: 75 | Nucleotide fragment of the third coding exon strain Ling-Q-S |
| SEQ ID No.: 76 | Nucleotide fragment of the third coding exon strain Mao-Q-S |
| SEQ ID No.: 77 | Nucleotide fragment of the third coding exon strain TemR-Q-S |
| SEQ ID No.: 78 | Nucleotide fragment of the third coding exon strain Uppsala-T***-S |
| SEQ ID No.: 79 | Nucleotide fragment of the third coding exon strain Trans-Q-S |
| SEQ ID No.: 80 | Nucleotide fragment of the third coding exon strain BEQ-Q-S |
| SEQ ID No.: 81 | Nucleotide fragment of the third coding exon strain BSQ-Q-S |
| SEQ ID No.: 82 | Nucleotide fragment of the third coding exon strain Brazza-Q-S |
| SEQ ID No.: 83 | Nucleotide fragment of the third coding exon strain Bouaké-Q-R |
| SEQ ID No.: 84 | Nucleotide fragment of the third coding exon strain Thai-Q-S |
| SEQ ID No.: 85 | Nucleotide fragment of the third coding exon strain Madurai-Q-S |
| SEQ ID No.: 86 | Nucleotide fragment of the third coding exon strain Recife-Q-R |
| SEQ ID No.: 87 | Nucleotide fragment of the third coding exon strain Brésil Q-S |
| SEQ ID No.: 88 | Nucleotide fragment of the third coding exon strain Moorea Q-S |
| SEQ ID No.: 89 | Nucleotide fragment of the third coding exon strain Killcare P-S |
| SEQ ID No.: 90 | (1) |
| SEQ ID No.: 91 | (1) |
| SEQ ID No.: 92 | (1) |
| SEQ ID No.: 93 | (1) |
| SEQ ID No.: 94 | (1) |
| SEQ ID No.: 95 | (1) |
| SEQ ID No.: 96 | (1) |
| SEQ ID No.: 97 | (1) |
| SEQ ID No.: 98 | (1) |
| SEQ ID No.: 99 | (1) |
| SEQ ID No.: 100 | (1) |
| SEQ ID No.: 101 | (1) |
| SEQ ID No.: 101 | (1) |
| SEQ ID No.: 102 | (1) |
| SEQ ID No.: 103 | (1) |
| SEQ ID No.: 104 | (1) |
| SEQ ID No.: 105 | (1) |
| SEQ ID No.: 106 | (1) |
| SEQ ID No.: 107 | (1) |
| SEQ ID No.: 108 | (1) |
| SEQ ID No.: 109 | (1) |
| SEQ ID No.: 110 | (1) |
| SEQ ID No.: 111 | (1) |
| SEQ ID No.: 111 | (1) |
| SEQ ID No.: 112 | (1) |
| SEQ ID No.: 113 | (1) |
| SEQ ID No.: 114 | (1) |
| SEQ ID No.: 115 | (1) |
| SEQ ID No.: 116 | (1) |
| SEQ ID No.: 117 | (1) |
| SEQ ID No.: 118 | (1) |
| SEQ ID No.: 119 | (1) |
| SEQ ID No.: 120 | *An. gambiae* strain YAO ace-1 gene |
| SEQ ID No.: 121 | *An. gambiae* strain YAO AChE1 cDNA (complete coding sequence) |
| SEQ ID No.: 122 | *An. gambiae* strain YAO AChE1 protein (complete sequence) |
| SEQ ID No.: 123 | Primer Ex3 AG dir |
| SEQ ID No.: 124 | Primer Ex3 AG rev |
| SEQ ID No.: 125 | *An. gambiae* strain KISUMU AChE1 cDNA (complete sequence) |
| SEQ ID No.: 126 | *An. gambiae* strain KISUMU AChE1 protein (complete sequence) |
| SEQ ID No.: 127 | *An. gambiae* ace-1 gene (including 2 5' non-coding exons) |
| SEQ ID No.: 128 | Primer Moustdir1 |
| SEQ ID No.: 129 | Primer Moustrev1 |

*P = *Culex pipiens pipiens* (subspecies *pipiens*)
**Q = *Culex pipiens quinquefasciatus* (subspecies *quinquefasciatus*)
***T = *Culex torrentium*
****R = resistant
*****S = sensitive
(1) peptide fragments of the third coding exon corresponding to the nucleotide fragments SEQ ID No.s. 60 to 89

The nucleotide sequences (SEQ ID NOs. 27 to 38) and the corresponding peptide sequences (SEQ ID NOs. 10 to 21) were submitted to various sequence libraries on Mar. 8, 2002, but were only made accessible on Nov. 30, 2002, in the EMBL sequence base and on Jan. 11, 2003, in the GENBANK sequence base.

EXAMPLE 1

Materials and Methods a) Strains and Crosses

Five *C. pipiens* strains were used: S-LAB, a standard insecticide-sensitive strain (Georghiou et al., 1996, Bull. Wld. Hlth Org., 35, 691-708), SA1, SA4 and EDIT, which have a single insecticide-sensitive AChE, and SR which is homozygous for an insecticide-insensitive AChE (Berticat et al., Genet. Res., 2002, 79, 41-47). The strains having a sensitive and insensitive AChE are referred to, respectively, as S and R.

b) Ace Gene Nomenclature and Amino Acid Sequence Numbering ace-1 represents the locus encoding a cholinergic AChE responsible for resistance to organophosphorus compounds and/or to carbamates in *C. pipiens* (AChE1), previously called Ace.1 (Raymond et al., Genetica, 2001, 112/113, 287-296). ace-2 represents the second ace locus, which is not involved in insecticide resistance in *C. pipiens* (previously called Ace.2), the function of which is unknown in *C. pipiens*. The single ace gene present in *Drosophila melanogaster*, which is homologous to ace-2, is therefore similarly named.

In the analyses which follow, the positions of the amino acid residues are indicated with reference to the sequence of the torpedo fish AChE [*Torpedo californica*; GENBANK P04058], according to the nomenclature recommended by Massoulié et al., 1992, In *Multidisciplinary approaches to cholinesterase functions*, eds, Schafferman, A. & Velan, B. (Plenum Press New York), p 285-288].

The amino acid sequence described by UniProtKB/SwissProt Accession Number P04058 is described by SEQ ID NO: 151 c) Analysis of Transmission of the Ace-1 Gene

With the females being indicated first, F1 crosses (S×R) and back crosses (F1×S-LAB and S-LAB×F1) were obtained by mass crossing of adults. A few larvae derived from the back crosses were treated with a dose of carbamate (propoxur, 4 mg/l) which kills 100% of sensitive larvae. The linkage between ace-1 and propoxur resistance was studied by RFLP in the surviving larvae, based on a 320 bp PCR product making it possible to identify the S and R alleles. The experiments were carried out independently, with S=SA1, S=SA4 and S=EDIT.

d) Sequence Analysis and Gene Assembly

All the sequence analyses were carried out based on the crude sequences of *Anopheles gambiae* available on the INFOBIOGEN server (available on the worldwide web at infobiogen.fr) and the tools available on the site (available on the worldwide web at ncbi.nlm.nih.gov/blast/blast). The genomic sequences encoding an AChE were identified using the TBLASTN and BLAST programs (Altschul et al., J. Biol. Mol., 1990, 215, 403-410). The genomic sequences identified were assembled using the ABI Prism Auto-Assembler program (v2.1, Perkin Elmer). The sequences were verified and corrected using the Ensembl Trace Server program (available at trace.ensembl.org/). Two concatenations of, respectively, 5195 and 6975 base pairs, encoding respectively AChE1 and AChE2, were assembled from, respectively, 64 and 74 independent sequences (mean redundancy of 10.5 and 6.5). The exons and the protein sequences were identified using a combination between the FGENESH (available on the worldwide web at sanger.uk) and BLASTX (available on the worldwide web at ncbi.nlm.nih.gov) programs. The genomic sequences of ascidian AChE were assembled from crude sequences deposited in the databases of the NCBI (*Ciona savignyi*) and of the Doe Joint Institute (*Ciona intestinalis*, available on the worldwide web at jgi.doe.gov/programs/ciona/ciona-mainage.html). The searches in the *Drosophila* databases were carried out using Flybase (available on the worldwide web at fruitfly.org/).

e) Sequence Comparisons

The sequences of the *Anopheles gambiae* AChE1 and AChE2 proteins deduced from the genomic sequences and the peptide sequences deduced from PCR fragments of *C. pipiens* and *A. aegypti* were aligned with those of known AChEs, by means of the ClustalW program, using a BLOSUM matrix and default parameters (Thompson et al., N.A.R., 1994, 22, 4673-4680).

A phylogenetic tree was constructed using the neighbor-joining algorithm of version DDBJ of Clustal W (available at hypemig.nig.ac.jp/homology/ex-clustalw-e.shtml). Bootstrap analysis (1000 counts and 111 entry values) was used to evaluate the degrees of confidence for the topology of the tree. The construction of the trees was carried out using the Treeview program (v1.6.6).

f) Accession Numbers

The numbers of the sequences (accession numbers in the databases or the identifying numbers in the sequence listing) which were used for the genetic analysis are as follows:

Craniata: *Homo sapiens*: NP_00046; *Bos taurus*: P23795; *Felix catus*: O6763; *Oryctolagus cuniculus*: Q29499; *Rattus norvegicus*: P36136; *Mus musculus*: P21836; *Gallus gallus*: CAC37792; *Danio reno*: Q9DDE3; *Electrophorus electricus*: 6730113; *Torpedo marmorata*: P07692; *Torpedo californica*: P04058; *Bungarus fasciatus*: Q92035; *Myxine glutinosa*: Q92081.

Cephalocordes: *Branchiostoma floridae*: O76998 and O76999; *Branchiostoma lanceolatum*: Q95000 and Q95001.

Urocordes: *Ciona intestinalis*: SEQ ID NO 51; *Ciona savignyi*: SEQ ID NO 52.

Nematodes: *Caenorhabditis elegans* (1 to 4): P38433, O61371, O61459 and O61372; *Caenorhabditis briggsae* (1 to 4) Q27459, O61378Q9NDG9 and Q9NDG8; *Dictyocaulus viviparus*: Q9GPLO.

Insects: *Anopheles gambiae* (1 and 2): SEQ ID NO 3 and SEQ ID NO 53 (BM 629847 anD BM 627478); *Aedes aegypti* (1 and 2): SEQ ID NO 9 and AAB3500; *An. stephensi*: P56161; *Culex pipiens*: SEQ ID NO 7 (ace-1) and Esther database for ace-2; *Drosophila melanogaster*: P07140; *Lucilia cuprina*: P91954; *Musca domestica*: AAK69132.1; *Leptinotarsa decemlineata*: Q27677; *Apis mellifera*: AAG43568; *Nephotettix cincticeps*: AF145235_1; *Schizaphis graminum*: Q9BMJ1.

Arachnids: *Rhipicephalus appendiculatus*: O62563; *Boophilus microplus* (1 and 2): O45210 and O61864; *Boophilus decoloratus*: O61987.

Mollusks: *Loligo opalescens*: O97110.

g) Cloning of the Fragment K and Genotyping of Ace-1 in *Culex pipiens*

The mosquito DNA was extracted as described in Rogers et al. [*Plant Molecular Biology* manual, 1988, eds. Gelvin, S. B.1 Schilperoot, R. A. (Kluwer Academic Publishers, Boston), Vol. A6, p 1-10]. The oligonucleotides PkdirAGSG (5'-ATMGWGTTYGAGTACACSGAYTGG-3', SEQ ID NO 39) and Pkrev AGSG (5'-GGCAAARTTKGWCCAG- TATCKCAT-3', SEQ ID NO 40) amplify a 320 bp fragment (fragment K) from the genomic DNA of several mosquitoes. 30 PCR amplification cycles were carried out under the following conditions: 94° C. for 30 s, 50° C. for 30 s and 72° C. for 30 s. The sequences were determined directly on the PCR products on an ABI prism 310 sequencer, using the Big Dye Terminator kit.

The genotyping of ace-1 *Culex* was carried out under the following conditions: the fragments K obtained as described above were digested with EcoRI and the digestion product was separated by electrophoresis on a 2% agarose gel. The restriction profiles show: 1 band (320 bp) in the resistant homozygous RR mosquitoes, 2 bands (106 bp and 214 bp) in the homozygous SS mosquitoes and 3 bands (103 bp, 214 bp and 320 bp) in the heterozygous RS mosquitoes.

h) Cloning of the Ace-1 cDNA in Sensitive and Resistant Individuals

The cDNA of the *Culex pipiens* ace-1 gene was obtained from the RNA extracted from individuals of the reference sensitive strain S-LAB and of the resistant strain SR, at the very first larval stage of the development L1. The reverse transcription was carried out with an 18T oligonucleotide and SuperScriptIIRNaseH (INVITROGEN), according to the conditions recommended by the manufacturer.

Strain S-LAB

Two cDNA fragments were amplified by PCR using degenerate oligonucleotides obtained from the alignment of the sequences of the *Anopheles gambiae* and *Schizaphis graminum* ace-1 genes:

```
a fragment b (193 bp) was amplified using the pair of primers PbdirAGSG (5'GGYGCKACMATGTGGAAYCC3', SEQ ID NO 41) and PbrevAGSG (5'ACCAMRATCACGTTYTCYT

CCGAC3', SEQ ID NO 42);

a fragment k (320 bp) was amplified using the pair of primers PkdirAGSG (5'ATMGWGTTYGAGTACACSGAYTG G3', SEQ ID NO 39) and PkrevAGSG (5'GGCAAARTTKGWCC

AGTATCKCAT3', SEQ ID NO 40).
```

The fragments b and k thus obtained were then cloned and sequenced, according to conventional techniques known in themselves to those skilled in the art, as described in Current Protocols in Molecular Biology (Frederick M. *AUSUBEL*, 2000, Wiley and Son Inc, Library of Congress, USA).

A larger cDNA fragment was amplified by PCR, using the *Culex pipiens*-specific primers deduced from the sequences of the fragments b and k obtained above. Namely:

a fragment CulexA (1127 bp) was amplified by PCR using the pair of primers: *culex*-bdir1 (5'TACATCAACGTG-GTCGTGCCACG3', SEQ ID NO 43) and *culex*-krev1 (5'GT-CACGGTTGCTGTTCGGG3', SEQ ID NO 44). The 1127 bp fragment CulexA thus obtained was then cloned and sequenced, as above.

The ends of the cDNAs were amplified by the RACE (Rapid Amplification of cDNA Ends) technique using a commercial kit (Gene Racer kit (INVITROGEN)) according to the conditions indicated in the instruction booklet. They were subsequently cloned and then sequenced, as above.

Strain SR

The complete sequence of the cDNA of the ace-1 gene of the resistant strain SR was amplified by PCR using the primers *culex*-5'dir (5'-CCACACGCCAGAAGAAAAGA-3', SEQ ID NO 54) and *culex*-3'dir (5'-AAAAACGGGAACGG-GAAAG-3', SEQ ID NO 55) and the 2497 bp fragment thus obtained was cloned and sequenced, as above.

i) Cloning of the Ace-1 Gene in Sensitive and Resistant Individuals

The genomic DNA of the strain KISUMU (reference sensitive strain from West Africa) and of the strain YAO (resistant strain isolated in Ivory Coast) of *A. gambiae* was extracted from homozygous individuals as described in Rogers et al. [*Plant Molecular Biology manual*, 1988, eds. Gelvin, S. I.1 Schilperoot, R. A. (Kluwer Academic Publishers, Boston) Vol. A6, p 1-10].

3 overlapping fragments (A, B and C) were amplified under the following conditions: 94° C. for 30 s, 50° C. for 30 s and 72° C. for 30 s (30 cycles), using the primers synthesized from the sequence of the ace-1 gene. Namely:

```
the fragment A (1130 bp) was amplified using the pair of primers AG1-Adir (5'CGACGCCACCTTCACA3', SEQ ID NO 45) and AG1-Arev (5'GATGGCCCGCTGGAACAGA

T3', SEQ ID NO 46), the fragment B (1167 bp) was amplified using the pair of primers AG1-Bdir (5'GGGTGCGGGACAACATTCA C3', SEQ ID NO 47) and AG1-brev (5'CCCCGACCGACGAAG

GA3', SEQ ID NO 48), and the fragment C (876 bp) was amplified using the pair of primers AG1-Cdir (5'AGATGGTGGGCGACTATCAC3'

SEQ ID NO 49) and AG1-Crev (5'CTCGTCCGCCACCACTTGT

T3', SEQ ID NO 50).
```

The sequences of the fragments A, B and C were determined directly on the PCR products, by means of internal oligonucleotides, included in these fragments, using the Big Dye Terminator kit and an ABI prism 310 sequencer.

j) Detection of the Mutation of the Third Coding Exon Responsible for the Insecticide Resistance in Mosquitoes of the Species *C. pipiens* and *An. gambiae*

The mosquito DNA was extracted as described in Rogers et al., mentioned above, and a fragment of the third coding exon was then amplified by PCR and sequenced, and the mutation in the coding sequence of the third coding exon was detected by PCR-RFLP, according to the principle as described above for the fragment K.

*C. pipiens*

A 520 bp fragment of the third coding exon was amplified from the genomic DNA of several mosquitoes, by PCR using the pair of primers:

Ex3dir 5'-CGACTCGGACCCACTGGT-3' (SEQ ID NO 58) and

Ex3rev 5'-GTTCTGATCAAACAGCCCCGC-3' (SEQ ID NO 59).

The fragment thus obtained was digested with Alu I and the digestion product was separated by electrophoresis on a 2% agarose gel. The expected restriction profiles are as follows: 1 fragment (520 bp) in the sensitive homozygous SS individuals, 2 fragments (357 bp and 163 bp) in the resistant homozygous RR individuals and 3 fragments (520 bp, 357 bp and 163 bp) in the resistant heterozygous RS individuals.

*An. gambiae*

A 541 bp fragment of the third coding exon was amplified from the genomic DNA of several individuals, by PCR using the pair of primers:

```
Ex3AGdir
5'-GATCGTGGACACCGTGTTCG-3'    (SEQ ID NO 123)
and

Ex3AGrev
5'-AGGATGGCCCGCTGGAACAG-3'.   (SEQ ID NO 124)
```

The fragment thus obtained was digested with Alu I and the digestion product was separated by electrophoresis on a 2% agarose gel. The expected restriction profiles are as follows: 2 fragments (403 bp and 138 bp) in the sensitive homozygous SS individuals, 3 fragments (253 bp, 150 bp and 138 bp) in the resistant homozygous RR individuals and 4 fragments (403 bp, 253 bp, 150 bp and 138 bp) in the resistant heterozygous RS individuals; given that the 150 bp and 138 bp fragments comigrate, the resistant homozygous and heterozygous individuals are detected, respectively, by the presence of 2 bands (253 bp and approximately 150 bp) and of 3 bands (403 bp, 253 bp and approximately 150 bp) in agarose gel.

*C. pipiens, An. gambiae* and *An. albimanus*

A 174 bp fragment of the third coding exon was amplified from the genomic DNA of several mosquitoes, by PCR using the pair of primers:

```
Moustdir1:
5' CCGGGNGCSACYATGTGGAA 3',    (SEQ ID NO 128)
and

Moustrev1:
5' ACGATMACGTTCTCYTCCGA 3'.    (SEQ ID NO 129)
```

The fragment thus obtained was digested with Alu I and the digestion product was separated by electrophoresis on a 2% agarose gel. The expected restriction profiles are as follows: 1 fragment (194 bp) in the sensitive homozygous SS individuals, 2 fragments (74 bp and 120 bp) in the resistant homozygous RR individuals and 3 fragments (194 bp, 74 bp and 120 bp) in the resistant heterozygous RS individuals.

The results are illustrated in FIG. 11.

FIG. 12 shows that, with resistant *An. albimanus* mosquitoes, the same propoxur-inhibition characteristics are obtained, by means of a conventional biochemical test, as for the *An. gambiae* and *C. pipiens* mosquitoes.

Application of the diagnostic test, also referred to as "G119S", using the Moustdir1 and Moustrev1 amplimer reveals the presence of an AluI site associated with resistance (FIG. 11). Sequencing of the amplified fragments of *An. albimanus* confirms the substitution of the Gly codon GGC, in the Ss individuals, to an Ser codon AGC in the RR individuals (FIGS. 13 and 14).

k) Measurement of the Acetylcholinesterase Activity

The cDNAs encoding the AChE1s of, respectively, the strain S-LAB and the strain SR were cloned in the eukaryotic expression vector pAc5.1/V5-His (INVITROGEN), according to conventional recombinant DNA techniques, by following standard protocols such as those described in *Current Protocols in Molecular Biology*, mentioned above. *Drosophila* cells (Schneider S2 cells) were transfected with the recombinant vectors thus obtained, using the Fugen® reagent (ROCHE), according to the manufacturer's instructions. 24 hours after transfection, the cells were harvested by centrifugation and then lyzed in a 0.25M phosphate buffer containing 1% Triton X-100. The acetylcholinesterase activity of the cell extracts obtained was measured, in the presence or in the absence of insecticide (propoxur), by the method as described in Bourguet et al., Biochemical Genetics, 1996, 34, 351-362.

EXAMPLE 2

Demonstration of 2 Ace Genes in *Anopheles gambiae*

Genes homologous to the human and *drosophila* acetylcholinesterase genes were sought based on sequence fragments deposited in the databases, using the TBLASTN program. Two groups of distinct fragments encoding an AChE very similar to that of *drosophila* were identified. Two genes of, respectively, 6975 bp (ace-1) and 5195 bp (ace-2) were reconstructed from overlapping fragments of each group. Analysis of the genes using the FGENESH and BLASTX programs shows that the ace-1 and ace-2 genes consist, respectively, of at least 7 and 8 exons encoding proteins of approximately 534 and 569 amino acids, respectively referred to as AChE1 and AChE2. However, this analysis did not make it possible to determine with certainty the sequence of the 5' and 3' ends of the cDNA and the $NH_2$ and COOH sequences of the corresponding proteins, which are not conserved between the various AChEs.

The amino acid sequence analysis confirms that the AChE1 and AChE2 proteins are highly homologous to the AChE of *Drosophila* (BLASTP:$P<e^{-180}$) and contain a canonic FGE-SAG motif around the serine at position 200, with reference to the sequence of the Torpedo AChE ($S_{200}$, FIG. 1), which is characteristic of the AChE active site. In addition, other motifs characteristic of AChEs were also found in the two sequences (AChE1 and AChE2): the choline-binding site (tryptophan residue at position 84, W84), the three residues of the catalytic triad (serine, glutamic acid and histidine residues, respectively at positions 200, 327 and 440: $S_{200}$, $E_{327}$ and $H_{440}$), the six cysteine residues potentially involved in conserved disulfide bridges ($C_{67}$-$C_{94}$; $C_{254}$-$C_{265}$; $C_{402}$-$C_{521}$), and aromatic residues bordering the active site gorge (10 and 11 residues, respectively, for AChE1 and AChE2).

In the two sequences, the presence of a phenylalanine residue is observed at position 290 (F290), but not at position 288; this characteristic common to invertebrate AChEs is responsible for a broader substrate specificity of invertebrate AChEs, compared with those of vertebrates.

Analysis of the C-terminal sequences of Diptera AChEs shows the presence of a hydrophobic peptide corresponding to a signal for the addition of a glycolipid, indicating post-translational cleavage of a C-terminal fragment and the addition of a glycolipid anchoring residue as in *Drosophila*, and other mosquito species. In all the sequences, the presence of a cysteine residue is also observed in the C-terminal sequence preceding the potential site of cleavage of the hydrophobic peptide. This cysteine residue could be involved in an intermolecular disulfide bond, linking the two catalytic subunits of the AChE dimer.

The AChE1 and AChE2 proteins of *An. gambiae* exhibit 53% similarity between one another and show, respectively: 76% and 55% similarity with the AChE of *Schizaphis graminum* (NCBI accession number AAK09373 or GENBANK accession number 12958609), 53% and 98% similarity with the AChE of *An. stephensi* (GENBANK 2494391), 54% and 95% similarity with the AChE of *Aedes aegypti* (GENBANK 2133626), and 52% and 83% similarity with the AChE of *Drosophila* (GENBANK 17136862).

The major difference between AChE1 and AChE2 lies in an insertion of 31 amino acids in the sequence of AChE2 (FIG.

1). This sequence, referred to as "hydrophilic insertion" in the AChE of *Drosophila* is absent in vertebrate and nematode AChEs and could be characteristic of AChE2, at least in the diptera.

These results demonstrate the presence of two ace genes in the genome of *Anopheles gambiae*, one encoding AChE1 which is related to the AChE of *Schizaphis graminum*, and the other encoding AChE2 which is related to the AChE of *Drosophila* and to the known AChEs of mosquitoes. The presence of other ace genes in *An. gambiae* is highly improbable insofar as complementary searches in the databases of the *An. gambiae* genome, using less stringent parameters, detected only sequences encoding alpha-esterases (EC 3.1.1) and carboxylesterases (EC 3.1.1.1).

EXAMPLE 3

Demonstration of a Single Ace Gene in *Drosophila melanogaster*

The presence of a gene homologous to the ace-1 gene was sought in the genome of *Drosophila*. TBLASTN searches made it possible to detect the ace gene identified above, homologous to the ace-2 gene of *Anopheles gambiae*, but did not make it possible to detect other sequences homologous to the ace-1 gene. Searches using less stringent parameters made it possible to detect only alpha- and carboxylesterases. These results demonstrate that the *drosophila* genome contains a single ace gene (ace-2).

EXAMPLE 4

Demonstration of at Least Two Ace Genes in the Other Mosquito Species

The presence of the ace-1 gene in the genome of other mosquito species was analyzed by PCR using degenerate oligonucleotides (PdirAGSG and PrevAGSG, SEQ ID NOs. 39 and 40) for amplifying an exon fragment (fragment K of approximately 320 bp, FIG. 1), corresponding to sequences that are conserved between the AChE1 sequences of *An. gambiae* and *Schizaphis graminum*, but divergent between the AChE1 and AChE2 sequences of *An. gambiae*.

The sequence of the PCR products obtained from the genomic DNA of various mosquito species shows a very high percentage identity between the sequences of *Anopheles*, *Culex* and *Aedes*. In addition, most of the substitutions are silent since the amino acid sequences deduced from these nucleotide sequences only differ from one another by 5 to 6 amino acids (FIG. 2A). The fragment K was also amplified by RT-PCR from the mRNA of *C. pipiens*, indicating that the ace-1 gene is expressed in the form of mRNA; this result is in agreement with the existence, in *C. pipiens*, of two AChEs having distinct catalytic properties.

EXAMPLE 5

Analysis of the Linkage Between the Ace-1 Gene and Insecticide Resistance

In order to analyze the linkage between the ace-1 gene and insecticide resistance, the fragment K amplified from the genomic DNA of resistant *C. pipiens* (strain R) was sequenced. Comparison of the fragment K sequences between the S and R strains shows differences of 3 nucleotides (silent substitutions, FIG. 2B). One of these substitutions affects an EcoRI site, which makes it possible to readily differentiate the ace-1 loci of the S and R strains by PCR-RFLP: the restriction profiles show 1 band (320 bp) in the resistant homozygous individuals, 2 bands (106 bp and 214 bp) in the homozygous SS mosquitoes and 3 bands (103 bp, 214 bp and 320 bp) in the heterozygous RS mosquitoes (FIG. 2C).

The linkage between the ace-1 gene and propoxur resistance was studied, in triplicate, in the following way: larvae from a backcross (S×R)×S were treated for a dose that is lethal for sensitive individuals and the ace-1 genotype was analyzed in the survivors, by PCR-RFLP.

The results show that exposure to propoxur kills 50% of the larvae in all the back crosses, i.e. all the sensitive individuals. All the surviving larvae (100 for each back cross, 300 in total) show a heterozygous profile by RFLP, indicating that they all have a copy of the ace-1 gene of the R strain.

These results demonstrate that the ace-1 gene is very closely linked with the insecticide resistance (less than 1% recombination with a degree of confidence of 0.05).

EXAMPLE 6

Analysis of the Phylogeny of the Ace-1 and Ace-2 Genes

Figure 1B:
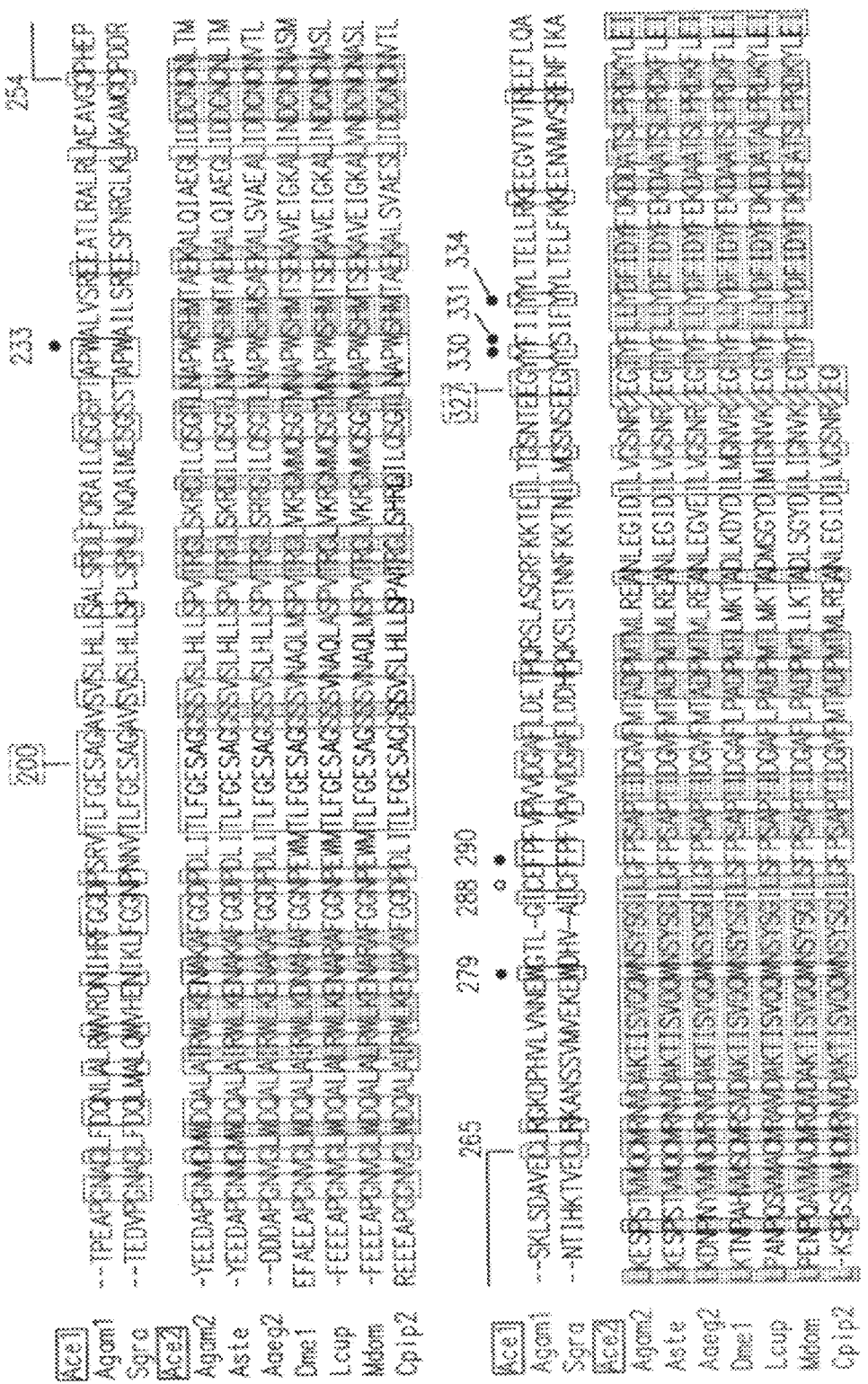
Figure 1C:
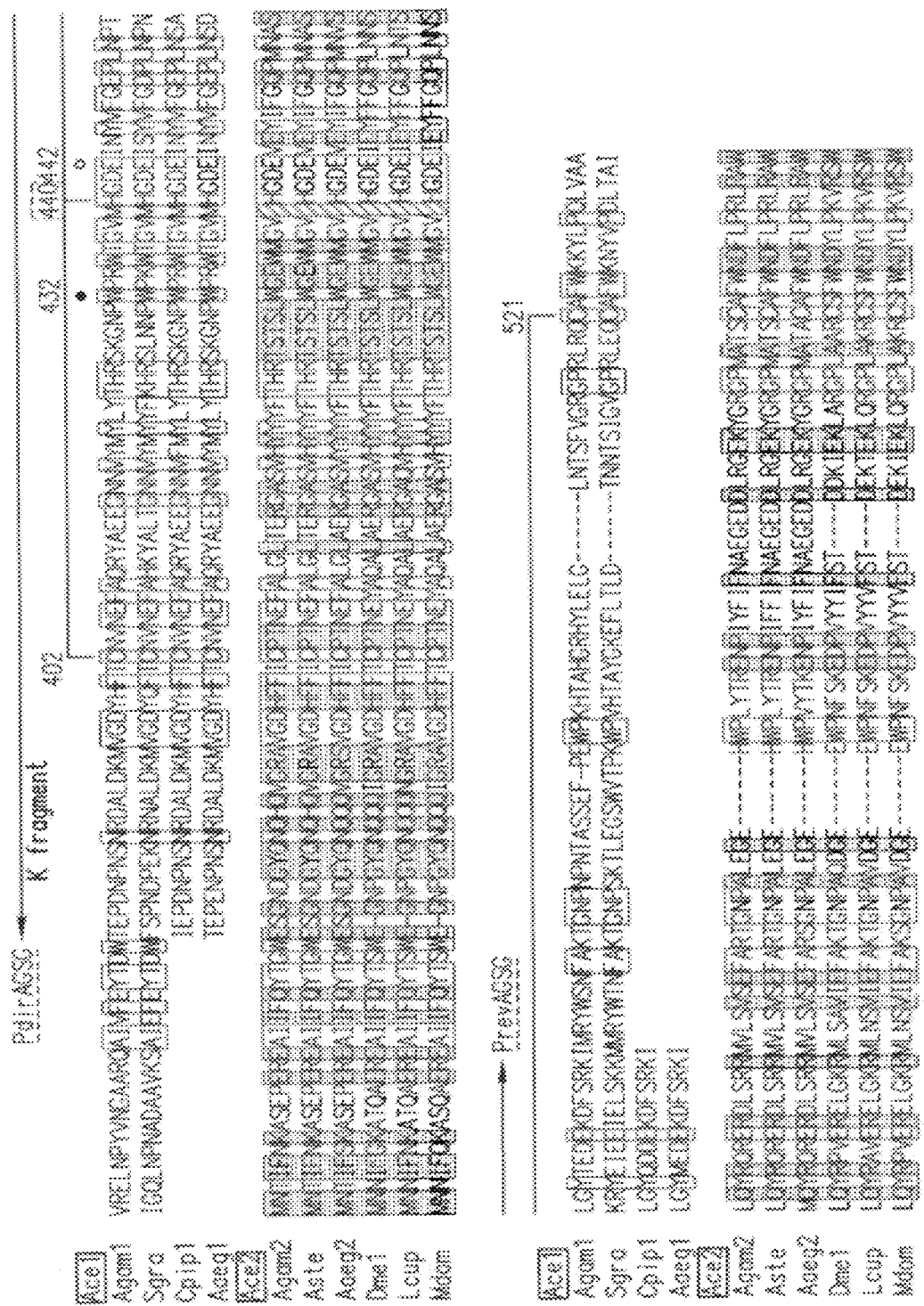

Phylogenetic trees were constructed from the sequences of the conserved regions of *An. gambiae* AChEs (SEQ ID NO 1 and fragment 34-393 of the sequence SEQ ID NO 53, FIG. 1), of the fragments K of *C. pipiens* and *Aedes aegypti* (SEQ ID NOs. 8 and 9) and from 33 AChE sequences available in GENBANK, using the neighbor-joining method, as described in the materials and methods.

FIG. 3 illustrates the heterogeneity of the number of ace genes in the course of the evolution of the animal kingdom. Among the chordates, the cephalochordates have at least two ace genes, whereas the urochordates have only a single one, as deduced from the analysis of their genome. Among the arthropods, the Diptera have either a single ace gene (*Drosophila* of the suborder Brachycera) or two ace genes (mosquitoes of the suborder nematocera). The topology of the tree shows that these two ace genes became duplicated very early in the course of evolution, probably before separation between protostomes and deuterostomes. These results are supported by the fact that mollusk, nematode and arthropod AChEs branch from the sequences of chordata (craniatia, cephalochordata and urochordata). The results show that arthropods and nematodes have a related AChE.

These results indicate that the ace-1 and ace-2 genes identified in insects originate from a very distant duplication event and that the absence of the ace-1 gene, at least in certain species of the suborder Brachycera (*Drosophila*), results from the loss of an ace gene rather than from a recent duplication of the ace gene in the nematocera. These results also suggest that the extrapolations made from studies in *D. melanogaster* are to be considered with reservation insofar as the situation in *Drosophila* is representative neither of the Diptera nor of the entire insect class.

EXAMPLE 7

Determination of the cDNA Sequence of the Ace-1 Gene

The ace-1 cDNA was cloned from two strains of *Anopheles gambiae* (sensitive strain KISUMU and resistant strain YAO)

and from two strains of *Culex pipiens* (sensitive strain S-LAB and resistant strain SR), as described in the materials and methods.

The complete sequence of the cDNA of the KISUMU strain corresponds to the sequence SEQ ID NO 125 which encodes a 737 amino acid protein (SEQ ID NO 126). The complete sequence of the cDNA and of the AChE1 protein of the strain YAO correspond, respectively, to the sequences SEQ ID NO 121 and SEQ ID NO 122.

The sequences SEQ ID NO 4 and SEQ ID NO 5 correspond to the virtually complete sequence (with the exception of the first coding exon of the ace-1 gene), respectively, of the cDNA and of the AChE1 protein of the strain KISUMU.

The complete sequence of the cDNA of the *C. pipiens* strains S-LAB and SR correspond, respectively, to the sequences SEQ ID NO 6 and SEQ ID NO 56 which encode a 702 amino acid protein (SEQ ID NO 7 and SEQ ID NO 57, respectively, for the strain S-LAB and the strain SR).

EXAMPLE 8

Determination of the Sequence of the Ace-1 Gene

The sequence of the ace-1 gene was determined from the genomic DNA of two strains of *Anopheles gambiae*, the reference sensitive strain from West Africa (strain KISUMU) and a resistant strain from Ivory Coast (strain YAO), as described in the materials and methods.

The complete *An. gambiae* sequence corresponds to the sequence SEQ ID NO 127 which has an intron-exon organization comprising at least 9 exons and including two 5' non-coding exons (table I).

The virtually complete sequence (with the exception of the first two 5' non-coding exons) of the ace-1 gene of the strain KISUMU corresponds to the sequence SEQ ID NO 23.

The virtually complete sequence (with the exception of the first two 5' non-coding exons and of the first coding exon) of the ace-1 gene of the strain YAO corresponds to the sequence SEQ ID NO 120.

EXAMPLE 9

Identification of (a) Mutation(s) in the Amino Acid Sequence of the AChE1 Protein that is (are) Responsible for the Insecticide Resistance in Mosquitoes of the Species *Culex pipiens* and *Anopheles gambiae*

The nucleotide sequence encoding the AChE1 protein (cDNA) was determined from two strains of *Anopheles gambiae* (sensitive strain KISUMU and resistant strain YAO) and from two strains of *Culex pipiens* (sensitive strain S-LAB and resistant strain SR), as described in example 7.

Figure 6C:
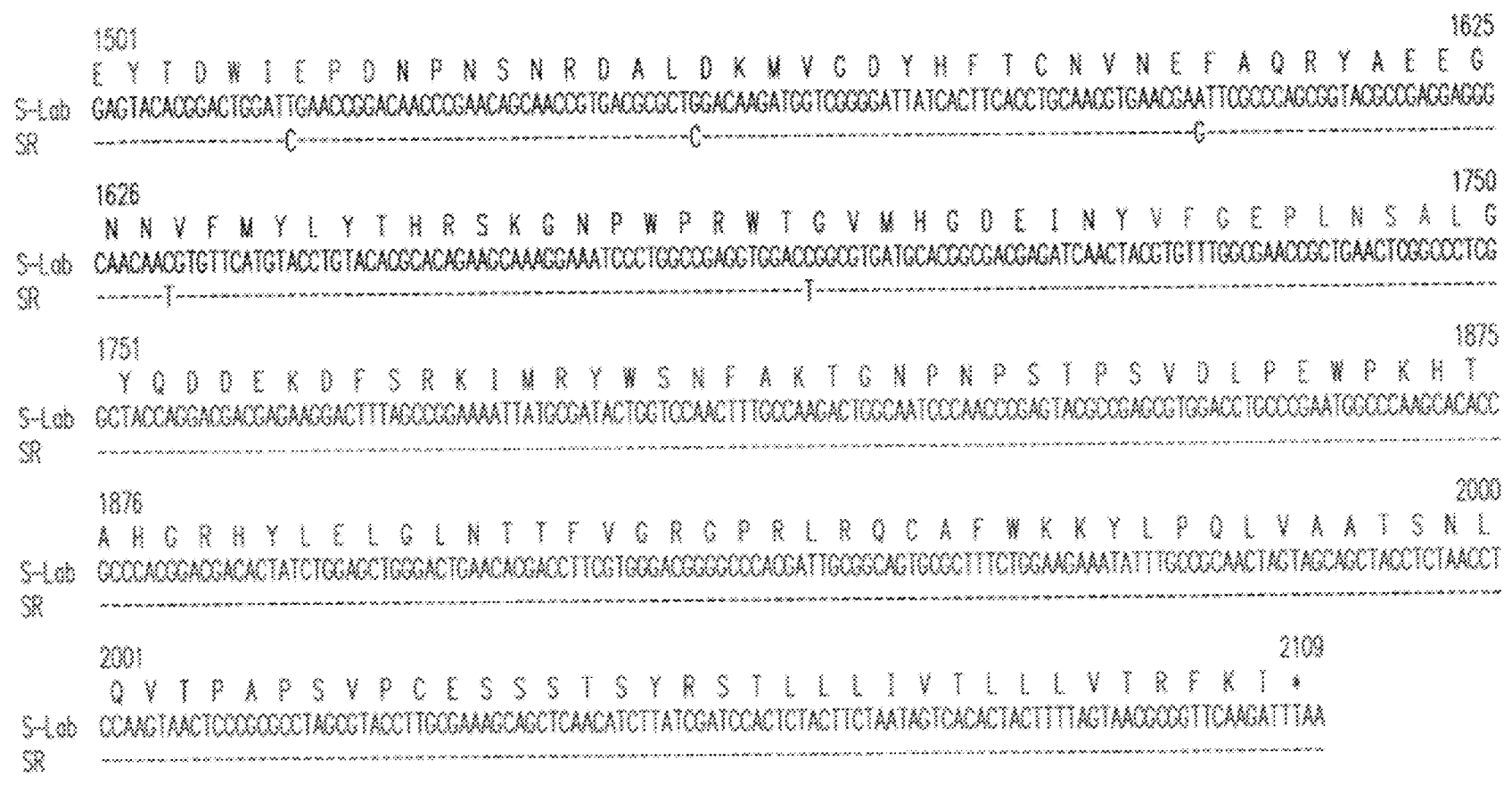

The amino acid sequences of the AChE1 protein of the sensitive and resistant strains, deduced from the above sequences, were then aligned (FIGS. 5, 6 and 9).

Comparison of the amino acid sequences of the *C. pipiens* AChE1 protein (FIGS. 5 and 6) shows that a single non-silent mutation exists between the insecticide-sensitive strain (S-LAB, SEQ ID NO 7) and the insecticide-resistant strain (strain SR, SEQ ID NO 57), located in the region encoded by the third coding exon of the ace-1 gene: the glycine (GGC) at position 247 (or at position 119, with reference to the sequence of the torpedo fish AChE) of the sensitive strain is replaced with a serine (AGC) in the resistant strain $(G_{247(119)} \rightarrow S_{247(119)})$.

The location of the amino acid at position 247 in the *C. pipiens* acetylcholinesterase structure and the effect of the glycine→serine substitution on this structure were analyzed by molecular modelling based on the structure of the torpedo fish acetylcholinesterase. The results are given in FIGS. 7 (A, B and C). FIG. 7A shows that the amino acid at position 119 is close to the residues of the catalytic site ($S_{200}$ and $H_{440}$). FIG. 7C shows that, by comparison with the glycine of the sensitive strain (FIG. 7B), the hindrance of the side chain of the serine in the resistant strain reduces the space of the catalytic site, which probably prevents the insecticide from interacting with the catalytic serine ($S_{200}$).

Comparison of the amino acid sequences of the *An. gambiae* AChE1 protein shows that two non-silent mutations exist between the insecticide-sensitive strain (KISUMU, SEQ ID NO 5) and the insecticide-resistant strain (strain YAO, SEQ ID NO 122): the first corresponds to the replacement of the valine (CGT) at position 33 of the sequence of the sensitive strain (SEQ ID NO 5) with an alanine (CGC) in the resistant strain, and the second is the same glycine→serine mutation as that found in *Culex pipiens*.

Given the external position of the valine in the acetylcholinesterase structure, this mutation is certainly not involved in the resistance in *Anopheles gambiae* and only the serine should be responsible for the insecticide resistance both in *Anopheles gambiae* and *Culex pipiens*.

EXAMPLE 10

Detection of the Mutation in the Third Coding Exon of the Ace-1 Gene that is Responsible for the Insecticide Resistance in Mosquitoes of the Species *Culex pipiens* and *Anopheles gambiae*

The restriction profile of the third coding exon of the ace-1 gene containing the glycine→serine mutation was verified in many populations and strains of mosquitoes of the species *C. pipiens* and *An. gambiae*, sensitive and resistant to insecticides of the organophosphorus compound and carbamate class, by PCR-RFLP according to the protocol as described in example 1.

More precisely:
in *C. pipiens*, the glycine (GGC)→serine (AGC) mutation introduces a unique Alu I site (AGCT) into the sequence of the resistant strain, which is demonstrated on the basis of a 520 bp PCR product amplified using the primers Ex3dir and Ex3rev, as illustrated in FIG. 6;
in *An. gambiae*, the glycine (GGC)→serine (AGC) mutation introduces a second Alu I site (AGCT) into the sequence of the resistant strain, which is demonstrated on the basis of a 541 bp PCR product amplified using the primers Ex3AGdir and Ex3AGrev, as illustrated in FIG. 9.

The PCR-RFLP results were then verified by sequencing the 520 bp or 541 bp PCR fragment of the third coding exon.

Species *C. pipiens*

The resistant (R) or sensitive (S) *Culex pipiens* strains and populations which were analyzed are given in table III below:

TABLE III

Strains and populations of the species *C. pipiens* analyzed

| Classification | Name | R/S* | Country | Reference |
|---|---|---|---|---|
| C. p. quinquefasciatus | BO | R | Burkina-Faso | Isolated by the inventors |
| | HARARE | R | Zimbabwe | Isolated by the inventors |
| | SUPERCAR | R | Ivory Coast | (F. Chandre, Doctoral Thesis, University Paris XII, 1998). |
| | DJI | R | Mali | Isolated by the inventors |
| | MARTINIQUE | R | Martinique | Bourguet et al., Biochem. Genet., 1996, 34, 351-362 |
| | RECIFE | R | Brazil | Isolated in 1995 by A.-B. Failloux, Pasteur Institute, Paris (France) |
| | PRO-R | S | United States | Georghiou et al., Bull. Wld Hlth Org., 1996, 35, 691-708. |
| | S-LAB | S | United States | Georghiou et al., Bull. Wld Hlth Org., 1996, 35, 691-708. |
| | TEM-R | S | United States | Georghiou et al., J. Econ. Entomol., 1978, 71, 201-205. |
| | TRANS-P | S | United States | Priester et al., J. Econ. Entomol., 1978, 71, 197-200. |
| | LING | S | China | Weill et al., J. American Mosquito Control Assoc., 2001, 17, 238-244 |
| | THAI | S | Thailand | Guillemaud et al., Heredity, 1996, 77, 535-543. |
| | MAO | S | China | Qiao et al., Biochem. Genet., 1998, 36, 417-426. |
| | MADURAI | S | India | Nielsen-Leroux, et al., J. Med. Entomol., 2002, 39, 729-735 |
| | BSQ | S | South Africa | Isolated in 1991 by A. J. Cornel (Sth Afr. Inst. Med. Res., South Africa) |
| | BED | S | South Africa | Isolated in 1991 by A. J. Cornel (Sth Afr. Inst. Med. Res., South Africa) |
| | BOUAKE | S | Ivory Coast | Magnin et al., J. Med. Entomol., 1988, 25, 99-104 |
| | BRAZZA | S | Congo | Beyssat-Arnaouty, Doctoral Thesis, University of Montpellier II (1989). |
| | BRESIL | S | Brazil | Isolated by the inventors |
| | MOOREA | S | Polynesia | N. Pasteur, et al., Genet. Res., 1995, 66, 139-146 |
| C. p. pipiens | ESPRO | R | Tunisia | H. Ben Cheikh et al., J. Am. Mosquito Control Assoc., 1993, 9, 335-337 |
| | PRAIAS | R | Portugal | Bourguet et al., J. Econ. Entomol., 1996, 89, 1060-1066 |
| | PADOVA | R | Italy | Bourguet et al., Genetics, 1997, 147, 1225-1234. |
| | BARRIOL | R | France | Chevillon et al., Evolution, 1995, 49, 997-1007. |
| | BRUGES-A | S | Belgium | Raymond et al., Genet. Res., 1996, 67, 19-26. |
| | BRUGES-B | S | Belgium | Raymond et al., Genet. Res., 1996, 67, 19-26. |
| | KILLCARE | S | Australia | Guillemaud et al., Proc. R. Soc. Lond. B, 1997, 264, 245-251. |
| | BLEUET | S | France | Rioux et al., C. R. Séances Soc. Biol. Fil., 1961, 155, 343-344 |
| | HETEREN | S | The Netherlands | Isolated by the inventors |
| C. torrentium | UPPSALA | S | Sweden | M. Raymond, Ent. Tidskr., 1995, 116, 65-66. |

*R/S resistant or sensitive to insecticides of the organophosphorus compound and carbamate class The PCR-RFLP analysis of all the mosquitoes of table III shows that a perfect correlation exists between the insecticide resistance and the restriction profile by PCR-RFLP, namely: 1 band (520 bp) is detected in the sensitive homozygous SS individuals, 2 bands (357 bp and 163 bp) are detected in the resistant homozygous RR individuals and 3 bands (520 bp, 357 bp and 163 bp) are detected in the resistant heterozygous RS individuals (FIG. 8).

These results were confirmed by sequencing the 520 bp PCR product for all the mosquitoes of table III analyzed by PCR-RFLP. Alignment of the sequences obtained (SEQ ID NOs. 60 to 89), illustrated in table IV below, shows that in the mosquitoes of the species *C. pipiens*, the glycine→serine mutation, located at position 739 with reference to the cDNA sequence of the ace-1 gene of the reference sensitive strain (strain S-LAB), which is responsible for the insecticide resistance, originates from two groups of independent mutations, respectively, in *C. pipiens pipiens* and *C. pipiens quinquefasciatus*.

TABLE IV

Analysis of the origin of the glycine → serine mutation responsible for the insecticide resistance in mosquitoes of the species C. pipiens Position of the mutations with reference to the cDNA sequence of the ace-1 gene of the strain S-LAB (SEQ ID NO. 6)

```
                         4 4 4 4 5 5 5 5 5 6 6 6 6 6 6 6 7 7 7 7 7 7 7 7 7 7 7 8 8
                         5 5 7 9 1 2 6 7 9 0 5 6 8 8 9 9 1 3 3 4 4 5 6 7 7 8 9 9 1 4
                         0 3 1 8 3 8 4 3 7 3 1 0 1 4 1 6 4 2 9 1 7 6 3 4 7 0 0 8 3 6

Strains of
C. pipiens
C. pipiens
quinquefasciatus

BO (R)*                  T C A T C G G G G C G G G C C C C A C C T C C C C G G A T
Harare (R)               - - - - - - - - - - - - - - - - - - - - - - - - - - - - - -
Supercar (R)             - - - - - - - - - - - - - - - - - - - - - - - - - - - - - -
```

TABLE IV-continued

Analysis of the origin of the glycine →
serine mutation responsible for the insecticide
resistance in mosquitoes of the species *C. pipiens*

Position of the mutations with reference
to the cDNA sequence of the ace-1 gene of
the strain S-LAB (SEQ ID NO. 6)

| Strain | Sequence |
|---|---|
| DJI (R) | - - - - - - - - - - - - - - - - - - - - - - - - - - - - - - |
| Martinique (R) | - - - - - - - - - - - - - - - - - - - - - - - - - - - - - - |
| Recife (R) | - - - - - - - - - - - - - - - - - - - - - - - - - - - - - - |
| ProR (S)* | - T - C - - - - - - - - - - - - - - - G - - - - - - - - - G |
| S-Lab (S) | - T - C - - - - - - - - - - - - - - - G - - - - - - - - - G |
| TemR (S) | - T - - - - A - - - - - - - - - - - - G - - - - - - - A - - |
| Trans (S) | - T - - - - A - - - - - - - - - - - - G - - - - - - - A - - |
| Ling (S | - T C C - - - - - - - - - - - - - - - G - - - - T - - - - - - |
| Thai (S) | - T C C - - - - - - - - - - - - - - - G - - - - - - - - - G |
| Mao (S) | - T - C - - - - - - - - - - - - - - - G - - - - - - - - - - |
| Madurai (S) | - T - C - - A - - - - - - - - - - - - G - - - - - - - - - G |
| BSQ (S) | - T C C - - - - - - - - - - - - - - - G - - - - - - - - - G |
| BE (S) | - T - - - - A - - - - - - - - - - - - G - - - - - - - - - - |
| Boualse (S) | - T - C - - - - - - - - - - - - - - - G - - - - - - - - - - |
| Brazza (S) | - T C C - - - - - - - - - - - - - - - G - - - - - - - - - G |
| Bresil (S) | - T - C - - - - - - - - - - - - - - - G - T - - - - - - - G |
| Moorea (S) | - T - - - - - - - - - - - - - - - - - G - - - - - - - - - G |

*C. pipiens*

*pipiens*

| Strain | Sequence |
|---|---|
| Espro (R) | A T - C - - - A - - C - - - A G T T A - - - T - T T - - G - |
| Praias (R) | A T - C - - - A - - C - - - A G T T A - - - T - T T - - G - |
| Padova (R) | A T - C - - - A - - C - - - A G T T A - - - T - T T - - G - |
| Barriol (R) | A T - C - - - A - - C - - - A G T T A - - - T - T T - - G - |
| BrugeA (S) | A T - C - - - A - - C - - - A G T T G - - - T - T T - - G - |
| BrugesB (S) | A T - C - - - A - - C - - - A G T T G - - - T - T T - - G - |
| Killcare (S) | A T - C - - - A - A C - - - A G T T G - - - T - T T - - G - |
| Bleuet (S) | A T - C - - - A - - C - - - A G T T G - - - T - T T - - G - |
| Heteren (S) | A T - C - A - A - A C - - - A G T - G - - - T - - T - A G - |

*(R) resistant to insecticides

*(S) sensitive to insecticides

*An. gambiae*

Sensitive strains KISUMU (reference sensitive strain from East Africa) and VK-PER (KDR reference strain from West Africa) and also sensitive populations from the Yaoundé region were tested by means of the PCR-RFLP test as described above.

The results of the PCR-RFLP test show that, for all the *An. gambiae* mosquitoes analyzed, a perfect correlation exists between the insecticide resistance and the restriction profile by PCR-RFLP, namely: 2 bands (403 bp and 138 bp) are detected in the sensitive homozygous SS individuals, 2 bands (253 bp and approximately 150 bp) or 3 bands (403 bp, 253 bp and approximately 150 bp) are detected in the resistant individuals, respectively in the homozygous (RR) and heterozygous (RS) individuals.

EXAMPLE 11

Analysis of the Acetylcholinesterase Activity of the Insecticide-Sensitive and Insecticide-Resistant AChE1 Proteins The recombinant AChE1s of, respectively, the strain S-LAB and the strain SR were expressed in insect cells and the acetylcholinesterase activity was measured using cell extracts as described in example 1.

The results given in FIG. 10 show that the single glycine$_{247(119)}$→serine$_{247(119)}$ mutation renders the acetylcholinesterase insensitive to the insecticide.

As emerges from the above, the invention is in no way limited to its methods of implementation, execution and application which have just been described more explicitly; on the contrary, it encompasses all the variants thereof which may occur to those skilled in the art, without departing from the context or the scope of the present invention.

The invention claimed is:

1. An isolated or purified polypeptide comprising the amino acid sequence of SEQ ID NO: 1.

2. The isolated or purified polypeptide of claim 1 that has acetylcholinesterase activity.

3. The isolated or purified polypeptide of claim 2 that is from an insect of the genus *Anopheles*.

4. The isolated or purified polypeptide of claim 2 that is sensitive to an organophosphorus or carbamate class insecticide, wherein sensitive means that acetylcholinesterase activity is inhibited by the presence of an organophosphorus or carbamate class insecticide.

5. The isolated or purified polypeptide of claim 2 that consists of a sequence selected from the group consisting of SEQ ID NO: 3, SEQ ID NO: 5 and SEQ ID NO: 126 of *Anopheles gambiae*.

6. An isolated or purified polypeptide comprising SEQ ID NO:1 except in that it contains a substitution mutation of the glycine residue located at position 117 of SEQ ID NO:1 with serine.

7. The isolated or purified polypeptide of claim 6 that is insensitive to an organophosphorus or carbamate class insecticide, wherein insensitive means that acetylcholinesterase activity is not inhibited by a concentration of an organophosphorus or carbamate class insecticide that inhibits the activity of the corresponding polypeptide that does not contain said substitutional mutation.

8. The isolated or purified polypeptide of claim 6 that consists of the sequence SEQ ID NO: 122.

* * *

SEQUENCE LISTING

```
<160> NUMBER OF SEQ ID NOS: 183

<210> SEQ ID NO 1
<211> LENGTH: 524
<212> TYPE: PRT
<213> ORGANISM: Anopheles gambiae

<400> SEQUENCE: 1

Asp Pro Leu Val Val Asn Thr Asp Lys Gly Arg Ile Arg Gly Ile Thr
1               5                   10                  15

Val Asp Ala Pro Ser Gly Lys Lys Val Asp Val Trp Leu Gly Ile Pro
            20                  25                  30

Tyr Ala Gln Pro Pro Val Gly Pro Leu Arg Phe Arg His Pro Arg Pro
        35                  40                  45

Ala Glu Lys Trp Thr Gly Val Leu Asn Thr Thr Thr Pro Pro Asn Ser
    50                  55                  60

Cys Val Gln Ile Val Asp Thr Val Phe Gly Asp Phe Pro Gly Ala Thr
65                  70                  75                  80

Met Trp Asn Pro Asn Thr Pro Leu Ser Glu Asp Cys Leu Tyr Ile Asn
                85                  90                  95

Val Val Ala Pro Arg Pro Arg Pro Lys Asn Ala Ala Val Met Leu Trp
            100                 105                 110

Ile Phe Gly Gly Gly Phe Tyr Ser Gly Thr Ala Thr Leu Asp Val Tyr
        115                 120                 125

Asp His Arg Ala Leu Ala Ser Glu Glu Asn Val Ile Val Val Ser Leu
    130                 135                 140

Gln Tyr Arg Val Ala Ser Leu Gly Phe Leu Phe Leu Gly Thr Pro Glu
145                 150                 155                 160

Ala Pro Gly Asn Ala Gly Leu Phe Asp Gln Asn Leu Ala Leu Arg Trp
                165                 170                 175

Val Arg Asp Asn Ile His Arg Phe Gly Gly Asp Pro Ser Arg Val Thr
            180                 185                 190

Leu Phe Gly Glu Ser Ala Gly Ala Val Ser Val Ser Leu His Leu Leu
        195                 200                 205

Ser Ala Leu Ser Arg Asp Leu Phe Gln Arg Ala Ile Leu Gln Ser Gly
    210                 215                 220

Ser Pro Thr Ala Pro Trp Ala Leu Val Ser Arg Glu Glu Ala Thr Leu
225                 230                 235                 240
```

```
Arg Ala Leu Arg Leu Ala Glu Ala Val Gly Cys Pro His Glu Pro Ser
                245                 250                 255

Lys Leu Ser Asp Ala Val Glu Cys Leu Arg Gly Lys Asp Pro His Val
            260                 265                 270

Leu Val Asn Asn Glu Trp Gly Thr Leu Gly Ile Cys Glu Phe Pro Phe
        275                 280                 285

Val Pro Val Val Asp Gly Ala Phe Leu Asp Glu Thr Pro Gln Arg Ser
    290                 295                 300

Leu Ala Ser Gly Arg Phe Lys Lys Thr Glu Ile Leu Thr Gly Ser Asn
305                 310                 315                 320

Thr Glu Glu Gly Tyr Tyr Phe Ile Ile Tyr Tyr Leu Thr Glu Leu Leu
                325                 330                 335

Arg Lys Glu Glu Gly Val Thr Val Thr Arg Glu Phe Leu Gln Ala
            340                 345                 350

Val Arg Glu Leu Asn Pro Tyr Val Asn Gly Ala Ala Arg Gln Ala Ile
        355                 360                 365

Val Phe Glu Tyr Thr Asp Trp Thr Glu Pro Asp Asn Pro Asn Ser Asn
    370                 375                 380

Arg Asp Ala Leu Asp Lys Met Val Gly Asp Tyr His Phe Thr Cys Asn
385                 390                 395                 400

Val Asn Glu Phe Ala Gln Arg Tyr Ala Glu Glu Gly Asn Asn Val Tyr
                405                 410                 415

Met Tyr Leu Tyr Thr His Arg Ser Lys Gly Asn Pro Trp Pro Arg Trp
            420                 425                 430

Thr Gly Val Met His Gly Asp Glu Ile Asn Tyr Val Phe Gly Glu Pro
        435                 440                 445

Leu Asn Pro Thr Leu Gly Tyr Thr Glu Asp Glu Lys Asp Phe Ser Arg
    450                 455                 460

Lys Ile Met Arg Tyr Trp Ser Asn Phe Ala Lys Thr Gly Asn Pro Asn
465                 470                 475                 480

Pro Asn Thr Ala Ser Ser Glu Phe Pro Glu Trp Pro Lys His Thr Ala
                485                 490                 495

His Gly Arg His Tyr Leu Glu Leu Gly Leu Asn Thr Ser Phe Val Gly
            500                 505                 510

Arg Gly Pro Arg Leu Arg Gln Cys Ala Phe Trp Lys
        515                 520

<210> SEQ ID NO 2
<211> LENGTH: 1932
<212> TYPE: DNA
<213> ORGANISM: Anopheles gambiae
<220> FEATURE:
<221> NAME/KEY: CDS
<222> LOCATION: (1)..(1932)

<400> SEQUENCE: 2 atg ttt gtg tgt tgt ttt ttc ttt ctc tct ctc tct ttc tgt ggt tcc      48
Met Phe Val Cys Cys Phe Phe Phe Leu Ser Leu Ser Phe Cys Gly Ser
1               5                   10                  15 aac att tca gac gca ttt ttt aca cca tat ata ggt cac ggt gag tcc      96
Asn Ile Ser Asp Ala Phe Phe Thr Pro Tyr Ile Gly His Gly Glu Ser
            20                  25                  30 gta cga att ata gat gcc gag ttg ggc acg ctc gag cat gtc cac agt     144
Val Arg Ile Ile Asp Ala Glu Leu Gly Thr Leu Glu His Val His Ser
        35                  40                  45 gga gca acg ccg cgg cga cgc ggc ctg acg agg cgc gag tca aac tcg     192
Gly Ala Thr Pro Arg Arg Arg Gly Leu Thr Arg Arg Glu Ser Asn Ser
```

```
                  50                    55                     60
gac gcg aac gac aac gat ccg ctg gtg gtc aac acg gat aag ggg cgc      240
Asp Ala Asn Asp Asn Asp Pro Leu Val Val Asn Thr Asp Lys Gly Arg
 65                  70                      75                  80 atc cgc ggc att acg gtc gat gcg ccc agc ggc aag aag gtg gac gtg      288
Ile Arg Gly Ile Thr Val Asp Ala Pro Ser Gly Lys Lys Val Asp Val
                     85                      90                  95 tgg ctc ggc att ccc tac gcc cag ccg ccg gtc ggg ccg cta cgg ttc      336
Trp Leu Gly Ile Pro Tyr Ala Gln Pro Pro Val Gly Pro Leu Arg Phe
                    100                     105             110 cgt cat ccg cgg ccg gcc gaa aag tgg acc ggc gtg ctg aac acg acc      384
Arg His Pro Arg Pro Ala Glu Lys Trp Thr Gly Val Leu Asn Thr Thr
                115                     120                 125 aca ccg ccc aac agc tgc gtg cag atc gtg gac acc gtg ttc ggc gac      432
Thr Pro Pro Asn Ser Cys Val Gln Ile Val Asp Thr Val Phe Gly Asp
130                 135                     140 ttc ccg ggc gcg acc atg tgg aac ccg aac acg ccc ctg tcc gag gac      480
Phe Pro Gly Ala Thr Met Trp Asn Pro Asn Thr Pro Leu Ser Glu Asp
145                 150                     155                 160 tgt ctg tac att aac gtg gtg gca ccg cga ccc cgg ccc aag aat gcg      528
Cys Leu Tyr Ile Asn Val Val Ala Pro Arg Pro Arg Pro Lys Asn Ala
                    165                     170                 175 gcc gtc atg ctg tgg atc ttc ggc ggc ggc ttc tac tcc ggc acc gcc      576
Ala Val Met Leu Trp Ile Phe Gly Gly Gly Phe Tyr Ser Gly Thr Ala
                180                     185                 190 acc ctg gac gtg tac gac cac cgg gcg ctt gcg tcg gag gag aac gtg      624
Thr Leu Asp Val Tyr Asp His Arg Ala Leu Ala Ser Glu Glu Asn Val
                195                     200                 205 atc gtg gtg tcg ctg cag tac cgc gtg gcc agt ctg ggc ttc ctg ttt      672
Ile Val Val Ser Leu Gln Tyr Arg Val Ala Ser Leu Gly Phe Leu Phe
            210                     215                 220 ctc ggc acc ccg gaa gcg ccg ggc aat gcg gga ctg ttc gat cag aac      720
Leu Gly Thr Pro Glu Ala Pro Gly Asn Ala Gly Leu Phe Asp Gln Asn
225                 230                     235                 240 ctt gcg cta cgc tgg gtg cgg gac aac att cac cgg ttc ggt ggc gat      768
Leu Ala Leu Arg Trp Val Arg Asp Asn Ile His Arg Phe Gly Gly Asp
                245                     250                 255 ccg tcg cgt gtg aca ctg ttc ggc gag agt gcc ggt gcc gtc tcg gtg      816
Pro Ser Arg Val Thr Leu Phe Gly Glu Ser Ala Gly Ala Val Ser Val
                260                     265                 270 tcg ctg cat ctg ctg tcc gcc ctt tcc cgc gat ctg ttc cag cgg gcc      864
Ser Leu His Leu Leu Ser Ala Leu Ser Arg Asp Leu Phe Gln Arg Ala
                275                     280                 285 atc ctg cag agc ggc tcg ccg acg gca ccg tgg gca ttg gta tcg cgc      912
Ile Leu Gln Ser Gly Ser Pro Thr Ala Pro Trp Ala Leu Val Ser Arg
            290                     295                 300 gag gaa gcc aca cta aga gca ctg cgg ttg gcc gag gcg gtc ggc tgc      960
Glu Glu Ala Thr Leu Arg Ala Leu Arg Leu Ala Glu Ala Val Gly Cys
305                 310                     315                 320 ccg cac gaa ccg agc aag ctg agc gat gcg gtc gag tgc ctg cgc ggc     1008
Pro His Glu Pro Ser Lys Leu Ser Asp Ala Val Glu Cys Leu Arg Gly
                325                     330                 335 aag gac ccg cac gtg ctg gtc aac aac gag tgg ggc acg ctc ggc att     1056
Lys Asp Pro His Val Leu Val Asn Asn Glu Trp Gly Thr Leu Gly Ile
                340                     345                 350 tgc gag ttc ccg ttc gtg ccg gtg gtc gac ggt gcg ttc ctg gac gag     1104
Cys Glu Phe Pro Phe Val Pro Val Val Asp Gly Ala Phe Leu Asp Glu
                355                     360                 365 acg ccg cag cgt tcg ctc gcc agc ggg cgc ttc aag aag acg gag atc     1152
Thr Pro Gln Arg Ser Leu Ala Ser Gly Arg Phe Lys Lys Thr Glu Ile
```

```
                370                 375                 380
ctc acc ggc agc aac acg gag gag ggc tac tac ttc atc atc tac tac    1200
Leu Thr Gly Ser Asn Thr Glu Glu Gly Tyr Tyr Phe Ile Ile Tyr Tyr
385                 390                 395                 400 ctg acc gag ctg ctg cgc aag gag gag ggc gtg acc gtg acg cgc gag    1248
Leu Thr Glu Leu Leu Arg Lys Glu Glu Gly Val Thr Val Thr Arg Glu
                405                 410                 415 gag ttc ctg cag gcg gtg cgc gag ctc aac ccg tac gtg aac ggg gcg    1296
Glu Phe Leu Gln Ala Val Arg Glu Leu Asn Pro Tyr Val Asn Gly Ala
            420                 425                 430 gcc cgg cag gcg atc gtg ttc gag tac acc gac tgg acc gag ccg gac    1344
Ala Arg Gln Ala Ile Val Phe Glu Tyr Thr Asp Trp Thr Glu Pro Asp
        435                 440                 445 aac ccg aac agc aac cgg gac gcg ctg gac aag atg gtg ggc gac tat    1392
Asn Pro Asn Ser Asn Arg Asp Ala Leu Asp Lys Met Val Gly Asp Tyr
450                 455                 460 cac ttc acc tgc aac gtg aac gag ttc gcg cag cgg tac gcc gag gag    1440
His Phe Thr Cys Asn Val Asn Glu Phe Ala Gln Arg Tyr Ala Glu Glu
465                 470                 475                 480 ggc aac aac gtc tac atg tat ctg tac acg cac cgc agc aaa ggc aac    1488
Gly Asn Asn Val Tyr Met Tyr Leu Tyr Thr His Arg Ser Lys Gly Asn
                485                 490                 495 ccg tgg ccg cgc tgg acg ggc gtg atg cac ggc gac gag atc aac tac    1536
Pro Trp Pro Arg Trp Thr Gly Val Met His Gly Asp Glu Ile Asn Tyr
            500                 505                 510 gtg ttc ggc gaa ccg ctc aac ccc acc ctc ggc tac acc gag gac gag    1584
Val Phe Gly Glu Pro Leu Asn Pro Thr Leu Gly Tyr Thr Glu Asp Glu
        515                 520                 525 aaa gac ttt agc cgg aag atc atg cga tac tgg tcc aac ttt gcc aaa    1632
Lys Asp Phe Ser Arg Lys Ile Met Arg Tyr Trp Ser Asn Phe Ala Lys
530                 535                 540 acc ggg aat cca aat ccc aac acg gcc agc agc gaa ttc ccc gag tgg    1680
Thr Gly Asn Pro Asn Pro Asn Thr Ala Ser Ser Glu Phe Pro Glu Trp
545                 550                 555                 560 ccc aag cac acc gcc cac gga cgg cac tat ctg gag ctg ggc ctc aac    1728
Pro Lys His Thr Ala His Gly Arg His Tyr Leu Glu Leu Gly Leu Asn
                565                 570                 575 acg tcc ttc gtc ggt cgg ggc cca cgg ttg agg cag tgt gcc ttc tgg    1776
Thr Ser Phe Val Gly Arg Gly Pro Arg Leu Arg Gln Cys Ala Phe Trp
            580                 585                 590 aag aag tac ctt ccc cag cta gtt gca gct acc tcg aac cta cca ggg    1824
Lys Lys Tyr Leu Pro Gln Leu Val Ala Ala Thr Ser Asn Leu Pro Gly
        595                 600                 605 cca gca ccg cct agt gaa ccg tgc gaa agc agc gca ttt ttt tac cga    1872
Pro Ala Pro Pro Ser Glu Pro Cys Glu Ser Ser Ala Phe Phe Tyr Arg
610                 615                 620 cct gat ctg atc gtg ctg ctg gtg tcg ctg ctt acg gcg acc gtc aga    1920
Pro Asp Leu Ile Val Leu Leu Val Ser Leu Leu Thr Ala Thr Val Arg
625                 630                 635                 640 ttc ata caa taa                                                    1932
Phe Ile Gln <210> SEQ ID NO 3
<211> LENGTH: 643
<212> TYPE: PRT
<213> ORGANISM: Anopheles gambiae

<400> SEQUENCE: 3

Met Phe Val Cys Cys Phe Phe Phe Leu Ser Leu Ser Phe Cys Gly Ser
1               5                   10                  15
```

```
Asn Ile Ser Asp Ala Phe Phe Thr Pro Tyr Ile Gly His Gly Glu Ser
             20                  25                  30

Val Arg Ile Ile Asp Ala Glu Leu Gly Thr Leu Glu Val His Ser
             35                  40                  45

Gly Ala Thr Pro Arg Arg Gly Leu Thr Arg Glu Ser Asn Ser
 50                  55                  60

Asp Ala Asn Asp Asn Asp Pro Leu Val Val Asn Thr Asp Lys Gly Arg
 65                  70                  75                  80

Ile Arg Gly Ile Thr Val Asp Ala Pro Ser Gly Lys Lys Val Asp Val
             85                  90                  95

Trp Leu Gly Ile Pro Tyr Ala Gln Pro Val Gly Pro Leu Arg Phe
             100                 105                 110

Arg His Pro Arg Pro Ala Glu Lys Trp Thr Gly Val Leu Asn Thr Thr
             115                 120                 125

Thr Pro Pro Asn Ser Cys Val Gln Ile Val Asp Thr Val Phe Gly Asp
             130                 135                 140

Phe Pro Gly Ala Thr Met Trp Asn Pro Asn Thr Pro Leu Ser Glu Asp
145                 150                 155                 160

Cys Leu Tyr Ile Asn Val Val Ala Pro Arg Pro Arg Pro Lys Asn Ala
             165                 170                 175

Ala Val Met Leu Trp Ile Phe Gly Gly Gly Phe Tyr Ser Gly Thr Ala
             180                 185                 190

Thr Leu Asp Val Tyr Asp His Arg Ala Leu Ala Ser Glu Glu Asn Val
             195                 200                 205

Ile Val Val Ser Leu Gln Tyr Arg Val Ala Ser Leu Gly Phe Leu Phe
             210                 215                 220

Leu Gly Thr Pro Glu Ala Pro Gly Asn Ala Gly Leu Phe Asp Gln Asn
225                 230                 235                 240

Leu Ala Leu Arg Trp Val Arg Asp Asn Ile His Arg Phe Gly Gly Asp
             245                 250                 255

Pro Ser Arg Val Thr Leu Phe Gly Glu Ser Ala Gly Ala Val Ser Val
             260                 265                 270

Ser Leu His Leu Leu Ser Ala Leu Ser Arg Asp Leu Phe Gln Arg Ala
             275                 280                 285

Ile Leu Gln Ser Gly Ser Pro Thr Ala Pro Trp Ala Leu Val Ser Arg
             290                 295                 300

Glu Glu Ala Thr Leu Arg Ala Leu Arg Leu Ala Glu Ala Val Gly Cys
305                 310                 315                 320

Pro His Glu Pro Ser Lys Leu Ser Asp Ala Val Glu Cys Leu Arg Gly
             325                 330                 335

Lys Asp Pro His Val Leu Val Asn Asn Glu Trp Gly Thr Leu Gly Ile
             340                 345                 350

Cys Glu Phe Pro Phe Val Pro Val Asp Gly Ala Phe Leu Asp Glu
             355                 360                 365

Thr Pro Gln Arg Ser Leu Ala Ser Gly Arg Phe Lys Lys Thr Glu Ile
             370                 375                 380

Leu Thr Gly Ser Asn Thr Glu Glu Gly Tyr Tyr Phe Ile Ile Tyr Tyr
385                 390                 395                 400

Leu Thr Glu Leu Leu Arg Lys Glu Glu Gly Val Thr Val Thr Arg Glu
             405                 410                 415

Glu Phe Leu Gln Ala Val Arg Glu Leu Asn Pro Tyr Val Asn Gly Ala
             420                 425                 430

Ala Arg Gln Ala Ile Val Phe Glu Tyr Thr Asp Trp Thr Glu Pro Asp
             435                 440                 445
```

```
Asn Pro Asn Ser Asn Arg Asp Ala Leu Asp Lys Met Val Gly Asp Tyr
    450                 455                 460
His Phe Thr Cys Asn Val Asn Glu Phe Ala Gln Arg Tyr Ala Glu Glu
465                 470                 475                 480
Gly Asn Asn Val Tyr Met Tyr Leu Tyr Thr His Arg Ser Lys Gly Asn
                485                 490                 495
Pro Trp Pro Arg Trp Thr Gly Val Met His Gly Asp Glu Ile Asn Tyr
            500                 505                 510
Val Phe Gly Glu Pro Leu Asn Pro Thr Leu Gly Tyr Thr Glu Asp Glu
        515                 520                 525
Lys Asp Phe Ser Arg Lys Ile Met Arg Tyr Trp Ser Asn Phe Ala Lys
    530                 535                 540
Thr Gly Asn Pro Asn Pro Asn Thr Ala Ser Ser Glu Phe Pro Glu Trp
545                 550                 555                 560
Pro Lys His Thr Ala His Gly Arg His Tyr Leu Glu Leu Gly Leu Asn
                565                 570                 575
Thr Ser Phe Val Gly Arg Gly Pro Arg Leu Arg Gln Cys Ala Phe Trp
            580                 585                 590
Lys Lys Tyr Leu Pro Gln Leu Val Ala Ala Thr Ser Asn Leu Pro Gly
        595                 600                 605
Pro Ala Pro Pro Ser Glu Pro Cys Glu Ser Ser Ala Phe Phe Tyr Arg
    610                 615                 620
Pro Asp Leu Ile Val Leu Leu Val Ser Leu Leu Thr Ala Thr Val Arg
625                 630                 635                 640
Phe Ile Gln

<210> SEQ ID NO 4
<211> LENGTH: 1932
<212> TYPE: DNA
<213> ORGANISM: Anopheles gambiae strain KISUMU
<220> FEATURE:
<221> NAME/KEY: CDS
<222> LOCATION: (1)..(1932)

<400> SEQUENCE: 4 atg ttt gtg tgt tgt ttt ttc ttt ctc tct ctc tct ctc tgt ggt tcc      48
Met Phe Val Cys Cys Phe Phe Phe Leu Ser Leu Ser Leu Cys Gly Ser
1               5                   10                  15 aac att tca gac gca ttt ttt aca cca tat ata ggt cac ggt gag tcc      96
Asn Ile Ser Asp Ala Phe Phe Thr Pro Tyr Ile Gly His Gly Glu Ser
            20                  25                  30 gta cga att ata gat gcc gag ttg ggc acg ctc gag cat gtc cac agt     144
Val Arg Ile Ile Asp Ala Glu Leu Gly Thr Leu Glu His Val His Ser
        35                  40                  45 gga gca acg ccg cgg cga cgc ggt ctg acg agg cgc gag tcc aac tcg     192
Gly Ala Thr Pro Arg Arg Arg Gly Leu Thr Arg Arg Glu Ser Asn Ser
    50                  55                  60 gac gcg aac gac aac gat ccg ctg gtg gtc aac acg gat aag ggg cgc     240
Asp Ala Asn Asp Asn Asp Pro Leu Val Val Asn Thr Asp Lys Gly Arg
65                  70                  75                  80 atc cgc ggc att acg gtc gat gcg ccc agc ggc aag aag gtg gac gtg     288
Ile Arg Gly Ile Thr Val Asp Ala Pro Ser Gly Lys Lys Val Asp Val
                85                  90                  95 tgg ctc ggc att ccc tac gcc cag ccg ccg gtc ggg ccg tta cgg ttc     336
Trp Leu Gly Ile Pro Tyr Ala Gln Pro Pro Val Gly Pro Leu Arg Phe
            100                 105                 110 cgt cat ccg cgg ccg gcc gaa aag tgg acc ggc gtg ctg aac acg acc     384
Arg His Pro Arg Pro Ala Glu Lys Trp Thr Gly Val Leu Asn Thr Thr
```

-continued

|   |   |   | 115 |   |   |   | 120 |   |   |   | 125 |   |   |   |   |
|---|---|---|---|---|---|---|---|---|---|---|---|---|---|---|---|

```
aca ccg ccc aac agc tgc gtg cag atc gtg gac acc gtg ttc ggc gac       432
Thr Pro Pro Asn Ser Cys Val Gln Ile Val Asp Thr Val Phe Gly Asp
    130                 135                 140 ttc ccg ggc gcg acc atg tgg aac ccg aac acg ccc ctg tcc gag gac       480
Phe Pro Gly Ala Thr Met Trp Asn Pro Asn Thr Pro Leu Ser Glu Asp
145                 150                 155                 160 tgt ctg tac att aac gtg gtg gca ccg cga ccc cgg ccc aag aat gcg       528
Cys Leu Tyr Ile Asn Val Val Ala Pro Arg Pro Arg Pro Lys Asn Ala
                165                 170                 175 gcc gtc atg ctg tgg atc ttc ggc ggc ggc ttc tac tcc ggc acc gcc       576
Ala Val Met Leu Trp Ile Phe Gly Gly Gly Phe Tyr Ser Gly Thr Ala
        180                 185                 190 acc ctg gac gtg tac gac cac cgg gcg ctt gcg tcg gag gag aac gtg       624
Thr Leu Asp Val Tyr Asp His Arg Ala Leu Ala Ser Glu Glu Asn Val
            195                 200                 205 atc gtg gtg tcg ctg cag tac cgc gtg gcc agt ctg ggc ttc ctg ttt       672
Ile Val Val Ser Leu Gln Tyr Arg Val Ala Ser Leu Gly Phe Leu Phe
    210                 215                 220 ctc ggc acc ccg gaa gcg ccg ggc aat gcg gga ctg ttc gat cag aac       720
Leu Gly Thr Pro Glu Ala Pro Gly Asn Ala Gly Leu Phe Asp Gln Asn
225                 230                 235                 240 ctt gcg cta cgc tgg gtg cgg gac aac att cac cgg ttc ggt ggt gat       768
Leu Ala Leu Arg Trp Val Arg Asp Asn Ile His Arg Phe Gly Gly Asp
                245                 250                 255 ccg tcg cgt gtg aca ctg ttc ggc gag agt gcc ggt gcc gtc tcg gtg       816
Pro Ser Arg Val Thr Leu Phe Gly Glu Ser Ala Gly Ala Val Ser Val
        260                 265                 270 tcg ctg cat ctg ctg tcc gcc ctg tcc cgc gat ctg ttc cag cgg gcc       864
Ser Leu His Leu Leu Ser Ala Leu Ser Arg Asp Leu Phe Gln Arg Ala
            275                 280                 285 atc ctg cag agc ggc tcg ccg acg gca ccg tgg gca ttg gta tcg cgc       912
Ile Leu Gln Ser Gly Ser Pro Thr Ala Pro Trp Ala Leu Val Ser Arg
    290                 295                 300 gag gaa gcc acg cta aga gca ctg cgg ttg gcc gag gcg gtc ggc tgc       960
Glu Glu Ala Thr Leu Arg Ala Leu Arg Leu Ala Glu Ala Val Gly Cys
305                 310                 315                 320 ccg cac gaa ccg agc aag ctg agc gat gcg gtc gag tgt ctg cgc ggc      1008
Pro His Glu Pro Ser Lys Leu Ser Asp Ala Val Glu Cys Leu Arg Gly
                325                 330                 335 aag gat ccg cac gtg ctg gtc aac aac gag tgg ggc acg ctc ggc att      1056
Lys Asp Pro His Val Leu Val Asn Asn Glu Trp Gly Thr Leu Gly Ile
        340                 345                 350 tgc gag ttc ccg ttc gtg ccg gtg gtc gac ggt gcg ttc ctg gac gag      1104
Cys Glu Phe Pro Phe Val Pro Val Val Asp Gly Ala Phe Leu Asp Glu
            355                 360                 365 acg ccg cag cgt tcg ctc gcc agc ggg cgc ttc aag aag acg gag atc      1152
Thr Pro Gln Arg Ser Leu Ala Ser Gly Arg Phe Lys Lys Thr Glu Ile
    370                 375                 380 ctc acc ggc agc aac acg gag gag ggc tac tac ttc atc atc tac tac      1200
Leu Thr Gly Ser Asn Thr Glu Glu Gly Tyr Tyr Phe Ile Ile Tyr Tyr
385                 390                 395                 400 ctg acc gag ctg ctg cgc aag gag gag ggc gtg acc gtg acg cgc gag      1248
Leu Thr Glu Leu Leu Arg Lys Glu Glu Gly Val Thr Val Thr Arg Glu
                405                 410                 415 gag ttc ctg cag gcg gtg cgc gag ctc aac ccg tac gtg aac ggg gcg      1296
Glu Phe Leu Gln Ala Val Arg Glu Leu Asn Pro Tyr Val Asn Gly Ala
        420                 425                 430 gcc cgg cag gcg atc gtg ttc gag tac acc gac tgg acc gag ccg gac      1344
Ala Arg Gln Ala Ile Val Phe Glu Tyr Thr Asp Trp Thr Glu Pro Asp
```

```
                           435                 440                 445
aac ccg aac agc aac cgg gac gcg ctg gac aag atg gtg ggc gac tat         1392
Asn Pro Asn Ser Asn Arg Asp Ala Leu Asp Lys Met Val Gly Asp Tyr
450                 455                 460 cac ttc acc tgc aac gtg aac gag ttc gcg cag cgg tac gcc gag gag         1440
His Phe Thr Cys Asn Val Asn Glu Phe Ala Gln Arg Tyr Ala Glu Glu
465                 470                 475                 480 ggc aac aac gtc tac atg tat ctg tac acg cac cgc agc aaa ggc aac         1488
Gly Asn Asn Val Tyr Met Tyr Leu Tyr Thr His Arg Ser Lys Gly Asn
                485                 490                 495 ccg tgg ccg cgc tgg acg ggc gtg atg cac ggc gac gag atc aac tac         1536
Pro Trp Pro Arg Trp Thr Gly Val Met His Gly Asp Glu Ile Asn Tyr
500                 505                 510 gtg ttc ggc gaa ccg ctc aac ccc acc ctc ggc tac acc gag gac gag         1584
Val Phe Gly Glu Pro Leu Asn Pro Thr Leu Gly Tyr Thr Glu Asp Glu
                515                 520                 525 aaa gac ttt agc cgg aag atc atg cga tac tgg tct aac ttt gcc aaa         1632
Lys Asp Phe Ser Arg Lys Ile Met Arg Tyr Trp Ser Asn Phe Ala Lys
530                 535                 540 acc ggg aat cca aat ccc aac acg gcc agc agc gaa ttc ccc gag tgg         1680
Thr Gly Asn Pro Asn Pro Asn Thr Ala Ser Ser Glu Phe Pro Glu Trp
545                 550                 555                 560 ccc aag cac acc gcc cac gga cgg cac tat ctg gag ctg ggc ctc aac         1728
Pro Lys His Thr Ala His Gly Arg His Tyr Leu Glu Leu Gly Leu Asn
                565                 570                 575 acg tcc ttc gtc ggt cgg ggc cca cgg ttg agg cag tgt gcc ttc tgg         1776
Thr Ser Phe Val Gly Arg Gly Pro Arg Leu Arg Gln Cys Ala Phe Trp
                580                 585                 590 aag aag tac ctt ccc cag cta gtt gca gct acc tcg aac cta cca ggg         1824
Lys Lys Tyr Leu Pro Gln Leu Val Ala Ala Thr Ser Asn Leu Pro Gly
                595                 600                 605 cca gca ccg ccc agt gaa ccg tgc gaa agc agc gca ttt ttt tac cga         1872
Pro Ala Pro Pro Ser Glu Pro Cys Glu Ser Ser Ala Phe Phe Tyr Arg
610                 615                 620 cct gat ctg atc gtg ctg ctg gtg tcg ctg ctt acg gcg acc gtc aga         1920
Pro Asp Leu Ile Val Leu Leu Val Ser Leu Leu Thr Ala Thr Val Arg
625                 630                 635                 640 ttc ata caa taa                                                         1932
Phe Ile Gln <210> SEQ ID NO 5
<211> LENGTH: 643
<212> TYPE: PRT
<213> ORGANISM: Anopheles gambiae strain KISUMU

<400> SEQUENCE: 5

Met Phe Val Cys Cys Phe Phe Phe Leu Ser Leu Ser Leu Cys Gly Ser
1               5                   10                  15

Asn Ile Ser Asp Ala Phe Phe Thr Pro Tyr Ile Gly His Gly Glu Ser
                20                  25                  30

Val Arg Ile Ile Asp Ala Glu Leu Gly Thr Leu Glu His Val His Ser
            35                  40                  45

Gly Ala Thr Pro Arg Arg Arg Gly Leu Thr Arg Arg Glu Ser Asn Ser
        50                  55                  60

Asp Ala Asn Asp Asn Asp Pro Leu Val Val Asn Thr Asp Lys Gly Arg
65                  70                  75                  80

Ile Arg Gly Ile Thr Val Asp Ala Pro Ser Gly Lys Lys Val Asp Val
                85                  90                  95

Trp Leu Gly Ile Pro Tyr Ala Gln Pro Pro Val Gly Pro Leu Arg Phe
```

-continued

```
                100             105             110
Arg His Pro Arg Pro Ala Glu Lys Trp Thr Gly Val Leu Asn Thr Thr
            115                 120                 125
Thr Pro Pro Asn Ser Cys Val Gln Ile Val Asp Thr Val Phe Gly Asp
        130                 135                 140
Phe Pro Gly Ala Thr Met Trp Asn Pro Asn Thr Pro Leu Ser Glu Asp
145                 150                 155                 160
Cys Leu Tyr Ile Asn Val Val Ala Pro Arg Pro Arg Pro Lys Asn Ala
                165                 170                 175
Ala Val Met Leu Trp Ile Phe Gly Gly Gly Phe Tyr Ser Gly Thr Ala
            180                 185                 190
Thr Leu Asp Val Tyr Asp His Arg Ala Leu Ala Ser Glu Glu Asn Val
        195                 200                 205
Ile Val Val Ser Leu Gln Tyr Arg Val Ala Ser Leu Gly Phe Leu Phe
    210                 215                 220
Leu Gly Thr Pro Glu Ala Pro Gly Asn Ala Gly Leu Phe Asp Gln Asn
225                 230                 235                 240
Leu Ala Leu Arg Trp Val Arg Asp Asn Ile His Arg Phe Gly Gly Asp
                245                 250                 255
Pro Ser Arg Val Thr Leu Phe Gly Glu Ser Ala Gly Ala Val Ser Val
            260                 265                 270
Ser Leu His Leu Leu Ser Ala Leu Ser Arg Asp Leu Phe Gln Arg Ala
        275                 280                 285
Ile Leu Gln Ser Gly Ser Pro Thr Ala Pro Trp Ala Leu Val Ser Arg
    290                 295                 300
Glu Glu Ala Thr Leu Arg Ala Leu Arg Leu Ala Glu Ala Val Gly Cys
305                 310                 315                 320
Pro His Glu Pro Ser Lys Leu Ser Asp Ala Val Glu Cys Leu Arg Gly
                325                 330                 335
Lys Asp Pro His Val Leu Val Asn Asn Glu Trp Gly Thr Leu Gly Ile
            340                 345                 350
Cys Glu Phe Pro Phe Val Pro Val Asp Gly Ala Phe Leu Asp Glu
        355                 360                 365
Thr Pro Gln Arg Ser Leu Ala Ser Gly Arg Phe Lys Lys Thr Glu Ile
    370                 375                 380
Leu Thr Gly Ser Asn Thr Glu Glu Gly Tyr Tyr Phe Ile Ile Tyr Tyr
385                 390                 395                 400
Leu Thr Glu Leu Leu Arg Lys Glu Glu Gly Val Thr Val Thr Arg Glu
                405                 410                 415
Glu Phe Leu Gln Ala Val Arg Glu Leu Asn Pro Tyr Val Asn Gly Ala
            420                 425                 430
Ala Arg Gln Ala Ile Val Phe Glu Tyr Thr Asp Trp Thr Glu Pro Asp
        435                 440                 445
Asn Pro Asn Ser Asn Arg Asp Ala Leu Asp Lys Met Val Gly Asp Tyr
    450                 455                 460
His Phe Thr Cys Asn Val Asn Glu Phe Ala Gln Arg Tyr Ala Glu Glu
465                 470                 475                 480
Gly Asn Asn Val Tyr Met Tyr Leu Tyr Thr His Arg Ser Lys Gly Asn
                485                 490                 495
Pro Trp Pro Arg Trp Thr Gly Val Met His Gly Asp Glu Ile Asn Tyr
            500                 505                 510
Val Phe Gly Glu Pro Leu Asn Pro Thr Leu Gly Tyr Thr Glu Asp Glu
        515                 520                 525
```

```
Lys Asp Phe Ser Arg Lys Ile Met Arg Tyr Trp Ser Asn Phe Ala Lys
            530                 535                 540

Thr Gly Asn Pro Asn Pro Asn Thr Ala Ser Ser Glu Phe Pro Glu Trp
545                 550                 555                 560

Pro Lys His Thr Ala His Gly Arg His Tyr Leu Glu Leu Gly Leu Asn
                565                 570                 575

Thr Ser Phe Val Gly Arg Gly Pro Arg Leu Arg Gln Cys Ala Phe Trp
            580                 585                 590

Lys Lys Tyr Leu Pro Gln Leu Val Ala Thr Ser Asn Leu Pro Gly
        595                 600                 605

Pro Ala Pro Pro Ser Glu Pro Cys Glu Ser Ser Ala Phe Phe Tyr Arg
            610                 615                 620

Pro Asp Leu Ile Val Leu Leu Val Ser Leu Leu Thr Ala Thr Val Arg
625                 630                 635                 640

Phe Ile Gln

<210> SEQ ID NO 6
<211> LENGTH: 3297
<212> TYPE: DNA
<213> ORGANISM: Culex pipiens strain S-LAB

<400> SEQUENCE: 6
ccagagcaga ccacgaacct cgtcggaaga gctgatgccg ttgtgacatt cgctccgatt      60
gtgtaagcaa ataaggttag gacacaccgt attcacgaac tctgacacca agctgtcata     120
gccgtcactg acgagaagaa aaagaaacaa gagtcgacaa cacactcaca gtctcacgcc     180
gccagagagc acaccaagag tcacattgag aaaaccacac gccagaagaa aagaagagtt     240
gttcaagaag gaagctaata ccacacacac acacactcac acacaccggg agaaaccgca     300
cagcaggcgg cgctgtgaaa ttcacacgtt cggtcggtga agtggtggaa ggaactcggc     360
gtcggagtag caattagtga attacaaaca aagggaaata agggaaggag tcaagagtca     420
accagtggaa ccagtggtgc agtgagtgat ttttttgtgt tgttgctgca gaaaggaacg     480
cgcgacgagc acactcttgt gaaatcggtg tcatcatcgt taaatgctct cgaccgtcaa     540
cttatagcta tcatatgcga tctctccaag ccatggagat ccgaggccta ataacccgat     600
tactgggtcc atgtcacctg cgacatctga tactgtgcag tttggggctg tactccatcc     660
tcgtgaagtc ggtccattgc cggcatcatg acatcggtag ttcggtggca caccagctag     720
gatcgaaata ctcacaatca tcctcgttat cgtcatcctc gcaatcgtca tcgtcgttag     780
ctgaagaggc cacgctgaat aaagattcag atgcattttt tacaccatat ataggtcacg     840
gagattctgt tcgaattgta gatgccgaat taggtacatt agagcgcgag cacatccata     900
gcactacgac ccggcggcgt ggcctgacgc ggagggagtc cagctccgat gccaccgact     960
cggacccact ggtcataacg acggacaagg gcaaaatccg tggaacgaca ctggaagcgc    1020
ctagtggaaa gaaggtggac gcatggatgg gcattccgta cgcgcagccc ccgctgggtc    1080
cgctccggtt tcgacatccg cgaccggccg aaagatggac cggtgtgctg aacgcgacca    1140
aaccgcccaa ctcctgcgtc cagatcgtgg acaccgtgtt cggtgacttc ccgggggcca    1200
ccatgtggaa cccgaacaca ccgctctcgg aggactgtct gtacatcaac gtggtcgtgc    1260
cacggcccag gccaagaat gccgccgtca tgctgtggat cttcggggt ggcttctact    1320 ccgggactgc cacgctggac gtgtacgacc atcggacgct ggcctcggag gagaacgtga    1380
tcgtagtttc gctgcagtac cgtgtcgcaa gtcttgggtt tctcttcctc ggcacaccgg    1440
aggcacccgg taacgcgggg ctgtttgatc agaacctggc actgagatgg gtccgcgaca    1500
```

```
acatccaccg gttcggcggt gacccctcgc gggtcacact gttcggcgag agcgccggag   1560
cggtctcggt ttcgctgcac ctgctgtcgg cgctctcgcg ggaccttgttc cagcgggcca  1620 tcctccagag tggctccccg acggcccgt gggcgctggt ttcgcgcgaa gaagctacgc   1680
ttagagctct tcgtctggcc gaggccgtca actgtccgca cgatgcgacc aagctgagcg   1740
atgccgtcga atgcctgcga accaaggatc cgaacgagct ggtcgacaac gagtggggca   1800
cgctggggat ctgcgagttt ccgttcgttc cggttgtgga cggagccttc ctcgatgaga   1860
caccgcagcg ttcgttggcc agcgggcgct tcaagaaaac ggacatcctg accggcagca   1920
acaccgagga gggttactac tttatcattt actatctaac cgagctgctc aggaaagagg   1980
aaggggtcac ggtaacacgc gaggagttcc tacaggccgt ccgggagttg aatccgtacg   2040
tgaacggtgc cgcccggcag gccatcgtgt tcgagtacac ggactggatt gaaccggaca   2100
acccgaacag caaccgtgac gcgctggaca agatggtcgg ggattatcac ttcacctgca   2160
acgtgaacga attcgcccag cggtacgccg aggagggcaa caacgtgttc atgtacctgt   2220
acacgcacag aagcaaagga aatccctggc cgaggtggac cggcgtgatg cacggcgacg   2280
agatcaacta cgtgtttggc gaaccgctga actcggccct cggctaccag gacgacgaga   2340
aggactttag ccggaaaatt atgcgatact ggtccaactt tgccaagact ggcaatccca   2400
acccgagtac gccgagcgtg gacctgcccg aatgggccaa gcacaccgcc cacggacgac   2460
actatctgga gctgggactg aacacgacct tcgtgggacg gggcccacga ttgcggcagt   2520
gcgctttctg gaagaaatat ttgccgcaac tagtagcagc tacctctaac ctccaagtaa   2580
ctcccgcgcc tagcgtacct tgcgaaagca gctcaacatc ttatcgatcc actctacttc   2640
taatagtcac actactttta gtaacgcggt tcaagattta aatccgtgtt ttctttcccg   2700
ttcccgtttt tccgttaaag cttctttagg tcaggtgaaa acatcaacaa gcagcatcaa   2760
ttctactact aatactatta ctactattaa ctgaaatgga acaataagat tacctttttc   2820
ttctaaattt gttcaactgc taattaaatt ctaaataggt gaatgcatct tgctctgcaa   2880
acgaacgatc ggacaattat gttgtattgt ttttttcttt gtaataatat tctgtaaaca   2940
gaggtgatat cattaatatt ttactaacca tacaataaac aaaatatttc ctgttataaa   3000
ttgtgatgaa tatttcgctt taactacacc attgaaggtt acttaagttg aaataacaaa   3060 aatttttatat aaacaactaa caaataaaac agctgctaga gacaactaga cattaaatcg   3120
aaaaaaacgt tattttgaaa aagagcgatt tatgcactag cggaggtgaa tcccttataa   3180
tcttgaaaag agaggaggaa tggaagaaga agaagaagaa aatattatga tacaataaaa   3240
ccaacatcta attctaacaa tcaactgttt actttactaa aaaaaaaaaa aaaaaaa     3297
```

<210> SEQ ID NO 7
<211> LENGTH: 702
<212> TYPE: PRT
<213> ORGANISM: Culex pipiens strain S-LAB

<400> SEQUENCE: 7

Met Glu Ile Arg Gly Leu Ile Thr Arg Leu Leu Gly Pro Cys His Leu
1               5                   10                  15

Arg His Leu Ile Leu Cys Ser Leu Gly Leu Tyr Ser Ile Leu Val Lys
            20                  25                  30

Ser Val His Cys Arg His His Asp Ile Gly Ser Ser Val Ala His Gln
        35                  40                  45

Leu Gly Ser Lys Tyr Ser Gln Ser Ser Leu Ser Ser Ser Ser Gln
    50                  55                  60

```
Ser Ser Ser Ser Leu Ala Glu Glu Ala Thr Leu Asn Lys Asp Ser Asp
 65                  70                  75                  80

Ala Phe Phe Thr Pro Tyr Ile Gly His Gly Asp Ser Val Arg Ile Val
                     85                  90                  95

Asp Ala Glu Leu Gly Thr Leu Glu Arg Glu His Ile His Ser Thr Thr
                100                 105                 110

Thr Arg Arg Arg Gly Leu Thr Arg Arg Glu Ser Ser Ser Asp Ala Thr
            115                 120                 125

Asp Ser Asp Pro Leu Val Ile Thr Thr Asp Lys Gly Lys Ile Arg Gly
130                 135                 140

Thr Thr Leu Glu Ala Pro Ser Gly Lys Lys Val Asp Ala Trp Met Gly
145                 150                 155                 160

Ile Pro Tyr Ala Gln Pro Pro Leu Gly Pro Leu Arg Phe Arg His Pro
                165                 170                 175

Arg Pro Ala Glu Arg Trp Thr Gly Val Leu Asn Ala Thr Lys Pro Pro
                180                 185                 190

Asn Ser Cys Val Gln Ile Val Asp Thr Val Phe Gly Asp Phe Pro Gly
            195                 200                 205

Ala Thr Met Trp Asn Pro Asn Thr Pro Leu Ser Glu Asp Cys Leu Tyr
            210                 215                 220

Ile Asn Val Val Pro Arg Pro Arg Pro Lys Asn Ala Ala Val Met
225                 230                 235                 240

Leu Trp Ile Phe Gly Gly Gly Phe Tyr Ser Gly Thr Ala Thr Leu Asp
                245                 250                 255

Val Tyr Asp His Arg Thr Leu Ala Ser Glu Glu Asn Val Ile Val Val
                260                 265                 270

Ser Leu Gln Tyr Arg Val Ala Ser Leu Gly Phe Leu Phe Leu Gly Thr
            275                 280                 285

Pro Glu Ala Pro Gly Asn Ala Gly Leu Phe Asp Gln Asn Leu Ala Leu
        290                 295                 300

Arg Trp Val Arg Asp Asn Ile His Arg Phe Gly Gly Asp Pro Ser Arg
305                 310                 315                 320

Val Thr Leu Phe Gly Glu Ser Ala Gly Ala Val Ser Val Ser Leu His
                325                 330                 335

Leu Leu Ser Ala Leu Ser Arg Asp Leu Phe Gln Arg Ala Ile Leu Gln
            340                 345                 350

Ser Gly Ser Pro Thr Ala Pro Trp Ala Leu Val Ser Arg Glu Glu Ala
        355                 360                 365

Thr Leu Arg Ala Leu Arg Leu Ala Glu Ala Val Asn Cys Pro His Asp
370                 375                 380

Ala Thr Lys Leu Ser Asp Ala Val Glu Cys Leu Arg Thr Lys Asp Pro
385                 390                 395                 400

Asn Glu Leu Val Asp Asn Glu Trp Gly Thr Leu Gly Ile Cys Glu Phe
                405                 410                 415

Pro Phe Val Pro Val Val Asp Gly Ala Phe Leu Asp Glu Thr Pro Gln
                420                 425                 430

Arg Ser Leu Ala Ser Gly Arg Phe Lys Lys Thr Asp Ile Leu Thr Gly
            435                 440                 445

Ser Asn Thr Glu Glu Gly Tyr Tyr Phe Ile Ile Tyr Tyr Leu Thr Glu
        450                 455                 460

Leu Leu Arg Lys Glu Glu Gly Val Thr Val Thr Arg Glu Glu Phe Leu
465                 470                 475                 480

Gln Ala Val Arg Glu Leu Asn Pro Tyr Val Asn Gly Ala Ala Arg Gln
```

```
                    485                 490                 495
Ala Ile Val Phe Glu Tyr Thr Asp Trp Ile Glu Pro Asp Asn Pro Asn
                500                 505                 510

Ser Asn Arg Asp Ala Leu Asp Lys Met Val Gly Asp Tyr His Phe Thr
            515                 520                 525

Cys Asn Val Asn Glu Phe Ala Gln Arg Tyr Ala Glu Glu Gly Asn Asn
        530                 535                 540

Val Phe Met Tyr Leu Tyr Thr His Arg Ser Lys Gly Asn Pro Trp Pro
545                 550                 555                 560

Arg Trp Thr Gly Val Met His Gly Asp Glu Ile Asn Tyr Val Phe Gly
                565                 570                 575

Glu Pro Leu Asn Ser Ala Leu Gly Tyr Gln Asp Asp Glu Lys Asp Phe
            580                 585                 590

Ser Arg Lys Ile Met Arg Tyr Trp Ser Asn Phe Ala Lys Thr Gly Asn
        595                 600                 605

Pro Asn Pro Ser Thr Pro Ser Val Asp Leu Pro Glu Trp Pro Lys His
    610                 615                 620

Thr Ala His Gly Arg His Tyr Leu Glu Leu Gly Leu Asn Thr Thr Phe
625                 630                 635                 640

Val Gly Arg Gly Pro Arg Leu Arg Gln Cys Ala Phe Trp Lys Lys Tyr
                645                 650                 655

Leu Pro Gln Leu Val Ala Ala Thr Ser Asn Leu Gln Val Thr Pro Ala
            660                 665                 670

Pro Ser Val Pro Cys Glu Ser Ser Ser Thr Ser Tyr Arg Ser Thr Leu
        675                 680                 685

Leu Leu Ile Val Thr Leu Leu Leu Val Thr Arg Phe Lys Ile
    690                 695                 700

<210> SEQ ID NO 8
<211> LENGTH: 91
<212> TYPE: PRT
<213> ORGANISM: Culex pipiens

<400> SEQUENCE: 8

Ile Glu Pro Asp Asn Pro Asn Ser Asn Arg Asp Ala Leu Asp Lys Met
1               5                   10                  15

Val Gly Asp Tyr His Phe Thr Cys Asn Val Asn Glu Phe Ala Gln Arg
            20                  25                  30

Tyr Ala Glu Glu Gly Asn Asn Val Phe Met Tyr Leu Tyr Thr His Arg
        35                  40                  45

Ser Lys Gly Asn Pro Trp Pro Arg Trp Thr Gly Val Met His Gly Asp
    50                  55                  60

Glu Ile Asn Tyr Val Phe Gly Glu Pro Leu Asn Ser Ala Leu Gly Tyr
65                  70                  75                  80

Gln Asp Asp Glu Lys Asp Phe Ser Arg Lys Ile
            85                  90

<210> SEQ ID NO 9
<211> LENGTH: 91
<212> TYPE: PRT
<213> ORGANISM: Aedes aegypti

<400> SEQUENCE: 9

Thr Glu Pro Glu Asn Pro Asn Ser Asn Arg Asp Ala Leu Asp Lys Met
1               5                   10                  15

Val Gly Asp Tyr His Phe Thr Cys Asn Val Asn Glu Phe Ala Gln Arg
            20                  25                  30
```

Tyr Ala Glu Glu Gly Asn Asn Val Tyr Met Tyr Leu Tyr Thr His Arg
        35                  40                  45

Ser Lys Gly Asn Pro Trp Pro Arg Trp Thr Gly Val Met His Gly Asp
    50                  55                  60

Glu Ile Asn Tyr Val Phe Gly Glu Pro Leu Asn Ser Asp Leu Gly Tyr
65                  70                  75                  80

Met Glu Asp Glu Lys Asp Phe Ser Arg Lys Ile
                85                  90

<210> SEQ ID NO 10
<211> LENGTH: 91
<212> TYPE: PRT
<213> ORGANISM: Aedes albopictus

<400> SEQUENCE: 10

Thr Glu Pro Glu Asn Pro Asn Ser Asn Arg Asp Ala Leu Asp Lys Met
1               5                   10                  15

Val Gly Asp Tyr His Phe Thr Cys Asn Val Asn Glu Phe Ala Gln Arg
                20                  25                  30

Tyr Ala Glu Glu Gly Asn Asn Val Tyr Met Tyr Leu Tyr Thr His Arg
        35                  40                  45

Ser Lys Gly Asn Pro Trp Pro Arg Trp Thr Gly Val Met His Gly Asp
    50                  55                  60

Glu Ile Asn Tyr Val Phe Gly Glu Pro Leu Asn Ser Asp Leu Gly Tyr
65                  70                  75                  80

Met Asp Asp Glu Lys Asp Phe Ser Arg Lys Ile
                85                  90

<210> SEQ ID NO 11
<211> LENGTH: 91
<212> TYPE: PRT
<213> ORGANISM: Anopheles darlingi

<400> SEQUENCE: 11

Thr Glu Pro Asp Asn Pro Asn Ser Asn Arg Asp Ala Leu Asp Lys Met
1               5                   10                  15

Val Gly Asp Tyr His Phe Thr Cys Asn Val Asn Glu Phe Ala Gln Arg
                20                  25                  30

Tyr Ala Glu Glu Gly Asn Asn Val Tyr Met Tyr Leu Tyr Thr His Arg
        35                  40                  45

Ser Lys Gly Asn Pro Trp Pro Arg Trp Thr Gly Val Met His Gly Asp
    50                  55                  60

Glu Ile Asn Tyr Val Phe Gly Glu Pro Leu Asn Pro Thr Leu Gly Tyr
65                  70                  75                  80

Thr Asp Asp Glu Lys Gly Phe Ser Arg Lys Ile
                85                  90

<210> SEQ ID NO 12
<211> LENGTH: 91
<212> TYPE: PRT
<213> ORGANISM: Anopheles sundaicus

<400> SEQUENCE: 12

Thr Glu Pro Asp Asn Pro Asn Ser Asn Arg Asp Ala Leu Asp Lys Met
1               5                   10                  15

Val Gly Asp Tyr His Phe Thr Cys Asn Val Asn Glu Phe Ala Gln Arg
                20                  25                  30

Tyr Ala Glu Glu Gly Asn Asn Val Tyr Met Tyr Leu Tyr Thr His Arg

```
                35                  40                  45
Ser Lys Gly Asn Pro Trp Pro Arg Trp Thr Gly Val Met His Gly Asp
 50                  55                  60

Glu Ile Asn Tyr Val Phe Gly Glu Pro Leu Asn Pro Thr Leu Gly Tyr
 65                  70                  75                  80

Thr Glu Asp Glu Lys Asp Phe Ser Arg Lys Ile
                 85                  90

<210> SEQ ID NO 13
<211> LENGTH: 91
<212> TYPE: PRT
<213> ORGANISM: Anopheles minimus

<400> SEQUENCE: 13

Thr Glu Pro Asp Asn Pro Asn Ser Asn Arg Asp Ala Leu Asp Lys Met
  1               5                  10                  15

Val Gly Asp Tyr His Phe Thr Cys Asn Val Asn Glu Phe Ala Gln Arg
                 20                  25                  30

Tyr Ala Glu Glu Gly Asn Asn Val Tyr Met Tyr Leu Tyr Thr His Arg
             35                  40                  45

Ser Lys Gly Asn Pro Trp Pro Arg Trp Thr Gly Val Met His Gly Asp
 50                  55                  60

Glu Ile Asn Tyr Val Phe Gly Glu Pro Leu Asn Pro Ser Leu Gly Tyr
 65                  70                  75                  80

Thr Glu Asp Glu Lys Asp Phe Ser Arg Lys Ile
                 85                  90

<210> SEQ ID NO 14
<211> LENGTH: 91
<212> TYPE: PRT
<213> ORGANISM: Anopheles moucheti

<400> SEQUENCE: 14

Thr Glu Pro Asp Asn Pro Asn Ser Asn Arg Asp Ala Leu Asp Lys Met
  1               5                  10                  15

Val Gly Asp Tyr His Phe Thr Cys Asn Val Asn Glu Phe Ala Gln Arg
                 20                  25                  30

Tyr Ala Glu Glu Gly Asn Asn Val Tyr Met Tyr Leu Tyr Thr His Arg
             35                  40                  45

Ser Lys Gly Asn Pro Trp Pro Arg Trp Thr Gly Val Met His Gly Asp
 50                  55                  60

Glu Ile Asn Tyr Val Phe Gly Glu Pro Leu Asn Pro Ser Leu Gly Tyr
 65                  70                  75                  80

Thr Glu Asp Glu Lys Asp Phe Ser Arg Lys Ile
                 85                  90

<210> SEQ ID NO 15
<211> LENGTH: 91
<212> TYPE: PRT
<213> ORGANISM: Anopheles arabiensis

<400> SEQUENCE: 15

Thr Glu Pro Asp Asn Pro Asn Ser Asn Arg Asp Ala Leu Asp Lys Met
  1               5                  10                  15

Val Gly Asp Tyr His Phe Thr Cys Asn Val Asn Glu Phe Ala Gln Arg
                 20                  25                  30

Tyr Ala Glu Glu Gly Asn Asn Val Tyr Met Tyr Leu Tyr Thr His Arg
             35                  40                  45
```

Ser Lys Gly Asn Pro Trp Pro Arg Trp Thr Gly Val Met His Gly Asp
         50                  55                  60

Glu Ile Asn Tyr Val Phe Gly Glu Pro Leu Asn Pro Thr Leu Gly Tyr
65                  70                  75                  80

Thr Glu Asp Glu Lys Asp Phe Ser Arg Lys Ile
                 85                  90

<210> SEQ ID NO 16
<211> LENGTH: 91
<212> TYPE: PRT
<213> ORGANISM: Anopheles funestus

<400> SEQUENCE: 16

Thr Glu Pro Asp Asn Pro Asn Ser Asn Arg Asp Ala Leu Asp Lys Met
1               5                   10                  15

Val Gly Asp Tyr His Phe Thr Cys Asn Val Asn Glu Phe Ala Gln Arg
            20                  25                  30

Tyr Ala Glu Glu Gly Asn Asn Val Tyr Met Tyr Leu Tyr Thr His Arg
        35                  40                  45

Ser Lys Gly Asn Pro Trp Pro Arg Trp Thr Gly Val Met His Gly Asp
    50                  55                  60

Glu Ile Asn Tyr Val Phe Gly Glu Pro Leu Asn Pro Ser Leu Gly Tyr
65                  70                  75                  80

Thr Glu Asp Glu Lys Asp Phe Ser Arg Lys Ile
                85                  90

<210> SEQ ID NO 17
<211> LENGTH: 91
<212> TYPE: PRT
<213> ORGANISM: Anopheles pseudopunctipennis

<400> SEQUENCE: 17

Thr Glu Pro Asp Asn Pro Asn Ser Asn Arg Asp Ala Leu Asp Lys Met
1               5                   10                  15

Val Gly Asp Tyr His Phe Thr Cys Asn Val Asn Glu Phe Ala Gln Arg
            20                  25                  30

Tyr Ala Glu Glu Gly Asn Asn Val Tyr Met Tyr Leu Tyr Thr His Arg
        35                  40                  45

Ser Lys Gly Asn Pro Trp Pro Arg Trp Thr Gly Val Met His Gly Asp
    50                  55                  60

Glu Ile Asn Tyr Val Phe Gly Glu Pro Leu Asn Pro Gly Leu Gly Tyr
65                  70                  75                  80

Thr Glu Asp Glu Lys Asp Phe Ser Arg Lys Ile
                85                  90

<210> SEQ ID NO 18
<211> LENGTH: 91
<212> TYPE: PRT
<213> ORGANISM: Anopheles sacharovi

<400> SEQUENCE: 18

Thr Glu Pro Asp Asn Pro Asn Ser Asn Arg Asp Ala Leu Asp Lys Met
1               5                   10                  15

Val Gly Asp Tyr His Phe Thr Cys Asn Val Asn Glu Phe Ala Gln Arg
            20                  25                  30

Tyr Ala Glu Glu Gly Asn Asn Val Tyr Met Tyr Leu Tyr Thr His Arg
        35                  40                  45

Ser Lys Gly Asn Pro Trp Pro Arg Trp Thr Gly Val Met His Gly Asp
    50                  55                  60

```
Glu Ile Asn Tyr Val Phe Gly Glu Pro Leu Asn Pro Ser Leu Gly Tyr
 65                  70                  75                  80

Thr Asp Asp Glu Lys Asp Phe Ser Arg Lys Ile
                 85                  90
```

```
<210> SEQ ID NO 19
<211> LENGTH: 91
<212> TYPE: PRT
<213> ORGANISM: Anopheles stephensi

<400> SEQUENCE: 19

Thr Glu Pro Asp Asn Pro Asn Ser Asn Arg Asp Ala Leu Asp Lys Met
  1               5                  10                  15

Val Gly Asp Tyr His Phe Thr Cys Asn Val Asn Glu Phe Ala Gln Arg
                 20                  25                  30

Tyr Ala Glu Glu Gly Asn Asn Val Tyr Met Tyr Leu Tyr Thr His Arg
             35                  40                  45

Ser Lys Gly Asn Pro Trp Pro Arg Trp Thr Gly Val Met His Gly Asp
         50                  55                  60

Glu Ile Asn Tyr Val Phe Gly Glu Pro Leu Asn Pro Ser Leu Gly Tyr
 65                  70                  75                  80

Thr Asp Asp Glu Lys Asp Phe Ser Arg Lys Ile
                 85                  90
```

```
<210> SEQ ID NO 20
<211> LENGTH: 91
<212> TYPE: PRT
<213> ORGANISM: Anopheles albimanus

<400> SEQUENCE: 20

Thr Glu Pro Asp Asn Pro Asn Ser Asn Arg Asp Ala Leu Asp Lys Met
  1               5                  10                  15

Val Gly Asp Tyr His Phe Thr Cys Asn Val Asn Glu Phe Ala Gln Arg
                 20                  25                  30

Tyr Ala Glu Glu Gly Asn Asn Val Tyr Met Tyr Leu Tyr Thr His Arg
             35                  40                  45

Ser Lys Gly Asn Pro Trp Pro Arg Trp Thr Gly Val Met His Gly Asp
         50                  55                  60

Glu Ile Asn Tyr Val Phe Gly Glu Pro Leu Asn Pro Thr Leu Gly Tyr
 65                  70                  75                  80

Thr Asp Asp Glu Lys Gly Phe Ser Arg Lys Ile
                 85                  90
```

```
<210> SEQ ID NO 21
<211> LENGTH: 91
<212> TYPE: PRT
<213> ORGANISM: Anopheles nili

<400> SEQUENCE: 21

Thr Glu Pro Asp Asn Pro Asn Ser Asn Arg Asp Ala Leu Asp Lys Met
  1               5                  10                  15

Val Gly Asp Tyr His Phe Thr Cys Asn Val Asn Glu Phe Ala Gln Arg
                 20                  25                  30

Tyr Ala Glu Glu Gly Asn Asn Val Tyr Met Tyr Leu Tyr Thr His Arg
             35                  40                  45

Ser Lys Gly Asn Pro Trp Pro Arg Trp Thr Gly Val Met His Gly Asp
         50                  55                  60

Glu Ile Asn Tyr Val Phe Gly Glu Pro Leu Asn Pro Ser Leu Gly Tyr
```

```
                65                  70                  75                  80
Thr Glu Asp Glu Lys Asp Phe Ser Arg Lys Met
                    85                  90

<210> SEQ ID NO 22
<211> LENGTH: 4209
<212> TYPE: DNA
<213> ORGANISM: Anopheles gambiae

<400> SEQUENCE: 22
tggtaattac aattcccaag tttgcgtatg acaatgttaa atgttaagac gctcaaatgc      60
aaccaataga gtataattac taaggcgggc agtagaaacc aaaatatctt aaataatgtc     120
aagcaaaaca aaaagaacaa ttccgttcac tgctcaaaga aagccctaac taactaccta     180
accttttcat cgatgaccct gtactgacat ggtaagatat tctttatcct ttaactcttc     240
tgcaccctac gcactcaatg caacacacgc actactatta ctgctactac tctcgcactc     300
acgagcacct acttgcactc aagccggcac tcaatgtact agcgaaacac gtcgcatcta     360
agcactcaca aggaagcaca catttgcaaa tagcacctac cggaacagct ttgaatgtgc     420
cagcacagca ttgaacaggt tcgcgccttt actcctgtgc tctgttttct cgatcggaat     480
gttcgaaagt tgaaaagcgc atttttcat ctctcttttt ctattcttct tcgtattttt      540
atccctctct cgtcgtgttt tttctaaaca ttaccatact tcttccgcta cgaactcgcc     600
aagaaccaga acgcagcgtg cgtgcggtgc ttgcggtgtg tgtgtgtgtg tgtgtattcc     660
acggctgcga gaagcaagat cggagaacag gcatcattcc cctttcacag acaattgcac     720
ttttgtacta gaacagaaaa cgagacagca taatttccaa cagcctcatt cactcatacc     780
aggctcacac cgacttttaa ccgaaacatg tactacagaa acaaaaacaa acaatatgga     840
gagtgctcgc gctgatacta agttaatatg aagagattac tggcgaggtc atcgatccca     900
tcccgacatc atcgctccag gctccagacc taccaagtcg cctaccatta cctacccacc     960
accgaccact actcacacag cattatcact tccgccgccg tcgccgccgc cgccgacgcc    1020
gccgacgcca ccaccttcac accgccctgc caaaatgaat gcgcattgtt gcgatagatt    1080
gaatttcctt ggttgttgtt gttgttggtt ttcttttgac atgtttgtgt gttgtttttt    1140
ctttctctct ctctctttct gtggttccaa catttcagac gcatttttta caccatatat    1200
aggtcacggt gagtccgtac gaattataga tgccgagttg ggcacgctcg agcatgtcca    1260
cagtggagca acgccgcggc gacgcggcct gacgaggcgc gagtcaaact cgggtaagta    1320
cgcgattgga agtgggggga cgtttaccct accgtgtact actacaacgc actttacccc    1380
cacgcacacg caccggcaga cgcgaacgac aacgatccgc tggtggtcaa cacggataag    1440
gggcgcatcc gcggcattac ggtcgatgcg cccagcggca agaaggtgga cgtgtggctc    1500
ggcattccct acgcccagcc gccggtcggg ccgctacggt tccgtcatcc gcggccggcc    1560
gaaaagtgga ccggcgtgct gaacacgacc acaccgccca acagctgcgt gcagatcgtg    1620
gacaccgtgt tcggcgactt cccgggcgcg accatgtgga acccgaacac gcccctgtcc    1680
gaggactgtc tgtacattaa cgtggtggca ccgcgacccc ggcccaagaa tgcggccgtc    1740
atgctgtgga tcttcggcgg cggcttctac tccggcaccg ccaccctgga cgtgtacgac    1800
cacccgggcgc ttgcgtcgga ggagaacgtg atcgtggtgt cgctgcagta ccgcgtggcc    1860
agtctgggct tcctgtttct cggcaccccg gaagcgccgg gcaatgcggg actgttcgat    1920
cagaaccttg cgctacggta ggtgtctttg catgtgtgaa tgagggtata gtattctaac    1980
gaggtgctct tcttcccatc acttcttggg agtcagctgg gtgcgggaca acattcaccg    2040
```

```
gttcggtggc gatccgtcgc gtgtgacact gttcggcgag agtgccggtg ccgtctcggt    2100
gtcgctgcat ctgctgtccg ccctttcccg cgatctgttc cagcgggcca tcctgcagag    2160
cggctcgccg acggcaccgt gggcattggt atcgcgcgag gaagccacac taaggtacgt    2220
gccagctgct gctttcccca aaccaccaac ccgcaacagc tcacacaacc ctcttttccg    2280
tcgctctttt ctcgctccag agcactgcgg ttggccgagg cggtcggctg cccgcacgaa    2340
ccgagcaagc tgagcgatgc ggtcgagtgc ctgcgcggca aggacccgca cgtgctggtc    2400
aacaacgagt ggggcacgct cggcatttgc gagttcccgt tcgtgccggt ggtcgacggt    2460
gcgttcctgg acgagacgcc gcagcgttcg ctcgccagcg ggcgcttcaa gaagacggag    2520
atcctcaccg gcagcaacac ggaggagggc tactacttca tcatctacta cctgaccgag    2580
ctgctgcgca aggaggaggg cgtgaccgtg acgcgcgagg agttcctgca ggcggtgcgc    2640
gagctcaacc cgtacgtgaa cggggcggcc cggcaggcga tcgtgttcga gtacaccgac    2700
tggaccgagc cggacaaccc gaacagcaac cgggacgcgc tggacaagat ggtgggcgac    2760
tatcacttca cctgcaacgt gaacgagttc gcgcagcggt acgccgagga gggcaacaac    2820
gtctacatgt atctgtacac gcaccgcagc aaaggcaacc cgtggccgcg ctggacgggc    2880
gtgatgcacg gcgacgagat caactacgtg ttcggcgaac cgctcaaccc caccctcggc    2940
tacaccgagg acgagaaaga ctttagccgg aagatcatgc gatactggtc caactttgcc    3000
aaaaccgggt aagtgtgtgt gtcaaacagc agagtgtcga tcgctctaac accagcgtct    3060
tctctcttct acagcaatcc aaatcccaac acggccagca gcgaattccc cgagtggccc    3120
aagcacaccg cccacggacg gcactatctg gagctgggcc tcaacacgtc cttcgtcggt    3180
cggggcccac ggttgaggca gtgtgccttc tggaagaagt accttcccca gctagttgca    3240
gctacctgta agtctcgtgc agcacttgaa acccctcccc acatcccat cagggtccag    3300 gttgcaataa taaatttcac tttctctctc tcacgtctct tttccccaaa acagcgaacc    3360
taccagggcc agcaccgcct agtgaaccgt gcgaaagcag cgcatttttt taccgacctg    3420
atctgatcgt gctgctggtg tcgctgctta cggcgaccgt cagattcata caataattac    3480
taccccatcc atggcctagt tcgtttaagc tttaagatag tgaggaacaa attttttccca    3540 aacaatttc ccccctttag agcagaaccg agggagagat aggactacat agcgaaaagg    3600
gaaaacaagt ggtggcggac gaggagagaa gaagcaaatc gaataatcga agcaacaaca    3660
acaacaacaa aaaaactgca accgggttca ctaaacccag ggggcagctc agtagcaaac    3720
tactacttaa ataactactt tcttatggca aattatggca agagcagtcg tgatgggttc    3780
gatcagtatc catctgaccg gagcagctga accgtttcat gggcagttgc tgcaatacac    3840
cacgacccgt acacacagta acacactttt tatagcttta cactaacaac cactctcccc    3900
acgctcctct tccccttccc ctccacacag acagcagcgc cgtttgtagc aggatctact    3960
accgtgcggt ttggtatggc ggccaacaac actaaacacc acacatctac taaaacacac    4020
cggaacaata aacaaatgtt aaacttacta tatgaatata catctagacg catatatacg    4080
catgaactac tacttcccct cgtggtctga caaaaacaca ttaccttgtc cccccttccc    4140
cctccgggtt gcttaccacc actgaccccc agtatgaatt tgttccataa taacgcttcg    4200
taactcgct                                                            4209
```

<210> SEQ ID NO 23
<211> LENGTH: 2557
<212> TYPE: DNA
<213> ORGANISM: Anopheles gambiae strain KISUMU

<400> SEQUENCE: 23

```
aatgaatgcg cattgttgcg atagattgaa tttccttggt tgttgttgtt gttggttttc      60
ttttgacatg tttgtgtgtt gttttttctt tctctctctc tctctctgtg gttccaacat     120
ttcagacgca ttttttacac catatatagg tcacggtgag tccgtacgaa ttatagatgc     180
cgagttgggc acgctcgagc atgtccacag tggagcaacg ccgcggcgac gcggtctgac     240
gaggcgcgag tccaactcgg gtaagtacgc gattggaagt gggggacgt ttaccctgcc      300
gtgtactaca atgcacttta cccccacgca cacgcaccgg cagacgcgaa cgacaacgat     360
ccgctggtgg tcaacacgga taaggggcgc atccgcggca ttacggtcga tgcgcccagc     420
ggcaagaagg tggacgtgtg gctcggcatt ccctacgccc agccgccggt cgggccgtta     480
cggttccgtc atccgcggcc ggccgaaaag tggaccggcg tgctgaacac gaccacaccg     540
cccaacagct gcgtgcagat cgtggacacc gtgttcggcg acttcccggg cgcgaccatg     600
tggaacccga acacgcccct gtccgaggac tgtctgtaca ttaacgtggt ggcaccgcga     660
ccccggccca agaatgcggc cgtcatgctg tggatcttcg gcggcggctt ctactccggc     720
accgccaccc tggacgtgta cgaccaccgg gcgcttgcgt cggaggagaa cgtgatcgtg     780
gtgtcgctgc agtaccgcgt ggccagtctg gcttcctgt ttctcggcac cccggaagcg      840
ccgggcaatg cgggactgtt cgatcagaac cttgcgctac ggtaggtgtc tttgcatggg     900
tgaatgaggg tatagtattc taacgaggtg ctcttcttcc catcacttct tgggagtcag     960
ctgggtgcgg gacaacattc accggttcgg tggtgatccg tcgcgtgtga cactgttcgg    1020
cgagagtgcc ggtgccgtct cggtgtcgct gcatctgctg tccgccctgt cccgcgatct    1080
gttccagcgg gccatcctgc agagcggctc gccgacggca ccgtgggcat ggtatcgcg    1140
cgaggaagcc acgctaaggt acgtgccagc tgctgctttc cccaaaccac caacccgcga    1200
cagctcacac aaccctcttt tccttcgctc ttttctcgct ccagagcact gcggttggcc    1260
gaggcggtcg gctgcccgca cgaaccgagc aagctgagcg atgcggtcga gtgtctgcgc    1320
ggcaaggatc cgcacgtgct ggtcaacaac gagtggggca cgctcggcat ttgcgagttc    1380
ccgttcgtgc cggtggtcga cggtgcgttc ctggacgaga cgccgcagcg ttcgctcgcc    1440
agcgggcgct tcaagaagac ggagatcctc accggcagca acacggagga gggctactac    1500
ttcatcatct actacctgac cgagctgctg cgcaaggagg agggcgtgac cgtgacgcgc    1560
gaggagttcc tgcaggcggt gcgcgagctc aacccgtacg tgaacggggc ggcccggcag    1620
gcgatcgtgt tcgagtacac cgactggacc gagccggaca acccgaacag caaccgggac    1680
gcgctggaca agatggtggg cgactatcac ttcacctgca acgtgaacga ttcgcgcag     1740
cggtacgccg aggagggcaa caacgtctac atgtatctgt acacgcaccg cagcaaaggc    1800
aacccgtggc cgcgctggac gggcgtgatg cacggcgacg agatcaacta cgtgttcggc    1860
gaaccgctca accccaccct cggctacacc gaggacgaga aagactttag ccggaagatc    1920
atgcgatact ggtctaactt tgccaaaacc gggtaagtgt gtgtgtgtgt gtgtgtcaaa    1980
cagcagagtg tcgatcgctc taacgccttc tctcttcaac agcaatccaa atcccaacac    2040
ggccagcagc gaattcccg agtggcccaa gcacaccgcc cacgacggc actatctgga      2100
gctgggcctc aacacgtcct tcgtcggtcg gggcccacgg ttgaggcagt gtgccttctg    2160
gaagaagtac cttccccagc tagttgcagc tacctgtaag tctcgtgcag cgcttgaaat    2220
cctctcccgc atcctcaaca gggtccaggt tgcaataaca aatgtatctc tctctctctc    2280
acgtctcttt tccccaaaac agcgaaccta ccagggccag caccgcccag tgaaccgtgc    2340
```

```
gaaagcagcg cattttttta ccgacctgat ctgatcgtgc tgctggtgtc gctgcttacg    2400
gcgaccgtca gattcataca ataattacta ccccatccat ggcctagttc ttttaagctt    2460
taagatagtg aggaacaaat ttttcctaac caatttccca acccccttta gagcagaacc    2520
gagggagaga taggactaca tagcgaaaag ggaaaac                              2557
```

<210> SEQ ID NO 24
<211> LENGTH: 273
<212> TYPE: DNA
<213> ORGANISM: Culex pipiens strain S-LAB

<400> SEQUENCE: 24

```
attgaaccgg acaacccgaa cagcaaccgt gacgcgctgg acaagatggt cggggattat     60
cacttcacct gcaacgtgaa cgaattcgcc cagcggtacg ccgaggaggg caacaacgtg    120
ttcatgtacc tgtacacgca cagaagcaaa ggaaatccct ggccgaggtg gaccggcgtg    180
atgcacggcg acgagatcaa ctacgtgttt ggcgaaccgc tgaactcggc cctcggctac    240
caggacgacg agaaggactt tagccggaaa att                                 273
```

<210> SEQ ID NO 25
<211> LENGTH: 273
<212> TYPE: DNA
<213> ORGANISM: Culex pipiens strain SR

<400> SEQUENCE: 25

```
atcgaaccgg acaacccgaa cagcaaccgt gacgcgctcg acaagatggt cggggattat     60
cacttcacct gcaacgtgaa cgagttcgcc cagcggtacg ccgaggaggg caacaatgtg    120
ttcatgtacc tgtacacgca cagaagcaaa ggaaatccct ggccgaggtg gactggcgtg    180
atgcacggcg acgagatcaa ctacgtgttt ggcgaaccgc tgaactcggc cctcggctac    240
caggacgacg agaaggactt tagccggaaa att                                 273
```

<210> SEQ ID NO 26
<211> LENGTH: 273
<212> TYPE: DNA
<213> ORGANISM: Aedes aegypti

<400> SEQUENCE: 26

```
actgaaccgg aaaatcccaa cagcaatcgg gatgcattgg acaaaatggt cggagattat     60
cacttcacgt gtaatgtgaa tgagtttgcc cagcgatatg cagaagaagg caacaatgtg    120
tacatgtatc tgtacactca tagaagcaaa ggtaaccect ggccacggtg gaccggtgtg    180
atgcatggtg acgagatcaa ttatgtgttc ggtgagcctc tgaactctga tctggggtac    240
atggaggatg aaaaagactt cagtaggaag att                                 273
```

<210> SEQ ID NO 27
<211> LENGTH: 273
<212> TYPE: DNA
<213> ORGANISM: Aedes albopictus

<400> SEQUENCE: 27

```
actgaaccag agaatcccaa cagcaatcgg gatgcgttgg acaaaatggt gggagattat     60
catttcacct gcaacgtgaa cgagtttgcc cagcgatatg cggaagaggg caacaacgtg    120
tacatgtatt tgtacactca cagaagcaaa ggtaacccett ggccacggtg gaccggggtg    180
atgcatggtg acgagatcaa ctatgtattc ggtgagccgt tgaattccga cctggggtac    240
atggacgatg agaaagattt cagtagaaag ata                                 273
```

<210> SEQ ID NO 28
<211> LENGTH: 273
<212> TYPE: DNA
<213> ORGANISM: Anopheles darlingi

<400> SEQUENCE: 28

```
acagaaccgg acaacccgaa cagtaaccgg gacgcgctgg acaagatggt cggtgattat      60
cacttcacgt gtaacgtcaa tgagtttgcg cagcggtacg ccgaggaggg caacaacgtc     120
tacatgtatc tgtacacgca ccgtagcaaa ggcaacccgt ggccccgctg gaccggggtg     180
atgcatggtg atgagattaa ctacgtgttc ggtgaaccgc tcaacccgac gctcggttac     240
accgacgatg agaagggttt cagccggaag att                                  273
```

<210> SEQ ID NO 29
<211> LENGTH: 273
<212> TYPE: DNA
<213> ORGANISM: Anopheles sundaicus

<400> SEQUENCE: 29

```
accgagccgg acaacccgaa cagcaaccga gacgcgctgg acaagatggt cggcgactat      60
cacttcaccc tgcaacgtcaa cgagttcgcc cagcggtacg ccgaggaggg caacaacgtc    120
tacatgtatc tgtacacgca ccgaagcaaa ggcaacccgt ggccacgctg gacgggtgtg     180
atgcacggtg acgagattaa ttacgtgttt ggagagccgc ttaaccccac gctcggatac     240
accgaggacg agaaggactt tagccggaag atc                                  273
```

<210> SEQ ID NO 30
<211> LENGTH: 273
<212> TYPE: DNA
<213> ORGANISM: Anopheles minimus

<400> SEQUENCE: 30

```
accgaaccag ataatccgaa cagcaaccgg gacgcactgg acaagatggt gggcgactac      60
catttcacct gtaacgtgaa cgagttcgca cagcggtacg ccgaggaggg caacaatgta     120
tacatgtacc tgtacacgca ccgaagcaaa ggcaacccgt ggccacgctg gaccggcgtt     180
atgcacggtg acgagattaa ctacgtgttc ggggaaccgc tcaacccaag cctcggctac     240
accgaagacg agaaagactt tagccggaag atc                                  273
```

<210> SEQ ID NO 31
<211> LENGTH: 273
<212> TYPE: DNA
<213> ORGANISM: Anopheles moucheti

<400> SEQUENCE: 31

```
accgaaccag ataatccgaa cagcaaccgg gacgcactgg acaagatggt gggcgactac      60
catttcacct gtaacgtgaa cgagttcgca cagcggtacg ccgaggaggg caacaatgta     120
tacatgtacc tgtacacgca ccgaagcaaa ggcaacccgt ggccacgctg gaccggcgtt     180
atgcacggtg acgagattaa ctacgtgttc ggggaaccgc tcaacccaag cctcggctac     240
accgaagacg agaaagactt tagccggaag atc                                  273
```

<210> SEQ ID NO 32
<211> LENGTH: 273
<212> TYPE: DNA
<213> ORGANISM: Anopheles arabiensis

<400> SEQUENCE: 32

```
accgagccgg acaacccgaa cagcaaccgg gacgcgttgg acaagatggt gggcgactat    60
cacttcacct gcaacgtgaa cgagttcgcg cagcggtacg ccgaggaggg caacaacgtc   120
tacatgtatc tgtacacgca ccgcagcaaa ggcaacccgt ggccgcgctg acgggcgtg    180 atgcacggcg acgagatcaa ctacgtgttc ggcgaaccgc tcaaccccac cctcggctac   240
accgaggacg agaaagactt tagccggaag atc                                273

<210> SEQ ID NO 33
<211> LENGTH: 273
<212> TYPE: DNA
<213> ORGANISM: Anopheles funestus

<400> SEQUENCE: 33
accgagccgg acaacccgaa cagcaaccgt gacgcgctcg acaaaatggt gggcgactat    60
catttcacct gcaacgtgaa cgagttcgcc cagcggtacg ccgaggaggg caacaatgta   120
tacatgtacc tgtacacgca ccgaagcaaa ggcaacccat ggccacgctg acgggcgtt    180 atgcacggtg atgagattaa ctatgtgttc ggggaaccgc tcaatcccag cctcggctac   240
accgaggacg agaaagactt tagccggaag atc                                273

<210> SEQ ID NO 34
<211> LENGTH: 273
<212> TYPE: DNA
<213> ORGANISM: Anopheles pseudopunctipennis

<400> SEQUENCE: 34
accgagccgg acaacccgaa cagcaaccgg gacgcgctgg acaagatggt gggcgactac    60
cacttcacgt gcaacgtgaa cgagttcgcc cagcgctacg ccgaagaggg caacaacgtg   120
tacatgtatc tgtacacgca ccgaagcaaa ggcaacccgt ggccgcgctg accggcgtc    180 atgcatgggg acgagattaa ctacgtgttt ggggaaccgc ttaacccggg gctcggctat   240
accgaggacg agaaggactt tagccgcaag atc                                273

<210> SEQ ID NO 35
<211> LENGTH: 273
<212> TYPE: DNA
<213> ORGANISM: Anopheles sacharovi

<400> SEQUENCE: 35
accgagccgg acaacccgaa cagcaaccgg gacgcgctgg acaagatggt cggtgactac    60
cacttcacct gcaacgtgaa cgagttcgcg cagcggtacg ccgaggaggg caacaacgtc   120
tacatgtacc tgtacacgca caggagcaaa ggcaacccat ggccgcgctg accggcgtc    180 atgcatggcg acgagatcaa ctacgtgttc ggcgaaccgc tcaatcccag cctaggctac   240
accgatgacg agaaagactt tagccggaag att                                273

<210> SEQ ID NO 36
<211> LENGTH: 273
<212> TYPE: DNA
<213> ORGANISM: Anopheles stephensi

<400> SEQUENCE: 36
accgaaccgg acaatccgaa cagcaaccgg gatgcattgg acaaaatggt gggcgattac    60
catttcacgt gcaacgtgaa cgagttcgca cagcgatacg ccgaggaggg caacaatgtg   120
tacatgtatc tgtacacgca ccgaagcaaa ggcaatccgt ggccacgctg accggcgtt    180 atgcatgggg acgaaattaa ctacgtgttc ggggaaccgc tcaaccctag ccttggttac   240
```

```
accgacgacg agaaagactt tagccggaag atc                                    273

<210> SEQ ID NO 37
<211> LENGTH: 273
<212> TYPE: DNA
<213> ORGANISM: Anopheles albimanus

<400> SEQUENCE: 37
acggagccgg acaatccgaa cagcaaccgg gacgcactgg acaagatggt cggcgattat        60
cactttacgt gcaacgtcaa cgagttcgcg cagcggtacg ccgaggaggg caacaacgtc       120
tacatgtatc tgtatacgca ccgcagcaaa ggcaatccgt ggccccgttg gacgggcgtg       180
atgcatggcg atgagatcaa ctacgtgttt ggtgaaccgc tgaacccgac gctcggctac       240
accgacgacg agaagggctt cagccggaag atc                                    273

<210> SEQ ID NO 38
<211> LENGTH: 273
<212> TYPE: DNA
<213> ORGANISM: Anopheles nili

<400> SEQUENCE: 38
accgagccgg ataacccgaa cagcaaccgg gacgcgttag acaagatggt gggcgactac        60
cacttcacgt gcaacgtgaa cgagttcgcc cagcggtacg ccgaggaggg caacaacgtc       120
tacatgtacc tctacacgca ccggagcaaa ggcaatccct ggccgcgttg gacgggcgtc       180
atgcacggtg acgagatcaa ctacgtgttc ggggaaccgc ttaacccgag cctcggctac       240
accgaggacg agaaggactt cagccgcaag atg                                    273

<210> SEQ ID NO 39
<211> LENGTH: 24
<212> TYPE: DNA
<213> ORGANISM: Artificial Sequence
<220> FEATURE:
<223> OTHER INFORMATION: Synthetic DNA

<400> SEQUENCE: 39
atmgwgttyg agtacacsga ytgg                                               24

<210> SEQ ID NO 40
<211> LENGTH: 24
<212> TYPE: DNA
<213> ORGANISM: Artificial Sequence
<220> FEATURE:
<223> OTHER INFORMATION: Synthetic DNA

<400> SEQUENCE: 40
ggcaaarttk gwccagtatc kcat                                               24

<210> SEQ ID NO 41
<211> LENGTH: 20
<212> TYPE: DNA
<213> ORGANISM: Artificial Sequence
<220> FEATURE:
<223> OTHER INFORMATION: Synthetic DNA

<400> SEQUENCE: 41
ggygckacma tgtggaaycc                                                    20

<210> SEQ ID NO 42
<211> LENGTH: 24
<212> TYPE: DNA
<213> ORGANISM: Artificial Sequence
```

```
<220> FEATURE:
<223> OTHER INFORMATION: Synthetic DNA

<400> SEQUENCE: 42
accamratca cgttytcytc cgac                                        24

<210> SEQ ID NO 43
<211> LENGTH: 23
<212> TYPE: DNA
<213> ORGANISM: Artificial Sequence
<220> FEATURE:
<223> OTHER INFORMATION: Synthetic DNA

<400> SEQUENCE: 43
tacatcaacg tggtcgtgcc acg                                         23

<210> SEQ ID NO 44
<211> LENGTH: 19
<212> TYPE: DNA
<213> ORGANISM: Artificial Sequence
<220> FEATURE:
<223> OTHER INFORMATION: Synthetic DNA

<400> SEQUENCE: 44
gtcacggttg ctgttcggg                                              19

<210> SEQ ID NO 45
<211> LENGTH: 16
<212> TYPE: DNA
<213> ORGANISM: Artificial Sequence
<220> FEATURE:
<223> OTHER INFORMATION: Synthetic DNA

<400> SEQUENCE: 45
cgacgccacc ttcaca                                                 16

<210> SEQ ID NO 46
<211> LENGTH: 20
<212> TYPE: DNA
<213> ORGANISM: Artificial Sequence
<220> FEATURE:
<223> OTHER INFORMATION: Synthetic DNA

<400> SEQUENCE: 46
gatggcccgc tggaacagat                                             20

<210> SEQ ID NO 47
<211> LENGTH: 20
<212> TYPE: DNA
<213> ORGANISM: Artificial Sequence
<220> FEATURE:
<223> OTHER INFORMATION: Synthetic DNA

<400> SEQUENCE: 47
gggtgcggga caacattcac                                             20

<210> SEQ ID NO 48
<211> LENGTH: 17
<212> TYPE: DNA
<213> ORGANISM: Artificial Sequence
<220> FEATURE:
<223> OTHER INFORMATION: Synthetic DNA

<400> SEQUENCE: 48
ccccgaccga cgaagga                                                17
```

<210> SEQ ID NO 49
<211> LENGTH: 20
<212> TYPE: DNA
<213> ORGANISM: Artificial Sequence
<220> FEATURE:
<223> OTHER INFORMATION: Synthetic DNA

<400> SEQUENCE: 49
agatggtggg cgactatcac                                        20

<210> SEQ ID NO 50
<211> LENGTH: 20
<212> TYPE: DNA
<213> ORGANISM: Artificial Sequence
<220> FEATURE:
<223> OTHER INFORMATION: Synthetic DNA

<400> SEQUENCE: 50
ctcgtccgcc accacttgtt                                        20

<210> SEQ ID NO 51
<211> LENGTH: 585
<212> TYPE: PRT
<213> ORGANISM: Ciona intestinalis

<400> SEQUENCE: 51

Leu Pro Arg Tyr Gly Ser Val Arg Gly Lys His Val Glu Ser Pro Pro
1               5                   10                  15

Arg His Gln Arg Ile Ala Ala Phe Leu Gly Ile Pro Phe Ala Ser Pro
            20                  25                  30

Pro Val Gly Glu Leu Arg Phe Ala Ala Pro Gln Pro Pro Leu Ser Trp
        35                  40                  45

Glu Pro Asp Val Arg Gln Thr Thr Glu Phe Gly Asn Ser Cys Val Gln
    50                  55                  60

Ile Asp Asp Glu Val Phe Gly Asn Phe Arg Glu Met Trp Asn Ala Pro
65                  70                  75                  80

Asn Leu Lys Ser Glu Asp Cys Leu Tyr Leu Asn Ile Trp Thr Pro Arg
                85                  90                  95

Ile Pro Thr Ser Thr Arg Ser Gln Pro Leu Ala Val Met Val Trp Ile
            100                 105                 110

Tyr Gly Gly Ser Phe Tyr Ser Gly Thr Thr Ala Leu Ala Leu Tyr Asp
        115                 120                 125

Gly Arg Tyr Leu Ala Ala Gln Gly Gly Val Val Val Ser Ile Asn
    130                 135                 140

Tyr Arg Leu Gly Pro Leu Gly Phe Leu Ala Pro Leu Ala Gly Thr Pro
145                 150                 155                 160

Gly Asn Ala Gly Leu Leu Asp Gln Gln Leu Ala Leu Lys Trp Val Arg
                165                 170                 175

Asp Asn Ile Arg Ala Phe Gly Gly Asn Pro Asp Asn Val Thr Leu Met
            180                 185                 190

Gly Glu Ser Ala Gly Ala Ala Ser Ile Gly Leu His Thr Val Ala Pro
        195                 200                 205

Ser Ser Arg Gly Leu Phe Asn Arg Val Ile Phe Gln Ser Gly Asn Gln
    210                 215                 220

Met Thr Pro Trp Ser Thr Ile Ser Leu Pro Thr Ser Leu Asn Arg Thr
225                 230                 235                 240

Arg Ile Leu Ala Ala Asn Leu Arg Cys Pro Asn Pro Arg Thr Ser Ser
                245                 250                 255

Glu Leu Asp Val Leu Thr Cys Leu Arg Ser His Ser Ala Val Asp Val

```
            260                 265                 270
Phe Ser Asn Ser Trp Ile Thr Gln Glu Ile Phe Asp Phe Pro Phe Val
        275                 280                 285
Pro Val His Gly Thr Ser Phe Leu Pro Glu His Pro His Glu Val Thr
    290                 295                 300
Arg Lys Gly Glu Gln Ala Asp Val Asp Val Met Ala Gly His Asn Thr
305                 310                 315                 320
Asn Glu Gly Ser Tyr Phe Thr Leu Tyr Thr Val Pro Gly Phe Asn Ile
                325                 330                 335
Ser Ser Gln Ser Ile Leu Ser Lys Lys Glu Tyr Ile Asp Gly Ile Ala
            340                 345                 350
Leu Ser Gly Ile Lys Thr Asn Glu Leu Gly Arg Ser Gly Ala Ala Phe
        355                 360                 365
Met Tyr Ala Asp Trp Glu Asn Pro Asp Asn Val Leu Gln Tyr Arg Asp
    370                 375                 380
Gly Val Asn Glu Ile Val Gly Asp Phe His Val Cys Pro Thr Val
385                 390                 395                 400
Leu Leu Thr Lys Arg His Ser Arg Thr Phe Ser Asn Asn Asn Val Tyr
                405                 410                 415
Leu Tyr His Leu Ser Tyr Arg Leu Ser Asn Asn Pro Trp Pro Ala Trp
            420                 425                 430
Met Gly Val Met His Gly Tyr Glu Ile Glu Leu Met Phe Gly Thr Pro
        435                 440                 445
Trp Phe Gly Thr Ser Gln Phe Thr Ser Gly Tyr Asn Asp Val Asp Arg
    450                 455                 460
Ser Val Ser Arg Arg Met Val His Tyr Trp Thr Asn Phe Ala Lys Phe
465                 470                 475                 480
Gly Asn Pro Asn Gly Leu Arg Ser Ala Asn Glu Leu Asp Leu Arg Ser
                485                 490                 495
Thr Asp Trp Pro Arg Phe Asp Asp Val Arg Gln Arg Tyr Leu Glu Ile
            500                 505                 510
Gly Ile Asp Asp Val Met Gly Pro Phe Pro Asn Ser Phe Arg Cys
        515                 520                 525
Ala Phe Trp Glu Arg Tyr Leu Pro Ser Leu Lys Leu Ala Ser Ser Ala
    530                 535                 540
Asp Met Asp Glu Val Glu Thr Lys Trp Lys Ile Glu Phe Asn Arg Trp
545                 550                 555                 560
Thr Glu Ser Met Asp Leu Trp Asp Arg Ser Phe Lys Ala Tyr Ser Lys
                565                 570                 575
Asp Gly Lys Gln Ser Ser Cys Pro Asn
            580                 585

<210> SEQ ID NO 52
<211> LENGTH: 583
<212> TYPE: PRT
<213> ORGANISM: Ciona savignyi

<400> SEQUENCE: 52

Gly Ser Ile Gln Gly Lys His Val Glu Val Thr Ala His Arg Gln Arg
1               5                   10                  15
Tyr Gly Arg Val Ala Thr Phe Gln Gly Ile Pro Phe Ala Gln Pro Pro
                20                  25                  30
Val Gly Glu Leu Arg Phe Ala Ala Pro Gln Pro Pro Leu Ser Trp Glu
            35                  40                  45
Pro Asp Val Lys Met Thr Ser Glu Phe Gly Asn Ser Cys Ile Gln Glu
```

```
                 50                  55                  60
Asp Asp Leu Val Phe Gly Asn Phe Thr Gly Gly Ser Gln Met Trp Asn
 65                  70                  75                  80

Ser Pro Asn Ala Lys Ser Glu Asp Cys Leu Tyr Leu Asn Val Trp Thr
                 85                  90                  95

Pro Val Arg Ser Arg His Ala Glu Pro Leu Ala Val Leu Val Trp Ile
                100                 105                 110

Tyr Gly Gly Ser Tyr Tyr Ser Gly Thr Ser Ser Leu Ala Leu Tyr Asp
                115                 120                 125

Gly Arg Tyr Leu Ala Ala Thr Gly Val Val Val Ser Leu Asn
130                 135                 140

Tyr Arg Leu Gly Pro Ile Gly Phe Leu Ala Pro Leu Ala Asp Glu Thr
145                 150                 155                 160

Pro Gly Asn Val Gly Leu Leu Asp Gln Gln Leu Ala Leu Lys Trp Val
                165                 170                 175

Arg Asp Asn Ile Arg Glu Phe Gly Gly Asn Pro Asn Asn Val Thr Val
                180                 185                 190

Met Gly Glu Ser Ala Gly Ala Ala Ser Ile Gly Leu His Thr Ile Ala
                195                 200                 205

Pro Ser Ser Arg Gly Leu Phe Ser Arg Val Ile Leu Gln Ser Gly Asn
210                 215                 220

Gln Met Thr Pro Trp Ser Thr Ile Ser Leu Glu Thr Ser Leu Asn Arg
225                 230                 235                 240

Thr Arg Thr Leu Ala Ala Asn Leu Asn Cys Pro Lys Pro Arg Thr Ala
                245                 250                 255

Ser Glu Ala Asp Ile Leu Ala Cys Leu Arg Thr His Thr Ala Asn Glu
                260                 265                 270

Val Phe Ala Gly Ser Trp Ile Thr Lys Glu Ile Phe Asp Phe Pro Phe
                275                 280                 285

Val Pro Val His Gly Thr Thr Phe Leu Pro Glu His Pro His Glu Val
                290                 295                 300

Thr Arg Arg Gly Asp Gln Ala Glu Val Asp Val Leu Ala Gly Tyr Asn
305                 310                 315                 320

Thr Asn Glu Gly Ser Tyr Phe Thr Ile Tyr Thr Val Pro Gly Tyr Asn
                325                 330                 335

Ile Thr Thr Asn Ser Val Leu Asn Arg Arg Gln Tyr Leu Ala Gly Val
                340                 345                 350

Asp Leu Ser Gly Leu Lys Thr Asn Thr Met Gly Arg Ser Ala Ala Ala
                355                 360                 365

Phe Met Tyr Thr Asp Trp Glu Asn Leu Asp Asn Glu Leu Gln Tyr Arg
370                 375                 380

Asp Ala Val Asn Glu Ile Val Gly Asp Phe His Val Val Cys Pro Thr
385                 390                 395                 400

Val Leu Val Ser Lys Arg His Ser Asn Ser Phe Pro Asn Arg Asn Val
                405                 410                 415

Phe Leu Tyr His Leu Ser Tyr Arg Val Ser Thr Asn Pro Trp Pro Ile
                420                 425                 430

Trp Met Gly Val Met His Gly Tyr Glu Ile Glu Leu Met Phe Gly Thr
                435                 440                 445

Pro Trp Phe Gly Asn Ser Lys Phe Thr Arg Gly Tyr Ser Asp Leu Asp
                450                 455                 460

Arg Ser Val Ser Arg Arg Met Val Arg Tyr Trp Thr Asn Phe Ala Lys
465                 470                 475                 480
```

-continued

```
Phe Gly Asn Pro Asn Gly Leu Arg Asn Gln Asn Gln Glu Leu Val Ser
                485                 490                 495

Asp Trp Pro Arg Phe Asn Asp Val Thr Gln Arg Tyr Leu Glu Ile Ala
            500                 505                 510

Asp Asp Asp Val Thr Met Ala Pro Phe Pro Asp Ser Phe Arg Cys Ala
        515                 520                 525

Phe Trp Gln Lys Tyr Leu Pro Ser Leu Gln Leu Ala Ser Ser Asn Met
    530                 535                 540

Asp Glu Val Glu Thr Lys Trp Lys Ile Glu Phe His Arg Trp Ser Glu
545                 550                 555                 560

Ser Met Asp Leu Trp Asp Arg Ser Phe Lys Ala Tyr Ser Ser Asp Asp
                565                 570                 575

Lys Gln Asn Ser Cys Pro Asn
            580

<210> SEQ ID NO 53
<211> LENGTH: 645
<212> TYPE: PRT
<213> ORGANISM: Anopheles gambiae

<400> SEQUENCE: 53

Met Ala Ser Ala Tyr Tyr His Gln Ser Ala Val Gly Val Gly Asn Val
1               5                   10                  15

Leu Val Leu Leu Leu Gly Ala Thr Val Ile Cys Pro Ala Tyr Ala Ile
                20                  25                  30

Ile Asp Arg Leu Val Val Gln Thr Ser Ser Gly Pro Ile Arg Gly Arg
            35                  40                  45

Ser Thr Met Val Gln Gly Arg Glu Val His Val Phe Asn Gly Val Pro
        50                  55                  60

Phe Ala Lys Pro Pro Val Asp Ser Leu Arg Phe Lys Lys Pro Val Pro
65                  70                  75                  80

Ala Glu Pro Trp His Gly Val Leu Asp Ala Thr Arg Leu Pro Pro Ser
                85                  90                  95

Cys Ile Gln Glu Arg Tyr Glu Tyr Phe Pro Gly Phe Ala Gly Glu Glu
                100                 105                 110

Met Trp Asn Pro Asn Thr Asn Val Ser Glu Asp Cys Leu Tyr Leu Asn
            115                 120                 125

Ile Trp Val Pro Thr Lys Thr Arg Leu Arg His Gly Arg Gly Leu Asn
        130                 135                 140

Phe Gly Ser Asn Asp Tyr Phe Gln Asp Asp Asp Phe Gln Arg Gln
145                 150                 155                 160

His Gln Ser Lys Gly Gly Leu Ala Met Leu Val Trp Ile Tyr Gly Gly
                165                 170                 175

Gly Phe Met Ser Gly Thr Ser Thr Leu Asp Ile Tyr Asn Ala Glu Ile
            180                 185                 190

Leu Ala Ala Val Gly Asn Val Ile Val Ala Ser Met Gln Tyr Arg Val
        195                 200                 205

Gly Ala Phe Gly Phe Leu Tyr Leu Ala Pro Tyr Ile Asn Gly Tyr Glu
    210                 215                 220

Glu Asp Ala Pro Gly Asn Met Gly Met Trp Asp Gln Ala Leu Ala Ile
225                 230                 235                 240

Arg Trp Leu Lys Glu Asn Ala Lys Ala Phe Gly Gly Asp Pro Asp Leu
                245                 250                 255

Ile Thr Leu Phe Gly Glu Ser Ala Gly Gly Ser Val Ser Leu His
                260                 265                 270
```

```
Leu Leu Ser Pro Val Thr Arg Gly Leu Ser Lys Arg Gly Ile Leu Gln
        275                 280                 285

Ser Gly Thr Leu Asn Ala Pro Trp Ser His Met Thr Ala Glu Lys Ala
290                 295                 300

Leu Gln Ile Ala Glu Gly Leu Ile Asp Asp Cys Asn Cys Asn Leu Thr
305                 310                 315                 320

Met Leu Lys Glu Ser Pro Ser Thr Val Met Gln Cys Met Arg Asn Val
                325                 330                 335

Asp Ala Lys Thr Ile Ser Val Gln Gln Trp Asn Ser Tyr Ser Gly Ile
                340                 345                 350

Leu Gly Phe Pro Ser Ala Pro Thr Ile Asp Gly Val Phe Met Thr Ala
            355                 360                 365

Asp Pro Met Thr Met Leu Arg Glu Ala Asn Leu Glu Gly Ile Asp Ile
370                 375                 380

Leu Val Gly Ser Asn Arg Asp Glu Gly Thr Tyr Phe Leu Leu Tyr Asp
385                 390                 395                 400

Phe Ile Asp Tyr Phe Glu Lys Asp Ala Ala Thr Ser Leu Pro Arg Asp
                405                 410                 415

Lys Phe Leu Glu Ile Met Asn Thr Ile Phe Asn Lys Ala Ser Glu Pro
                420                 425                 430

Glu Arg Glu Ala Ile Ile Phe Gln Tyr Thr Gly Trp Glu Ser Gly Asn
            435                 440                 445

Asp Gly Tyr Gln Asn Gln His Gln Val Gly Arg Ala Val Gly Asp His
450                 455                 460

Phe Phe Ile Cys Pro Thr Asn Glu Phe Ala Leu Gly Leu Thr Glu Arg
465                 470                 475                 480

Gly Ala Ser Val His Tyr Tyr Tyr Phe Thr His Arg Thr Ser Thr Ser
                485                 490                 495

Leu Trp Gly Glu Trp Met Gly Val Leu His Gly Asp Glu Val Glu Tyr
            500                 505                 510

Ile Phe Gly Gln Pro Met Asn Ala Ser Leu Gln Tyr Arg Gln Arg Glu
            515                 520                 525

Arg Asp Leu Ser Arg Arg Met Val Leu Ser Val Ser Glu Phe Ala Arg
530                 535                 540

Thr Gly Asn Pro Ala Leu Glu Gly Glu His Trp Pro Leu Tyr Thr Arg
545                 550                 555                 560

Glu Asn Pro Ile Tyr Phe Ile Phe Asn Ala Glu Gly Glu Asp Asp Leu
                565                 570                 575

Arg Gly Glu Lys Tyr Gly Arg Gly Pro Met Ala Thr Ser Cys Ala Phe
                580                 585                 590

Trp Asn Asp Phe Leu Pro Arg Leu Arg Ala Trp Ser Val Pro Leu Lys
            595                 600                 605

Asp Pro Cys Lys Leu Asp Asp His Thr Ser Ile Ala Ser Thr Ala Arg
610                 615                 620

Ala Ala Pro Thr Val Ala Leu Leu Ile Ala Leu Ser Leu Ala Val Ala
625                 630                 635                 640

Arg Leu Val Ala Ala
                645

<210> SEQ ID NO 54
<211> LENGTH: 20
<212> TYPE: DNA
<213> ORGANISM: Artificial Sequence
<220> FEATURE:
<223> OTHER INFORMATION: Synthetic DNA
```

-continued

```
<400> SEQUENCE: 54
ccacacgcca gaagaaaaga                                                    20

<210> SEQ ID NO 55
<211> LENGTH: 19
<212> TYPE: DNA
<213> ORGANISM: Artificial Sequence
<220> FEATURE:
<223> OTHER INFORMATION: Synthetic DNA

<400> SEQUENCE: 55
aaaaacggga acgggaaag                                                     19

<210> SEQ ID NO 56
<211> LENGTH: 2109
<212> TYPE: DNA
<213> ORGANISM: Culex pipiens strain SR
<220> FEATURE:
<221> NAME/KEY: CDS
<222> LOCATION: (1)..(2106)

<400> SEQUENCE: 56 atg gag atc cga ggc cta ata acc cga tta ctg ggt cca tgt cac ctg         48
Met Glu Ile Arg Gly Leu Ile Thr Arg Leu Leu Gly Pro Cys His Leu
1               5                   10                  15 cga cat ctg ata ctg tgc agt ttg ggg ctg tac tcc atc ctc gtg cag         96
Arg His Leu Ile Leu Cys Ser Leu Gly Leu Tyr Ser Ile Leu Val Gln
            20                  25                  30 tcg gtc cat tgc cgg cat cat gac atc ggt agt tcg gtg gca cac cag        144
Ser Val His Cys Arg His His Asp Ile Gly Ser Ser Val Ala His Gln
        35                  40                  45 cta gga tcg aaa tac tca caa tca tcc tcg tta tcg tca tcc tcg caa        192
Leu Gly Ser Lys Tyr Ser Gln Ser Ser Ser Leu Ser Ser Ser Ser Gln
    50                  55                  60 tcg tca tcg tcg tta gct gaa gag gcc acg ctg aat aaa gat tca gat        240
Ser Ser Ser Ser Leu Ala Glu Glu Ala Thr Leu Asn Lys Asp Ser Asp
65                  70                  75                  80 gca ttt ttt aca cca tat ata ggt cac gga gat tct gtt cga att gta        288
Ala Phe Phe Thr Pro Tyr Ile Gly His Gly Asp Ser Val Arg Ile Val
                85                  90                  95 gat gcc gaa tta ggt aca tta gag cgc gag cat atc cat agc act acg        336
Asp Ala Glu Leu Gly Thr Leu Glu Arg Glu His Ile His Ser Thr Thr
            100                 105                 110 acc cgg cgg cgt ggc ctg acc cgg agg gag tcc agc tcc gat gcc acc        384
Thr Arg Arg Arg Gly Leu Thr Arg Arg Glu Ser Ser Ser Asp Ala Thr
        115                 120                 125 gac tcg gac cca ctg gta ata acg acg gac aag ggc aaa atc cgt gga        432
Asp Ser Asp Pro Leu Val Ile Thr Thr Asp Lys Gly Lys Ile Arg Gly
    130                 135                 140 acg aca ctg gaa gcg cca agt gga aag aag gtg gac gca tgg atg ggc        480
Thr Thr Leu Glu Ala Pro Ser Gly Lys Lys Val Asp Ala Trp Met Gly
145                 150                 155                 160 att ccg tac gcg cag ccc ccg ctg ggt ccg ctc cgg ttt cga cat ccg        528
Ile Pro Tyr Ala Gln Pro Pro Leu Gly Pro Leu Arg Phe Arg His Pro
                165                 170                 175 cga ccc gcc gaa aga tgg acc ggt gtg ctg aac gcg acc aaa cca ccc        576
Arg Pro Ala Glu Arg Trp Thr Gly Val Leu Asn Ala Thr Lys Pro Pro
            180                 185                 190 aac tcc tgc gtc cag atc gtg gac acc gtg ttc ggt gac ttc ccg ggc        624
Asn Ser Cys Val Gln Ile Val Asp Thr Val Phe Gly Asp Phe Pro Gly
        195                 200                 205 gcg acc atg tgg aac ccg aac aca ccc ctc tcg gag gac tgt ctg tac        672
Ala Thr Met Trp Asn Pro Asn Thr Pro Leu Ser Glu Asp Cys Leu Tyr
```

```
                Ala Thr Met Trp Asn Pro Asn Thr Pro Leu Ser Glu Asp Cys Leu Tyr
                    210                 215                 220 atc aac gtg gtc gtg cca agg ccg agg ccc aag aat gcc gct gtc atg          720
Ile Asn Val Val Val Pro Arg Pro Arg Pro Lys Asn Ala Ala Val Met
225                 230                 235                 240 ctg tgg atc ttt ggg ggt agc ttc tac tcc ggg act gcc acg ttg gac          768
Leu Trp Ile Phe Gly Gly Ser Phe Tyr Ser Gly Thr Ala Thr Leu Asp
                245                 250                 255 gtg tac gat cat cgg acg ctg gcc tcg gag gag aac gtg atc gtg gtt          816
Val Tyr Asp His Arg Thr Leu Ala Ser Glu Glu Asn Val Ile Val Val
            260                 265                 270 tcg ctg cag tac cgt gtc gca agt ctt ggt ttt ctc ttc ctg ggc act          864
Ser Leu Gln Tyr Arg Val Ala Ser Leu Gly Phe Leu Phe Leu Gly Thr
        275                 280                 285 ccg gag gca cct ggt aac gcg ggg ctg ttt gat caa aac ctg gca ctg          912
Pro Glu Ala Pro Gly Asn Ala Gly Leu Phe Asp Gln Asn Leu Ala Leu
    290                 295                 300 aga tgg gtc cgc gac aac atc cac cgg ttc ggc ggt gac ccc tcg cgg          960
Arg Trp Val Arg Asp Asn Ile His Arg Phe Gly Gly Asp Pro Ser Arg
305                 310                 315                 320 gtc aca ctg ttc ggc gag agc gcc gga gcg gtc tcg gtt tcg ctg cac         1008
Val Thr Leu Phe Gly Glu Ser Ala Gly Ala Val Ser Val Ser Leu His
                325                 330                 335 ctg ctg tcg gcg ctc tcg cgg gac ctg ttc cag cgg gcc atc ctc cag         1056
Leu Leu Ser Ala Leu Ser Arg Asp Leu Phe Gln Arg Ala Ile Leu Gln
            340                 345                 350 agt ggc tcc ccg acg gcc cca tgg gcg ctg gtt tcg cgc gaa gaa gct         1104
Ser Gly Ser Pro Thr Ala Pro Trp Ala Leu Val Ser Arg Glu Glu Ala
        355                 360                 365 acg ctt aga gct ctt cgt ctg gcc gag gcc gtc aac tgt ccg cac gat         1152
Thr Leu Arg Ala Leu Arg Leu Ala Glu Ala Val Asn Cys Pro His Asp
    370                 375                 380 gcg acc aag ctg agc gat gcc gtc gaa tgt ctg cga acc aag gat ccg         1200
Ala Thr Lys Leu Ser Asp Ala Val Glu Cys Leu Arg Thr Lys Asp Pro
385                 390                 395                 400 aac gag ctg gtc gac aat gag tgg ggc acg ctg ggg atc tgc gag ttt         1248
Asn Glu Leu Val Asp Asn Glu Trp Gly Thr Leu Gly Ile Cys Glu Phe
                405                 410                 415 ccg ttc gtt ccg gtt gtg gac ggt gcc ttc ctc gat gag aca ccg cag         1296
Pro Phe Val Pro Val Val Asp Gly Ala Phe Leu Asp Glu Thr Pro Gln
            420                 425                 430 cgt tcg ttg gcc agc ggt cgc ttc aag aaa acg gac atc ctg acc ggc         1344
Arg Ser Leu Ala Ser Gly Arg Phe Lys Lys Thr Asp Ile Leu Thr Gly
        435                 440                 445 agc aac acc gag gag ggt tac tac ttt atc att tac tat cta acc gaa         1392
Ser Asn Thr Glu Glu Gly Tyr Tyr Phe Ile Ile Tyr Tyr Leu Thr Glu
    450                 455                 460 ctg ctc agg aaa gag gaa ggg gtc acg gta aca cgc gag gag ttc cta         1440
Leu Leu Arg Lys Glu Glu Gly Val Thr Val Thr Arg Glu Glu Phe Leu
465                 470                 475                 480 cag gcc gtc cgg gag ttg aat ccg tac gtg aac ggt gcc gcc cgg cag         1488
Gln Ala Val Arg Glu Leu Asn Pro Tyr Val Asn Gly Ala Ala Arg Gln
                485                 490                 495 gcc atc gtg ttc gag tac acg gac tgg atc gaa ccg gac aac ccg aac         1536
Ala Ile Val Phe Glu Tyr Thr Asp Trp Ile Glu Pro Asp Asn Pro Asn
            500                 505                 510 agc aac cgt gac gcg ctc gac aag atg gtc ggg gat tat cac ttc acc         1584
Ser Asn Arg Asp Ala Leu Asp Lys Met Val Gly Asp Tyr His Phe Thr
        515                 520                 525 tgc aac gtg aac gag ttc gcc cag cgg tac gcc gag gag ggc aac aat         1632
```

```
Cys Asn Val Asn Glu Phe Ala Gln Arg Tyr Ala Glu Glu Gly Asn Asn
        530                 535                 540 gtg ttc atg tac ctg tac acg cac aga agc aaa gga aat ccc tgg ccg      1680
Val Phe Met Tyr Leu Tyr Thr His Arg Ser Lys Gly Asn Pro Trp Pro
545                 550                 555                 560 agg tgg act ggc gtg atg cac ggc gac gag atc aac tac gtg ttt ggc      1728
Arg Trp Thr Gly Val Met His Gly Asp Glu Ile Asn Tyr Val Phe Gly
                565                 570                 575 gaa ccg ctg aac tcg gcc ctc ggc tac cag gac gac gag aag gac ttt      1776
Glu Pro Leu Asn Ser Ala Leu Gly Tyr Gln Asp Asp Glu Lys Asp Phe
            580                 585                 590 agc cgg aaa att atg cga tac tgg tcc aac ttt gcc aag act ggc aat      1824
Ser Arg Lys Ile Met Arg Tyr Trp Ser Asn Phe Ala Lys Thr Gly Asn
        595                 600                 605 cca aac ccg agt acg ccg agc gtg gac ctg ccc gaa tgg ccc aag cac      1872
Pro Asn Pro Ser Thr Pro Ser Val Asp Leu Pro Glu Trp Pro Lys His
    610                 615                 620 acc gcc cac gga cga cac tat ctg gag ctg gga ctg aac acg acc ttc      1920
Thr Ala His Gly Arg His Tyr Leu Glu Leu Gly Leu Asn Thr Thr Phe
625                 630                 635                 640 gtg gga cgg ggc cca cga ttg cgg cag tgc gct ttc tgg aag aaa tat      1968
Val Gly Arg Gly Pro Arg Leu Arg Gln Cys Ala Phe Trp Lys Lys Tyr
                645                 650                 655 ttg ccg caa cta gta gca gct acc tct aac ctc caa gta act ccc gcg      2016
Leu Pro Gln Leu Val Ala Ala Thr Ser Asn Leu Gln Val Thr Pro Ala
            660                 665                 670 cct agc gta cct tgc gaa agc agc tca aca tct tat cga tcc act cta      2064
Pro Ser Val Pro Cys Glu Ser Ser Ser Thr Ser Tyr Arg Ser Thr Leu
        675                 680                 685 ctt cta ata gtc aca cta ctt tta gta acg cgg ttc aag att taa          2109
Leu Leu Ile Val Thr Leu Leu Leu Val Thr Arg Phe Lys Ile
    690                 695                 700

<210> SEQ ID NO 57
<211> LENGTH: 702
<212> TYPE: PRT
<213> ORGANISM: Culex pipiens strain SR

<400> SEQUENCE: 57

Met Glu Ile Arg Gly Leu Ile Thr Arg Leu Leu Gly Pro Cys His Leu
1               5                   10                  15

Arg His Leu Ile Leu Cys Ser Leu Gly Leu Tyr Ser Ile Leu Val Gln
            20                  25                  30

Ser Val His Cys Arg His His Asp Ile Gly Ser Ser Val Ala His Gln
        35                  40                  45

Leu Gly Ser Lys Tyr Ser Gln Ser Ser Ser Leu Ser Ser Ser Ser Gln
    50                  55                  60

Ser Ser Ser Ser Leu Ala Glu Glu Ala Thr Leu Asn Lys Asp Ser Asp
65                  70                  75                  80

Ala Phe Phe Thr Pro Tyr Ile Gly His Gly Asp Ser Val Arg Ile Val
                85                  90                  95

Asp Ala Glu Leu Gly Thr Leu Glu Arg Glu His Ile His Ser Thr Thr
            100                 105                 110

Thr Arg Arg Arg Gly Leu Thr Arg Arg Glu Ser Ser Ser Asp Ala Thr
        115                 120                 125

Asp Ser Asp Pro Leu Val Ile Thr Thr Asp Lys Gly Lys Ile Arg Gly
    130                 135                 140

Thr Thr Leu Glu Ala Pro Ser Gly Lys Lys Val Asp Ala Trp Met Gly
145                 150                 155                 160
```

```
Ile Pro Tyr Ala Gln Pro Pro Leu Gly Pro Leu Arg Phe Arg His Pro
                165                 170                 175
Arg Pro Ala Glu Arg Trp Thr Gly Val Leu Asn Ala Thr Lys Pro Pro
            180                 185                 190
Asn Ser Cys Val Gln Ile Val Asp Thr Val Phe Gly Asp Phe Pro Gly
        195                 200                 205
Ala Thr Met Trp Asn Pro Asn Thr Pro Leu Ser Glu Asp Cys Leu Tyr
    210                 215                 220
Ile Asn Val Val Val Pro Arg Pro Arg Pro Lys Asn Ala Ala Val Met
225                 230                 235                 240
Leu Trp Ile Phe Gly Gly Ser Phe Tyr Ser Gly Thr Ala Thr Leu Asp
                245                 250                 255
Val Tyr Asp His Arg Thr Leu Ala Ser Glu Glu Asn Val Ile Val Val
            260                 265                 270
Ser Leu Gln Tyr Arg Val Ala Ser Leu Gly Phe Leu Phe Leu Gly Thr
        275                 280                 285
Pro Glu Ala Pro Gly Asn Ala Gly Leu Phe Asp Gln Asn Leu Ala Leu
    290                 295                 300
Arg Trp Val Arg Asp Asn Ile His Arg Phe Gly Gly Asp Pro Ser Arg
305                 310                 315                 320
Val Thr Leu Phe Gly Glu Ser Ala Gly Ala Val Ser Val Ser Leu His
                325                 330                 335
Leu Leu Ser Ala Leu Ser Arg Asp Leu Phe Gln Arg Ala Ile Leu Gln
            340                 345                 350
Ser Gly Ser Pro Thr Ala Pro Trp Ala Leu Val Ser Arg Glu Glu Ala
        355                 360                 365
Thr Leu Arg Ala Leu Arg Leu Ala Glu Ala Val Asn Cys Pro His Asp
    370                 375                 380
Ala Thr Lys Leu Ser Asp Ala Val Glu Cys Leu Arg Thr Lys Asp Pro
385                 390                 395                 400
Asn Glu Leu Val Asp Asn Glu Trp Gly Thr Leu Gly Ile Cys Glu Phe
                405                 410                 415
Pro Phe Val Pro Val Val Asp Gly Ala Phe Leu Asp Glu Thr Pro Gln
            420                 425                 430
Arg Ser Leu Ala Ser Gly Arg Phe Lys Lys Thr Asp Ile Leu Thr Gly
        435                 440                 445
Ser Asn Thr Glu Glu Gly Tyr Tyr Phe Ile Ile Tyr Tyr Leu Thr Glu
    450                 455                 460
Leu Leu Arg Lys Glu Glu Gly Val Thr Val Thr Arg Glu Glu Phe Leu
465                 470                 475                 480
Gln Ala Val Arg Glu Leu Asn Pro Tyr Val Asn Gly Ala Ala Arg Gln
                485                 490                 495
Ala Ile Val Phe Glu Tyr Thr Asp Trp Ile Glu Pro Asp Asn Pro Asn
            500                 505                 510
Ser Asn Arg Asp Ala Leu Asp Lys Met Val Gly Asp Tyr His Phe Thr
        515                 520                 525
Cys Asn Val Asn Glu Phe Ala Gln Arg Tyr Ala Glu Glu Gly Asn Asn
    530                 535                 540
Val Phe Met Tyr Leu Tyr Thr His Arg Ser Lys Gly Asn Pro Trp Pro
545                 550                 555                 560
Arg Trp Thr Gly Val Met His Gly Asp Glu Ile Asn Tyr Val Phe Gly
                565                 570                 575
Glu Pro Leu Asn Ser Ala Leu Gly Tyr Gln Asp Asp Glu Lys Asp Phe
```

-continued

```
                       580                 585                 590
Ser Arg Lys Ile Met Arg Tyr Trp Ser Asn Phe Ala Lys Thr Gly Asn
                595                 600                 605

Pro Asn Pro Ser Thr Pro Ser Val Asp Leu Pro Glu Trp Pro Lys His
            610                 615                 620

Thr Ala His Gly Arg His Tyr Leu Glu Leu Gly Leu Asn Thr Thr Phe
625                 630                 635                 640

Val Gly Arg Gly Pro Arg Leu Arg Gln Cys Ala Phe Trp Lys Lys Tyr
                645                 650                 655

Leu Pro Gln Leu Val Ala Ala Thr Ser Asn Leu Gln Val Thr Pro Ala
            660                 665                 670

Pro Ser Val Pro Cys Glu Ser Ser Thr Ser Tyr Arg Ser Thr Leu
        675                 680                 685

Leu Leu Ile Val Thr Leu Leu Leu Val Thr Arg Phe Lys Ile
            690                 695                 700
```

```
<210> SEQ ID NO 58
<211> LENGTH: 18
<212> TYPE: DNA
<213> ORGANISM: Artificial Sequence
<220> FEATURE:
<223> OTHER INFORMATION: Synthetic DNA

<400> SEQUENCE: 58
cgactcggac ccactggt                                                   18

<210> SEQ ID NO 59
<211> LENGTH: 21
<212> TYPE: DNA
<213> ORGANISM: Artificial Sequence
<220> FEATURE:
<223> OTHER INFORMATION: Synthetic DNA

<400> SEQUENCE: 59
gttctgatca aacagccccg c                                               21

<210> SEQ ID NO 60
<211> LENGTH: 459
<212> TYPE: DNA
<213> ORGANISM: Culex pipiens pipiens strain Espro (R)
<220> FEATURE:
<221> NAME/KEY: CDS
<222> LOCATION: (3)..(458)

<400> SEQUENCE: 60 ag ggc aaa atc cgt gga acg aca ctg gaa gcg cca agt gga aag aag    47
   Gly Lys Ile Arg Gly Thr Thr Leu Glu Ala Pro Ser Gly Lys Lys
    1               5                  10                  15 gtg gac gca tgg atg ggc att ccg tac gcg cag ccc ccg ctg ggt ccg    95
Val Asp Ala Trp Met Gly Ile Pro Tyr Ala Gln Pro Pro Leu Gly Pro
                 20                  25                  30 ctc cgg ttt cga cat ccg cga ccc gcc gaa aga tgg acc ggt gtg ctg   143
Leu Arg Phe Arg His Pro Arg Pro Ala Glu Arg Trp Thr Gly Val Leu
             35                  40                  45 aac gcg acc aaa cca ccc aac tcc tgc gtc cag atc gtg gac acc gtg   191
Asn Ala Thr Lys Pro Pro Asn Ser Cys Val Gln Ile Val Asp Thr Val
         50                  55                  60 ttc ggt gac ttc ccg ggg gcc acc atg tgg aac ccg aac aca ccc ctc   239
Phe Gly Asp Phe Pro Gly Ala Thr Met Trp Asn Pro Asn Thr Pro Leu
     65                  70                  75 tcg gag gac tgt ctg tac atc aac gtg gtc gtg cca agg ccg agg ccc   287
Ser Glu Asp Cys Leu Tyr Ile Asn Val Val Val Pro Arg Pro Arg Pro
```

-continued

```
            80                  85                  90                  95
aag aat gcc gct gtc atg ctg tgg atc ttt ggg ggt agc ttc tac tcc         335
Lys Asn Ala Ala Val Met Leu Trp Ile Phe Gly Gly Ser Phe Tyr Ser
                100                 105                 110 ggg act gcc acg ttg gac gtg tac gat cat cgg acg ctg gcc tcg gag         383
Gly Thr Ala Thr Leu Asp Val Tyr Asp His Arg Thr Leu Ala Ser Glu
            115                 120                 125 gag aac gtg atc gtg gtt tcg ctg cag tac cgt gtc gca agt ctt ggt         431
Glu Asn Val Ile Val Val Ser Leu Gln Tyr Arg Val Ala Ser Leu Gly
        130                 135                 140 ttt ctc ttc ctg ggc aca ccg gag gca c                                   459
Phe Leu Phe Leu Gly Thr Pro Glu Ala
    145                 150

<210> SEQ ID NO 61
<211> LENGTH: 152
<212> TYPE: PRT
<213> ORGANISM: Culex pipiens pipiens strain Espro (R)

<400> SEQUENCE: 61

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
            85                  90                  95

Asn Ala Ala Val Met Leu Trp Ile Phe Gly Gly Ser Phe Tyr Ser Gly
        100                 105                 110

Thr Ala Thr Leu Asp Val Tyr Asp His Arg Thr Leu Ala Ser Glu Glu
    115                 120                 125

Asn Val Ile Val Val Ser Leu Gln Tyr Arg Val Ala Ser Leu Gly Phe
130                 135                 140

Leu Phe Leu Gly Thr Pro Glu Ala
145                 150

<210> SEQ ID NO 62
<211> LENGTH: 461
<212> TYPE: DNA
<213> ORGANISM: Culex pipiens quinquefasciatus strain ProR(S)
<220> FEATURE:
<221> NAME/KEY: CDS
<222> LOCATION: (3)..(458)

<400> SEQUENCE: 62 ac aag ggc aaa atc cgt gga acg aca ctg gaa gcg cct agt gga aag         47
   Lys Gly Lys Ile Arg Gly Thr Thr Leu Glu Ala Pro Ser Gly Lys
       1               5                   10                  15 aag gtg gac gca tgg atg ggc att ccg tac gcg cag ccc ccg ctg ggt        95
Lys Val Asp Ala Trp Met Gly Ile Pro Tyr Ala Gln Pro Pro Leu Gly
            20                  25                  30 ccg ctc cgg ttt cga cat ccg cga ccc gcc gaa aga tgg acc ggt gtg       143
Pro Leu Arg Phe Arg His Pro Arg Pro Ala Glu Arg Trp Thr Gly Val
        35                  40                  45 ctg aac gcg acc aaa ccg ccc aac tcc tgc gtc cag atc gtg gac acc       191
Leu Asn Ala Thr Lys Pro Pro Asn Ser Cys Val Gln Ile Val Asp Thr
```

```
Leu Asn Ala Thr Lys Pro Pro Asn Ser Cys Val Gln Ile Val Asp Thr
         50                  55                  60 gtg ttc ggt gac ttc ccg ggg gcc acc atg tgg aac ccg aac aca ccg      239
Val Phe Gly Asp Phe Pro Gly Ala Thr Met Trp Asn Pro Asn Thr Pro
 65                  70                  75 ctc tcg gag gac tgt ctg tac atc aac gtg gtc gtg cca cgg ccc agg      287
Leu Ser Glu Asp Cys Leu Tyr Ile Asn Val Val Val Pro Arg Pro Arg
 80                  85                  90                  95 ccc aag aat gcc gcc gtc atg ctg tgg atc ttc ggg ggt ggc ttc tac      335
Pro Lys Asn Ala Ala Val Met Leu Trp Ile Phe Gly Gly Gly Phe Tyr
                100                 105                 110 tcc ggg act gcc acg ctg gac gtg tac gac cac cgg acg ctg gcc tcg      383
Ser Gly Thr Ala Thr Leu Asp Val Tyr Asp His Arg Thr Leu Ala Ser
            115                 120                 125 gag gag aac gtg atc gta gtt tcg ctg cag tac cgt gtc gca agt ctt      431
Glu Glu Asn Val Ile Val Val Ser Leu Gln Tyr Arg Val Ala Ser Leu
        130                 135                 140 ggg ttt ctc ttc ctg ggc aca ccg gag gca                              461
Gly Phe Leu Phe Leu Gly Thr Pro Glu Ala
145                 150

<210> SEQ ID NO 63
<211> LENGTH: 152
<212> TYPE: PRT
<213> ORGANISM: Culex pipiens quinquefasciatus strain ProR(S)

<400> SEQUENCE: 63

Lys Gly Lys Ile Arg Gly Thr Thr Leu Glu Ala Pro Ser Gly Lys Lys
  1               5                  10                  15

Val Asp Ala Trp Met Gly Ile Pro Tyr Ala Gln Pro Pro Leu Gly Pro
             20                  25                  30

Leu Arg Phe Arg His Pro Arg Pro Ala Glu Arg Trp Thr Gly Val Leu
         35                  40                  45

Asn Ala Thr Lys Pro Pro Asn Ser Cys Val Gln Ile Val Asp Thr Val
     50                  55                  60

Phe Gly Asp Phe Pro Gly Ala Thr Met Trp Asn Pro Asn Thr Pro Leu
 65                  70                  75                  80

Ser Glu Asp Cys Leu Tyr Ile Asn Val Val Val Pro Arg Pro Arg Pro
                 85                  90                  95

Lys Asn Ala Ala Val Met Leu Trp Ile Phe Gly Gly Gly Phe Tyr Ser
            100                 105                 110

Gly Thr Ala Thr Leu Asp Val Tyr Asp His Arg Thr Leu Ala Ser Glu
        115                 120                 125

Glu Asn Val Ile Val Val Ser Leu Gln Tyr Arg Val Ala Ser Leu Gly
    130                 135                 140

Phe Leu Phe Leu Gly Thr Pro Glu
145                 150

<210> SEQ ID NO 64
<211> LENGTH: 448
<212> TYPE: DNA
<213> ORGANISM: Culex pipiens pipiens strain S-LAB (S)
<220> FEATURE:
<221> NAME/KEY: CDS
<222> LOCATION: (3)..(446)

<400> SEQUENCE: 64 ag ggc aaa atc cgt gga acg aca ctg gaa gcg cct agt gga aag aag       47
   Gly Lys Ile Arg Gly Thr Thr Leu Glu Ala Pro Ser Gly Lys Lys
    1               5                  10                  15
```

| | | | | | | | | | | | | | | | | |
|---|---|---|---|---|---|---|---|---|---|---|---|---|---|---|---|---|
| gtg | gac | gca | tgg | atg | ggc | att | ccg | tac | gcg | cag | ccc | ccg | ctg | ggt | ccg | 95 |
| Val | Asp | Ala | Trp | Met | Gly | Ile | Pro | Tyr | Ala | Gln | Pro | Pro | Leu | Gly | Pro | |
| | | | 20 | | | | | 25 | | | | | 30 | | | |
| ctc | cgg | ttt | cga | cat | ccg | cga | ccc | gcc | gaa | aga | tgg | acc | ggt | gtg | ctg | 143 |
| Leu | Arg | Phe | Arg | His | Pro | Arg | Pro | Ala | Glu | Arg | Trp | Thr | Gly | Val | Leu | |
| | | 35 | | | | | 40 | | | | | 45 | | | | |
| aac | gcg | acc | aaa | ccg | ccc | aac | tcc | tgc | gtc | cag | atc | gtg | gac | acc | gtg | 191 |
| Asn | Ala | Thr | Lys | Pro | Pro | Asn | Ser | Cys | Val | Gln | Ile | Val | Asp | Thr | Val | |
| | | | 50 | | | | | 55 | | | | | 60 | | | |
| ttc | ggt | gac | ttc | ccg | ggg | gcc | acc | atg | tgg | aac | ccg | aac | aca | ccg | ctc | 239 |
| Phe | Gly | Asp | Phe | Pro | Gly | Ala | Thr | Met | Trp | Asn | Pro | Asn | Thr | Pro | Leu | |
| 65 | | | | | 70 | | | | | 75 | | | | | | |
| tcg | gag | gac | tgt | ctg | tac | atc | aac | gtg | gtc | gtg | cca | cgg | ccc | agg | ccc | 287 |
| Ser | Glu | Asp | Cys | Leu | Tyr | Ile | Asn | Val | Val | Val | Pro | Arg | Pro | Arg | Pro | |
| 80 | | | | | 85 | | | | | 90 | | | | | 95 | |
| aag | aat | gcc | gcc | gtc | atg | ctg | tgg | atc | ttc | ggg | ggt | ggc | ttc | tac | tcc | 335 |
| Lys | Asn | Ala | Ala | Val | Met | Leu | Trp | Ile | Phe | Gly | Gly | Gly | Phe | Tyr | Ser | |
| | | | | 100 | | | | | 105 | | | | | 110 | | |
| ggg | act | gcc | acg | ctg | gac | gtg | tac | gac | cac | cgg | acg | ctg | gcc | tcg | gag | 383 |
| Gly | Thr | Ala | Thr | Leu | Asp | Val | Tyr | Asp | His | Arg | Thr | Leu | Ala | Ser | Glu | |
| | | | 115 | | | | | 120 | | | | | 125 | | | |
| gag | aac | gtg | atc | gta | gtt | tcg | ctg | cag | tac | cgt | gtc | gca | agt | ctt | ggg | 431 |
| Glu | Asn | Val | Ile | Val | Val | Ser | Leu | Gln | Tyr | Arg | Val | Ala | Ser | Leu | Gly | |
| | | 130 | | | | | 135 | | | | | 140 | | | | |
| ttt | ctc | ttc | ctg | ggc | ac | | | | | | | | | | | 448 |
| Phe | Leu | Phe | Leu | Gly | | | | | | | | | | | | |
| | | 145 | | | | | | | | | | | | | | |

<210> SEQ ID NO 65
<211> LENGTH: 148
<212> TYPE: PRT
<213> ORGANISM: Culex pipiens pipiens strain S-LAB (S)

<400> SEQUENCE: 65

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Val Pro Arg Pro Arg Pro Lys
                85                  90                  95

Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140

Leu Phe Leu Gly
145

<210> SEQ ID NO 66
<211> LENGTH: 459
<212> TYPE: DNA
<213> ORGANISM: Culex pipiens pipiens strain Padova (R)
<220> FEATURE:

```
<221> NAME/KEY: CDS
<222> LOCATION: (3)..(458)

<400> SEQUENCE: 66 ag ggc aaa atc cgt gga acg aca ctg gaa gcg cca agt gga aag aag      47
   Gly Lys Ile Arg Gly Thr Thr Leu Glu Ala Pro Ser Gly Lys Lys
    1               5                  10                  15 gtg gac gca tgg atg ggc att ccg tac gcg cag ccc ccg ctg ggt ccg     95
Val Asp Ala Trp Met Gly Ile Pro Tyr Ala Gln Pro Pro Leu Gly Pro
                 20                  25                  30 ctc cgg ttt cga cat ccg cga ccc gcc gaa aga tgg acc ggt gtg ctg    143
Leu Arg Phe Arg His Pro Arg Pro Ala Glu Arg Trp Thr Gly Val Leu
             35                  40                  45 aac gcg acc aaa cca ccc aac tcc tgc gtc cag atc gtg gac acc gtg    191
Asn Ala Thr Lys Pro Pro Asn Ser Cys Val Gln Ile Val Asp Thr Val
         50                  55                  60 ttc ggt gac ttc ccg ggg gcc acc atg tgg aac ccg aac aca ccc ctc    239
Phe Gly Asp Phe Pro Gly Ala Thr Met Trp Asn Pro Asn Thr Pro Leu
 65                  70                  75                  80 tcg gag gac tgt ctg tac atc aac gtg gtc gtg cca agg ccg agg ccc    287
Ser Glu Asp Cys Leu Tyr Ile Asn Val Val Val Pro Arg Pro Arg Pro
                 85                  90                  95 aag aat gcc gct gtc atg ctg tgg atc ttt ggg ggt agc ttc tac tcc    335
Lys Asn Ala Ala Val Met Leu Trp Ile Phe Gly Gly Ser Phe Tyr Ser
            100                 105                 110 ggg act gcc acg ttg gac gtg tac gat cat cgg acg ctg gcc tcg gag    383
Gly Thr Ala Thr Leu Asp Val Tyr Asp His Arg Thr Leu Ala Ser Glu
        115                 120                 125 gag aac gtg atc gtg gtt tcg ctg cag tac cgt gtc gca agt ctt ggt    431
Glu Asn Val Ile Val Val Ser Leu Gln Tyr Arg Val Ala Ser Leu Gly
    130                 135                 140 ttt ctc ttc ctg ggc aca ccg gag gca c                              459
Phe Leu Phe Leu Gly Thr Pro Glu Ala
145                 150

<210> SEQ ID NO 67
<211> LENGTH: 152
<212> TYPE: PRT
<213> ORGANISM: Culex pipiens pipiens strain Padova (R)

<400> SEQUENCE: 67

Gly Lys Ile Arg Gly Thr Thr Leu Glu Ala Pro Ser Gly Lys Lys Val
  1               5                  10                  15

Asp Ala Trp Met Gly Ile Pro Tyr Ala Gln Pro Pro Leu Gly Pro Leu
                 20                  25                  30

Arg Phe Arg His Pro Arg Pro Ala Glu Arg Trp Thr Gly Val Leu Asn
             35                  40                  45

Ala Thr Lys Pro Pro Asn Ser Cys Val Gln Ile Val Asp Thr Val Phe
         50                  55                  60

Gly Asp Phe Pro Gly Ala Thr Met Trp Asn Pro Asn Thr Pro Leu Ser
 65                  70                  75                  80

Glu Asp Cys Leu Tyr Ile Asn Val Val Val Pro Arg Pro Arg Pro Lys
                 85                  90                  95

Asn Ala Ala Val Met Leu Trp Ile Phe Gly Gly Ser Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140
```

Leu Phe Leu Gly Thr Pro Glu Ala
145              150

<210> SEQ ID NO 68
<211> LENGTH: 463
<212> TYPE: DNA
<213> ORGANISM: Culex pipiens pipiens strain Praias (R)
<220> FEATURE:
<221> NAME/KEY: CDS
<222> LOCATION: (1)..(462)

<400> SEQUENCE: 68 gac aag ggc aaa atc cgt gga acg aca ctg gaa gcg cca agt gga aag        48
Asp Lys Gly Lys Ile Arg Gly Thr Thr Leu Glu Ala Pro Ser Gly Lys
1               5                   10                  15 aag gtg gac gca tgg atg ggc att ccg tac gcg cag ccc ccg ctg ggt        96
Lys Val Asp Ala Trp Met Gly Ile Pro Tyr Ala Gln Pro Pro Leu Gly
            20                  25                  30 ccg ctc cgg ttt cga cat ccg cga ccc gcc gaa aga tgg acc ggt gtg       144
Pro Leu Arg Phe Arg His Pro Arg Pro Ala Glu Arg Trp Thr Gly Val
        35                  40                  45 ctg aac gcg acc aaa cca ccc aac tcc tgc gtc cag atc gtg gac acc       192
Leu Asn Ala Thr Lys Pro Pro Asn Ser Cys Val Gln Ile Val Asp Thr
    50                  55                  60 gtg ttc ggt gac ttc ccg ggg gcc acc atg tgg aac ccg aac aca ccc       240
Val Phe Gly Asp Phe Pro Gly Ala Thr Met Trp Asn Pro Asn Thr Pro
65                  70                  75                  80 ctc tcg gag gac tgt ctg tac atc aac gtg gtc gtg cca agg ccg agg       288
Leu Ser Glu Asp Cys Leu Tyr Ile Asn Val Val Val Pro Arg Pro Arg
                85                  90                  95 ccc aag aat gcc gct gtc atg ctg tgg atc ttt ggg ggt agc ttc tac       336
Pro Lys Asn Ala Ala Val Met Leu Trp Ile Phe Gly Gly Ser Phe Tyr
            100                 105                 110 tcc ggg act gcc acg ttg gac gtg tac gat cat cgg acg ctg gcc tcg       384
Ser Gly Thr Ala Thr Leu Asp Val Tyr Asp His Arg Thr Leu Ala Ser
        115                 120                 125 gag gag aac gtg atc gtg gtt tcg ctg cag tac cgt gtc gca agt ctt       432
Glu Glu Asn Val Ile Val Val Ser Leu Gln Tyr Arg Val Ala Ser Leu
    130                 135                 140 ggt ttt ctc ttc ctg ggc aca ccg gag gca c                              463
Gly Phe Leu Phe Leu Gly Thr Pro Glu Ala
145              150

<210> SEQ ID NO 69
<211> LENGTH: 154
<212> TYPE: PRT
<213> ORGANISM: Culex pipiens pipiens strain Praias (R)

<400> SEQUENCE: 69

Asp Lys Gly Lys Ile Arg Gly Thr Thr Leu Glu Ala Pro Ser Gly Lys
1               5                   10                  15

Lys Val Asp Ala Trp Met Gly Ile Pro Tyr Ala Gln Pro Pro Leu Gly
            20                  25                  30

Pro Leu Arg Phe Arg His Pro Arg Pro Ala Glu Arg Trp Thr Gly Val
        35                  40                  45

Leu Asn Ala Thr Lys Pro Pro Asn Ser Cys Val Gln Ile Val Asp Thr
    50                  55                  60

Val Phe Gly Asp Phe Pro Gly Ala Thr Met Trp Asn Pro Asn Thr Pro
65                  70                  75                  80

Leu Ser Glu Asp Cys Leu Tyr Ile Asn Val Val Val Pro Arg Pro Arg
                85                  90                  95

```
Pro Lys Asn Ala Ala Val Met Leu Trp Ile Phe Gly Gly Ser Phe Tyr
            100                 105                 110

Ser Gly Thr Ala Thr Leu Asp Val Tyr Asp His Arg Thr Leu Ala Ser
            115                 120                 125

Glu Glu Asn Val Ile Val Val Ser Leu Gln Tyr Arg Val Ala Ser Leu
        130                 135                 140

Gly Phe Leu Phe Leu Gly Thr Pro Glu Ala
145                 150

<210> SEQ ID NO 70
<211> LENGTH: 463
<212> TYPE: DNA
<213> ORGANISM: Culex pipiens quinquefasciatus strain Supercar (R)
<220> FEATURE:
<221> NAME/KEY: CDS
<222> LOCATION: (1)..(462)

<400> SEQUENCE: 70 gac aag ggc aaa atc cgt gga acg aca ctg gaa gcg cca agt gga aag      48
Asp Lys Gly Lys Ile Arg Gly Thr Thr Leu Glu Ala Pro Ser Gly Lys
1               5                   10                  15 aag gtg gac gca tgg atg ggc att ccg tac gcg cag ccc ccg ctg ggt      96
Lys Val Asp Ala Trp Met Gly Ile Pro Tyr Ala Gln Pro Pro Leu Gly
            20                  25                  30 ccg ctc cgg ttt cga cat ccg cga ccc gcc gaa aga tgg acc ggt gtg     144
Pro Leu Arg Phe Arg His Pro Arg Pro Ala Glu Arg Trp Thr Gly Val
        35                  40                  45 ctg aac gcg acc aaa cca ccc aac tcc tgc gtc cag atc gtg gac acc     192
Leu Asn Ala Thr Lys Pro Pro Asn Ser Cys Val Gln Ile Val Asp Thr
    50                  55                  60 gtg ttc ggt gac ttc ccg ggg gcc acc atg tgg aac ccg aac aca ccc     240
Val Phe Gly Asp Phe Pro Gly Ala Thr Met Trp Asn Pro Asn Thr Pro
65                  70                  75                  80 ctc tcg gag gac tgt ctg tac atc aac gtg gtc gtg cca agg ccg agg     288
Leu Ser Glu Asp Cys Leu Tyr Ile Asn Val Val Val Pro Arg Pro Arg
                85                  90                  95 ccc aag aat gcc gct gtc atg ctg tgg atc ttt ggg ggt agc ttc tac     336
Pro Lys Asn Ala Ala Val Met Leu Trp Ile Phe Gly Gly Ser Phe Tyr
            100                 105                 110 tcc ggg act gcc acg ttg gac gtg tac gat cat cgg acg ctg gcc tcg     384
Ser Gly Thr Ala Thr Leu Asp Val Tyr Asp His Arg Thr Leu Ala Ser
        115                 120                 125 gag gag aac gtg atc gtg gtt tcg ctg cag tac cgt gtc gca agt ctt     432
Glu Glu Asn Val Ile Val Val Ser Leu Gln Tyr Arg Val Ala Ser Leu
    130                 135                 140 ggt ttt ctc ttc ctg ggc aca ccg gag gca c                           463
Gly Phe Leu Phe Leu Gly Thr Pro Glu Ala
145                 150

<210> SEQ ID NO 71
<211> LENGTH: 154
<212> TYPE: PRT
<213> ORGANISM: Culex pipiens quinquefasciatus strain Supercar (R)

<400> SEQUENCE: 71

Asp Lys Gly Lys Ile Arg Gly Thr Thr Leu Glu Ala Pro Ser Gly Lys
1               5                   10                  15

Lys Val Asp Ala Trp Met Gly Ile Pro Tyr Ala Gln Pro Pro Leu Gly
            20                  25                  30

Pro Leu Arg Phe Arg His Pro Arg Pro Ala Glu Arg Trp Thr Gly Val
        35                  40                  45
```

```
Leu Asn Ala Thr Lys Pro Pro Asn Ser Cys Val Gln Ile Val Asp Thr
         50                  55                  60

Val Phe Gly Asp Phe Pro Gly Ala Thr Met Trp Asn Pro Asn Thr Pro
 65                  70                  75                  80

Leu Ser Glu Asp Cys Leu Tyr Ile Asn Val Val Pro Arg Pro Arg
                 85                  90                  95

Pro Lys Asn Ala Ala Val Met Leu Trp Ile Phe Gly Gly Ser Phe Tyr
            100                 105                 110

Ser Gly Thr Ala Thr Leu Asp Val Tyr Asp His Arg Thr Leu Ala Ser
            115                 120                 125

Glu Glu Asn Val Ile Val Val Ser Leu Gln Tyr Arg Val Ala Ser Leu
        130                 135                 140

Gly Phe Leu Phe Leu Gly Thr Pro Glu Ala
145                 150

<210> SEQ ID NO 72
<211> LENGTH: 448
<212> TYPE: DNA
<213> ORGANISM: Culex pipiens pipiens strain Bruges A (S)
<220> FEATURE:
<221> NAME/KEY: CDS
<222> LOCATION: (3)..(446)

<400> SEQUENCE: 72 ag ggc aaa atc cgt gga acg aca ctg gaa gcg cca agt gga aag aag        47
   Gly Lys Ile Arg Gly Thr Thr Leu Glu Ala Pro Ser Gly Lys Lys
   1               5                  10                  15 gtg gac gca tgg atg ggc att ccg tac gcg cag ccc ccg ctg ggt ccg       95
Val Asp Ala Trp Met Gly Ile Pro Tyr Ala Gln Pro Pro Leu Gly Pro
                20                  25                  30 ctc cgg ttt cga cat ccg cga ccc gcc gaa aga tgg acc ggt gtg ctg      143
Leu Arg Phe Arg His Pro Arg Pro Ala Glu Arg Trp Thr Gly Val Leu
             35                  40                  45 aac gcg acc aaa cca ccc aac tcc tgc gtc cag atc gtg gac acc gtg      191
Asn Ala Thr Lys Pro Pro Asn Ser Cys Val Gln Ile Val Asp Thr Val
         50                  55                  60 ttc ggt gac ttc ccg ggg gcc acc atg tgg aac ccg aac aca ccc ctc      239
Phe Gly Asp Phe Pro Gly Ala Thr Met Trp Asn Pro Asn Thr Pro Leu
 65                  70                  75 tcg gag gac tgt ctg tac atc aac gtg gtc gtg cca agg ccg agg ccc      287
Ser Glu Asp Cys Leu Tyr Ile Asn Val Val Val Pro Arg Pro Arg Pro
 80                  85                  90                  95 aag aat gcc gct gtc atg ctg tgg atc ttt ggg ggt ggc ttc tac tcc      335
Lys Asn Ala Ala Val Met Leu Trp Ile Phe Gly Gly Gly Phe Tyr Ser
            100                 105                 110 ggg act gcc acg ttg gac gtg tac gat cat cgg acg ctg gcc tcg gag      383
Gly Thr Ala Thr Leu Asp Val Tyr Asp His Arg Thr Leu Ala Ser Glu
            115                 120                 125 gag aac gtg atc gtg gtt tcg ctg cag tac cgt gtc gca agt ctt ggt      431
Glu Asn Val Ile Val Val Ser Leu Gln Tyr Arg Val Ala Ser Leu Gly
        130                 135                 140 ttt ctc ttc ctg ggc ac                                               448
Phe Leu Phe Leu Gly
    145

<210> SEQ ID NO 73
<211> LENGTH: 148
<212> TYPE: PRT
<213> ORGANISM: Culex pipiens pipiens strain Bruges A (S)

<400> SEQUENCE: 73
```

```
Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
                20                  25                  30

Arg Phe Arg His Pro Arg Pro Ala Glu Arg Trp Thr Gly Val Leu Asn
            35                  40                  45

Ala Thr Lys Pro Pro Asn Ser Cys Val Gln Ile Val Asp Thr Val Phe
        50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Val Pro Arg Pro Arg Pro Lys
                85                  90                  95

Asn Ala Ala Val Met Leu Trp Ile Phe Gly Gly Gly Phe Tyr Ser Gly
                100                 105                 110

Thr Ala Thr Leu Asp Val Tyr Asp His Arg Thr Leu Ala Ser Glu Glu
            115                 120                 125

Asn Val Ile Val Val Ser Leu Gln Tyr Arg Val Ala Ser Leu Gly Phe
        130                 135                 140

Leu Phe Leu Gly
145
```

<210> SEQ ID NO 74
<211> LENGTH: 457
<212> TYPE: DNA
<213> ORGANISM: Culex pipiens quinquefasciatus strain BO (R)
<220> FEATURE:
<221> NAME/KEY: CDS
<222> LOCATION: (1)..(456)

<400> SEQUENCE: 74

```
ggc aaa atc cgt gga acg aca ctg gaa gcg cct agc gga aag aag gtg      48
Gly Lys Ile Arg Gly Thr Thr Leu Glu Ala Pro Ser Gly Lys Lys Val
1               5                   10                  15 gac gca tgg atg ggc att ccg tac gcg cag cct ccg ctg ggt ccg ctc      96
Asp Ala Trp Met Gly Ile Pro Tyr Ala Gln Pro Pro Leu Gly Pro Leu
                20                  25                  30 cgg ttt cga cat ccg cga ccc gcc gaa aga tgg acc ggt gtg ctg aac     144
Arg Phe Arg His Pro Arg Pro Ala Glu Arg Trp Thr Gly Val Leu Asn
            35                  40                  45 gcg acc aaa ccg ccc aac tcc tgc gtc cag atc gtg gac acc gtg ttc     192
Ala Thr Lys Pro Pro Asn Ser Cys Val Gln Ile Val Asp Thr Val Phe
        50                  55                  60 ggt gac ttc ccg ggg gcc acc atg tgg aac ccg aac aca ccg ctc tcg     240
Gly Asp Phe Pro Gly Ala Thr Met Trp Asn Pro Asn Thr Pro Leu Ser
65                  70                  75                  80 gag gac tgt ctg tac atc aac gtg gtc gtg cca cgg ccc agg ccc aag     288
Glu Asp Cys Leu Tyr Ile Asn Val Val Val Pro Arg Pro Arg Pro Lys
                85                  90                  95 aat gcc gcc gtc atg ctg tgg atc ttc ggg ggt agc ttc tac tcc ggg     336
Asn Ala Ala Val Met Leu Trp Ile Phe Gly Gly Ser Phe Tyr Ser Gly
                100                 105                 110 act gcc acg ctg gac gtg tac gac cac cgg acg ctg gcc tcg gag gag     384
Thr Ala Thr Leu Asp Val Tyr Asp His Arg Thr Leu Ala Ser Glu Glu
            115                 120                 125 aac gtg atc gta gtt tcg ctg cag tac cgt gtc gca agt ctt ggt ttt     432
Asn Val Ile Val Val Ser Leu Gln Tyr Arg Val Ala Ser Leu Gly Phe
        130                 135                 140 ctc ttc ctg ggc aca ccg gag gca c                                   457
Leu Phe Leu Gly Thr Pro Glu Ala
145                 150
```

<210> SEQ ID NO 75
<211> LENGTH: 152
<212> TYPE: PRT
<213> ORGANISM: Culex pipiens quinquefasciatus strain BO (R)

<400> SEQUENCE: 75

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Ser Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140

Leu Phe Leu Gly Thr Pro Glu Ala
145                 150

<210> SEQ ID NO 76
<211> LENGTH: 447
<212> TYPE: DNA
<213> ORGANISM: Culex pipiens quinquefasciatus strain DJI (R)
<220> FEATURE:
<221> NAME/KEY: CDS
<222> LOCATION: (1)..(444)

<400> SEQUENCE: 76 ggc aaa atc cgt gga acg aca ctg gaa gcg cct agc gga aag aag gtg     48
Gly Lys Ile Arg Gly Thr Thr Leu Glu Ala Pro Ser Gly Lys Lys Val
1               5                   10                  15 gac gca tgg atg ggc att ccg tac gcg cag cct ccg ctg ggt ccg ctc     96
Asp Ala Trp Met Gly Ile Pro Tyr Ala Gln Pro Pro Leu Gly Pro Leu
            20                  25                  30 cgg ttt cga cat ccg cga ccc gcc gaa aga tgg acc ggt gtg ctg aac    144
Arg Phe Arg His Pro Arg Pro Ala Glu Arg Trp Thr Gly Val Leu Asn
        35                  40                  45 gcg acc aaa ccg ccc aac tcc tgc gtc cag atc gtg gac acc gtg ttc    192
Ala Thr Lys Pro Pro Asn Ser Cys Val Gln Ile Val Asp Thr Val Phe
    50                  55                  60 ggt gac ttc ccg ggg gcc acc atg tgg aac ccg aac aca ccg ctc tcg    240
Gly Asp Phe Pro Gly Ala Thr Met Trp Asn Pro Asn Thr Pro Leu Ser
65                  70                  75                  80 gag gac tgt ctg tac atc aac gtg gtc gtg cca cgg ccc agg ccc aag    288
Glu Asp Cys Leu Tyr Ile Asn Val Val Val Pro Arg Pro Arg Pro Lys
                85                  90                  95 aat gcc gcc gtc atg ctg tgg atc ttc ggg ggt agc ttc tac tcc ggg    336
Asn Ala Ala Val Met Leu Trp Ile Phe Gly Gly Ser Phe Tyr Ser Gly
            100                 105                 110 act gcc acg ctg gac gtg tac gac cac cgg acg ctg gcc tcg gag gag    384
Thr Ala Thr Leu Asp Val Tyr Asp His Arg Thr Leu Ala Ser Glu Glu -continued

```
                115                 120                 125
aac gtg atc gta gtt tcg ctg cag tac cgt gtc gca agt ctt ggt ttt      432
Asn Val Ile Val Val Ser Leu Gln Tyr Arg Val Ala Ser Leu Gly Phe
        130                 135                 140 ctc ttc ctg ggc aca                                                   447
Leu Phe Leu Gly
145
```

<210> SEQ ID NO 77
<211> LENGTH: 148
<212> TYPE: PRT
<213> ORGANISM: Culex pipiens quinquefasciatus strain DJI (R)

<400> SEQUENCE: 77

```
Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Val Pro Arg Pro Arg Pro Lys
                85                  90                  95

Asn Ala Ala Val Met Leu Trp Ile Phe Gly Gly Ser Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140

Leu Phe Leu Gly
145
```

<210> SEQ ID NO 78
<211> LENGTH: 457
<212> TYPE: DNA
<213> ORGANISM: Culex pipiens quinquefasciatus strain Harare (R)
<220> FEATURE:
<221> NAME/KEY: CDS
<222> LOCATION: (1)..(456)

<400> SEQUENCE: 78

```
ggc aaa atc cgt gga acg aca ctg gaa gcg cct agc gga aag aag gtg      48
Gly Lys Ile Arg Gly Thr Thr Leu Glu Ala Pro Ser Gly Lys Lys Val
1               5                   10                  15 gac gca tgg atg ggc att ccg tac gcg cag cct ccg ctg ggt ccg ctc      96
Asp Ala Trp Met Gly Ile Pro Tyr Ala Gln Pro Pro Leu Gly Pro Leu
            20                  25                  30 cgg ttt cga cat ccg cga ccc gcc gaa aga tgg acc ggt gtg ctg aac      144
Arg Phe Arg His Pro Arg Pro Ala Glu Arg Trp Thr Gly Val Leu Asn
        35                  40                  45 gcg acc aaa ccg ccc aac tcc tgc gtc cag atc gtg gac acc gtg ttc      192
Ala Thr Lys Pro Pro Asn Ser Cys Val Gln Ile Val Asp Thr Val Phe
    50                  55                  60 ggt gac ttc ccg ggg gcc acc atg tgg aac ccg aac aca ccg ctc tcg      240
Gly Asp Phe Pro Gly Ala Thr Met Trp Asn Pro Asn Thr Pro Leu Ser
65                  70                  75                  80 gag gac tgt ctg tac atc aac gtg gtc gtg cca cgg ccc agg ccc aag      288
```

```
Glu Asp Cys Leu Tyr Ile Asn Val Val Val Pro Arg Pro Arg Pro Lys
                85                  90                  95 aat gcc gcc gtc atg ctg tgg atc ttc ggg ggt agc ttc tac tcc ggg      336
Asn Ala Ala Val Met Leu Trp Ile Phe Gly Gly Ser Phe Tyr Ser Gly
            100                 105                 110 act gcc acg ctg gac gtg tac gac cac cgg acg ctg gcc tcg gag gag      384
Thr Ala Thr Leu Asp Val Tyr Asp His Arg Thr Leu Ala Ser Glu Glu
            115                 120                 125 aac gtg atc gta gtt tcg ctg cag tac cgt gtc gca agt ctt ggt ttt      432
Asn Val Ile Val Val Ser Leu Gln Tyr Arg Val Ala Ser Leu Gly Phe
            130                 135                 140 ctc ttc ctg ggc aca ccg gag gca c                                    457
Leu Phe Leu Gly Thr Pro Glu Ala
145                 150

<210> SEQ ID NO 79
<211> LENGTH: 152
<212> TYPE: PRT
<213> ORGANISM: Culex pipiens quinquefasciatus strain Harare (R)

<400> SEQUENCE: 79

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Val Pro Arg Pro Arg Pro Lys
                85                  90                  95

Asn Ala Ala Val Met Leu Trp Ile Phe Gly Gly Ser Phe Tyr Ser Gly
            100                 105                 110

Thr Ala Thr Leu Asp Val Tyr Asp His Arg Thr Leu Ala Ser Glu Glu
            115                 120                 125

Asn Val Ile Val Val Ser Leu Gln Tyr Arg Val Ala Ser Leu Gly Phe
            130                 135                 140

Leu Phe Leu Gly Thr Pro Glu Ala
145                 150

<210> SEQ ID NO 80
<211> LENGTH: 458
<212> TYPE: DNA
<213> ORGANISM: Culex pipiens quinquefasciatus strain Martinique (R)
<220> FEATURE:
<221> NAME/KEY: CDS
<222> LOCATION: (1)..(456)

<400> SEQUENCE: 80 ggc aaa atc cgt gga acg aca ctg gaa gcg cct agc gga aag aag gtg       48
Gly Lys Ile Arg Gly Thr Thr Leu Glu Ala Pro Ser Gly Lys Lys Val
1               5                   10                  15 gac gca tgg atg ggc att ccg tac gcg cag cct ccg ctg ggt ccg ctc       96
Asp Ala Trp Met Gly Ile Pro Tyr Ala Gln Pro Pro Leu Gly Pro Leu
            20                  25                  30 cgg ttt cga cat ccg cga ccc gcc gaa aga tgg acc ggt gtg ctg aac      144
Arg Phe Arg His Pro Arg Pro Ala Glu Arg Trp Thr Gly Val Leu Asn
        35                  40                  45
```

```
gcg acc aaa ccg ccc aac tcc tgc gtc cag atc gtg gac acc gtg ttc     192
Ala Thr Lys Pro Pro Asn Ser Cys Val Gln Ile Val Asp Thr Val Phe
 50              55                  60 ggt gac ttc ccg ggg gcc acc atg tgg aac ccg aac aca ccg ctc tcg     240
Gly Asp Phe Pro Gly Ala Thr Met Trp Asn Pro Asn Thr Pro Leu Ser
 65              70                  75                  80 gag gac tgt ctg tac atc aac gtg gtc gtg cca cgg ccc agg ccc aag     288
Glu Asp Cys Leu Tyr Ile Asn Val Val Val Pro Arg Pro Arg Pro Lys
                 85                  90                  95 aat gcc gcc gtc atg ctg tgg atc ttc ggg ggt agc ttc tac tcc ggg     336
Asn Ala Ala Val Met Leu Trp Ile Phe Gly Gly Ser Phe Tyr Ser Gly
            100                 105                 110 act gcc acg ctg gac gtg tac gac cac cgg acg ctg gcc tcg gag gag     384
Thr Ala Thr Leu Asp Val Tyr Asp His Arg Thr Leu Ala Ser Glu Glu
        115                 120                 125 aac gtg atc gta gtt tcg ctg cag tac cgt gtc gca agt ctt ggt ttt     432
Asn Val Ile Val Val Ser Leu Gln Tyr Arg Val Ala Ser Leu Gly Phe
130                 135                 140 ctc ttc ctg ggc aca ccg gag gca cc                                  458
Leu Phe Leu Gly Thr Pro Glu Ala
145                 150

<210> SEQ ID NO 81
<211> LENGTH: 152
<212> TYPE: PRT
<213> ORGANISM: Culex pipiens quinquefasciatus strain Martinique (R)

<400> SEQUENCE: 81

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Val Pro Arg Pro Arg Pro Lys
                85                  90                  95

Asn Ala Ala Val Met Leu Trp Ile Phe Gly Gly Ser Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140

Leu Phe Leu Gly Thr Pro Glu Ala
145                 150

<210> SEQ ID NO 82
<211> LENGTH: 447
<212> TYPE: DNA
<213> ORGANISM: Culex pipiens pipiens strain Barriol (R)
<220> FEATURE:
<221> NAME/KEY: CDS
<222> LOCATION: (3)..(446)

<400> SEQUENCE: 82 ag ggc aaa atc cgt gga acg aca ctg gaa gcg cca agt gga aag aag       47
   Gly Lys Ile Arg Gly Thr Thr Leu Glu Ala Pro Ser Gly Lys Lys
    1               5                   10                  15
```

```
gtg gac gca tgg atg ggc att ccg tac gcg cag ccc ccg ctg ggt ccg     95
Val Asp Ala Trp Met Gly Ile Pro Tyr Ala Gln Pro Pro Leu Gly Pro
             20                  25                  30 ctc cgg ttt cga cat ccg cga ccc gcc gaa aga tgg acc ggt gtg ctg    143
Leu Arg Phe Arg His Pro Arg Pro Ala Glu Arg Trp Thr Gly Val Leu
         35                  40                  45 aac gcg acc aaa cca ccc aac tcc tgc gtc cag atc gtg gac acc gtg    191
Asn Ala Thr Lys Pro Pro Asn Ser Cys Val Gln Ile Val Asp Thr Val
 50                  55                  60 ttc ggt gac ttc ccg ggg gcc acc atg tgg aac ccg aac aca ccc ctc    239
Phe Gly Asp Phe Pro Gly Ala Thr Met Trp Asn Pro Asn Thr Pro Leu
             65                  70                  75 tcg gag gac tgt ctg tac atc aac gtg gtc gtg cca agg ccg agg ccc    287
Ser Glu Asp Cys Leu Tyr Ile Asn Val Val Val Pro Arg Pro Arg Pro
 80                  85                  90                  95 aag aat gcc gct gtc atg ctg tgg atc ttt ggg ggt agc ttc tac tcc    335
Lys Asn Ala Ala Val Met Leu Trp Ile Phe Gly Gly Ser Phe Tyr Ser
                 100                 105                 110 ggg act gcc acg ttg gac gtg tac gat cat cgg acg ctg gcc tcg gag    383
Gly Thr Ala Thr Leu Asp Val Tyr Asp His Arg Thr Leu Ala Ser Glu
             115                 120                 125 gag aac gtg atc gtg gtt tcg ctg cag tac cgt gtc gca agt ctt ggt    431
Glu Asn Val Ile Val Val Ser Leu Gln Tyr Arg Val Ala Ser Leu Gly
         130                 135                 140 ttt ctc ttc ctg ggc a                                              447
Phe Leu Phe Leu Gly
    145

<210> SEQ ID NO 83
<211> LENGTH: 148
<212> TYPE: PRT
<213> ORGANISM: Culex pipiens pipiens strain Barriol (R)

<400> SEQUENCE: 83

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
             20                  25                  30

Arg Phe Arg His Pro Arg Pro Ala Glu Arg Trp Thr Gly Val Leu Asn
         35                  40                  45

Ala Thr Lys Pro Pro Asn Ser Cys Val Gln Ile Val Asp Thr Val Phe
     50                  55                  60

Gly Asp Phe Pro Gly Ala Thr Met Trp Asn Pro Asn Thr Pro Leu Ser
 65                  70                  75                  80

Glu Asp Cys Leu Tyr Ile Asn Val Val Val Pro Arg Pro Arg Pro Lys
                 85                  90                  95

Asn Ala Ala Val Met Leu Trp Ile Phe Gly Gly Ser Phe Tyr Ser Gly
             100                 105                 110

Thr Ala Thr Leu Asp Val Tyr Asp His Arg Thr Leu Ala Ser Glu Glu
         115                 120                 125

Asn Val Ile Val Val Ser Leu Gln Tyr Arg Val Ala Ser Leu Gly Phe
     130                 135                 140

Leu Phe Leu Gly
145

<210> SEQ ID NO 84
<211> LENGTH: 447
<212> TYPE: DNA
<213> ORGANISM: Culex pipiens pipiens strain Bleuet (S)
```

```
<220> FEATURE:
<221> NAME/KEY: CDS
<222> LOCATION: (3)..(446)

<400> SEQUENCE: 84 ag ggc aaa atc cgt gga acg aca ctg gaa gcg cca agt gga aag aag        47
   Gly Lys Ile Arg Gly Thr Thr Leu Glu Ala Pro Ser Gly Lys Lys
    1               5                  10                  15 gtg gac gca tgg atg ggc att ccg tac gcg cag ccc ccg ctg ggt ccg       95
Val Asp Ala Trp Met Gly Ile Pro Tyr Ala Gln Pro Pro Leu Gly Pro
                    20                  25                  30 ctc cgg ttt cga cat ccg cga ccc gcc gaa aga tgg acc ggt gtg ctg      143
Leu Arg Phe Arg His Pro Arg Pro Ala Glu Arg Trp Thr Gly Val Leu
                35                  40                  45 aac gcg acc aaa cca ccc aac tcc tgc gtc cag atc gtg gac acc gtg      191
Asn Ala Thr Lys Pro Pro Asn Ser Cys Val Gln Ile Val Asp Thr Val
            50                  55                  60 ttc ggt gac ttc ccg ggg gcc acc atg tgg aac ccg aac aca ccc ctc      239
Phe Gly Asp Phe Pro Gly Ala Thr Met Trp Asn Pro Asn Thr Pro Leu
65                  70                  75 tcg gag gac tgt ctg tac atc aac gtg gtc gtg cca agg ccg agg ccc      287
Ser Glu Asp Cys Leu Tyr Ile Asn Val Val Val Pro Arg Pro Arg Pro
80                  85                  90                  95 aag aat gcc gct gtc atg ctg tgg atc ttt ggg ggt ggc ttc tac tcc      335
Lys Asn Ala Ala Val Met Leu Trp Ile Phe Gly Gly Gly Phe Tyr Ser
                    100                 105                 110 ggg act gcc acg ttg gac gtg tac gat cat cgg acg ctg gcc tcg gag      383
Gly Thr Ala Thr Leu Asp Val Tyr Asp His Arg Thr Leu Ala Ser Glu
                115                 120                 125 gag aac gtg atc gtg gtt tcg ctg cag tac cgt gtc gca agt ctt ggt      431
Glu Asn Val Ile Val Val Ser Leu Gln Tyr Arg Val Ala Ser Leu Gly
            130                 135                 140 ttt ctc ttc ctg ggc a                                                447
Phe Leu Phe Leu Gly
        145

<210> SEQ ID NO 85
<211> LENGTH: 148
<212> TYPE: PRT
<213> ORGANISM: Culex pipiens pipiens strain Bleuet (S)

<400> SEQUENCE: 85

Gly Lys Ile Arg Gly Thr Thr Leu Glu Ala Pro Ser Gly Lys Lys Val
  1               5                  10                  15

Asp Ala Trp Met Gly Ile Pro Tyr Ala Gln Pro Pro Leu Gly Pro Leu
                 20                  25                  30

Arg Phe Arg His Pro Arg Pro Ala Glu Arg Trp Thr Gly Val Leu Asn
             35                  40                  45

Ala Thr Lys Pro Pro Asn Ser Cys Val Gln Ile Val Asp Thr Val Phe
         50                  55                  60

Gly Asp Phe Pro Gly Ala Thr Met Trp Asn Pro Asn Thr Pro Leu Ser
 65                  70                  75                  80

Glu Asp Cys Leu Tyr Ile Asn Val Val Val Pro Arg Pro Arg Pro Lys
                 85                  90                  95

Asn Ala Ala Val Met Leu Trp Ile Phe Gly Gly Gly Phe Tyr Ser Gly
             100                 105                 110

Thr Ala Thr Leu Asp Val Tyr Asp His Arg Thr Leu Ala Ser Glu Glu
         115                 120                 125

Asn Val Ile Val Val Ser Leu Gln Tyr Arg Val Ala Ser Leu Gly Phe
     130                 135                 140
```

```
Leu Phe Leu Gly
145

<210> SEQ ID NO 86
<211> LENGTH: 448
<212> TYPE: DNA
<213> ORGANISM: Culex pipiens pipiens strain Bruges B (S)
<220> FEATURE:
<221> NAME/KEY: CDS
<222> LOCATION: (3)..(446)

<400> SEQUENCE: 86 ag ggc aaa atc cgt gga acg aca ctg gaa gcg cca agt gga aag aag        47
   Gly Lys Ile Arg Gly Thr Thr Leu Glu Ala Pro Ser Gly Lys Lys
     1               5                  10                  15 gtg gac gca tgg atg ggc att ccg tac gcg cag ccc ccg ctg ggt ccg        95
Val Asp Ala Trp Met Gly Ile Pro Tyr Ala Gln Pro Pro Leu Gly Pro
                 20                  25                  30 ctc cgg ttt cga cat ccg cga ccc gcc gaa aga tgg acc ggt gtg ctg       143
Leu Arg Phe Arg His Pro Arg Pro Ala Glu Arg Trp Thr Gly Val Leu
             35                  40                  45 aac gcg acc aaa cca ccc aac tcc tgc gtc cag atc gtg gac acc gtg       191
Asn Ala Thr Lys Pro Pro Asn Ser Cys Val Gln Ile Val Asp Thr Val
         50                  55                  60 ttc ggt gac ttc ccg ggg gcc acc atg tgg aac ccg aac aca ccc ctc       239
Phe Gly Asp Phe Pro Gly Ala Thr Met Trp Asn Pro Asn Thr Pro Leu
     65                  70                  75 tcg gag gac tgt ctg tac atc aac gtg gtc gtg cca agg ccg agg ccc       287
Ser Glu Asp Cys Leu Tyr Ile Asn Val Val Val Pro Arg Pro Arg Pro
 80                  85                  90                  95 aag aat gcc gct gtc atg ctg tgg atc ttt ggg ggt ggc ttc tac tcc       335
Lys Asn Ala Ala Val Met Leu Trp Ile Phe Gly Gly Gly Phe Tyr Ser
                100                 105                 110 ggg act gcc acg ttg gac gtg tac gat cat cgg acg ctg gcc tcg gag       383
Gly Thr Ala Thr Leu Asp Val Tyr Asp His Arg Thr Leu Ala Ser Glu
            115                 120                 125 gag aac gtg atc gtg gtt tcg ctg cag tac cgt gtc gca agt ctt ggt       431
Glu Asn Val Ile Val Val Ser Leu Gln Tyr Arg Val Ala Ser Leu Gly
        130                 135                 140 ttt ctc ttc ctg ggc ac                                                448
Phe Leu Phe Leu Gly
    145

<210> SEQ ID NO 87
<211> LENGTH: 148
<212> TYPE: PRT
<213> ORGANISM: Culex pipiens pipiens strain Bruges B (S)

<400> SEQUENCE: 87

Gly Lys Ile Arg Gly Thr Thr Leu Glu Ala Pro Ser Gly Lys Lys Val
 1               5                  10                  15

Asp Ala Trp Met Gly Ile Pro Tyr Ala Gln Pro Pro Leu Gly Pro Leu
                 20                  25                  30

Arg Phe Arg His Pro Arg Pro Ala Glu Arg Trp Thr Gly Val Leu Asn
             35                  40                  45

Ala Thr Lys Pro Pro Asn Ser Cys Val Gln Ile Val Asp Thr Val Phe
         50                  55                  60

Gly Asp Phe Pro Gly Ala Thr Met Trp Asn Pro Asn Thr Pro Leu Ser
 65                  70                  75                  80

Glu Asp Cys Leu Tyr Ile Asn Val Val Val Pro Arg Pro Arg Pro Lys
                 85                  90                  95
```

```
Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140

Leu Phe Leu Gly
145

<210> SEQ ID NO 88
<211> LENGTH: 447
<212> TYPE: DNA
<213> ORGANISM: Culex pipiens pipiens strain Heteren (S)
<220> FEATURE:
<221> NAME/KEY: CDS
<222> LOCATION: (3)..(446)

<400> SEQUENCE: 88 ag ggc aaa atc cgt gga acg aca ctg gaa gcg cca agt gga aag aag      47
   Gly Lys Ile Arg Gly Thr Thr Leu Glu Ala Pro Ser Gly Lys Lys
   1               5                   10                  15 gtg gac gca tgg atg ggc att ccg tac gcg cag ccc ccg ctg ggt ccg     95
Val Asp Ala Trp Met Gly Ile Pro Tyr Ala Gln Pro Pro Leu Gly Pro
                20                  25                  30 ctc cgg ttt cga cat cca cga ccc gcc gaa aga tgg acc ggt gtg ctg    143
Leu Arg Phe Arg His Pro Arg Pro Ala Glu Arg Trp Thr Gly Val Leu
            35                  40                  45 aac gcg acc aaa cca ccc aac tcc tgc gtc cag atc gtg gac aca gtg    191
Asn Ala Thr Lys Pro Pro Asn Ser Cys Val Gln Ile Val Asp Thr Val
        50                  55                  60 ttc ggt gac ttc ccg ggg gcc acc atg tgg aac ccg aac aca ccc ctc    239
Phe Gly Asp Phe Pro Gly Ala Thr Met Trp Asn Pro Asn Thr Pro Leu
65                  70                  75 tcg gag gac tgt ctg tac atc aac gtg gtc gtg cca agg ccg agg ccc    287
Ser Glu Asp Cys Leu Tyr Ile Asn Val Val Val Pro Arg Pro Arg Pro
80                  85                  90                  95 aag aat gcc gct gtc atg ctg tgg atc ttt ggg ggt ggc ttc tac tcc    335
Lys Asn Ala Ala Val Met Leu Trp Ile Phe Gly Gly Gly Phe Tyr Ser
                100                 105                 110 ggg act gcc acg ttg gac gtg tac gac cat cgg acg ctg gcc tcg gaa    383
Gly Thr Ala Thr Leu Asp Val Tyr Asp His Arg Thr Leu Ala Ser Glu
            115                 120                 125 gag aac gtg atc gtg gtt tcg ctg cag tac cgt gtc gca agt ctt ggt    431
Glu Asn Val Ile Val Val Ser Leu Gln Tyr Arg Val Ala Ser Leu Gly
        130                 135                 140 ttt ctc ttc ctg ggc a                                              447
Phe Leu Phe Leu Gly
    145

<210> SEQ ID NO 89
<211> LENGTH: 148
<212> TYPE: PRT
<213> ORGANISM: Culex pipiens pipiens strain Heteren (S)

<400> SEQUENCE: 89

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45
```

```
Ala Thr Lys Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Ala Ser Glu Glu
            115                 120                 125

Asn Val Ile Val Val Ser Leu Gln Tyr Arg Val Ala Ser Leu Gly Phe
    130                 135                 140

Leu Phe Leu Gly
145

<210> SEQ ID NO 90
<211> LENGTH: 450
<212> TYPE: DNA
<213> ORGANISM: Culex pipiens quinquefasciatus strain Ling (S)
<220> FEATURE:
<221> NAME/KEY: CDS
<222> LOCATION: (1)..(447)

<400> SEQUENCE: 90 cag ggc aaa atc cgt gga acg aca ctg gaa gcg cct agt gga aag aag      48
Gln Gly Lys Ile Arg Gly Thr Thr Leu Glu Ala Pro Ser Gly Lys Lys
1               5                   10                  15 gtg gac gcc tgg atg ggc att ccg tac gcg cag ccc ccg ctg ggt ccg      96
Val Asp Ala Trp Met Gly Ile Pro Tyr Ala Gln Pro Pro Leu Gly Pro
                20                  25                  30 ctc cgg ttt cga cat ccg cga ccc gcc gaa aga tgg acc ggt gtg ctg     144
Leu Arg Phe Arg His Pro Arg Pro Ala Glu Arg Trp Thr Gly Val Leu
            35                  40                  45 aac gcg acc aaa ccg ccc aac tcc tgc gtc cag atc gtg gac acc gtg     192
Asn Ala Thr Lys Pro Pro Asn Ser Cys Val Gln Ile Val Asp Thr Val
        50                  55                  60 ttc ggt gac ttc ccg ggg gcc acc atg tgg aac ccg aac aca ccg ctc     240
Phe Gly Asp Phe Pro Gly Ala Thr Met Trp Asn Pro Asn Thr Pro Leu
65                  70                  75                  80 tcg gag gac tgt ctg tac atc aac gtg gtc gtg cca cgg ccc agg ccc     288
Ser Glu Asp Cys Leu Tyr Ile Asn Val Val Val Pro Arg Pro Arg Pro
                85                  90                  95 aag aat gcc gcc gtc atg ctg tgg atc ttc ggg ggt ggc ttc tac tcc     336
Lys Asn Ala Ala Val Met Leu Trp Ile Phe Gly Gly Gly Phe Tyr Ser
            100                 105                 110 ggg act gcc acg ctg gac gtg tat gac cac cgg acg ctg gcc tcg gag     384
Gly Thr Ala Thr Leu Asp Val Tyr Asp His Arg Thr Leu Ala Ser Glu
        115                 120                 125 gag aac gtg atc gta gtt tcg ctg cag tac cgt gtc gca agt ctt ggt     432
Glu Asn Val Ile Val Val Ser Leu Gln Tyr Arg Val Ala Ser Leu Gly
    130                 135                 140 ttt ctc ttc ctg ggc aca                                             450
Phe Leu Phe Leu Gly
145

<210> SEQ ID NO 91
<211> LENGTH: 149
<212> TYPE: PRT
<213> ORGANISM: Culex pipiens quinquefasciatus strain Ling (S)

<400> SEQUENCE: 91
```

```
Gln Gly Lys Ile Arg Gly Thr Thr Leu Glu Ala Pro Ser Gly Lys Lys
  1               5                   10                  15

Val Asp Ala Trp Met Gly Ile Pro Tyr Ala Gln Pro Pro Leu Gly Pro
             20                  25                  30

Leu Arg Phe Arg His Pro Arg Pro Ala Glu Arg Trp Thr Gly Val Leu
         35                  40                  45

Asn Ala Thr Lys Pro Pro Asn Ser Cys Val Gln Ile Val Asp Thr Val
     50                  55                  60

Phe Gly Asp Phe Pro Gly Ala Thr Met Trp Asn Pro Asn Thr Pro Leu
 65                  70                  75                  80

Ser Glu Asp Cys Leu Tyr Ile Asn Val Val Pro Arg Pro Arg Pro
             85                  90                  95

Lys Asn Ala Ala Val Met Leu Trp Ile Phe Gly Gly Phe Tyr Ser
            100                 105                 110

Gly Thr Ala Thr Leu Asp Val Tyr Asp His Arg Thr Leu Ala Ser Glu
            115                 120                 125

Glu Asn Val Ile Val Val Ser Leu Gln Tyr Arg Val Ala Ser Leu Gly
        130                 135                 140

Phe Leu Phe Leu Gly
145

<210> SEQ ID NO 92
<211> LENGTH: 448
<212> TYPE: DNA
<213> ORGANISM: Culex pipiens quinquefasciatus strain Mao (S)
<220> FEATURE:
<221> NAME/KEY: CDS
<222> LOCATION: (3)..(446)

<400> SEQUENCE: 92 ac ggc aaa atc cgt gga acg aca ctg gaa gcg cct agt gga aag aag         47
   Gly Lys Ile Arg Gly Thr Thr Leu Glu Ala Pro Ser Gly Lys Lys
     1               5                  10                  15 gtg gac gca tgg atg ggc att ccg tac gcg cag ccc ccg ctg ggt ccg        95
Val Asp Ala Trp Met Gly Ile Pro Tyr Ala Gln Pro Pro Leu Gly Pro
             20                  25                  30 ctc cgg ttt cga cat ccg cga ccc gcc gaa aga tgg acc ggt gtg ctg       143
Leu Arg Phe Arg His Pro Arg Pro Ala Glu Arg Trp Thr Gly Val Leu
         35                  40                  45 aac gcg acc aaa ccg ccc aac tcc tgc gtc cag atc gtg gac acc gtg       191
Asn Ala Thr Lys Pro Pro Asn Ser Cys Val Gln Ile Val Asp Thr Val
     50                  55                  60 ttc ggt gac ttc ccg ggg gcc acc atg tgg aac ccg aac aca ccg ctc       239
Phe Gly Asp Phe Pro Gly Ala Thr Met Trp Asn Pro Asn Thr Pro Leu
 65                  70                  75 tcg gag gac tgt ctg tac atc aac gtg gtc gtg cca cgg ccc agg ccc       287
Ser Glu Asp Cys Leu Tyr Ile Asn Val Val Val Pro Arg Pro Arg Pro
80                   85                  90                  95 aag aat gcc gcc gtc atg ctg tgg atc ttc ggg ggt ggc ttc tac tcc       335
Lys Asn Ala Ala Val Met Leu Trp Ile Phe Gly Gly Gly Phe Tyr Ser
            100                 105                 110 ggg act gcc acg ctg gac gtg tac gac cac cgg acg ctg gcc tcg gag       383
Gly Thr Ala Thr Leu Asp Val Tyr Asp His Arg Thr Leu Ala Ser Glu
            115                 120                 125 gag aac gtg atc gta gtt tcg ctg cag tac cgt gtc gca agt ctt ggt       431
Glu Asn Val Ile Val Val Ser Leu Gln Tyr Arg Val Ala Ser Leu Gly
        130                 135                 140 ttt ctc ttc ctg ggc ac                                                 448
Phe Leu Phe Leu Gly
```

<210> SEQ ID NO 93
<211> LENGTH: 148
<212> TYPE: PRT
<213> ORGANISM: Culex pipiens quinquefasciatus strain Mao (S)

<400> SEQUENCE: 93

```
Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140

Leu Phe Leu Gly
145
```

<210> SEQ ID NO 94
<211> LENGTH: 433
<212> TYPE: DNA
<213> ORGANISM: Culex pipiens quinquefasciatus strain TemR (S)
<220> FEATURE:
<221> NAME/KEY: CDS
<222> LOCATION: (1)..(432)

<400> SEQUENCE: 94

```
aaa atc cgt gga acg aca ctg gaa gcg cct agt gga aag aag gtg gac      48
Lys Ile Arg Gly Thr Thr Leu Glu Ala Pro Ser Gly Lys Lys Val Asp
1               5                   10                  15 gca tgg atg ggc att ccg tac gcg cag cct ccg ctg ggt ccg ctc cgg      96
Ala Trp Met Gly Ile Pro Tyr Ala Gln Pro Pro Leu Gly Pro Leu Arg
            20                  25                  30 ttt cga cat ccg cga ccc gcc gaa aga tgg acc ggt gtg ctg aac gcg     144
Phe Arg His Pro Arg Pro Ala Glu Arg Trp Thr Gly Val Leu Asn Ala
        35                  40                  45 acc aaa cca ccc aac tcc tgc gtc cag atc gtg gac acc gtg ttc ggt     192
Thr Lys Pro Pro Asn Ser Cys Val Gln Ile Val Asp Thr Val Phe Gly
    50                  55                  60 gac ttc ccg ggg gcc acc atg tgg aac ccg aac aca ccg ctc tcg gag     240
Asp Phe Pro Gly Ala Thr Met Trp Asn Pro Asn Thr Pro Leu Ser Glu
65                  70                  75                  80 gac tgt ctg tac atc aac gtg gtc gtg cca cgg ccc agg ccc aag aat     288
Asp Cys Leu Tyr Ile Asn Val Val Val Pro Arg Pro Arg Pro Lys Asn
                85                  90                  95 gcc gcc gtc atg ctg tgg atc ttc ggg ggt ggc ttc tac tcc ggg act     336
Ala Ala Val Met Leu Trp Ile Phe Gly Gly Gly Phe Tyr Ser Gly Thr
            100                 105                 110 gcc acg ctg gac gtg tac gac cac cgg acg ctg acc tcg gag gag aac     384
```

```
                                    Ala Thr Leu Asp Val Tyr Asp His Arg Thr Leu Thr Ser Glu Glu Asn
                                            115                 120                 125 gtg atc gta gtt tcg ctg cag tac cgt gtc gca agt ctt ggt ttt ctc t                  433
Val Ile Val Val Ser Leu Gln Tyr Arg Val Ala Ser Leu Gly Phe Leu
    130                 135                 140

<210> SEQ ID NO 95
<211> LENGTH: 144
<212> TYPE: PRT
<213> ORGANISM: Culex pipiens quinquefasciatus strain TemR (S)

<400> SEQUENCE: 95

Lys Ile Arg Gly Thr Thr Leu Glu Ala Pro Ser Gly Lys Lys Val Asp
1               5                   10                  15

Ala Trp Met Gly Ile Pro Tyr Ala Gln Pro Pro Leu Gly Pro Leu Arg
            20                  25                  30

Phe Arg His Pro Arg Pro Ala Glu Arg Trp Thr Gly Val Leu Asn Ala
        35                  40                  45

Thr Lys Pro Pro Asn Ser Cys Val Gln Ile Val Asp Thr Val Phe Gly
    50                  55                  60

Asp Phe Pro Gly Ala Thr Met Trp Asn Pro Asn Thr Pro Leu Ser Glu
65                  70                  75                  80

Asp Cys Leu Tyr Ile Asn Val Val Pro Arg Pro Arg Pro Lys Asn
                85                  90                  95

Ala Ala Val Met Leu Trp Ile Phe Gly Gly Gly Phe Tyr Ser Gly Thr
            100                 105                 110

Ala Thr Leu Asp Val Tyr Asp His Arg Thr Leu Thr Ser Glu Glu Asn
        115                 120                 125

Val Ile Val Val Ser Leu Gln Tyr Arg Val Ala Ser Leu Gly Phe Leu
    130                 135                 140

<210> SEQ ID NO 96
<211> LENGTH: 448
<212> TYPE: DNA
<213> ORGANISM: Culex torrentium strain Uppsala
<220> FEATURE:
<221> NAME/KEY: CDS
<222> LOCATION: (3)..(446)

<400> SEQUENCE: 96 ag ggc aaa atc cgt gga acg aca ctg gaa gcg cca agt gga aag aag         47
   Gly Lys Ile Arg Gly Thr Thr Leu Glu Ala Pro Ser Gly Lys Lys
   1               5                   10                  15 gtg gac gca tgg atg ggc att ccg tac gcg cag cct ccg ctg ggt ccg        95
Val Asp Ala Trp Met Gly Ile Pro Tyr Ala Gln Pro Pro Leu Gly Pro
            20                  25                  30 ctt cgg ttt cga cat cca cga ccc gcc gaa aga tgg acc ggt gtg ctg       143
Leu Arg Phe Arg His Pro Arg Pro Ala Glu Arg Trp Thr Gly Val Leu
        35                  40                  45 aac gcg acc aaa cca ccc aac tcc tgc gtc cag atc gtc gac acc gtg       191
Asn Ala Thr Lys Pro Pro Asn Ser Cys Val Gln Ile Val Asp Thr Val
    50                  55                  60 ttc ggt gac ttc ccg ggg gcc acc atg tgg aac ccg aac aca ccc ctc       239
Phe Gly Asp Phe Pro Gly Ala Thr Met Trp Asn Pro Asn Thr Pro Leu
65                  70                  75 tcg gaa gac tgt ctg tac atc aac gtt gtg gtg cca cgg ccg agg ccc       287
Ser Glu Asp Cys Leu Tyr Ile Asn Val Val Val Pro Arg Pro Arg Pro
80                  85                  90                  95 aag aat gcc gcc gtc atg ctg tgg atc ttc ggg ggt gga ttc tac tcc       335
Lys Asn Ala Ala Val Met Leu Trp Ile Phe Gly Gly Gly Phe Tyr Ser
            100                 105                 110
```

```
ggg acc gcc acg ctg gac gtg tac gac cac cgg acg ctg gcc tcg gag      383
Gly Thr Ala Thr Leu Asp Val Tyr Asp His Arg Thr Leu Ala Ser Glu
            115                 120                 125 gag aac gtg atc gtg gtt tcg ctg cag tac cgt gtc gca agt ctt ggt      431
Glu Asn Val Ile Val Val Ser Leu Gln Tyr Arg Val Ala Ser Leu Gly
        130                 135                 140 ttt ctc ttc ctg ggc ac                                                448
Phe Leu Phe Leu Gly
    145
```

<210> SEQ ID NO 97
<211> LENGTH: 148
<212> TYPE: PRT
<213> ORGANISM: Culex torrentium strain Uppsala

<400> SEQUENCE: 97

```
Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140

Leu Phe Leu Gly
145
```

<210> SEQ ID NO 98
<211> LENGTH: 448
<212> TYPE: DNA
<213> ORGANISM: Culex pipiens quinquefasciatus strain Trans (S)
<220> FEATURE:
<221> NAME/KEY: CDS
<222> LOCATION: (3)..(446)

<400> SEQUENCE: 98

```
ag ggc aaa atc cgt gga acg aca ctg gaa gcg cct agt gga aag aag       47
   Gly Lys Ile Arg Gly Thr Thr Leu Glu Ala Pro Ser Gly Lys Lys
   1               5                   10                  15 gtg gac gca tgg atg ggc att ccg tac gcg cag cct ccg ctg ggt ccg      95
Val Asp Ala Trp Met Gly Ile Pro Tyr Ala Gln Pro Pro Leu Gly Pro
            20                  25                  30 ctc cgg ttt cga cat ccg cga ccc gcc gaa aga tgg acc ggt gtg ctg     143
Leu Arg Phe Arg His Pro Arg Pro Ala Glu Arg Trp Thr Gly Val Leu
        35                  40                  45 aac gcg acc aaa cca ccc aac tcc tgc gtc cag atc gtg gac acc gtg     191
Asn Ala Thr Lys Pro Pro Asn Ser Cys Val Gln Ile Val Asp Thr Val
    50                  55                  60 ttc ggt gac ttc ccg ggg gcc acc atg tgg aac ccg aac aca ccg ctc     239
Phe Gly Asp Phe Pro Gly Ala Thr Met Trp Asn Pro Asn Thr Pro Leu
```

```
tcg gag gac tgt ctg tac atc aac gtg gtc gtg cca cgg ccc agg ccc      287
Ser Glu Asp Cys Leu Tyr Ile Asn Val Val Val Pro Arg Pro Arg Pro
 80                  85                  90                  95 aag aat gcc gcc gtc atg ctg tgg atc ttc ggg ggt ggc ttc tac tcc      335
Lys Asn Ala Ala Val Met Leu Trp Ile Phe Gly Gly Gly Phe Tyr Ser
                100                 105                 110 ggg act gcc acg ctg gac gtg tac gac cac cgg acg ctg acc tcg gag      383
Gly Thr Ala Thr Leu Asp Val Tyr Asp His Arg Thr Leu Thr Ser Glu
            115                 120                 125 gag aac gtg atc gta gtt tcg ctg cag tac cgt gtc gca agt ctt ggt      431
Glu Asn Val Ile Val Val Ser Leu Gln Tyr Arg Val Ala Ser Leu Gly
        130                 135                 140 ttt ctc ttc ctg ggc ac                                              448
Phe Leu Phe Leu Gly
    145
```

<210> SEQ ID NO 99
<211> LENGTH: 148
<212> TYPE: PRT
<213> ORGANISM: Culex pipiens quinquefasciatus strain Trans (S)

<400> SEQUENCE: 99

```
Gly Lys Ile Arg Gly Thr Thr Leu Glu Ala Pro Ser Gly Lys Lys Val
 1               5                  10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
 65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Thr Ser Glu Glu
        115                 120                 125

Asn Val Ile Val Val Ser Leu Gln Tyr Arg Val Ala Ser Leu Gly Phe
    130                 135                 140

Leu Phe Leu Gly
145
```

<210> SEQ ID NO 100
<211> LENGTH: 412
<212> TYPE: DNA
<213> ORGANISM: Culex pipiens quinquefasciatus strain BED (S)
<220> FEATURE:
<221> NAME/KEY: CDS
<222> LOCATION: (1)..(411)

<400> SEQUENCE: 100

```
aca ctg gaa gcg cct agt gga aag aag gtg gac gca tgg atg ggc att      48
Thr Leu Glu Ala Pro Ser Gly Lys Lys Val Asp Ala Trp Met Gly Ile
 1               5                  10                  15 ccg tac gcg cag cct ccg ctg ggt ccg ctc cgg ttt cga cat ccg cga      96
Pro Tyr Ala Gln Pro Pro Leu Gly Pro Leu Arg Phe Arg His Pro Arg
            20                  25                  30 ccc gcc gaa aga tgg acc ggt gtg ctg aac gcg acc aaa cca ccc aac      144
```

```
Pro Ala Glu Arg Trp Thr Gly Val Leu Asn Ala Thr Lys Pro Pro Asn
         35                  40                  45 tcc tgc gtc cag atc gtg gac acc gtg ttc ggt gac ttc ccg ggg gcc    192
Ser Cys Val Gln Ile Val Asp Thr Val Phe Gly Asp Phe Pro Gly Ala
 50                  55                  60 acc atg tgg aac ccg aac aca ccg ctc tcg gag gac tgt ctg tac atc    240
Thr Met Trp Asn Pro Asn Thr Pro Leu Ser Glu Asp Cys Leu Tyr Ile
 65                  70                  75                  80 aac gtg gtc gtg cca cgg ccc agg ccc aag aat gcc gcc gtc atg ctg    288
Asn Val Val Val Pro Arg Pro Arg Pro Lys Asn Ala Ala Val Met Leu
                 85                  90                  95 tgg atc ttc ggg ggt ggc ttc tac tcc ggg act gcc acg ctg gac gtg    336
Trp Ile Phe Gly Gly Gly Phe Tyr Ser Gly Thr Ala Thr Leu Asp Val
            100                 105                 110 tac gac cac cgg acg ctg gcc tcg gag gag aac gtg atc gta gtt tcg    384
Tyr Asp His Arg Thr Leu Ala Ser Glu Glu Asn Val Ile Val Val Ser
        115                 120                 125 ctg cag tac cgt gtc gca agt ctt ggt t                              412
Leu Gln Tyr Arg Val Ala Ser Leu Gly
    130                 135

<210> SEQ ID NO 101
<211> LENGTH: 137
<212> TYPE: PRT
<213> ORGANISM: Culex pipiens quinquefasciatus strain BED (S)

<400> SEQUENCE: 101

Thr Leu Glu Ala Pro Ser Gly Lys Lys Val Asp Ala Trp Met Gly Ile
 1               5                  10                  15

Pro Tyr Ala Gln Pro Pro Leu Gly Pro Leu Arg Phe Arg His Pro Arg
             20                  25                  30

Pro Ala Glu Arg Trp Thr Gly Val Leu Asn Ala Thr Lys Pro Pro Asn
         35                  40                  45

Ser Cys Val Gln Ile Val Asp Thr Val Phe Gly Asp Phe Pro Gly Ala
 50                  55                  60

Thr Met Trp Asn Pro Asn Thr Pro Leu Ser Glu Asp Cys Leu Tyr Ile
 65                  70                  75                  80

Asn Val Val Val Pro Arg Pro Arg Pro Lys Asn Ala Ala Val Met Leu
                 85                  90                  95

Trp Ile Phe Gly Gly Gly Phe Tyr Ser Gly Thr Ala Thr Leu Asp Val
            100                 105                 110

Tyr Asp His Arg Thr Leu Ala Ser Glu Glu Asn Val Ile Val Val Ser
        115                 120                 125

Leu Gln Tyr Arg Val Ala Ser Leu Gly
    130                 135

<210> SEQ ID NO 102
<211> LENGTH: 437
<212> TYPE: DNA
<213> ORGANISM: Culex pipiens quinquefasciatus strain BSQ (S)
<220> FEATURE:
<221> NAME/KEY: CDS
<222> LOCATION: (3)..(434)

<400> SEQUENCE: 102 ag ggc aaa atc cgt gga acg aca ctg gaa gcg cct agt gga aag aag      47
   Gly Lys Ile Arg Gly Thr Thr Leu Glu Ala Pro Ser Gly Lys Lys
    1               5                  10                  15 gtg gac gcc tgg atg ggc att ccg tac gcg cag ccc ccg ctg ggt ccg     95
Val Asp Ala Trp Met Gly Ile Pro Tyr Ala Gln Pro Pro Leu Gly Pro
             20                  25                  30
```

```
ctc cgg ttt cga cat ccg cga ccc gcc gaa aga tgg acc ggt gtg ctg      143
Leu Arg Phe Arg His Pro Arg Pro Ala Glu Arg Trp Thr Gly Val Leu
         35                  40                  45 aac gcg acc aaa ccg ccc aac tcc tgc gtc cag atc gtg gac acc gtg      191
Asn Ala Thr Lys Pro Pro Asn Ser Cys Val Gln Ile Val Asp Thr Val
 50                  55                  60 ttc ggt gac ttc ccg ggg gcc acc atg tgg aac ccg aac aca ccg ctc      239
Phe Gly Asp Phe Pro Gly Ala Thr Met Trp Asn Pro Asn Thr Pro Leu
 65                  70                  75 tcg gag gac tgt ctg tac atc aac gtg gtc gtg cca cgg ccc agg ccc      287
Ser Glu Asp Cys Leu Tyr Ile Asn Val Val Val Pro Arg Pro Arg Pro
80                   85                  90                  95 aag aat gcc gcc gtc atg ctg tgg atc ttc ggg ggt ggc ttc tac tcc      335
Lys Asn Ala Ala Val Met Leu Trp Ile Phe Gly Gly Gly Phe Tyr Ser
             100                 105                 110 ggg act gcc acg ctg gac gtg tac gac cac cgg acg ctg gcc tcg gag      383
Gly Thr Ala Thr Leu Asp Val Tyr Asp His Arg Thr Leu Ala Ser Glu
             115                 120                 125 gag aac gtg atc gta gtt tcg ctg cag tac cgt gtc gca agt ctt ggg      431
Glu Asn Val Ile Val Val Ser Leu Gln Tyr Arg Val Ala Ser Leu Gly
             130                 135                 140 ttt ctc                                                              437
Phe

<210> SEQ ID NO 103
<211> LENGTH: 144
<212> TYPE: PRT
<213> ORGANISM: Culex pipiens quinquefasciatus strain BSQ (S)

<400> SEQUENCE: 103

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Val Pro Arg Pro Arg Pro Lys
                85                  90                  95

Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140

<210> SEQ ID NO 104
<211> LENGTH: 414
<212> TYPE: DNA
<213> ORGANISM: Culex pipiens quinquefasciatus strain Brazza (S)
<220> FEATURE:
<221> NAME/KEY: CDS
<222> LOCATION: (2)..(412)

<400> SEQUENCE: 104 a ctg gaa gcg cct agt gga aag aag gtg gac gcc tgg atg ggc att ccg    49
  Leu Glu Ala Pro Ser Gly Lys Lys Val Asp Ala Trp Met Gly Ile Pro
```

```
                1               5                   10                  15
tac  gcg  cag  ccc  ccg  ctg  ggt  ccg  ctc  cgg  ttt  cga  cat  ccg  cga  ccc        97
Tyr  Ala  Gln  Pro  Pro  Leu  Gly  Pro  Leu  Arg  Phe  Arg  His  Pro  Arg  Pro
               20                  25                  30 gcc  gaa  aga  tgg  acc  ggt  gtg  ctg  aac  gcg  acc  aaa  ccg  ccc  aac  tcc       145
Ala  Glu  Arg  Trp  Thr  Gly  Val  Leu  Asn  Ala  Thr  Lys  Pro  Pro  Asn  Ser
               35                  40                  45 tgc  gtc  cag  atc  gtg  gac  acc  gtg  ttc  ggt  gac  ttc  ccg  ggg  gcc  acc       193
Cys  Val  Gln  Ile  Val  Asp  Thr  Val  Phe  Gly  Asp  Phe  Pro  Gly  Ala  Thr
50                  55                  60 atg  tgg  aac  ccg  aac  aca  ccg  ctc  tcg  gag  gac  tgt  ctg  tac  atc  aac       241
Met  Trp  Asn  Pro  Asn  Thr  Pro  Leu  Ser  Glu  Asp  Cys  Leu  Tyr  Ile  Asn
65                  70                  75                  80 gtg  gtc  gtg  cca  cgg  ccc  agg  ccc  aag  aat  gcc  gcc  gtc  atg  ctg  tgg       289
Val  Val  Val  Pro  Arg  Pro  Arg  Pro  Lys  Asn  Ala  Ala  Val  Met  Leu  Trp
               85                  90                  95 atc  ttc  ggg  ggt  ggc  ttc  tac  tcc  ggg  act  gcc  acg  ctg  gac  gtg  tac       337
Ile  Phe  Gly  Gly  Gly  Phe  Tyr  Ser  Gly  Thr  Ala  Thr  Leu  Asp  Val  Tyr
               100                 105                 110 gac  cac  cgg  acg  ctg  gcc  tcg  gag  gag  aac  gtg  atc  gta  gtt  tcg  ctg       385
Asp  His  Arg  Thr  Leu  Ala  Ser  Glu  Glu  Asn  Val  Ile  Val  Val  Ser  Leu
               115                 120                 125 cag  tac  cgt  gtc  gca  agt  ctt  ggg  ttt  ct                                      414
Gln  Tyr  Arg  Val  Ala  Ser  Leu  Gly  Phe
               130                 135
```

<210> SEQ ID NO 105
<211> LENGTH: 137
<212> TYPE: PRT
<213> ORGANISM: Culex pipiens quinquefasciatus strain Brazza (S)

<400> SEQUENCE: 105

```
Leu  Glu  Ala  Pro  Ser  Gly  Lys  Lys  Val  Asp  Ala  Trp  Met  Gly  Ile  Pro
1               5                   10                  15

Tyr  Ala  Gln  Pro  Pro  Leu  Gly  Pro  Leu  Arg  Phe  Arg  His  Pro  Arg  Pro
               20                  25                  30

Ala  Glu  Arg  Trp  Thr  Gly  Val  Leu  Asn  Ala  Thr  Lys  Pro  Pro  Asn  Ser
               35                  40                  45

Cys  Val  Gln  Ile  Val  Asp  Thr  Val  Phe  Gly  Asp  Phe  Pro  Gly  Ala  Thr
50                  55                  60

Met  Trp  Asn  Pro  Asn  Thr  Pro  Leu  Ser  Glu  Asp  Cys  Leu  Tyr  Ile  Asn
65                  70                  75                  80

Val  Val  Val  Pro  Arg  Pro  Arg  Pro  Lys  Asn  Ala  Ala  Val  Met  Leu  Trp
               85                  90                  95

Ile  Phe  Gly  Gly  Gly  Phe  Tyr  Ser  Gly  Thr  Ala  Thr  Leu  Asp  Val  Tyr
               100                 105                 110

Asp  His  Arg  Thr  Leu  Ala  Ser  Glu  Glu  Asn  Val  Ile  Val  Val  Ser  Leu
               115                 120                 125

Gln  Tyr  Arg  Val  Ala  Ser  Leu  Gly  Phe
               130                 135
```

<210> SEQ ID NO 106
<211> LENGTH: 437
<212> TYPE: DNA
<213> ORGANISM: Culex pipiens quinquefasciatus strain Bouake (R)
<220> FEATURE:
<221> NAME/KEY: CDS
<222> LOCATION: (3)..(434)

<400> SEQUENCE: 106

```
ag ggc aaa atc cgt gga acg aca ctg gaa gcg cct agt gga aag aag      47
   Gly Lys Ile Arg Gly Thr Thr Leu Glu Ala Pro Ser Gly Lys Lys
    1               5                  10                  15 gtg gac gca tgg atg ggc att ccg tac gcg cag ccc ccg ctg ggt ccg      95
Val Asp Ala Trp Met Gly Ile Pro Tyr Ala Gln Pro Pro Leu Gly Pro
                 20                  25                  30 ctc cgg ttt cga cat ccg cga ccc gcc gaa aga tgg acc ggt gtg ctg     143
Leu Arg Phe Arg His Pro Arg Pro Ala Glu Arg Trp Thr Gly Val Leu
             35                  40                  45 aac gcg acc aaa ccg ccc aac tcc tgc gtc cag atc gtg gac acc gtg     191
Asn Ala Thr Lys Pro Pro Asn Ser Cys Val Gln Ile Val Asp Thr Val
         50                  55                  60 ttc ggt gac ttc ccg ggg gcc acc atg tgg aac ccg aac aca ccg ctc     239
Phe Gly Asp Phe Pro Gly Ala Thr Met Trp Asn Pro Asn Thr Pro Leu
     65                  70                  75 tcg gag gac tgt ctg tac atc aac gtg gtc gtg cca cgg ccc agg ccc     287
Ser Glu Asp Cys Leu Tyr Ile Asn Val Val Val Pro Arg Pro Arg Pro
 80                  85                  90                  95 aag aat gcc gcc gtc atg ctg tgg atc ttc ggg ggt ggc ttc tac tcc     335
Lys Asn Ala Ala Val Met Leu Trp Ile Phe Gly Gly Gly Phe Tyr Ser
                100                 105                 110 ggg act gcc acg ctg gac gtg tac gac cac cgg acg ctg gcc tcg gag     383
Gly Thr Ala Thr Leu Asp Val Tyr Asp His Arg Thr Leu Ala Ser Glu
            115                 120                 125 gag aac gtg atc gta gtt tcg ctg cag tac cgt gtc gca agt ctt ggt     431
Glu Asn Val Ile Val Val Ser Leu Gln Tyr Arg Val Ala Ser Leu Gly
        130                 135                 140 ttt ctc                                                              437
Phe

<210> SEQ ID NO 107
<211> LENGTH: 144
<212> TYPE: PRT
<213> ORGANISM: Culex pipiens quinquefasciatus strain Bouake (R)

<400> SEQUENCE: 107

Gly Lys Ile Arg Gly Thr Thr Leu Glu Ala Pro Ser Gly Lys Lys Val
 1               5                  10                  15

Asp Ala Trp Met Gly Ile Pro Tyr Ala Gln Pro Pro Leu Gly Pro Leu
             20                  25                  30

Arg Phe Arg His Pro Arg Pro Ala Glu Arg Trp Thr Gly Val Leu Asn
         35                  40                  45

Ala Thr Lys Pro Pro Asn Ser Cys Val Gln Ile Val Asp Thr Val Phe
     50                  55                  60

Gly Asp Phe Pro Gly Ala Thr Met Trp Asn Pro Asn Thr Pro Leu Ser
 65                  70                  75                  80

Glu Asp Cys Leu Tyr Ile Asn Val Val Val Pro Arg Pro Arg Pro Lys
                 85                  90                  95

Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140

<210> SEQ ID NO 108
<211> LENGTH: 416
<212> TYPE: DNA
<213> ORGANISM: Culex pipiens quinquefasciatus strain Thai (S)
<220> FEATURE:
```

-continued

```
<221> NAME/KEY: CDS
<222> LOCATION: (1)..(414)

<400> SEQUENCE: 108 aca ctg gaa gcg cct agt gga aag aag gtg gac gcc tgg atg ggc att      48
Thr Leu Glu Ala Pro Ser Gly Lys Lys Val Asp Ala Trp Met Gly Ile
1               5                   10                  15 ccg tac gcg cag ccc ccg ctg ggt ccg ctc cgg ttt cga cat ccg cga      96
Pro Tyr Ala Gln Pro Pro Leu Gly Pro Leu Arg Phe Arg His Pro Arg
            20                  25                  30 ccc gcc gaa aga tgg acc ggt gtg ctg aac gcg acc aaa ccg ccc aac     144
Pro Ala Glu Arg Trp Thr Gly Val Leu Asn Ala Thr Lys Pro Pro Asn
        35                  40                  45 tcc tgc gtc cag atc gtg gac acc gtg ttc ggt gac ttc ccg ggg gcc     192
Ser Cys Val Gln Ile Val Asp Thr Val Phe Gly Asp Phe Pro Gly Ala
    50                  55                  60 acc atg tgg aac ccg aac aca ccg ctc tcg gag gac tgt ctg tac atc     240
Thr Met Trp Asn Pro Asn Thr Pro Leu Ser Glu Asp Cys Leu Tyr Ile
65                  70                  75                  80 aac gtg gtc gtg cca cgg ccc agg ccc aag aat gcc gcc gtc atg ctg     288
Asn Val Val Val Pro Arg Pro Arg Pro Lys Asn Ala Ala Val Met Leu
                85                  90                  95 tgg atc ttc ggg ggt ggc ttc tac tcc ggg act gcc acg ctg gac gtg     336
Trp Ile Phe Gly Gly Gly Phe Tyr Ser Gly Thr Ala Thr Leu Asp Val
            100                 105                 110 tac gac cac cgg acg ctg gcc tcg gag gag aac gtg atc gta gtt tcg     384
Tyr Asp His Arg Thr Leu Ala Ser Glu Glu Asn Val Ile Val Val Ser
        115                 120                 125 ctg cag tac cgt gtc gca agt ctt ggg ttt ct                          416
Leu Gln Tyr Arg Val Ala Ser Leu Gly Phe
    130                 135

<210> SEQ ID NO 109
<211> LENGTH: 138
<212> TYPE: PRT
<213> ORGANISM: Culex pipiens quinquefasciatus strain Thai (S)

<400> SEQUENCE: 109

Thr Leu Glu Ala Pro Ser Gly Lys Lys Val Asp Ala Trp Met Gly Ile
1               5                   10                  15

Pro Tyr Ala Gln Pro Pro Leu Gly Pro Leu Arg Phe Arg His Pro Arg
            20                  25                  30

Pro Ala Glu Arg Trp Thr Gly Val Leu Asn Ala Thr Lys Pro Pro Asn
        35                  40                  45

Ser Cys Val Gln Ile Val Asp Thr Val Phe Gly Asp Phe Pro Gly Ala
    50                  55                  60

Thr Met Trp Asn Pro Asn Thr Pro Leu Ser Glu Asp Cys Leu Tyr Ile
65                  70                  75                  80

Asn Val Val Val Pro Arg Pro Arg Pro Lys Asn Ala Ala Val Met Leu
                85                  90                  95

Trp Ile Phe Gly Gly Gly Phe Tyr Ser Gly Thr Ala Thr Leu Asp Val
            100                 105                 110

Tyr Asp His Arg Thr Leu Ala Ser Glu Glu Asn Val Ile Val Val Ser
        115                 120                 125

Leu Gln Tyr Arg Val Ala Ser Leu Gly Phe
    130                 135

<210> SEQ ID NO 110
<211> LENGTH: 426
<212> TYPE: DNA
```

<213> ORGANISM: Culex pipiens quinquefasciatus strain Madurai (S)
<220> FEATURE:
<221> NAME/KEY: CDS
<222> LOCATION: (3)..(425)

<400> SEQUENCE: 110

```
ca ctg gaa gcg cct agt gga aag aag gtg gac gca tgg atg ggc att        47
   Leu Glu Ala Pro Ser Gly Lys Lys Val Asp Ala Trp Met Gly Ile
   1               5                  10                  15 ccg tac gcg cag ccc ccg ctg ggt ccg ctc cgg ttt cga cat ccg cga       95
Pro Tyr Ala Gln Pro Pro Leu Gly Pro Leu Arg Phe Arg His Pro Arg
                20                  25                  30 ccc gcc gaa aga tgg acc ggt gtg ctg aac gca acc aaa ccg ccc aac      143
Pro Ala Glu Arg Trp Thr Gly Val Leu Asn Ala Thr Lys Pro Pro Asn
            35                  40                  45 tcc tgc gtc cag atc gtg gac acc gtg ttc ggt gac ttc ccg ggg gcc      191
Ser Cys Val Gln Ile Val Asp Thr Val Phe Gly Asp Phe Pro Gly Ala
        50                  55                  60 acc atg tgg aac ccg aac aca ccg ctc tcg gag gac tgt ctg tac atc      239
Thr Met Trp Asn Pro Asn Thr Pro Leu Ser Glu Asp Cys Leu Tyr Ile
    65                  70                  75 aac gtg gtc gtg cca cgg ccc agg ccc aag aat gcc gcc gtc atg ctg      287
Asn Val Val Val Pro Arg Pro Arg Pro Lys Asn Ala Ala Val Met Leu
80                  85                  90                  95 tgg atc ttc ggg ggt ggc ttc tac tcc ggg act gcc acg ctg gac gtg      335
Trp Ile Phe Gly Gly Gly Phe Tyr Ser Gly Thr Ala Thr Leu Asp Val
                100                 105                 110 tac gac cac cgg acg ctg gcc tcg gag gag aac gtg atc gta gtt tcg      383
Tyr Asp His Arg Thr Leu Ala Ser Glu Glu Asn Val Ile Val Val Ser
            115                 120                 125 ctg cag tac cgt gtc gca agt ctt ggg ttt ctc ttc ctg ggc a            426
Leu Gln Tyr Arg Val Ala Ser Leu Gly Phe Leu Phe Leu Gly
        130                 135                 140
```

<210> SEQ ID NO 111
<211> LENGTH: 141
<212> TYPE: PRT
<213> ORGANISM: Culex pipiens quinquefasciatus strain Madurai (S)

<400> SEQUENCE: 111

```
Leu Glu Ala Pro Ser Gly Lys Lys Val Asp Ala Trp Met Gly Ile Pro
1               5                  10                  15

Tyr Ala Gln Pro Pro Leu Gly Pro Leu Arg Phe Arg His Pro Arg Pro
            20                  25                  30

Ala Glu Arg Trp Thr Gly Val Leu Asn Ala Thr Lys Pro Pro Asn Ser
        35                  40                  45

Cys Val Gln Ile Val Asp Thr Val Phe Gly Asp Phe Pro Gly Ala Thr
    50                  55                  60

Met Trp Asn Pro Asn Thr Pro Leu Ser Glu Asp Cys Leu Tyr Ile Asn
65                  70                  75                  80

Val Val Val Pro Arg Pro Arg Pro Lys Asn Ala Ala Val Met Leu Trp
                85                  90                  95

Ile Phe Gly Gly Gly Phe Tyr Ser Gly Thr Ala Thr Leu Asp Val Tyr
            100                 105                 110

Asp His Arg Thr Leu Ala Ser Glu Glu Asn Val Ile Val Val Ser Leu
        115                 120                 125

Gln Tyr Arg Val Ala Ser Leu Gly Phe Leu Phe Leu Gly
    130                 135                 140
```

<210> SEQ ID NO 112

-continued

```
<211> LENGTH: 423
<212> TYPE: DNA
<213> ORGANISM: Culex pipiens quinquefasciatus strain Recife (R)
<220> FEATURE:
<221> NAME/KEY: CDS
<222> LOCATION: (1)..(423)

<400> SEQUENCE: 112 ctg gaa gcg cct agc gga aag aag gtg gac gca tgg atg ggc att ccg     48
Leu Glu Ala Pro Ser Gly Lys Lys Val Asp Ala Trp Met Gly Ile Pro
1               5                   10                  15 tac gcg cag cct ccg ctg ggt ccg ctc cgg ttt cga cat ccg cga ccc     96
Tyr Ala Gln Pro Pro Leu Gly Pro Leu Arg Phe Arg His Pro Arg Pro
                20                  25                  30 gcc gaa aga tgg acc ggt gtg ctg aac gcg acc aaa ccg ccc aac tcc    144
Ala Glu Arg Trp Thr Gly Val Leu Asn Ala Thr Lys Pro Pro Asn Ser
            35                  40                  45 tgc gtc cag atc gtg gac acc gtg ttc ggt gac ttc ccg ggg gcc acc    192
Cys Val Gln Ile Val Asp Thr Val Phe Gly Asp Phe Pro Gly Ala Thr
        50                  55                  60 atg tgg aac ccg aac aca ccg ctc tcg gag gac tgt ctg tac atc aac    240
Met Trp Asn Pro Asn Thr Pro Leu Ser Glu Asp Cys Leu Tyr Ile Asn
65                  70                  75                  80 gtg gtc gtg cca cgg ccc agg ccc aag aat gcc gcc gtc atg ctg tgg    288
Val Val Val Pro Arg Pro Arg Pro Lys Asn Ala Ala Val Met Leu Trp
                85                  90                  95 atc ttc ggg ggt agc ttc tac tcc ggg act gcc acg ctg gac gtg tac    336
Ile Phe Gly Gly Ser Phe Tyr Ser Gly Thr Ala Thr Leu Asp Val Tyr
                100                 105                 110 gac cac cgg acg ctg gcc tcg gag gag aac gtg atc gta gtt tcg ctg    384
Asp His Arg Thr Leu Ala Ser Glu Glu Asn Val Ile Val Val Ser Leu
            115                 120                 125 cag tac cgt gtc gca agt ctt ggt ttt ctc ttc ctg ggc                423
Gln Tyr Arg Val Ala Ser Leu Gly Phe Leu Phe Leu Gly
        130                 135                 140

<210> SEQ ID NO 113
<211> LENGTH: 141
<212> TYPE: PRT
<213> ORGANISM: Culex pipiens quinquefasciatus strain Recife (R)

<400> SEQUENCE: 113

Leu Glu Ala Pro Ser Gly Lys Lys Val Asp Ala Trp Met Gly Ile Pro
1               5                   10                  15

Tyr Ala Gln Pro Pro Leu Gly Pro Leu Arg Phe Arg His Pro Arg Pro
                20                  25                  30

Ala Glu Arg Trp Thr Gly Val Leu Asn Ala Thr Lys Pro Pro Asn Ser
            35                  40                  45

Cys Val Gln Ile Val Asp Thr Val Phe Gly Asp Phe Pro Gly Ala Thr
        50                  55                  60

Met Trp Asn Pro Asn Thr Pro Leu Ser Glu Asp Cys Leu Tyr Ile Asn
65                  70                  75                  80

Val Val Val Pro Arg Pro Arg Pro Lys Asn Ala Ala Val Met Leu Trp
                85                  90                  95

Ile Phe Gly Gly Ser Phe Tyr Ser Gly Thr Ala Thr Leu Asp Val Tyr
                100                 105                 110

Asp His Arg Thr Leu Ala Ser Glu Glu Asn Val Ile Val Val Ser Leu
            115                 120                 125

Gln Tyr Arg Val Ala Ser Leu Gly Phe Leu Phe Leu Gly
        130                 135                 140
```

-continued

```
<210> SEQ ID NO 114
<211> LENGTH: 416
<212> TYPE: DNA
<213> ORGANISM: Culex pipiens quinquefasciatus strain Bresil (S)
<220> FEATURE:
<221> NAME/KEY: CDS
<222> LOCATION: (3)..(413)

<400> SEQUENCE: 114 ca ctg gaa gcg cct agt gga aag aag gtg gac gca tgg atg ggc att        47
   Leu Glu Ala Pro Ser Gly Lys Lys Val Asp Ala Trp Met Gly Ile
   1               5                  10                  15 ccg tac gcg cag ccc ccg ctg ggt ccg ctc cgg ttt cga cat ccg cga       95
Pro Tyr Ala Gln Pro Pro Leu Gly Pro Leu Arg Phe Arg His Pro Arg
                20                  25                  30 ccc gcc gaa aga tgg acc ggt gtg ctg aac gcg acc aaa ccg ccc aac      143
Pro Ala Glu Arg Trp Thr Gly Val Leu Asn Ala Thr Lys Pro Pro Asn
            35                  40                  45 tcc tgc gtc cag atc gtg gac acc gtg ttc ggt gac ttc ccg ggg gcc      191
Ser Cys Val Gln Ile Val Asp Thr Val Phe Gly Asp Phe Pro Gly Ala
        50                  55                  60 acc atg tgg aac ccg aac aca ccg ctc tcg gag gac tgt ctg tac atc      239
Thr Met Trp Asn Pro Asn Thr Pro Leu Ser Glu Asp Cys Leu Tyr Ile
    65                  70                  75 aac gtg gtc gtg cca cgg ccc agg ccc aag aat gcc gcc gtc atg ctg      287
Asn Val Val Val Pro Arg Pro Arg Pro Lys Asn Ala Ala Val Met Leu
80                  85                  90                  95 tgg atc ttc ggg ggt ggc ttc tat tcc ggg act gcc acg ctg gac gtg      335
Trp Ile Phe Gly Gly Gly Phe Tyr Ser Gly Thr Ala Thr Leu Asp Val
                100                 105                 110 tac gac cac cgg acg ctg gcc tcg gag gag aac gtg atc gta gtt tcg      383
Tyr Asp His Arg Thr Leu Ala Ser Glu Glu Asn Val Ile Val Val Ser
            115                 120                 125 ctg cag tac cgt gtc gca agt ctt ggg ttt ctc                          416
Leu Gln Tyr Arg Val Ala Ser Leu Gly Phe
        130                 135

<210> SEQ ID NO 115
<211> LENGTH: 137
<212> TYPE: PRT
<213> ORGANISM: Culex pipiens quinquefasciatus strain Bresil (S)

<400> SEQUENCE: 115

Leu Glu Ala Pro Ser Gly Lys Lys Val Asp Ala Trp Met Gly Ile Pro
1               5                   10                  15

Tyr Ala Gln Pro Pro Leu Gly Pro Leu Arg Phe Arg His Pro Arg Pro
            20                  25                  30

Ala Glu Arg Trp Thr Gly Val Leu Asn Ala Thr Lys Pro Pro Asn Ser
        35                  40                  45

Cys Val Gln Ile Val Asp Thr Val Phe Gly Asp Phe Pro Gly Ala Thr
    50                  55                  60

Met Trp Asn Pro Asn Thr Pro Leu Ser Glu Asp Cys Leu Tyr Ile Asn
65                  70                  75                  80

Val Val Val Pro Arg Pro Arg Pro Lys Asn Ala Ala Val Met Leu Trp
                85                  90                  95

Ile Phe Gly Gly Gly Phe Tyr Ser Gly Thr Ala Thr Leu Asp Val Tyr
            100                 105                 110

Asp His Arg Thr Leu Ala Ser Glu Glu Asn Val Ile Val Val Ser Leu
        115                 120                 125

Gln Tyr Arg Val Ala Ser Leu Gly Phe
        130                 135
```

<210> SEQ ID NO 116
<211> LENGTH: 418
<212> TYPE: DNA
<213> ORGANISM: Culex pipiens quinquefasciatus strain Moorea (S)
<220> FEATURE:
<221> NAME/KEY: CDS
<222> LOCATION: (1)..(417)

<400> SEQUENCE: 116

```
aca ctg gaa gcg cct agt gga aag aag gtg gac gca tgg atg ggc att      48
Thr Leu Glu Ala Pro Ser Gly Lys Lys Val Asp Ala Trp Met Gly Ile
1               5                   10                  15 ccg tac gcg cag cct ccg ctg ggt ccg ctc cgg ttt cga cat ccg cga      96
Pro Tyr Ala Gln Pro Pro Leu Gly Pro Leu Arg Phe Arg His Pro Arg
            20                  25                  30 ccc gcc gaa aga tgg acc ggt gtg ctg aac gcg acc aaa ccg ccc aac     144
Pro Ala Glu Arg Trp Thr Gly Val Leu Asn Ala Thr Lys Pro Pro Asn
        35                  40                  45 tcc tgc gtc cag atc gtg gac acc gtg ttc ggt gac ttc ccg ggg gcc     192
Ser Cys Val Gln Ile Val Asp Thr Val Phe Gly Asp Phe Pro Gly Ala
    50                  55                  60 acc atg tgg aac ccg aac aca ccg ctc tcg gag gac tgt ctg tac atc     240
Thr Met Trp Asn Pro Asn Thr Pro Leu Ser Glu Asp Cys Leu Tyr Ile
65                  70                  75                  80 aac gtg gtc gtg cca cgg ccc agg ccc aag aat gcc gcc gtc atg ctg     288
Asn Val Val Val Pro Arg Pro Arg Pro Lys Asn Ala Ala Val Met Leu
                85                  90                  95 tgg atc ttc ggg ggt ggc ttc tac tcc ggg act gcc acg ctg gac gtg     336
Trp Ile Phe Gly Gly Gly Phe Tyr Ser Gly Thr Ala Thr Leu Asp Val
            100                 105                 110 tac gac cac cgg acg ctg gcc tcg gag gag aac gtg atc gta gtt tcg     384
Tyr Asp His Arg Thr Leu Ala Ser Glu Glu Asn Val Ile Val Val Ser
        115                 120                 125 ctg cag tac cgt gtc gca agt ctt ggg ttt ctc t                       418
Leu Gln Tyr Arg Val Ala Ser Leu Gly Phe Leu
    130                 135
```

<210> SEQ ID NO 117
<211> LENGTH: 139
<212> TYPE: PRT
<213> ORGANISM: Culex pipiens quinquefasciatus strain Moorea (S)

<400> SEQUENCE: 117

```
Thr Leu Glu Ala Pro Ser Gly Lys Lys Val Asp Ala Trp Met Gly Ile
1               5                   10                  15

Pro Tyr Ala Gln Pro Pro Leu Gly Pro Leu Arg Phe Arg His Pro Arg
            20                  25                  30

Pro Ala Glu Arg Trp Thr Gly Val Leu Asn Ala Thr Lys Pro Pro Asn
        35                  40                  45

Ser Cys Val Gln Ile Val Asp Thr Val Phe Gly Asp Phe Pro Gly Ala
    50                  55                  60

Thr Met Trp Asn Pro Asn Thr Pro Leu Ser Glu Asp Cys Leu Tyr Ile
65                  70                  75                  80

Asn Val Val Val Pro Arg Pro Arg Pro Lys Asn Ala Ala Val Met Leu
                85                  90                  95

Trp Ile Phe Gly Gly Gly Phe Tyr Ser Gly Thr Ala Thr Leu Asp Val
            100                 105                 110

Tyr Asp His Arg Thr Leu Ala Ser Glu Glu Asn Val Ile Val Val Ser
        115                 120                 125
```

```
Leu Gln Tyr Arg Val Ala Ser Leu Gly Phe Leu
    130                 135

<210> SEQ ID NO 118
<211> LENGTH: 402
<212> TYPE: DNA
<213> ORGANISM: Culex pipiens pipiens strain Killcare (S)
<220> FEATURE:
<221> NAME/KEY: CDS
<222> LOCATION: (1)..(402)

<400> SEQUENCE: 118 agt gga aag aag gtg gac gca tgg atg ggc att ccg tac gcg cag ccc       48
Ser Gly Lys Lys Val Asp Ala Trp Met Gly Ile Pro Tyr Ala Gln Pro
1               5                   10                  15 ccg ctg ggt ccg ctc cgg ttt cga cat ccg cga ccc gcc gaa aga tgg       96
Pro Leu Gly Pro Leu Arg Phe Arg His Pro Arg Pro Ala Glu Arg Trp
            20                  25                  30 acc ggt gtg ctg aac gcg acc aaa cca ccc aac tcc tgc gtc cag atc      144
Thr Gly Val Leu Asn Ala Thr Lys Pro Pro Asn Ser Cys Val Gln Ile
        35                  40                  45 gtg gac aca gtg ttc ggt gac ttc ccg ggg gcc acc atg tgg aac ccg      192
Val Asp Thr Val Phe Gly Asp Phe Pro Gly Ala Thr Met Trp Asn Pro
    50                  55                  60 aac aca ccc ctc tcg gag gac tgt ctg tac atc aac gtg gtc gtg cca      240
Asn Thr Pro Leu Ser Glu Asp Cys Leu Tyr Ile Asn Val Val Val Pro
65                  70                  75                  80 agg ccg agg ccc aag aat gcc gct gtc atg ctg tgg atc ttc ggg ggt      288
Arg Pro Arg Pro Lys Asn Ala Ala Val Met Leu Trp Ile Phe Gly Gly
                85                  90                  95 ggc ttc tac tcc ggg act gcc acg ttg gac gtg tac gat cat cgg acg      336
Gly Phe Tyr Ser Gly Thr Ala Thr Leu Asp Val Tyr Asp His Arg Thr
            100                 105                 110 ctg gcc tcg gag gag aac gtg atc gtg gtt tcg ctg cag tac cgt gtc      384
Leu Ala Ser Glu Glu Asn Val Ile Val Val Ser Leu Gln Tyr Arg Val
        115                 120                 125 gca agt ctt ggt ttt ctc                                              402
Ala Ser Leu Gly Phe Leu
    130

<210> SEQ ID NO 119
<211> LENGTH: 134
<212> TYPE: PRT
<213> ORGANISM: Culex pipiens pipiens strain Killcare (S)

<400> SEQUENCE: 119

Ser Gly Lys Lys Val Asp Ala Trp Met Gly Ile Pro Tyr Ala Gln Pro
1               5                   10                  15

Pro Leu Gly Pro Leu Arg Phe Arg His Pro Arg Pro Ala Glu Arg Trp
            20                  25                  30

Thr Gly Val Leu Asn Ala Thr Lys Pro Pro Asn Ser Cys Val Gln Ile
        35                  40                  45

Val Asp Thr Val Phe Gly Asp Phe Pro Gly Ala Thr Met Trp Asn Pro
    50                  55                  60

Asn Thr Pro Leu Ser Glu Asp Cys Leu Tyr Ile Asn Val Val Val Pro
65                  70                  75                  80

Arg Pro Arg Pro Lys Asn Ala Ala Val Met Leu Trp Ile Phe Gly Gly
                85                  90                  95

Gly Phe Tyr Ser Gly Thr Ala Thr Leu Asp Val Tyr Asp His Arg Thr
            100                 105                 110
```

```
Leu Ala Ser Glu Glu Asn Val Ile Val Val Ser Leu Gln Tyr Arg Val
        115                 120                 125

Ala Ser Leu Gly Phe Leu
    130
```

<210> SEQ ID NO 120
<211> LENGTH: 152
<212> TYPE: PRT
<213> ORGANISM: Culex pipiens pipiens strain Espro (R)

<400> SEQUENCE: 120

```
Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Ser Phe Tyr Ser Gly
                100                 105                 110

Thr Ala Thr Leu Asp Val Tyr Asp His Arg Thr Leu Ala Ser Glu Glu
            115                 120                 125

Asn Val Ile Val Val Ser Leu Gln Tyr Arg Val Ala Ser Leu Gly Phe
    130                 135                 140

Leu Phe Leu Gly Thr Pro Glu Ala
145                 150
```

<210> SEQ ID NO 121
<211> LENGTH: 152
<212> TYPE: PRT
<213> ORGANISM: Culex pipiens quinquefasciatus strain ProR(S)

<400> SEQUENCE: 121

```
Lys Gly Lys Ile Arg Gly Thr Thr Leu Glu Ala Pro Ser Gly Lys Lys
1               5                   10                  15

Val Asp Ala Trp Met Gly Ile Pro Tyr Ala Gln Pro Pro Leu Gly Pro
            20                  25                  30

Leu Arg Phe Arg His Pro Arg Pro Ala Glu Arg Trp Thr Gly Val Leu
        35                  40                  45

Asn Ala Thr Lys Pro Pro Asn Ser Cys Val Gln Ile Val Asp Thr Val
    50                  55                  60

Phe Gly Asp Phe Pro Gly Ala Thr Met Trp Asn Pro Asn Thr Pro Leu
65                  70                  75                  80

Ser Glu Asp Cys Leu Tyr Ile Asn Val Val Pro Arg Pro Arg Pro
                85                  90                  95

Lys Asn Ala Ala Val Met Leu Trp Ile Phe Gly Gly Phe Tyr Ser
                100                 105                 110

Gly Thr Ala Thr Leu Asp Val Tyr Asp His Arg Thr Leu Ala Ser Glu
            115                 120                 125

Glu Asn Val Ile Val Val Ser Leu Gln Tyr Arg Val Ala Ser Leu Gly
    130                 135                 140

Phe Leu Phe Leu Gly Thr Pro Glu
```

<210> SEQ ID NO 122
<211> LENGTH: 148
<212> TYPE: PRT
<213> ORGANISM: Culex pipiens pipiens strain S-LAB (S)

<400> SEQUENCE: 122

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140

Leu Phe Leu Gly
145

<210> SEQ ID NO 123
<211> LENGTH: 152
<212> TYPE: PRT
<213> ORGANISM: Culex pipiens pipiens strain Padova (R)

<400> SEQUENCE: 123

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Ser Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140

Leu Phe Leu Gly Thr Pro Glu Ala
145                 150

<210> SEQ ID NO 124

```
<211> LENGTH: 154
<212> TYPE: PRT
<213> ORGANISM: Culex pipiens pipiens strain Praias (R)

<400> SEQUENCE: 124

Asp Lys Gly Lys Ile Arg Gly Thr Thr Leu Glu Ala Pro Ser Gly Lys
1               5                   10                  15

Lys Val Asp Ala Trp Met Gly Ile Pro Tyr Ala Gln Pro Pro Leu Gly
            20                  25                  30

Pro Leu Arg Phe Arg His Pro Arg Pro Ala Glu Arg Trp Thr Gly Val
        35                  40                  45

Leu Asn Ala Thr Lys Pro Pro Asn Ser Cys Val Gln Ile Val Asp Thr
    50                  55                  60

Val Phe Gly Asp Phe Pro Gly Ala Thr Met Trp Asn Pro Asn Thr Pro
65                  70                  75                  80

Leu Ser Glu Asp Cys Leu Tyr Ile Asn Val Val Pro Arg Pro Arg
                85                  90                  95

Pro Lys Asn Ala Ala Val Met Leu Trp Ile Phe Gly Gly Ser Phe Tyr
            100                 105                 110

Ser Gly Thr Ala Thr Leu Asp Val Tyr Asp His Arg Thr Leu Ala Ser
        115                 120                 125

Glu Glu Asn Val Ile Val Val Ser Leu Gln Tyr Arg Val Ala Ser Leu
    130                 135                 140

Gly Phe Leu Phe Leu Gly Thr Pro Glu Ala
145                 150

<210> SEQ ID NO 125
<211> LENGTH: 154
<212> TYPE: PRT
<213> ORGANISM: Culex pipiens quinquefasciatus strain Supercar (R)

<400> SEQUENCE: 125

Asp Lys Gly Lys Ile Arg Gly Thr Thr Leu Glu Ala Pro Ser Gly Lys
1               5                   10                  15

Lys Val Asp Ala Trp Met Gly Ile Pro Tyr Ala Gln Pro Pro Leu Gly
            20                  25                  30

Pro Leu Arg Phe Arg His Pro Arg Pro Ala Glu Arg Trp Thr Gly Val
        35                  40                  45

Leu Asn Ala Thr Lys Pro Pro Asn Ser Cys Val Gln Ile Val Asp Thr
    50                  55                  60

Val Phe Gly Asp Phe Pro Gly Ala Thr Met Trp Asn Pro Asn Thr Pro
65                  70                  75                  80

Leu Ser Glu Asp Cys Leu Tyr Ile Asn Val Val Pro Arg Pro Arg
                85                  90                  95

Pro Lys Asn Ala Ala Val Met Leu Trp Ile Phe Gly Gly Ser Phe Tyr
            100                 105                 110

Ser Gly Thr Ala Thr Leu Asp Val Tyr Asp His Arg Thr Leu Ala Ser
        115                 120                 125

Glu Glu Asn Val Ile Val Val Ser Leu Gln Tyr Arg Val Ala Ser Leu
    130                 135                 140

Gly Phe Leu Phe Leu Gly Thr Pro Glu Ala
145                 150

<210> SEQ ID NO 126
<211> LENGTH: 148
<212> TYPE: PRT
<213> ORGANISM: Culex pipiens pipiens strain Bruges A (S)
```

<400> SEQUENCE: 126

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Phe Tyr Ser Gly
                100                 105                 110

Thr Ala Thr Leu Asp Val Tyr Asp His Arg Thr Leu Ala Ser Glu Glu
            115                 120                 125

Asn Val Ile Val Val Ser Leu Gln Tyr Arg Val Ala Ser Leu Gly Phe
        130                 135                 140

Leu Phe Leu Gly
145

<210> SEQ ID NO 127
<211> LENGTH: 152
<212> TYPE: PRT
<213> ORGANISM: Culex pipiens quinquefasciatus strain BO (R)

<400> SEQUENCE: 127

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Ser Phe Tyr Ser Gly
                100                 105                 110

Thr Ala Thr Leu Asp Val Tyr Asp His Arg Thr Leu Ala Ser Glu Glu
            115                 120                 125

Asn Val Ile Val Val Ser Leu Gln Tyr Arg Val Ala Ser Leu Gly Phe
        130                 135                 140

Leu Phe Leu Gly Thr Pro Glu Ala
145                 150

<210> SEQ ID NO 128
<211> LENGTH: 148
<212> TYPE: PRT
<213> ORGANISM: Culex pipiens quinquefasciatus strain DJI (R)

<400> SEQUENCE: 128

Gly Lys Ile Arg Gly Thr Thr Leu Glu Ala Pro Ser Gly Lys Lys Val
1               5                   10                  15

```
Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Ser Phe Tyr Ser Gly
                100                 105                 110

Thr Ala Thr Leu Asp Val Tyr Asp His Arg Thr Leu Ala Ser Glu Glu
            115                 120                 125

Asn Val Ile Val Val Ser Leu Gln Tyr Arg Val Ala Ser Leu Gly Phe
        130                 135                 140

Leu Phe Leu Gly
145

<210> SEQ ID NO 129
<211> LENGTH: 152
<212> TYPE: PRT
<213> ORGANISM: Culex pipiens quinquefasciatus strain Harare (R)

<400> SEQUENCE: 129

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Ser Phe Tyr Ser Gly
                100                 105                 110

Thr Ala Thr Leu Asp Val Tyr Asp His Arg Thr Leu Ala Ser Glu Glu
            115                 120                 125

Asn Val Ile Val Val Ser Leu Gln Tyr Arg Val Ala Ser Leu Gly Phe
        130                 135                 140

Leu Phe Leu Gly Thr Pro Glu Ala
145                 150

<210> SEQ ID NO 130
<211> LENGTH: 152
<212> TYPE: PRT
<213> ORGANISM: Culex pipiens quinquefasciatus strain Martinique (R)

<400> SEQUENCE: 130

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30
```

Arg Phe Arg His Pro Arg Pro Ala Glu Arg Trp Thr Gly Val Leu Asn
    35                  40                  45

Ala Thr Lys Pro Pro Asn Ser Cys Val Gln Ile Val Asp Thr Val Phe
 50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Ser Phe Tyr Ser Gly
                100                 105                 110

Thr Ala Thr Leu Asp Val Tyr Asp His Arg Thr Leu Ala Ser Glu Glu
                115                 120                 125

Asn Val Ile Val Val Ser Leu Gln Tyr Arg Val Ala Ser Leu Gly Phe
            130                 135                 140

Leu Phe Leu Gly Thr Pro Glu Ala
145                 150

<210> SEQ ID NO 131
<211> LENGTH: 148
<212> TYPE: PRT
<213> ORGANISM: Culex pipiens pipiens strain Barriol (R)

<400> SEQUENCE: 131

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
                20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
 50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Ser Phe Tyr Ser Gly
                100                 105                 110

Thr Ala Thr Leu Asp Val Tyr Asp His Arg Thr Leu Ala Ser Glu Glu
                115                 120                 125

Asn Val Ile Val Val Ser Leu Gln Tyr Arg Val Ala Ser Leu Gly Phe
            130                 135                 140

Leu Phe Leu Gly
145

<210> SEQ ID NO 132
<211> LENGTH: 148
<212> TYPE: PRT
<213> ORGANISM: Culex pipiens pipiens strain Bleuet (S)

<400> SEQUENCE: 132

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
                20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe

```
                50                  55                  60
Gly Asp Phe Pro Gly Ala Thr Met Trp Asn Pro Asn Thr Pro Leu Ser
 65                  70                  75                  80

Glu Asp Cys Leu Tyr Ile Asn Val Val Pro Arg Pro Arg Pro Lys
                 85                  90                  95

Asn Ala Ala Val Met Leu Trp Ile Phe Gly Gly Gly Phe Tyr Ser Gly
                100                 105                 110

Thr Ala Thr Leu Asp Val Tyr Asp His Arg Thr Leu Ala Ser Glu Glu
                115                 120                 125

Asn Val Ile Val Val Ser Leu Gln Tyr Arg Val Ala Ser Leu Gly Phe
                130                 135                 140

Leu Phe Leu Gly
145

<210> SEQ ID NO 133
<211> LENGTH: 148
<212> TYPE: PRT
<213> ORGANISM: Culex pipiens pipiens strain Bruges B (S)

<400> SEQUENCE: 133

Gly Lys Ile Arg Gly Thr Thr Leu Glu Ala Pro Ser Gly Lys Lys Val
 1               5                  10                  15

Asp Ala Trp Met Gly Ile Pro Tyr Ala Gln Pro Pro Leu Gly Pro Leu
                20                  25                  30

Arg Phe Arg His Pro Arg Pro Ala Glu Arg Trp Thr Gly Val Leu Asn
                35                  40                  45

Ala Thr Lys Pro Pro Asn Ser Cys Val Gln Ile Val Asp Thr Val Phe
 50                  55                  60

Gly Asp Phe Pro Gly Ala Thr Met Trp Asn Pro Asn Thr Pro Leu Ser
 65                  70                  75                  80

Glu Asp Cys Leu Tyr Ile Asn Val Val Pro Arg Pro Arg Pro Lys
                 85                  90                  95

Asn Ala Ala Val Met Leu Trp Ile Phe Gly Gly Gly Phe Tyr Ser Gly
                100                 105                 110

Thr Ala Thr Leu Asp Val Tyr Asp His Arg Thr Leu Ala Ser Glu Glu
                115                 120                 125

Asn Val Ile Val Val Ser Leu Gln Tyr Arg Val Ala Ser Leu Gly Phe
                130                 135                 140

Leu Phe Leu Gly
145

<210> SEQ ID NO 134
<211> LENGTH: 148
<212> TYPE: PRT
<213> ORGANISM: Culex pipiens pipiens strain Heteren (S)

<400> SEQUENCE: 134

Gly Lys Ile Arg Gly Thr Thr Leu Glu Ala Pro Ser Gly Lys Lys Val
 1               5                  10                  15

Asp Ala Trp Met Gly Ile Pro Tyr Ala Gln Pro Pro Leu Gly Pro Leu
                20                  25                  30

Arg Phe Arg His Pro Arg Pro Ala Glu Arg Trp Thr Gly Val Leu Asn
                35                  40                  45

Ala Thr Lys Pro Pro Asn Ser Cys Val Gln Ile Val Asp Thr Val Phe
 50                  55                  60

Gly Asp Phe Pro Gly Ala Thr Met Trp Asn Pro Asn Thr Pro Leu Ser
 65                  70                  75                  80
```

```
Glu Asp Cys Leu Tyr Ile Asn Val Val Pro Arg Pro Arg Pro Lys
                85                  90                  95

Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Ala Ser Glu Glu
            115                 120                 125

Asn Val Ile Val Val Ser Leu Gln Tyr Arg Val Ala Ser Leu Gly Phe
        130                 135                 140

Leu Phe Leu Gly
145

<210> SEQ ID NO 135
<211> LENGTH: 149
<212> TYPE: PRT
<213> ORGANISM: Culex pipiens quinquefasciatus strain Ling (S)

<400> SEQUENCE: 135

Gln Gly Lys Ile Arg Gly Thr Thr Leu Glu Ala Pro Ser Gly Lys Lys
1               5                   10                  15

Val Asp Ala Trp Met Gly Ile Pro Tyr Ala Gln Pro Leu Gly Pro
            20                  25                  30

Leu Arg Phe Arg His Pro Arg Pro Ala Glu Arg Trp Thr Gly Val Leu
        35                  40                  45

Asn Ala Thr Lys Pro Pro Asn Ser Cys Val Gln Ile Val Asp Thr Val
    50                  55                  60

Phe Gly Asp Phe Pro Gly Ala Thr Met Trp Asn Pro Asn Thr Pro Leu
65                  70                  75                  80

Ser Glu Asp Cys Leu Tyr Ile Asn Val Val Pro Arg Pro Arg Pro
                85                  90                  95

Lys Asn Ala Ala Val Met Leu Trp Ile Phe Gly Gly Gly Phe Tyr Ser
            100                 105                 110

Gly Thr Ala Thr Leu Asp Val Tyr Asp His Arg Thr Leu Ala Ser Glu
            115                 120                 125

Glu Asn Val Ile Val Val Ser Leu Gln Tyr Arg Val Ala Ser Leu Gly
        130                 135                 140

Phe Leu Phe Leu Gly
145

<210> SEQ ID NO 136
<211> LENGTH: 148
<212> TYPE: PRT
<213> ORGANISM: Culex pipiens quinquefasciatus strain Mao (S)

<400> SEQUENCE: 136

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95
```

```
Asn Ala Ala Val Met Leu Trp Ile Phe Gly Gly Gly Phe Tyr Ser Gly
                100                 105                 110

Thr Ala Thr Leu Asp Val Tyr Asp His Arg Thr Leu Ala Ser Glu Glu
            115                 120                 125

Asn Val Ile Val Val Ser Leu Gln Tyr Arg Val Ala Ser Leu Gly Phe
        130                 135                 140

Leu Phe Leu Gly
145

<210> SEQ ID NO 137
<211> LENGTH: 144
<212> TYPE: PRT
<213> ORGANISM: Culex pipiens quinquefasciatus strain TemR (S)

<400> SEQUENCE: 137

Lys Ile Arg Gly Thr Thr Leu Glu Ala Pro Ser Gly Lys Lys Val Asp
1               5                   10                  15

Ala Trp Met Gly Ile Pro Tyr Ala Gln Pro Pro Leu Gly Pro Leu Arg
            20                  25                  30

Phe Arg His Pro Arg Pro Ala Glu Arg Trp Thr Gly Val Leu Asn Ala
        35                  40                  45

Thr Lys Pro Pro Asn Ser Cys Val Gln Ile Val Asp Thr Val Phe Gly
    50                  55                  60

Asp Phe Pro Gly Ala Thr Met Trp Asn Pro Thr Pro Leu Ser Glu
65                  70                  75                  80

Asp Cys Leu Tyr Ile Asn Val Val Pro Arg Pro Arg Pro Lys Asn
                85                  90                  95

Ala Ala Val Met Leu Trp Ile Phe Gly Gly Gly Phe Tyr Ser Gly Thr
            100                 105                 110

Ala Thr Leu Asp Val Tyr Asp His Arg Thr Leu Thr Ser Glu Glu Asn
        115                 120                 125

Val Ile Val Val Ser Leu Gln Tyr Arg Val Ala Ser Leu Gly Phe Leu
    130                 135                 140

<210> SEQ ID NO 138
<211> LENGTH: 148
<212> TYPE: PRT
<213> ORGANISM: Culex torrentium strain Uppsala

<400> SEQUENCE: 138

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
```

```
            130                 135                 140
Leu Phe Leu Gly
145

<210> SEQ ID NO 139
<211> LENGTH: 148
<212> TYPE: PRT
<213> ORGANISM: Culex pipiens quinquefasciatus strain Trans (S)

<400> SEQUENCE: 139

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Thr Ser Glu Glu
        115                 120                 125

Asn Val Ile Val Val Ser Leu Gln Tyr Arg Val Ala Ser Leu Gly Phe
    130                 135                 140

Leu Phe Leu Gly
145

<210> SEQ ID NO 140
<211> LENGTH: 137
<212> TYPE: PRT
<213> ORGANISM: Culex pipiens quinquefasciatus strain BED (S)

<400> SEQUENCE: 140

Thr Leu Glu Ala Pro Ser Gly Lys Lys Val Asp Ala Trp Met Gly Ile
1               5                   10                  15

Pro Tyr Ala Gln Pro Pro Leu Gly Pro Leu Arg Phe Arg His Pro Arg
            20                  25                  30

Pro Ala Glu Arg Trp Thr Gly Val Leu Asn Ala Thr Lys Pro Pro Asn
        35                  40                  45

Ser Cys Val Gln Ile Val Asp Thr Val Phe Gly Asp Phe Pro Gly Ala
    50                  55                  60

Thr Met Trp Asn Pro Asn Thr Pro Leu Ser Glu Asp Cys Leu Tyr Ile
65                  70                  75                  80

Asn Val Val Pro Arg Pro Arg Pro Lys Asn Ala Ala Val Met Leu
                85                  90                  95

Trp Ile Phe Gly Gly Gly Phe Tyr Ser Gly Thr Ala Thr Leu Asp Val
            100                 105                 110

Tyr Asp His Arg Thr Leu Ala Ser Glu Glu Asn Val Ile Val Val Ser
        115                 120                 125

Leu Gln Tyr Arg Val Ala Ser Leu Gly
    130                 135

<210> SEQ ID NO 141
```

```
<211> LENGTH: 144
<212> TYPE: PRT
<213> ORGANISM: Culex pipiens quinquefasciatus strain BSQ (S)

<400> SEQUENCE: 141
```

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu
            20                  25                  30

Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140

```
<210> SEQ ID NO 142
<211> LENGTH: 137
<212> TYPE: PRT
<213> ORGANISM: Culex pipiens quinquefasciatus strain Brazza (S)

<400> SEQUENCE: 142
```

Leu Glu Ala Pro Ser Gly Lys Lys Val Asp Ala Trp Met Gly Ile Pro
1               5                   10                  15

Tyr Ala Gln Pro Pro Leu Gly Pro Leu Arg Phe Arg His Pro Arg Pro
            20                  25                  30

Ala Glu Arg Trp Thr Gly Val Leu Asn Ala Thr Lys Pro Pro Asn Ser
        35                  40                  45

Cys Val Gln Ile Val Asp Thr Val Phe Gly Asp Phe Pro Gly Ala Thr
    50                  55                  60

Met Trp Asn Pro Asn Thr Pro Leu Ser Glu Asp Cys Leu Tyr Ile Asn
65                  70                  75                  80

Val Val Val Pro Arg Pro Arg Pro Lys Asn Ala Ala Val Met Leu Trp
                85                  90                  95

Ile Phe Gly Gly Gly Phe Tyr Ser Gly Thr Ala Thr Leu Asp Val Tyr
            100                 105                 110

Asp His Arg Thr Leu Ala Ser Glu Glu Asn Val Ile Val Val Ser Leu
        115                 120                 125

Gln Tyr Arg Val Ala Ser Leu Gly Phe
    130                 135

```
<210> SEQ ID NO 143
<211> LENGTH: 144
<212> TYPE: PRT
<213> ORGANISM: Culex pipiens quinquefasciatus strain Bouake (R)

<400> SEQUENCE: 143
```

Gly Lys Ile Arg Gly Thr Thr Leu Glu Ala Pro Ser Gly Lys Lys Val
1               5                   10                  15

Asp Ala Trp Met Gly Ile Pro Tyr Ala Gln Pro Pro Leu Gly Pro Leu

```
              20                  25                  30
Arg Phe Arg His Pro Arg Pro Ala Glu Arg Trp Thr Gly Val Leu Asn
        35                  40                  45

Ala Thr Lys Pro Pro Asn Ser Cys Val Gln Ile Val Asp Thr Val Phe
    50                  55                  60

Gly Asp Phe Pro Gly Ala Thr Met Trp Asn Pro Asn Thr Pro Leu Ser
65                  70                  75                  80

Glu Asp Cys Leu Tyr Ile Asn Val Val Pro Arg Pro Arg Pro Lys
                85                  90                  95

Asn Ala Ala Val Met Leu Trp Ile Phe Gly Gly Gly Phe Tyr Ser Gly
            100                 105                 110

Thr Ala Thr Leu Asp Val Tyr Asp His Arg Thr Leu Ala Ser Glu Glu
        115                 120                 125

Asn Val Ile Val Val Ser Leu Gln Tyr Arg Val Ala Ser Leu Gly Phe
    130                 135                 140

<210> SEQ ID NO 144
<211> LENGTH: 138
<212> TYPE: PRT
<213> ORGANISM: Culex pipiens quinquefasciatus strain Thai (S)

<400> SEQUENCE: 144

Thr Leu Glu Ala Pro Ser Gly Lys Lys Val Asp Ala Trp Met Gly Ile
1               5                   10                  15

Pro Tyr Ala Gln Pro Pro Leu Gly Pro Leu Arg Phe Arg His Pro Arg
            20                  25                  30

Pro Ala Glu Arg Trp Thr Gly Val Leu Asn Ala Thr Lys Pro Pro Asn
        35                  40                  45

Ser Cys Val Gln Ile Val Asp Thr Val Phe Gly Asp Phe Pro Gly Ala
    50                  55                  60

Thr Met Trp Asn Pro Asn Thr Pro Leu Ser Glu Asp Cys Leu Tyr Ile
65                  70                  75                  80

Asn Val Val Pro Arg Pro Arg Pro Lys Asn Ala Ala Val Met Leu
            85                  90                  95

Trp Ile Phe Gly Gly Gly Phe Tyr Ser Gly Thr Ala Thr Leu Asp Val
            100                 105                 110

Tyr Asp His Arg Thr Leu Ala Ser Glu Glu Asn Val Ile Val Val Ser
        115                 120                 125

Leu Gln Tyr Arg Val Ala Ser Leu Gly Phe
    130                 135

<210> SEQ ID NO 145
<211> LENGTH: 141
<212> TYPE: PRT
<213> ORGANISM: Culex pipiens quinquefasciatus strain Madurai (S)

<400> SEQUENCE: 145

Leu Glu Ala Pro Ser Gly Lys Lys Val Asp Ala Trp Met Gly Ile Pro
1               5                   10                  15

Tyr Ala Gln Pro Pro Leu Gly Pro Leu Arg Phe Arg His Pro Arg Pro
            20                  25                  30

Ala Glu Arg Trp Thr Gly Val Leu Asn Ala Thr Lys Pro Pro Asn Ser
        35                  40                  45

Cys Val Gln Ile Val Asp Thr Val Phe Gly Asp Phe Pro Gly Ala Thr
    50                  55                  60

Met Trp Asn Pro Asn Thr Pro Leu Ser Glu Asp Cys Leu Tyr Ile Asn
65                  70                  75                  80
```

Val Val Val Pro Arg Pro Arg Pro Lys Asn Ala Ala Val Met Leu Trp
            85                  90                  95

Ile Phe Gly Gly Gly Phe Tyr Ser Gly Thr Ala Thr Leu Asp Val Tyr
            100                 105                 110

Asp His Arg Thr Leu Ala Ser Glu Glu Asn Val Ile Val Val Ser Leu
            115                 120                 125

Gln Tyr Arg Val Ala Ser Leu Gly Phe Leu Phe Leu Gly
            130                 135                 140

<210> SEQ ID NO 146
<211> LENGTH: 141
<212> TYPE: PRT
<213> ORGANISM: Culex pipiens quinquefasciatus strain Recife (R)

<400> SEQUENCE: 146

Leu Glu Ala Pro Ser Gly Lys Lys Val Asp Ala Trp Met Gly Ile Pro
1               5                   10                  15

Tyr Ala Gln Pro Pro Leu Gly Pro Leu Arg Phe Arg His Pro Arg Pro
            20                  25                  30

Ala Glu Arg Trp Thr Gly Val Leu Asn Ala Thr Lys Pro Pro Asn Ser
            35                  40                  45

Cys Val Gln Ile Val Asp Thr Val Phe Gly Asp Phe Pro Gly Ala Thr
    50                  55                  60

Met Trp Asn Pro Asn Thr Pro Leu Ser Glu Asp Cys Leu Tyr Ile Asn
65                  70                  75                  80

Val Val Val Pro Arg Pro Arg Pro Lys Asn Ala Ala Val Met Leu Trp
            85                  90                  95

Ile Phe Gly Gly Ser Phe Tyr Ser Gly Thr Ala Thr Leu Asp Val Tyr
            100                 105                 110

Asp His Arg Thr Leu Ala Ser Glu Glu Asn Val Ile Val Val Ser Leu
            115                 120                 125

Gln Tyr Arg Val Ala Ser Leu Gly Phe Leu Phe Leu Gly
            130                 135                 140

<210> SEQ ID NO 147
<211> LENGTH: 137
<212> TYPE: PRT
<213> ORGANISM: Culex pipiens quinquefasciatus strain Bresil (S)

<400> SEQUENCE: 147

Leu Glu Ala Pro Ser Gly Lys Lys Val Asp Ala Trp Met Gly Ile Pro
1               5                   10                  15

Tyr Ala Gln Pro Pro Leu Gly Pro Leu Arg Phe Arg His Pro Arg Pro
            20                  25                  30

Ala Glu Arg Trp Thr Gly Val Leu Asn Ala Thr Lys Pro Pro Asn Ser
            35                  40                  45

Cys Val Gln Ile Val Asp Thr Val Phe Gly Asp Phe Pro Gly Ala Thr
    50                  55                  60

Met Trp Asn Pro Asn Thr Pro Leu Ser Glu Asp Cys Leu Tyr Ile Asn
65                  70                  75                  80

Val Val Val Pro Arg Pro Arg Pro Lys Asn Ala Ala Val Met Leu Trp
            85                  90                  95

Ile Phe Gly Gly Gly Phe Tyr Ser Gly Thr Ala Thr Leu Asp Val Tyr
            100                 105                 110

Asp His Arg Thr Leu Ala Ser Glu Glu Asn Val Ile Val Val Ser Leu
            115                 120                 125

Gln Tyr Arg Val Ala Ser Leu Gly Phe
    130                 135

<210> SEQ ID NO 148
<211> LENGTH: 139
<212> TYPE: PRT
<213> ORGANISM: Culex pipiens quinquefasciatus strain Moorea (S)

<400> SEQUENCE: 148

Thr Leu Glu Ala Pro Ser Gly Lys Lys Val Asp Ala Trp Met Gly Ile
1               5                   10                  15

Pro Tyr Ala Gln Pro Pro Leu Gly Pro Leu Arg Phe Arg His Pro Arg
            20                  25                  30

Pro Ala Glu Arg Trp Thr Gly Val Leu Asn Ala Thr Lys Pro Pro Asn
        35                  40                  45

Ser Cys Val Gln Ile Val Asp Thr Val Phe Gly Asp Phe Pro Gly Ala
    50                  55                  60

Thr Met Trp Asn Pro Asn Thr Pro Leu Ser Glu Asp Cys Leu Tyr Ile
65                  70                  75                  80

Asn Val Val Pro Arg Pro Arg Pro Lys Asn Ala Ala Val Met Leu
                85                  90                  95

Trp Ile Phe Gly Gly Gly Phe Tyr Ser Gly Thr Ala Thr Leu Asp Val
            100                 105                 110

Tyr Asp His Arg Thr Leu Ala Ser Glu Glu Asn Val Ile Val Val Ser
        115                 120                 125

Leu Gln Tyr Arg Val Ala Ser Leu Gly Phe Leu
    130                 135

<210> SEQ ID NO 149
<211> LENGTH: 134
<212> TYPE: PRT
<213> ORGANISM: Culex pipiens pipiens strain Killcare (S)

<400> SEQUENCE: 149

Ser Gly Lys Lys Val Asp Ala Trp Met Gly Ile Pro Tyr Ala Gln Pro
1               5                   10                  15

Pro Leu Gly Pro Leu Arg Phe Arg His Pro Arg Pro Ala Glu Arg Trp
            20                  25                  30

Thr Gly Val Leu Asn Ala Thr Lys Pro Pro Asn Ser Cys Val Gln Ile
        35                  40                  45

Val Asp Thr Val Phe Gly Asp Phe Pro Gly Ala Thr Met Trp Asn Pro
    50                  55                  60

Asn Thr Pro Leu Ser Glu Asp Cys Leu Tyr Ile Asn Val Val Val Pro
65                  70                  75                  80

Arg Pro Arg Pro Lys Asn Ala Ala Val Met Leu Trp Ile Phe Gly Gly
                85                  90                  95

Gly Phe Tyr Ser Gly Thr Ala Thr Leu Asp Val Tyr Asp His Arg Thr
            100                 105                 110

Leu Ala Ser Glu Glu Asn Val Ile Val Val Ser Leu Gln Tyr Arg Val
        115                 120                 125

Ala Ser Leu Gly Phe Leu
    130

<210> SEQ ID NO 150
<211> LENGTH: 2527
<212> TYPE: DNA
<213> ORGANISM: Anopheles gambiae strain YAO

<400> SEQUENCE: 150

```
gaatgcgcat tgttgcgata gattgaattt ccttggttgt tgttgttgtt ggttttcttt      60
tgacatgttt gtgtgttgtt ttttctttct ctctctctct ctttctgtgg ttccaacatt     120
tcagacgcat ttttttacacc atatataggt cacggtgagt ccgcacgaat tatagatgcc    180
gagttgggca cgctcgagca tgtacacagt ggagcaacgc cgcggcgacg cggtctgacg     240
aggcgcgagt caaactcggg taagtacgcg attggaagtg ggggggacgtt taccctaccg    300
tgtactacaa cgcactttac ccccacgcac acgcaccggc agacgcgaac gacaacgatc     360
cgctggtggt caacacggat aaggggcgca tccgcggcat tacggtcgat gcccccagcg     420
gcaagaaggt ggacgtgtgg ctcggcattc cctacgccca gccgccggtc gggccgctac     480
ggttccgtca tccgcggccg gccgaaaagt ggaccggcgt gctgaacacg accacaccgc     540
ccaacagctg cgtgcagatc gtggacaccg tgttcggcga cttcccgggc gcgaccatgt     600
ggaacccgaa cacgcccctg tccgaggact gtctgtacat taacgtggtg gcaccgcggc     660
cccggcccaa gaatgcggcc gtcatgctgt ggatcttcgg cggcagcttc tactccggca     720
ccgccaccct ggacgtgtac gaccaccggg cgcttgcgtc ggaggagaac gtgatcgtgg     780
tgtcgctgca gtaccgcgtg gccagtctgg gcttcctgtt tctcggcacc ccggaagcgc     840
cgggcaatgc gggactgttc gatcagaacc ttgcgctacg gtaggtgtct ttgcgtgtgt     900
gtctgtagtt atagtattct aacgaggtgc tcttcttccc atcacttctt gggagtcagc     960
tgggtgcggg acaacattca ccggttcggt ggtgatccgt cgcgcgtgac actgttcggc    1020
gagagtgccg gtgccgtctc ggtgtcgctg catctgctgt ccgccctttc ccgcgatctg    1080
ttccagcggg ccatcctgca gagcggctcg ccgacggcac cgtgggcatt ggtatcgcgc    1140
gaggaagcca cgctaaggta cgtgccagct gctgctttcc ccaaaccacc aacccgcaac    1200
agctcacaca accctctttt ccgtcgctct tttctcgctc cagagcactg cggttggccg    1260
aggcggtcgg ctgcccgcac gaaccgagca agctgagcga tgcggtcgag tgtctgcgcg    1320
gcaaggatcc gcacgtgctg gtcaacaacg agtggggcac gctcggcatt tgcgagttcc    1380
cgttcgtgcc ggtggtcgac ggtgcgttcc tggacgagac gccgcagcgt tcgctcgcca    1440
gcgggcgctt caagaagacg gagatcctca ccggcagcaa cacggaggag ggctactact    1500
tcatcatcta ctacctgacc gagctgctgc gcaaggagga gggcgtgacc gtgacgcgcg    1560
aggagttcct gcaggcggtg cgcgagctca acccgtacgt gaacggggcg gcccggcagg    1620
cgatcgtgtt cgagtacacc gactggaccg agcggacaa cccgaacagc aaccgggacg     1680
cgctggacaa gatggtgggc gactatcact tcacctgcaa cgtgaacgag ttcgcgcagc    1740
ggtacgccga ggagggcaac aacgtctaca tgtatctgta cacgcaccgc agcaaaggca    1800
acccgtggcc gcgctggacg ggcgtgatgc acggcgacga gatcaactac gtgttcggcg    1860
aaccgctcaa ccccacccct ggctacaccg aggacgagaa agactttagc cggaagatca    1920
tgcgatactg gtctaacttt gccaaaaccg ggtaagtgtg tgtgtcaaac agcaaagtgc    1980
caatagctct aacaccagcg tcttctctct tctacagcaa tccaaatccc aacacagcca    2040
gcagcgaatt ccccgagtgg cccaagcaca ccgcccacgg acggcactat ctggagctgg    2100
gcctcaacac gtccttcgtc ggtcggggcc cacggttgag gcagtgtgcc ttctggaaga    2160
agtaccttcc ccagctagtt gcagctacct gtaagtctag ttgctgcacg agaaaccccc    2220
tctcgcgtcc ccatcagggt ccagattaca ataacaaatg tatctctctc tcacgtatct    2280
tttcccaaa acagcgaacc taccaggggc agcaccgccc agtgaaccgt gcgaaagcag     2340
cgcattttttt taccgacctg atctgatcgt gctgctggtg tcgctgctta cggcgaccgt    2400
```

```
cagattcata caataattac tacccccatcc atggcctagt tcgtttaagc tttaagatag    2460
tgaggaacaa attttttccta accaatttcc ccccccttta gagcagaacc gagggagaga   2520
taggact                                                               2527

<210> SEQ ID NO 151
<211> LENGTH: 2214
<212> TYPE: DNA
<213> ORGANISM: Anopheles gambiae strain YAO
<220> FEATURE:
<221> NAME/KEY: CDS
<222> LOCATION: (1)..(2214)

<400> SEQUENCE: 151 atg gag atc cga ggg ctg ctg atg ggt aga ctg cgg tta gga cgg cgg    48
Met Glu Ile Arg Gly Leu Leu Met Gly Arg Leu Arg Leu Gly Arg Arg
1               5                  10                  15 atg gtt ccg ctg ggt ctg ctc ggc gtg acc gcg ctg cta cta atc ctg    96
Met Val Pro Leu Gly Leu Leu Gly Val Thr Ala Leu Leu Leu Ile Leu
            20                  25                  30 cca ccc tcc gcg ctg gtg cag ggc cgg cac cac gag ctc aac aat ggt   144
Pro Pro Ser Ala Leu Val Gln Gly Arg His His Glu Leu Asn Asn Gly
        35                  40                  45 gcc gcc atc gga tcg cat cag ctg tcg gct gcc gcc ggt gtt ggc ctt   192
Ala Ala Ile Gly Ser His Gln Leu Ser Ala Ala Ala Gly Val Gly Leu
    50                  55                  60 tcc tcc cag tcc gcc cag tcc gga tcg ctc gca tcc ggt gtg atg tca   240
Ser Ser Gln Ser Ala Gln Ser Gly Ser Leu Ala Ser Gly Val Met Ser
65                  70                  75                  80 tcc gtt cct gct gcc gga gcg tca tcc tcc tcc tcg tcg tcg ctg ctg   288
Ser Val Pro Ala Ala Gly Ala Ser Ser Ser Ser Ser Ser Leu Leu
                85                  90                  95 tca tcg tca gcc gag gac gac gtg gcg cgc att act ctc agc aag gac   336
Ser Ser Ser Ala Glu Asp Asp Val Ala Arg Ile Thr Leu Ser Lys Asp
            100                 105                 110 gca gac gca ttt ttt aca cca tat ata ggt cac ggt gag tcc gca cga   384
Ala Asp Ala Phe Phe Thr Pro Tyr Ile Gly His Gly Glu Ser Ala Arg
        115                 120                 125 att ata gat gcc gag ttg ggc acg ctc gag cat gta cac agt gga gca   432
Ile Ile Asp Ala Glu Leu Gly Thr Leu Glu His Val His Ser Gly Ala
    130                 135                 140 acg ccg cgg cga cgc ggt ctg acg agg cgc gag tca aac tcg gac gcg   480
Thr Pro Arg Arg Arg Gly Leu Thr Arg Arg Glu Ser Asn Ser Asp Ala
145                 150                 155                 160 aac gac aac gat ccg ctg gtg gtc aac acg gat aag ggg cgc atc cgc   528
Asn Asp Asn Asp Pro Leu Val Val Asn Thr Asp Lys Gly Arg Ile Arg
                165                 170                 175 ggc att acg gtc gat gcc ccc agc ggc aag aag gtg gac gtg tgg ctc   576
Gly Ile Thr Val Asp Ala Pro Ser Gly Lys Lys Val Asp Val Trp Leu
            180                 185                 190 ggc att ccc tac gcc cag ccg ccg gtc ggg ccg cta cgg ttc cgt cat   624
Gly Ile Pro Tyr Ala Gln Pro Pro Val Gly Pro Leu Arg Phe Arg His
        195                 200                 205 ccg cgg ccg gcc gaa aag tgg acc ggc gtg ctg aac acg acc aca ccg   672
Pro Arg Pro Ala Glu Lys Trp Thr Gly Val Leu Asn Thr Thr Thr Pro
    210                 215                 220 ccc aac agc tgc gtg cag atc gtg gac acc gtg ttc ggc gac ttc ccg   720
Pro Asn Ser Cys Val Gln Ile Val Asp Thr Val Phe Gly Asp Phe Pro
225                 230                 235                 240 ggc gcg acc atg tgg aac ccg aac acg ccc ctg tcc gag gac tgt ctg   768
Gly Ala Thr Met Trp Asn Pro Asn Thr Pro Leu Ser Glu Asp Cys Leu
```

```
                        245                     250                     255
tac att aac gtg gtg gca ccg cgg ccc cgg ccc aag aat gcg gcc gtc         816
Tyr Ile Asn Val Val Ala Pro Arg Pro Arg Pro Lys Asn Ala Ala Val
            260                     265                     270 atg ctg tgg atc ttc ggc ggc agc ttc tac tcc ggc acc gcc acc ctg         864
Met Leu Trp Ile Phe Gly Gly Ser Phe Tyr Ser Gly Thr Ala Thr Leu
            275                     280                     285 gac gtg tac gac cac cgg gcg ctt gcg tcg gag gag aac gtg atc gtg         912
Asp Val Tyr Asp His Arg Ala Leu Ala Ser Glu Glu Asn Val Ile Val
            290                     295                     300 gtg tcg ctg cag tac cgc gtg gcc agt ctg ggc ttc ctg ttt ctc ggc         960
Val Ser Leu Gln Tyr Arg Val Ala Ser Leu Gly Phe Leu Phe Leu Gly
305                     310                     315                 320 acc ccg gaa gcg ccg ggc aat gcg gga ctg ttc gat cag aac ctt gcg        1008
Thr Pro Glu Ala Pro Gly Asn Ala Gly Leu Phe Asp Gln Asn Leu Ala
                325                     330                     335 cta cgc tgg gtg cgg gac aac att cac cgg ttc ggt ggt gat ccg tcg        1056
Leu Arg Trp Val Arg Asp Asn Ile His Arg Phe Gly Gly Asp Pro Ser
                340                     345                     350 cgc gtg aca ctg ttc ggc gag agt gcc ggt gcc gtc tcg gtg tcg ctg        1104
Arg Val Thr Leu Phe Gly Glu Ser Ala Gly Ala Val Ser Val Ser Leu
                355                     360                     365 cat ctg ctg tcc gcc ctt tcc cgc gat ctg ttc cag cgg gcc atc ctg        1152
His Leu Leu Ser Ala Leu Ser Arg Asp Leu Phe Gln Arg Ala Ile Leu
370                     375                     380 cag agc ggc tcg ccg acg gca ccg tgg gca ttg gta tcg cgc gag gaa        1200
Gln Ser Gly Ser Pro Thr Ala Pro Trp Ala Leu Val Ser Arg Glu Glu
385                     390                     395                 400 gcc acg cta aga gca ctg cgg ttg gcc gag gcg gtc ggc tgc ccg cac        1248
Ala Thr Leu Arg Ala Leu Arg Leu Ala Glu Ala Val Gly Cys Pro His
                405                     410                     415 gaa ccg agc aag ctg agc gat gcg gtc gag tgt ctg cgc ggc aag gat        1296
Glu Pro Ser Lys Leu Ser Asp Ala Val Glu Cys Leu Arg Gly Lys Asp
                420                     425                     430 ccg cac gtg ctg gtc aac aac gag tgg ggc acg ctc ggc att tgc gag        1344
Pro His Val Leu Val Asn Asn Glu Trp Gly Thr Leu Gly Ile Cys Glu
                435                     440                     445 ttc ccg ttc gtg ccg gtg gtc gac ggt gcg ttc ctg gac gag acg ccg        1392
Phe Pro Phe Val Pro Val Val Asp Gly Ala Phe Leu Asp Glu Thr Pro
450                     455                     460 cag cgt tcg ctc gcc agc ggg cgc ttc aag aag acg gag atc ctc acc        1440
Gln Arg Ser Leu Ala Ser Gly Arg Phe Lys Lys Thr Glu Ile Leu Thr
465                     470                     475                 480 ggc agc aac acg gag gag ggc tac tac ttc atc atc tac tac ctg acc        1488
Gly Ser Asn Thr Glu Glu Gly Tyr Tyr Phe Ile Ile Tyr Tyr Leu Thr
                485                     490                     495 gag ctg ctg cgc aag gag gag ggc gtg acc gtg acg cgc gag gag ttc        1536
Glu Leu Leu Arg Lys Glu Glu Gly Val Thr Val Thr Arg Glu Glu Phe
                500                     505                     510 ctg cag gcg gtg cgc gag ctc aac ccg tac gtg aac ggg gcg gcc cgg        1584
Leu Gln Ala Val Arg Glu Leu Asn Pro Tyr Val Asn Gly Ala Ala Arg
                515                     520                     525 cag gcg atc gtg ttc gag tac acc gac tgg acc gag ccg gac aac ccg        1632
Gln Ala Ile Val Phe Glu Tyr Thr Asp Trp Thr Glu Pro Asp Asn Pro
                530                     535                     540 aac agc aac cgg gac gcg ctg gac aag atg gtg ggc gac tat cac ttc        1680
Asn Ser Asn Arg Asp Ala Leu Asp Lys Met Val Gly Asp Tyr His Phe
545                     550                     555                 560 acc tgc aac gtg aac gag ttc gcg cag cgg tac gcc gag gag ggc aac        1728
Thr Cys Asn Val Asn Glu Phe Ala Gln Arg Tyr Ala Glu Glu Gly Asn
```

```
                    565                 570                 575
aac gtc tac atg tat ctg tac acg cac cgc agc aaa ggc aac ccg tgg        1776
Asn Val Tyr Met Tyr Leu Tyr Thr His Arg Ser Lys Gly Asn Pro Trp
            580                 585                 590 ccg cgc tgg acg ggc gtg atg cac ggc gac gag atc aac tac gtg ttc        1824
Pro Arg Trp Thr Gly Val Met His Gly Asp Glu Ile Asn Tyr Val Phe
            595                 600                 605 ggc gaa ccg ctc aac ccc acc ctc ggc tac acc gag gac gag aaa gac        1872
Gly Glu Pro Leu Asn Pro Thr Leu Gly Tyr Thr Glu Asp Glu Lys Asp
610                 615                 620 ttt agc cgg aag atc atg cga tac tgg tct aac ttt gcc aaa acc ggc        1920
Phe Ser Arg Lys Ile Met Arg Tyr Trp Ser Asn Phe Ala Lys Thr Gly
625                 630                 635                 640 aat cca aat ccc aac aca gcc agc agc gaa ttc ccc gag tgg ccc aag        1968
Asn Pro Asn Pro Asn Thr Ala Ser Ser Glu Phe Pro Glu Trp Pro Lys
            645                 650                 655 cac acc gcc cac gga cgg cac tat ctg gag ctg ggc ctc aac acg tcc        2016
His Thr Ala His Gly Arg His Tyr Leu Glu Leu Gly Leu Asn Thr Ser
            660                 665                 670 ttc gtc ggt cgg ggc cca cgg ttg agg cag tgt gcc ttc tgg aag aag        2064
Phe Val Gly Arg Gly Pro Arg Leu Arg Gln Cys Ala Phe Trp Lys Lys
            675                 680                 685 tac ctt ccc cag cta gtt gca gct acc tcg aac cta cca ggg cca gca        2112
Tyr Leu Pro Gln Leu Val Ala Ala Thr Ser Asn Leu Pro Gly Pro Ala
690                 695                 700 ccg ccc agt gaa ccg tgc gaa agc agc gca ttt ttt tac cga cct gat        2160
Pro Pro Ser Glu Pro Cys Glu Ser Ser Ala Phe Phe Tyr Arg Pro Asp
705                 710                 715                 720 ctg atc gtg ctg ctg gtg tcg ctg ctt acg gcg acc gtc aga ttc ata        2208
Leu Ile Val Leu Leu Val Ser Leu Leu Thr Ala Thr Val Arg Phe Ile
            725                 730                 735 caa taa                                                                  2214
Gln <210> SEQ ID NO 152
<211> LENGTH: 737
<212> TYPE: PRT
<213> ORGANISM: Anopheles gambiae strain YAO

<400> SEQUENCE: 152

Met Glu Ile Arg Gly Leu Leu Met Gly Arg Leu Arg Leu Gly Arg Arg
1               5                   10                  15

Met Val Pro Leu Gly Leu Leu Gly Val Thr Ala Leu Leu Leu Ile Leu
            20                  25                  30

Pro Pro Ser Ala Leu Val Gln Gly Arg His His Glu Leu Asn Asn Gly
        35                  40                  45

Ala Ala Ile Gly Ser His Gln Leu Ser Ala Ala Gly Val Gly Leu
    50                  55                  60

Ser Ser Gln Ser Ala Gln Ser Gly Ser Leu Ala Ser Gly Val Met Ser
65                  70                  75                  80

Ser Val Pro Ala Ala Gly Ala Ser Ser Ser Ser Ser Ser Leu Leu
            85                  90                  95

Ser Ser Ser Ala Glu Asp Val Ala Arg Ile Thr Leu Ser Lys Asp
            100                 105                 110

Ala Asp Ala Phe Phe Thr Pro Tyr Ile Gly His Gly Glu Ser Ala Arg
        115                 120                 125

Ile Ile Asp Ala Glu Leu Gly Thr Leu Glu His Val His Ser Gly Ala
    130                 135                 140
```

```
Thr Pro Arg Arg Arg Gly Leu Thr Arg Glu Ser Asn Ser Asp Ala
145                 150                 155                 160

Asn Asp Asn Asp Pro Leu Val Val Asn Thr Asp Lys Gly Arg Ile Arg
            165                 170                 175

Gly Ile Thr Val Asp Ala Pro Ser Gly Lys Lys Val Asp Val Trp Leu
        180                 185                 190

Gly Ile Pro Tyr Ala Gln Pro Val Gly Pro Leu Arg Phe Arg His
    195                 200                 205

Pro Arg Pro Ala Glu Lys Trp Thr Gly Val Leu Asn Thr Thr Pro
210                 215                 220

Pro Asn Ser Cys Val Gln Ile Val Asp Thr Val Phe Gly Asp Phe Pro
225                 230                 235                 240

Gly Ala Thr Met Trp Asn Pro Asn Thr Pro Leu Ser Glu Asp Cys Leu
                245                 250                 255

Tyr Ile Asn Val Val Ala Pro Arg Pro Arg Pro Lys Asn Ala Ala Val
                260                 265                 270

Met Leu Trp Ile Phe Gly Gly Ser Phe Tyr Ser Gly Thr Ala Thr Leu
            275                 280                 285

Asp Val Tyr Asp His Arg Ala Leu Ala Ser Glu Glu Asn Val Ile Val
290                 295                 300

Val Ser Leu Gln Tyr Arg Val Ala Ser Leu Gly Phe Leu Phe Leu Gly
305                 310                 315                 320

Thr Pro Glu Ala Pro Gly Asn Ala Gly Leu Phe Asp Gln Asn Leu Ala
                325                 330                 335

Leu Arg Trp Val Arg Asp Asn Ile His Arg Phe Gly Gly Asp Pro Ser
            340                 345                 350

Arg Val Thr Leu Phe Gly Glu Ser Ala Gly Ala Val Ser Val Ser Leu
            355                 360                 365

His Leu Leu Ser Ala Leu Ser Arg Asp Leu Phe Gln Arg Ala Ile Leu
            370                 375                 380

Gln Ser Gly Ser Pro Thr Ala Pro Trp Ala Leu Val Ser Arg Glu Glu
385                 390                 395                 400

Ala Thr Leu Arg Ala Leu Arg Leu Ala Glu Ala Val Gly Cys Pro His
                405                 410                 415

Glu Pro Ser Lys Leu Ser Asp Ala Val Glu Cys Leu Arg Gly Lys Asp
                420                 425                 430

Pro His Val Leu Val Asn Asn Glu Trp Gly Thr Leu Gly Ile Cys Glu
            435                 440                 445

Phe Pro Phe Val Pro Val Val Asp Gly Ala Phe Leu Asp Glu Thr Pro
            450                 455                 460

Gln Arg Ser Leu Ala Ser Gly Arg Phe Lys Lys Thr Glu Ile Leu Thr
465                 470                 475                 480

Gly Ser Asn Thr Glu Glu Gly Tyr Tyr Phe Ile Ile Tyr Tyr Leu Thr
                485                 490                 495

Glu Leu Leu Arg Lys Glu Gly Val Thr Val Thr Arg Glu Glu Phe
            500                 505                 510

Leu Gln Ala Val Arg Glu Leu Asn Pro Tyr Val Asn Gly Ala Ala Arg
            515                 520                 525

Gln Ala Ile Val Phe Glu Tyr Thr Asp Trp Thr Glu Pro Asp Asn Pro
            530                 535                 540

Asn Ser Asn Arg Asp Ala Leu Asp Lys Met Val Gly Asp Tyr His Phe
545                 550                 555                 560

Thr Cys Asn Val Asn Glu Phe Ala Gln Arg Tyr Ala Glu Glu Gly Asn
                565                 570                 575
```

-continued

```
Asn Val Tyr Met Tyr Leu Tyr Thr His Arg Ser Lys Gly Asn Pro Trp
                580                 585                 590

Pro Arg Trp Thr Gly Val Met His Gly Asp Glu Ile Asn Tyr Val Phe
            595                 600                 605

Gly Glu Pro Leu Asn Pro Thr Leu Gly Tyr Thr Glu Asp Glu Lys Asp
        610                 615                 620

Phe Ser Arg Lys Ile Met Arg Tyr Trp Ser Asn Phe Ala Lys Thr Gly
625                 630                 635                 640

Asn Pro Asn Pro Asn Thr Ala Ser Ser Glu Phe Pro Glu Trp Pro Lys
                645                 650                 655

His Thr Ala His Gly Arg His Tyr Leu Glu Leu Gly Leu Asn Thr Ser
            660                 665                 670

Phe Val Gly Arg Gly Pro Arg Leu Arg Gln Cys Ala Phe Trp Lys Lys
        675                 680                 685

Tyr Leu Pro Gln Leu Val Ala Ala Thr Ser Asn Leu Pro Gly Pro Ala
    690                 695                 700

Pro Pro Ser Glu Pro Cys Glu Ser Ser Ala Phe Phe Tyr Arg Pro Asp
705                 710                 715                 720

Leu Ile Val Leu Leu Val Ser Leu Leu Thr Ala Thr Val Arg Phe Ile
                725                 730                 735

Gln

<210> SEQ ID NO 153
<211> LENGTH: 20
<212> TYPE: DNA
<213> ORGANISM: Artificial Sequence
<220> FEATURE:
<223> OTHER INFORMATION: Synthetic DNA

<400> SEQUENCE: 153
gatcgtggac accgtgttcg                                               20

<210> SEQ ID NO 154
<211> LENGTH: 20
<212> TYPE: DNA
<213> ORGANISM: Artificial Sequence
<220> FEATURE:
<223> OTHER INFORMATION: Synthetic DNA

<400> SEQUENCE: 154
aggatggccc gctggaacag                                               20

<210> SEQ ID NO 155
<211> LENGTH: 2214
<212> TYPE: DNA
<213> ORGANISM: Anopheles gambiae strain KISUMU
<220> FEATURE:
<221> NAME/KEY: CDS
<222> LOCATION: (1)..(2214)

<400> SEQUENCE: 155 atg gag atc cga ggg ctg ctg atg ggt aga cta cgg tta gga cgg cgg      48
Met Glu Ile Arg Gly Leu Leu Met Gly Arg Leu Arg Leu Gly Arg Arg
1               5                   10                  15 atg gtt ccg ctg ggt ctg ctc ggc gtg acc gcg ctg cta cta atc ctg      96
Met Val Pro Leu Gly Leu Leu Gly Val Thr Ala Leu Leu Leu Ile Leu
            20                  25                  30 cca ccc tcc gcg ctg gtg cag ggc cgg cac cac gag ctc aac aat ggt     144
Pro Pro Ser Ala Leu Val Gln Gly Arg His His Glu Leu Asn Asn Gly
        35                  40                  45
```

```
gcc gcc atc gga tcg cat cag ctg tcg gct gcc gcc ggt gtt ggc ctt    192
Ala Ala Ile Gly Ser His Gln Leu Ser Ala Ala Ala Gly Val Gly Leu
     50                  55                  60 tcc tcc cag tcc gcc cag tcc gga tcg ctc gca tcc ggt gtg atg tca    240
Ser Ser Gln Ser Ala Gln Ser Gly Ser Leu Ala Ser Gly Val Met Ser
65                  70                  75                  80 tcc gtt cct gct gcc gga gcg tca tcc tcc tcc tcg tcg ctg ctg        288
Ser Val Pro Ala Ala Gly Ala Ser Ser Ser Ser Ser Ser Leu Leu
                85                  90                  95 tca tcg tca gcc gag gac gac gtg gcg cgc att act ctc agc aag gac    336
Ser Ser Ser Ala Glu Asp Asp Val Ala Arg Ile Thr Leu Ser Lys Asp
            100                 105                 110 gca gac gca ttt ttt aca cca tat ata ggt cac ggt gag tcc gta cga    384
Ala Asp Ala Phe Phe Thr Pro Tyr Ile Gly His Gly Glu Ser Val Arg
        115                 120                 125 att ata gat gcc gag ttg ggc acg ctc gag cat gtc cac agt gga gca    432
Ile Ile Asp Ala Glu Leu Gly Thr Leu Glu His Val His Ser Gly Ala
    130                 135                 140 acg ccg cgg cga cgc ggt ctg acg agg cgc gag tcc aac tcg gac gcg    480
Thr Pro Arg Arg Arg Gly Leu Thr Arg Arg Glu Ser Asn Ser Asp Ala
145                 150                 155                 160 aac gac aac gat ccg ctg gtg gtc aac acg gat aag ggg cgc atc cgc    528
Asn Asp Asn Asp Pro Leu Val Val Asn Thr Asp Lys Gly Arg Ile Arg
                165                 170                 175 ggc att acg gtc gat gcg ccc agc ggc aag aag gtg gac gtg tgg ctc    576
Gly Ile Thr Val Asp Ala Pro Ser Gly Lys Lys Val Asp Val Trp Leu
            180                 185                 190 ggc att ccc tac gcc cag ccg ccg gtc ggg ccg tta cgg ttc cgt cat    624
Gly Ile Pro Tyr Ala Gln Pro Pro Val Gly Pro Leu Arg Phe Arg His
        195                 200                 205 ccg cgg ccg gcc gaa aag tgg acc ggc gtg ctg aac acg acc aca ccg    672
Pro Arg Pro Ala Glu Lys Trp Thr Gly Val Leu Asn Thr Thr Thr Pro
    210                 215                 220 ccc aac agc tgc gtg cag atc gtg gac acc gtg ttc ggc gac ttc ccg    720
Pro Asn Ser Cys Val Gln Ile Val Asp Thr Val Phe Gly Asp Phe Pro
225                 230                 235                 240 ggc gcg acc atg tgg aac ccg aac acg ccc ctg tcc gag gac tgt ctg    768
Gly Ala Thr Met Trp Asn Pro Asn Thr Pro Leu Ser Glu Asp Cys Leu
                245                 250                 255 tac att aac gtg gtg gca ccg cga ccc cgg ccc aag aat gcg gcc gtc    816
Tyr Ile Asn Val Val Ala Pro Arg Pro Arg Pro Lys Asn Ala Ala Val
            260                 265                 270 atg ctg tgg atc ttc ggc ggc ggc ttc tac tcc ggc acc gcc acc ctg    864
Met Leu Trp Ile Phe Gly Gly Gly Phe Tyr Ser Gly Thr Ala Thr Leu
        275                 280                 285 gac gtg tac gac cac cgg gcg ctt gcg tcg gag gag aac gtg atc gtg    912
Asp Val Tyr Asp His Arg Ala Leu Ala Ser Glu Glu Asn Val Ile Val
    290                 295                 300 gtg tcg ctg cag tac cgc gtg gcc agt ctg ggc ttc ctg ttt ctc ggc    960
Val Ser Leu Gln Tyr Arg Val Ala Ser Leu Gly Phe Leu Phe Leu Gly
305                 310                 315                 320 acc ccg gaa gcg ccg ggc aat gcg gga ctg ttc gat cag aac ctt gcg   1008
Thr Pro Glu Ala Pro Gly Asn Ala Gly Leu Phe Asp Gln Asn Leu Ala
                325                 330                 335 cta cgc tgg gtg cgg gac aac att cac cgg ttc ggt ggt gat ccg tcg   1056
Leu Arg Trp Val Arg Asp Asn Ile His Arg Phe Gly Gly Asp Pro Ser
            340                 345                 350 cgt gtg aca ctg ttc ggc gag agt gcc ggt gcc gtc tcg gtg tcg ctg   1104
Arg Val Thr Leu Phe Gly Glu Ser Ala Gly Ala Val Ser Val Ser Leu
        355                 360                 365
```

```
cat ctg ctg tcc gcc ctg tcc cgc gat ctg ttc cag cgg gcc atc ctg    1152
His Leu Leu Ser Ala Leu Ser Arg Asp Leu Phe Gln Arg Ala Ile Leu
    370             375             380 cag agc ggc tcg ccg acg gca ccg tgg gca ttg gta tcg cgc gag gaa    1200
Gln Ser Gly Ser Pro Thr Ala Pro Trp Ala Leu Val Ser Arg Glu Glu
385             390             395             400 gcc acg cta aga gca ctg cgg ttg gcc gag gcg gtc ggc tgc ccg cac    1248
Ala Thr Leu Arg Ala Leu Arg Leu Ala Glu Ala Val Gly Cys Pro His
            405             410             415 gaa ccg agc aag ctg agc gat gcg gtc gag tgt ctg cgc ggc aag gat    1296
Glu Pro Ser Lys Leu Ser Asp Ala Val Glu Cys Leu Arg Gly Lys Asp
        420             425             430 ccg cac gtg ctg gtc aac aac gag tgg ggc acg ctc ggc att tgc gag    1344
Pro His Val Leu Val Asn Asn Glu Trp Gly Thr Leu Gly Ile Cys Glu
            435             440             445 ttc ccg ttc gtg ccg gtg gtc gac ggt gcg ttc ctg gac gag acg ccg    1392
Phe Pro Phe Val Pro Val Val Asp Gly Ala Phe Leu Asp Glu Thr Pro
450             455             460 cag cgt tcg ctc gcc agc ggg cgc ttc aag aag acg gag atc ctc acc    1440
Gln Arg Ser Leu Ala Ser Gly Arg Phe Lys Lys Thr Glu Ile Leu Thr
465             470             475             480 ggc agc aac acg gag gag ggc tac tac ttc atc atc tac tac ctg acc    1488
Gly Ser Asn Thr Glu Glu Gly Tyr Tyr Phe Ile Ile Tyr Tyr Leu Thr
            485             490             495 gag ctg ctg cgc aag gag gag ggc gtg acc gtg acg cgc gag gag ttc    1536
Glu Leu Leu Arg Lys Glu Glu Gly Val Thr Val Thr Arg Glu Glu Phe
        500             505             510 ctg cag gcg gtg cgc gag ctc aac ccg tac gtg aac ggg gcg gcc cgg    1584
Leu Gln Ala Val Arg Glu Leu Asn Pro Tyr Val Asn Gly Ala Ala Arg
            515             520             525 cag gcg atc gtg ttc gag tac acc gac tgg acc gag ccg gac aac ccg    1632
Gln Ala Ile Val Phe Glu Tyr Thr Asp Trp Thr Glu Pro Asp Asn Pro
530             535             540 aac agc aac cgg gac gcg ctg gac aag atg gtg ggc gac tat cac ttc    1680
Asn Ser Asn Arg Asp Ala Leu Asp Lys Met Val Gly Asp Tyr His Phe
545             550             555             560 acc tgc aac gtg aac gag ttc gcg cag cgg tac gcc gag gag ggc aac    1728
Thr Cys Asn Val Asn Glu Phe Ala Gln Arg Tyr Ala Glu Glu Gly Asn
            565             570             575 aac gtc tac atg tat ctg tac acg cac cgc agc aaa ggc aac ccg tgg    1776
Asn Val Tyr Met Tyr Leu Tyr Thr His Arg Ser Lys Gly Asn Pro Trp
        580             585             590 ccg cgc tgg acg ggc gtg atg cac ggc gac gag atc aac tac gtg ttc    1824
Pro Arg Trp Thr Gly Val Met His Gly Asp Glu Ile Asn Tyr Val Phe
            595             600             605 ggc gaa ccg ctc aac ccc acc ctc ggc tac acc gag gac gag aaa gac    1872
Gly Glu Pro Leu Asn Pro Thr Leu Gly Tyr Thr Glu Asp Glu Lys Asp
610             615             620 ttt agc cgg aag atc atg cga tac tgg tct aac ttt gcc aaa acc ggc    1920
Phe Ser Arg Lys Ile Met Arg Tyr Trp Ser Asn Phe Ala Lys Thr Gly
625             630             635             640 aat cca aat ccc aac acg gcc agc agc gaa ttc ccc gag tgg ccc aag    1968
Asn Pro Asn Pro Asn Thr Ala Ser Ser Glu Phe Pro Glu Trp Pro Lys
            645             650             655 cac acc gcc cac gga cgg cac tat ctg gag ctg ggc ctc aac acg tcc    2016
His Thr Ala His Gly Arg His Tyr Leu Glu Leu Gly Leu Asn Thr Ser
        660             665             670 ttc gtc ggt cgg ggc cca cgg ttg agg cag tgt gcc ttc tgg aag aag    2064
Phe Val Gly Arg Gly Pro Arg Leu Arg Gln Cys Ala Phe Trp Lys Lys
            675             680             685
```

-continued

| | | | | | | | | | | | | |
|---|---|---|---|---|---|---|---|---|---|---|---|---|
| tac | ctt | ccc | cag | cta | gtt | gca | gct | acc | tcg | aac | cta | cca | ggg | cca | gca | 2112 |
| Tyr | Leu | Pro | Gln | Leu | Val | Ala | Ala | Thr | Ser | Asn | Leu | Pro | Gly | Pro | Ala | |
| | 690 | | | | 695 | | | | | 700 | | | | | | |
| ccg | ccc | agt | gaa | ccg | tgc | gaa | agc | agc | gca | ttt | ttt | tac | cga | cct | gat | 2160 |
| Pro | Pro | Ser | Glu | Pro | Cys | Glu | Ser | Ser | Ala | Phe | Phe | Tyr | Arg | Pro | Asp | |
| 705 | | | | 710 | | | | | 715 | | | | | 720 | | |
| ctg | atc | gtg | ctg | ctg | gtg | tcg | ctg | ctt | acg | gcg | acc | gtc | aga | ttc | ata | 2208 |
| Leu | Ile | Val | Leu | Leu | Val | Ser | Leu | Leu | Thr | Ala | Thr | Val | Arg | Phe | Ile | |
| | | | | 725 | | | | | 730 | | | | 735 | | | |
| caa | taa | | | | | | | | | | | | | | | 2214 |
| Gln | | | | | | | | | | | | | | | | |

<210> SEQ ID NO 156
<211> LENGTH: 737
<212> TYPE: PRT
<213> ORGANISM: Anopheles gambiae strain KISUMU

<400> SEQUENCE: 156

Met Glu Ile Arg Gly Leu Leu Met Gly Arg Leu Arg Leu Gly Arg Arg
1               5                   10                  15

Met Val Pro Leu Gly Leu Leu Gly Val Thr Ala Leu Leu Ile Leu
        20                  25                  30

Pro Pro Ser Ala Leu Val Gln Gly Arg His His Glu Leu Asn Asn Gly
        35                  40                  45

Ala Ala Ile Gly Ser His Gln Leu Ser Ala Ala Gly Val Gly Leu
50                  55                  60

Ser Ser Gln Ser Ala Gln Ser Gly Ser Leu Ala Ser Gly Val Met Ser
65                  70                  75                  80

Ser Val Pro Ala Ala Gly Ala Ser Ser Ser Ser Ser Ser Leu Leu
            85                  90                  95

Ser Ser Ser Ala Glu Asp Asp Val Ala Arg Ile Thr Leu Ser Lys Asp
            100                 105                 110

Ala Asp Ala Phe Phe Thr Pro Tyr Ile Gly His Gly Glu Ser Val Arg
        115                 120                 125

Ile Ile Asp Ala Glu Leu Gly Thr Leu Glu His Val His Ser Gly Ala
130                 135                 140

Thr Pro Arg Arg Arg Gly Leu Thr Arg Arg Glu Ser Asn Ser Asp Ala
145                 150                 155                 160

Asn Asp Asn Asp Pro Leu Val Val Asn Thr Asp Lys Gly Arg Ile Arg
                165                 170                 175

Gly Ile Thr Val Asp Ala Pro Ser Gly Lys Lys Val Asp Val Trp Leu
            180                 185                 190

Gly Ile Pro Tyr Ala Gln Pro Pro Val Gly Pro Leu Arg Phe Arg His
        195                 200                 205

Pro Arg Pro Ala Glu Lys Trp Thr Gly Val Leu Asn Thr Thr Thr Pro
    210                 215                 220

Pro Asn Ser Cys Val Gln Ile Val Asp Thr Val Phe Gly Asp Phe Pro
225                 230                 235                 240

Gly Ala Thr Met Trp Asn Pro Asn Thr Pro Leu Ser Glu Asp Cys Leu
                245                 250                 255

Tyr Ile Asn Val Val Ala Pro Arg Pro Arg Pro Lys Asn Ala Ala Val
            260                 265                 270

Met Leu Trp Ile Phe Gly Gly Gly Phe Tyr Ser Gly Thr Ala Thr Leu
        275                 280                 285

Asp Val Tyr Asp His Arg Ala Leu Ala Ser Glu Glu Asn Val Ile Val
    290                 295                 300

```
Val Ser Leu Gln Tyr Arg Val Ala Ser Leu Gly Phe Leu Phe Leu Gly
305                 310                 315                 320

Thr Pro Glu Ala Pro Gly Asn Ala Gly Leu Phe Asp Gln Asn Leu Ala
                325                 330                 335

Leu Arg Trp Val Arg Asp Asn Ile His Arg Phe Gly Gly Asp Pro Ser
            340                 345                 350

Arg Val Thr Leu Phe Gly Glu Ser Ala Gly Ala Val Ser Val Ser Leu
        355                 360                 365

His Leu Leu Ser Ala Leu Ser Arg Asp Leu Phe Gln Arg Ala Ile Leu
    370                 375                 380

Gln Ser Gly Ser Pro Thr Ala Pro Trp Ala Leu Val Ser Arg Glu Glu
385                 390                 395                 400

Ala Thr Leu Arg Ala Leu Arg Leu Ala Glu Ala Val Gly Cys Pro His
                405                 410                 415

Glu Pro Ser Lys Leu Ser Asp Ala Val Glu Cys Leu Arg Gly Lys Asp
            420                 425                 430

Pro His Val Leu Val Asn Asn Glu Trp Gly Thr Leu Gly Ile Cys Glu
        435                 440                 445

Phe Pro Phe Val Pro Val Asp Gly Ala Phe Leu Asp Glu Thr Pro
450                 455                 460

Gln Arg Ser Leu Ala Ser Gly Arg Phe Lys Lys Thr Glu Ile Leu Thr
465                 470                 475                 480

Gly Ser Asn Thr Glu Glu Gly Tyr Tyr Phe Ile Ile Tyr Tyr Leu Thr
                485                 490                 495

Glu Leu Leu Arg Lys Glu Gly Val Thr Val Thr Arg Glu Glu Phe
            500                 505                 510

Leu Gln Ala Val Arg Glu Leu Asn Pro Tyr Val Asn Gly Ala Ala Arg
    515                 520                 525

Gln Ala Ile Val Phe Glu Tyr Thr Asp Trp Thr Glu Pro Asp Asn Pro
530                 535                 540

Asn Ser Asn Arg Asp Ala Leu Asp Lys Met Val Gly Asp Tyr His Phe
545                 550                 555                 560

Thr Cys Asn Val Asn Glu Phe Ala Gln Arg Tyr Ala Glu Glu Gly Asn
                565                 570                 575

Asn Val Tyr Met Tyr Leu Tyr Thr His Arg Ser Lys Gly Asn Pro Trp
            580                 585                 590

Pro Arg Trp Thr Gly Val Met His Gly Asp Glu Ile Asn Tyr Val Phe
        595                 600                 605

Gly Glu Pro Leu Asn Pro Thr Leu Gly Tyr Thr Glu Asp Glu Lys Asp
    610                 615                 620

Phe Ser Arg Lys Ile Met Arg Tyr Trp Ser Asn Phe Ala Lys Thr Gly
625                 630                 635                 640

Asn Pro Asn Pro Asn Thr Ala Ser Ser Glu Phe Pro Glu Trp Pro Lys
                645                 650                 655

His Thr Ala His Gly Arg His Tyr Leu Glu Leu Gly Leu Asn Thr Ser
            660                 665                 670

Phe Val Gly Arg Gly Pro Arg Leu Arg Gln Cys Ala Phe Trp Lys Lys
        675                 680                 685

Tyr Leu Pro Gln Leu Val Ala Ala Thr Ser Asn Leu Pro Gly Pro Ala
    690                 695                 700

Pro Pro Ser Glu Pro Cys Glu Ser Ser Ala Phe Phe Tyr Arg Pro Asp
705                 710                 715                 720

Leu Ile Val Leu Leu Val Ser Leu Leu Thr Ala Thr Val Arg Phe Ile
                725                 730                 735
```

Gln

<210> SEQ ID NO 157
<211> LENGTH: 10700
<212> TYPE: DNA
<213> ORGANISM: Anopheles gambiae

<400> SEQUENCE: 157

```
cagtgttaaa cgctttccaa ccgcaacatc aatattggcc taaagacggg cccgacagct     60
acattggatg atgccagttc tgaaacgggg gaaaaagtaa acgaacgtt gcccttcaca    120
ttgacgatgt gtgcgagcag cggcggcaaa tacacggagg gcacataaat tagccacatc    180
aaccgatatc cgcttagcga attaagtcgt tcgccgagct tcaaacgtgt gcagtgtgtt    240
gccagctttg ctggccgcgg ctgaatacgc ggctggcaaa tgtttgcaaa tccttagcaa    300
gtaattaaat gtaaatcaaa tgagcaaaat cttgtgtttc gctcttgaaa tgtggtgtgc    360
taattggcag ccgatcttat gcgagcgaga tagagagtgc atatatgctg tagacttcat    420
tagtaaaagc agctttgctt tctttacgca tgatacttat cgcttatcgc tctcacaaat    480
aaatgaaata ctcaagacag tgaatgttga tattcaagag atatttacag caaaaagtgg    540
taataatgtt caatacgtgg atgattgtga tacaagcact agaatgttgt tcacaattat    600
tccgggaatc aacattaaac gttcagtatc atgtgacaac cttccaagga cgcttccaat    660
atcacaatcg atggatggat gaacctgcat cgagacctgg gcaaaaaaat gccacccaaa    720
cagctgtatt acctgcacga cacattacta agtaaaacact agccgctgtc ggcctcccac    780
agcacccttc ctcacacttc ttccttcatc cactgtttgg ggtagcgtcg aaatatgtcc    840
taagccctcc aggctattat tggatcatta ccgggctcga ccatgaaccg agttggcagg    900
aagtgtgtcg gggtgagtcg gtggggcggc tgatgctctt ccttacgtcc actcccagtc    960
ccaacgaccg agcccaccac tctcccccct ccctgcagca ctaatcgggc caccatcatt   1020
atgcattaat aaataactgc ccactttggt ggaataatct ccgttagggg cgcttcgtta   1080
aactaattaa atggcatttg agtggcagcg gcagtgatcg gtttgatcgt gcctcccaca   1140
accgaacctg agggggggt ctggaaatcg gcaggatact gctgcagcag ccgcgcgtgt   1200
accaccgttc ggcattgtgt gcagcatcat gttcaatggg cttctctcc gcagccattg   1260
tgcgtccagt gtcgtgtcga tataatcgga ttctaccgat aggctcgtta tcttgttacg   1320
cggtgttgtg cggcgtacgt gtgattgaaa gcgatcgagc ggctgtgcgg catagtttgt   1380
tgcgaattcg ctgtaaacat gcttatgcaa tggtgagtgc tactttttc gtagcccaaa   1440
tttaagacaa tccaaagctc acttcagtcg agagggaaca aacacgcccc agcgggaaga   1500
aataaatatt agcgtaagtg tttacttatt gattattatt aaaccataga tgaagaaatg   1560
aatatccaat ttatatagcc tttcttccag ccacctttt tctaatcttt ttgccatttt    1620
tgcatttttt tataatcgga ttagatgaac taaacccgaa attaataaga attccgcttc   1680
ggaagatatt acggcagcca tcattaggag ggagagaaaa cagtaaaaca atttcccgcg   1740
gtcaatgagt acttcagata caccattgaa agctgaaagc tcatcagcga gaacggggct   1800
caaatctacg acgactatga tgataaagct attttctgcc aattctgcaa ctttcgcaaa   1860
aaaggaagaa atgactcaag agcgttgcga caactgtgtg cgaaagagga tgatttcgga   1920
aaaggttgca cacacataca cacacgggca aacacactca gtgcacatgg tggacgtaaa   1980
tgggaatgct atttttatct attagaagca tgaattattg atgaaacatg ctgataatct   2040
ttctcccggc cccggcattg ccccgtttgc agtccggcga gacccgcgcc atctgccatc   2100
```

```
cgtccacaca acggcttttt gagggactgc ggataccagt gacagtgtag catgaaatat    2160
ttatcagttc ttataattga gtgtcggtgt gattccgttc ccaaaaaaaa aaaacggtga    2220
agcgcgaaag acgggaacga agtggatccg tcgaaacttc cgtcgaaaca ccacacctca    2280
cctcacacgt tggttggccc agggacgaca gggaatcgcg gtcaccgaac cagcatcgcg    2340
ggaaacattt tgacgtcaca cgtctctgtg atatttgccg tagctgccgg ttggtttatc    2400
gaagtgtgta tgtggatggc attttccacg ctactttgca tcggacgagc gcaacctgac    2460
gagtccctgc ccacactcat actattcgcg tgaaaaacgg tagagcgaat ccttccgttt    2520
tcaattagga ccgtgacatt tgtttcgacg tttcttgtgc gctcgtgtgt gtgtgtgtgt    2580
gtgtgtgtgt agtgcttttt ggaacaggaa aggcaaaaac catgatgcga cgtcgttttg    2640
acaaacgctt cagatgatcg gattgtggtt tgctggaagg attatcttgc aaagcggttg    2700
aaggattcat agcaatccga gcacaacgcg cttcacggta ttatggccag cgtgggataa    2760
gtgaaataag tttaaggata gctgaaataa gattgctgat ccagctatac agccgctaga    2820
tgcttcaacg caagaaaaag cacatgctaa cagacttaaa aggacaacac tgcaaagcgt    2880
attgcatact ttgaggcgta ttacttcgaa taacgtgcaa atatattatt actacttatc    2940
attaaccctc atattatcca ctaaattata attataatcg ctttctcaca aacccgatga    3000
tatcccactt cacggaggta actttattat tctcttttaa acagctctct ttcaccaact    3060
gcaccttata cttagggcga aatcccctaa tcccgcttca tagcgaacca aacgcaacca    3120
aaccaccata aacccgtcgc cctcgtgtgc tctcgattgg tttggggaca gaaatgaaag    3180
catcataaaa tatgaatgaa attgacgtgc cagtgcgaaa aaggtgttaa ttaaataaac    3240
tttcatcttc gtttcttgcc gtttcgagcc gttcagttg ctttgggtta gcctggctta    3300
gcaagagggc aaggcatatt acgcaccatt ttatgtttac accccattac accagtcgat    3360
ccgcgggccc gacatcggcc gacaccgtct cgtggcacag ttggggttga atgccggtcg    3420
cagagcggat tcgattttcc gttaagaaac tcccggagta cggttacgga tattgatccg    3480
caaaacaagt cccagctctt agataagccg tcgactcgga acgaatgcag caaagcaagt    3540
tctcttccac ctcaagaatc ggtggccggg gtagagcata caagcagctg gcaaaagttc    3600
tgccagcgag agtaaacagg gaaaacttta ataaggaatt taattaaaag aaaacaacac    3660
ccgggcacac agtgcgcaga accagggcac gattatccca cggcgtggtt gggacggtgg    3720 gggggaaac ttctgcacgc ctgtcaagcc tgaagagcca acaaacatgg gccggaataa    3780
ttcaactcgc cataaacgga atgccacggc acgggtctgg cagccgaatt attgtcctgt    3840
ccgttccgat cgtaaagtcg ccggaaggag aattatggcc gataaattag gaccaccggg    3900
ttccggcatg gcgcatggac gtgcggagaa ggcgaaggga gggtccttaa atactgatga    3960
cttgctcctt tttcggtcac atttcggatc ggtcgaaacc ggtacgaatg attatgcagc    4020
ggcacgaagc ttgggtttcg ttgtgagtgt tgagcgcttc cgaaagggc atccgtgagc    4080 ttaattcaaa tcactcgtgc gagcagaaag ttaatgctga tgctgaaaat caatcaacgg    4140
tttacattgt aaccaatgtg acttttaaac cggataaaca tttcggcaag acttttggca    4200
ggttttgggt tacttccact gaaagggcaa ggatcacgat gctcgatgtc cttttttgttg    4260 catactatgt tttattgatg tttgtgttat taagacacat ttgcagcatt tagttactga    4320
aaataggcat taaaccactg ttgaaatgta gtccaagtat aaacattaat tcttttaaat    4380
ctctaaagta cctgtaagtc ccaacaatga ctcatcgcat gaaaaaccct catctgaagc    4440
taagtcggca aacagttcca aacattggaa tgtttcgaga tgtatttata ttccatcgta    4500
```

```
atccacactt tcatcccgga gttcttaaaa agacgtacga tccaaacaag caccettctg    4560
aggcattgaa acattttcga cgcccagtgg tagattagca tttctgcaca ttagtcgctc    4620
aagctgtttt gttggagtat tacgaggaaa gaaagctccg ttccgatgcc caaacccttα    4680
cctgccaggc cacggaagct cccatgcgaa caccgagaac tgccaaataa tggaacagcg    4740
gcttttcaag agcacggatt cggcttgtgc ctcatttgaa aagaatctgg tagggaatta    4800
gaaattccgt gatgctgtgt ggcgtgcgct ctaatcctgc ccgagagggt aagaacgatt    4860
ggcctgaaca aaatcagcgc gttttaatcc cgcgctgtaa ttactatcat caccaatccg    4920
tacctcggac gattgccaaa gcgggcgtgt tgtgccgttg tgccgagcca attccatttc    4980
cgccggaacg cacgattgac tatgaatatt aaacttcagc cgtcgaaaag gaagcaaaaa    5040
aaaaagccaa ccctcatcgc cgcaaaatgg ccaccgagcc ccgtttgccc cgagtcaagc    5100
ttggttcgtg taccgaaaga agcgcatggg aaatttgcgt cggatttagc tttaagtttt    5160
cttaaattt atctgtaagc tctaacgcct tcttctgccg tcctgggtag atgtcgcagt    5220
agtctgagct ggcagtacga gaaaaaacga accgcatact aaaccaaacc aacggctaat    5280
ccacaacttc tgatatcttt tactcttttc ttcacatttt tccggttctt tctgtagcgc    5340
tctccgcccg tgccgatgga gatccgaggg ctgctgatgg gtagactacg gttaggacgg    5400
cggatggttc cgctgggtct gctcggcgtg accgcgctgc tactaatcct gccacccttc    5460
gcgctggtgc agggccggca ccacgagctc aacaatggtg ccgccatcgg atcgcatcag    5520
ctgtcggctg ccgccggtgt tggccttgcc tcccagtccg cccagtccgg atcgctcgca    5580
tccggtgtga tgtcatccgt tcctgctgcc ggagcgtcat cctcctcctc gtcgtcgctg    5640
ctgtcatcgt cagccgagga cgacgtggcg cgcattactc tcagcaagga cgcaggtcgg    5700
ttggatggcg tccgaaatcg gaccatcatt cttacataaa tacagattca cccacacaca    5760
cacaaagaac acagatatac agatccctca ccaacaaaaa aaaaacgggt tcatcgtct    5820
gactccacct gacagaggca aacacgccgg ggtcgaggtg gattggtacg gattggtcat    5880
ttccgttctt cttcatgtgc gtttcttact ctcctgcctt tcaaacgaa cttcagaacg    5940
aaaaaaaaca cgcgacggag agtaagaagc tgtacagaca ctctagtcct cacacacaca    6000
acttgcttac tttgtccgtc cgtttgattc cgctctttct atgtgtgact ttctggcacc    6060
ctttacttcg tcactattca tttcatttcc aataaacttt taatgtgtct ttctttttta    6120
ttctaaatat ctatagtaaa tgttctgtag caagtatctt gtagtagaat tgtatagaag    6180
tagattttg tatgagtttg catcatccct tcccaatggg gttgactccg tttcaaccaa    6240
cgccaaaagc tatcggcata aagtatggtt ccttgcaaag gcttttatga aacacgaatg    6300
tgttgaaagc ttttgcaaat ggaaatgtta aagcctttaa gttccaatcg cttttgtat    6360
ccatttagtt tgcatgaaca acaggaaatc aaaatattgg taacgacaat cgctggcggg    6420
cgttcctttc ttgtctaatc aaatcatcta cgattgtaat tacaaacttc caagtttgcg    6480
tatgacaatg ttaaatgtct aagacgctca aatgcaacca atagagtata attactaagg    6540
cgggcagtag aaaccaaaat atcttaaata atgtcaagca aaacaaaaag aacaattccg    6600
ttcactgctc aaagaaagcc ctaactaact acctaacctt ttcatcgatg accctgtact    6660
gacatggtaa gatattcttt atcctttaac tcttctgcac cctacgcact caatgcaaca    6720
cacgcactac tattactgct actactctcg cactcacgag cacctacttg cactcaagcc    6780
ggcactcaat gtactagcga aacacgtcgc atctaagcac tcacaaggaa gcacacattt    6840
gcaaatagca cctaccggaa cagctttgaa tgtgccagca cagcattgaa caggttcgcg    6900
```

```
cctttactcc tgtgctctgt tttctcgatc ggaatgttcg aaagttgaaa agcgcatttt    6960
ttcatctctc ttttttctatt cttcttcgta tttttatccc tctctcgtcg tgttttttct   7020
aaacattacc atacttcttc cgctacgaac tcgccaagaa ccagaacgca gcgtgcgtgc    7080
ggtgcttgcg gtgtgtgtgt gtgtgtgtgt attccacggc tgcgagaagc aagatcggag    7140
aacaggcatc attcccctttt cacagacaat tgcacttttg tactagaaca gaaaacgaga   7200
cagcataatt tccaacagcc tcattcactc ataccaggct cacaccgact tttaaccgaa    7260
acatgtacta cagaaacaaa aacaaacaat atggagagtg ctcgcgctga tactaagtta    7320
atatgaagag attactggcg aggtcatcga tcccatcccg acatcatcgc tccaggctcc    7380
agacctacca gtcgcctac cattacctac ccaccaccga ccactactca cacagcatta     7440
tcacttccgc cgccgtcgcc gccgccgccg acgccgccga cgccaccacc ttcacaccgc    7500
cctgccaaaa tgaatgcgca ttgttgcgat agattgaatt tccttggttg ttgttgttgt    7560
tggttttctt ttgacatgtt tgtgtgttgt tttttctttc tctctctctc tttctgtggt    7620
tccaacattt cagacgcatt ttttacacca tatataggtc acggtgagtc cgtacgaatt    7680
atagatgccg agttgggcac gctcgagcat gtccacagtg gagcaacgcc gcggcgacgc    7740
ggcctgacga ggcgcgagtc aaactcgggt aagtacgcga ttggaagtgg ggggacgttt    7800
accctaccgt gtactactac aacgcacttt acccccacgc acacgcaccg gcagacgcga    7860
acgacaacga tccgctggtg gtcaacacgg ataaggggcg catccgcggc attacggtcg    7920
atgcgcccag cggcaagaag gtggacgtgt ggctcggcat tccctacgcc cagccgccgg    7980
tcgggccgct acggttccgt catccgcggc cggccgaaaa gtggaccggc gtgctgaaca    8040
cgaccacacc gcccaacagc tgcgtgcaga tcgtggacac cgtgttcggc gacttcccgg    8100
gcgcgaccat gtggaacccg aacacgcccc tgtccgagga ctgtctgtac attaacgtgg    8160
tggcaccgcg accccggccc aagaatgcgg ccgtcatgct gtggatcttc ggcggcggct    8220
tctactccgg caccgccacc ctggacgtgt acgaccaccg ggcgcttgcg tcggaggaga    8280
acgtgatcgt ggtgtcgctg cagtaccgcg tggccagtct gggcttcctg tttctcggca    8340
ccccggaagc gccgggcaat gcgggactgt tcgatcagaa ccttgcgcta cggtaggtgt    8400
ctttgcatgt gtgaatgagg gtatagtatt ctaacgaggt gctcttcttc ccatcacttc    8460
ttgggagtca gctgggtgcg ggacaacatt caccggttcg gtggcgatcc gtcgcgtgtg    8520
acactgttcg gcgagagtgc cggtgccgtc tcggtgtcgc tgcatctgct gtccgccctt    8580
tcccgcgatc tgttccagcg ggccatcctg cagagcggct cgccgacggc accgtgggca    8640
ttggtatcgc gcgaggaagc cacactaagg tacgtgccag ctgctgctttt ccccaaacca   8700
ccaacccgca acagctcaca caaccctctt ttccgtcgct cttttctcgc tccagagcac    8760
tgcggttggc cgaggcggtc ggctgcccgc acgaaccgag caagctgagc gatgcggtcg    8820
agtgcctgcg cggcaaggac ccgcacgtgc tggtcaacaa cgagtggggc acgctcggca    8880
tttgcgagtt cccgttcgtg ccggtggtcg acggtgcgtt cctggacgag acgccgcagc    8940
gttcgctcgc cagcgggcgc ttcaagaaga cggagatcct caccggcagc aacacggagg    9000
agggctacta cttcatcatc tactacctga ccgagctgct gcgcaaggag gagggcgtga    9060
ccgtgacgcg cgaggagttc ctgcaggcgg tgcgcgagct caacccgtac gtgaacgggg    9120
cggcccggca ggcgatcgtg ttcgagtaca ccgactggac cgagccggac aacccgaaca    9180
gcaacccggga cgcgctggac aagatggtgg gcgactatca cttcacctgc aacgtgaacg    9240
agttcgcgca gcggtacgcc gaggagggca acaacgtcta catgtatctg tacacgcacc    9300
```

-continued

```
gcagcaaagg caacccgtgg ccgcgctgga cgggcgtgat gcacggcgac gagatcaact    9360
acgtgttcgg cgaaccgctc aaccccaccc tcggctacac cgaggacgag aaagacttta    9420
gccggaagat catgcgatac tggtccaact ttgccaaaac cgggtaagtg tgtgtgtcaa    9480
acagcagagt gtcgatcgct ctaacaccag cgtcttctct cttctacagc aatccaaatc    9540
ccaacacggc cagcagcgaa ttccccgagt ggcccaagca caccgcccac ggacggcact    9600
atctggagct gggcctcaac acgtccttcg tcggtcgggg cccacggttg aggcagtgtg    9660
ccttctggaa gaagtacctt ccccagctag ttgcagctac ctgtaagtct cgtgcagcac    9720
ttgaaacccc ctcccacatc cccatcaggg tccaggttgc aataataaat ttcactttct    9780
ctctctcacg tctcttttcc ccaaaacagc gaacctacca gggccagcac cgcctagtga    9840
accgtgcgaa agcagcgcat tttttaccg acctgatctg atcgtgctgc tggtgtcgct    9900
gcttacggcg accgtcagat tcatacaata attactaccc catccatggc ctagttcgtt    9960
taagctttaa gatagtgagg aacaaatttt tcccaaacaa ttttcccccc tttagagcag   10020
aaccgaggga gagataggac tacatagcga aagggaaaa caagtggtgg cggacgagga    10080
gagaagaagc aaatcgaata atcgaagcaa caacaacaac aacaaaaaaa ctgcaaccgg   10140
gttcactaaa cccaggggc agctcagtag caaactacta cttaaataac tactttctta    10200
tgcaaatta tggcaagagc agtcgtgatg ggttcgatca gtatccatct gaccggagca    10260
gctgaaccgt ttcatgggca gttgctgcaa tacaccacga cccgtacaca cagtaacaca   10320
ctttttatag ctttacacta caaccactc tccccacgct cctcttcccc ttcccctcca    10380
cacagacagc agcgccgttt gtagcaggat ctactaccgt gcggtttggt atggcggcca   10440
acaacactaa acaccacaca tctactaaaa cacaccggaa caataaacaa atgttaaact   10500
tactatatga atatacatct agacgcatat atacgcatga actactactt ccctcgtgtt   10560
ctgacaaaac acattccctt gtcccccctc cccctccggt ttgcttacca ccactgcacc   10620
accagtatga atttgttcca taataacgct tcgtaactcg ttaccaggag cacaactggg   10680
tcgttggcgg agtgctgcgc                                              10700
```

<210> SEQ ID NO 158
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: MISC_FEATURE
<222> LOCATION: (6)..(6)
<223> OTHER INFORMATION: n=a,c,g, or t
<400> SEQUENCE: 158
ccgggngcsa cyatgtggaa                                                20

<210> SEQ ID NO 159
<211> LENGTH: 20
<212> TYPE: DNA
<213> ORGANISM: Artificial Sequence
<220> FEATURE:
<223> OTHER INFORMATION: Synthetic DNA
<400> SEQUENCE: 159
acgatmacgt tctcytccga                                                20

<210> SEQ ID NO 160
<211> LENGTH: 676

<212> TYPE: PRT
<213> ORGANISM: Schizaphis graminum

<400> SEQUENCE: 160

```
Met Asp Gln Trp Leu Leu Trp Phe Gly Tyr Leu Val Ala Ser Thr Tyr
1               5                   10                  15

Gly Leu Ser Leu Arg His Ala Arg His Gln Ser Val Gly Thr Pro Thr
            20                  25                  30

Ala Glu Glu Ile Leu Glu Pro Gln Ile Leu Ile Glu Asp Thr Asp His
        35                  40                  45

Val Phe Arg Gln Arg Ala Ser Asp Met Phe Ala Gln Glu Pro Glu Tyr
    50                  55                  60

Thr Glu Lys Arg Asn Leu Asn His Arg Arg Ser Glu Phe Ser Gly
65                  70                  75                  80

Asn Gln Asp Thr Asp Phe Ala Ser Ser Gly Glu Thr Tyr Ser Ala Tyr
                85                  90                  95

Thr Ser Asp Pro Leu Ile Ile His Thr Asn Lys Gly Lys Ile Arg
            100                 105                 110

Gly Ile Thr Gln Thr Ala Thr Thr Gly Lys Leu Val Asp Ala Trp Leu
        115                 120                 125

Gly Ile Pro Tyr Ala Lys Lys Pro Ile Gly Asp Leu Arg Phe Arg His
    130                 135                 140

Pro Arg Pro Ile Asp Arg Trp Asp Thr Thr Pro Glu Thr Ile Leu
145                 150                 155                 160

Asn Cys Thr Thr Pro Pro Asn Thr Cys Val Gln Ile Phe Asp Thr Leu
                165                 170                 175

Phe Gly Asp Phe Pro Gly Ala Thr Met Trp Asn Pro Asn Ser Pro Val
            180                 185                 190

Ser Glu Asp Cys Leu Tyr Ile Asn Val Val Pro Lys Pro Arg Pro
        195                 200                 205

Gln Asn Ala Ala Val Met Val Trp Ile Phe Gly Gly Phe Tyr Ser
    210                 215                 220

Gly Ser Ala Thr Leu Asp Ile Tyr Asp Pro Lys Ile Leu Val Ser Glu
225                 230                 235                 240

Glu Asn Val Ile Leu Val Ser Met Gln Tyr Arg Val Ala Ser Leu Gly
                245                 250                 255

Phe Leu Tyr Phe Asp Thr Glu Asp Val Pro Gly Asn Ala Gly Leu Phe
            260                 265                 270

Asp Gln Leu Met Ala Leu Gln Trp Val His Glu Asn Ile Lys Leu Phe
        275                 280                 285

Gly Gly Asn Pro Asn Asn Val Thr Leu Phe Gly Glu Ser Ala Gly Ala
    290                 295                 300

Val Ser Val Ser Leu His Leu Leu Ser Pro Leu Ser Arg Asn Leu Phe
305                 310                 315                 320

Asn Gln Ala Ile Met Glu Ser Gly Ser Ser Thr Ala Pro Trp Ala Ile
                325                 330                 335

Leu Ser Arg Glu Glu Ser Phe Asn Arg Gly Leu Lys Leu Ala Lys Ala
            340                 345                 350

Met Gly Cys Pro Asp Asp Arg Asn Thr Ile His Lys Thr Val Glu Cys
        355                 360                 365

Leu Arg Lys Ala Asn Ser Ser Val Met Val Glu Lys Glu Trp Asp His
    370                 375                 380

Val Ala Ile Cys Phe Phe Pro Val Pro Val Val Asp Gly Ala Phe
385                 390                 395                 400
```

```
Leu Asp Asp His Pro Gln Lys Ser Leu Ser Thr Asn Phe Lys Lys
            405                 410                 415

Thr Asn Ile Leu Met Gly Ser Asn Ser Glu Glu Gly Tyr Tyr Ser Ile
            420                 425                 430

Phe Tyr Tyr Leu Thr Glu Leu Phe Lys Lys Glu Glu Asn Val Met Val
            435                 440                 445

Ser Arg Glu Asn Phe Ile Lys Ala Ile Gly Gln Leu Asn Pro Asn Ala
450                 455                 460

Asp Ala Ala Val Lys Ser Ala Ile Glu Phe Glu Tyr Thr Asp Trp Phe
465                 470                 475                 480

Ser Pro Asn Asp Pro Glu Lys Asn Arg Asn Ala Leu Asp Lys Met Val
                485                 490                 495

Gly Asp Tyr Gln Phe Thr Cys Asn Val Asn Glu Phe Ala His Lys Tyr
                500                 505                 510

Ala Leu Thr Gly Asn Asn Val Tyr Met Tyr Tyr Phe Lys His Arg Ser
            515                 520                 525

Leu Asn Asn Pro Trp Pro Lys Trp Thr Gly Val Met His Gly Asp Glu
            530                 535                 540

Ile Ser Tyr Val Phe Gly Asp Pro Leu Asn Pro Asn Lys Arg Tyr Glu
545                 550                 555                 560

Ile Glu Glu Ile Glu Leu Ser Lys Lys Met Met Arg Tyr Trp Thr Asn
                565                 570                 575

Phe Ala Lys Thr Gly Asn Pro Ser Lys Thr Leu Glu Gly Ser Trp Val
                580                 585                 590

Thr Pro Lys Trp Pro Val His Thr Ala Tyr Gly Lys Glu Phe Leu Thr
            595                 600                 605

Leu Asp Thr Asn Asn Thr Ser Ile Gly Val Gly Pro Arg Leu Glu Gln
            610                 615                 620

Cys Ala Phe Trp Lys Asn Tyr Val Pro Asp Leu Thr Ala Ile Ser Lys
625                 630                 635                 640

Ser Met Lys Ser Asp Lys Asn Cys Thr Thr Ile Ser Gly Gly Thr Lys
                645                 650                 655

Thr Asn Val Ile Glu Leu Ser Val Trp Thr Ile Val Met Thr Thr Ala
                660                 665                 670

Val Leu Met Leu
            675

<210> SEQ ID NO 161
<211> LENGTH: 737
<212> TYPE: PRT
<213> ORGANISM: Schizaphis graminum

<400> SEQUENCE: 161

Met Glu Ile Arg Gly Leu Leu Met Gly Arg Leu Arg Leu Gly Arg Arg
1               5                   10                  15

Met Val Pro Leu Gly Leu Leu Gly Val Thr Ala Leu Leu Leu Ile Leu
            20                  25                  30

Pro Pro Ser Ala Leu Val Gln Gly Arg His His Glu Leu Asn Asn Gly
        35                  40                  45

Ala Ala Ile Gly Ser His Gln Leu Ser Ala Ala Gly Val Gly Leu
    50                  55                  60

Ser Ser Gln Ser Ala Gln Ser Gly Ser Leu Ala Ser Gly Val Met Ser
65                  70                  75                  80

Ser Val Pro Ala Ala Gly Ala Ser Ser Ser Ser Ser Ser Leu Leu
                85                  90                  95
```

```
Ser Ser Ser Ala Glu Asp Asp Val Ala Arg Ile Thr Leu Ser Lys Asp
            100                 105                 110

Ala Asp Ala Phe Phe Thr Pro Tyr Ile Gly His Gly Glu Ser Val Arg
        115                 120                 125

Ile Ile Asp Ala Glu Leu Gly Thr Leu Glu His Val His Ser Gly Ala
    130                 135                 140

Thr Pro Arg Arg Arg Gly Leu Thr Arg Arg Glu Ser Asn Ser Asp Ala
145                 150                 155                 160

Asn Asp Asn Asp Pro Leu Val Val Asn Thr Asp Lys Gly Arg Ile Arg
                165                 170                 175

Gly Ile Thr Val Asp Ala Pro Ser Gly Lys Lys Val Asp Val Trp Leu
            180                 185                 190

Gly Ile Pro Tyr Ala Gln Pro Val Gly Pro Leu Arg Phe Arg His
        195                 200                 205

Pro Arg Pro Ala Glu Lys Trp Thr Gly Val Leu Asn Thr Thr Thr Pro
    210                 215                 220

Pro Asn Ser Cys Val Gln Ile Val Asp Thr Val Phe Gly Asp Phe Pro
225                 230                 235                 240

Gly Ala Thr Met Trp Asn Pro Asn Thr Pro Leu Ser Glu Asp Cys Leu
                245                 250                 255

Tyr Ile Asn Val Val Ala Pro Arg Pro Arg Pro Lys Asn Ala Ala Val
            260                 265                 270

Met Leu Trp Ile Phe Gly Gly Phe Tyr Ser Gly Thr Ala Thr Leu
        275                 280                 285

Asp Val Tyr Asp His Arg Ala Leu Ala Ser Glu Asn Val Ile Val
    290                 295                 300

Val Ser Leu Gln Tyr Arg Val Ala Ser Leu Gly Phe Leu Phe Leu Gly
305                 310                 315                 320

Thr Pro Glu Ala Pro Gly Asn Ala Gly Leu Phe Asp Gln Asn Leu Ala
                325                 330                 335

Leu Arg Trp Val Arg Asp Asn Ile His Arg Phe Gly Gly Asp Pro Ser
            340                 345                 350

Arg Val Thr Leu Phe Gly Glu Ser Ala Gly Ala Val Ser Val Ser Leu
        355                 360                 365

His Leu Leu Ser Ala Leu Ser Arg Asp Leu Phe Gln Arg Ala Ile Leu
    370                 375                 380

Gln Ser Gly Ser Pro Thr Ala Pro Trp Ala Leu Val Ser Arg Glu Glu
385                 390                 395                 400

Ala Thr Leu Arg Ala Leu Arg Leu Ala Glu Ala Val Gly Cys Pro His
                405                 410                 415

Glu Pro Ser Lys Leu Ser Asp Ala Val Glu Cys Leu Arg Gly Lys Asp
            420                 425                 430

Pro His Val Leu Val Asn Asn Glu Trp Gly Thr Leu Gly Ile Cys Glu
        435                 440                 445

Phe Pro Phe Val Pro Val Val Asp Gly Ala Phe Leu Asp Glu Thr Pro
    450                 455                 460

Gln Arg Ser Leu Ala Ser Gly Arg Phe Lys Lys Thr Glu Ile Leu Thr
465                 470                 475                 480

Gly Ser Asn Thr Glu Glu Gly Tyr Tyr Phe Ile Ile Tyr Tyr Leu Thr
                485                 490                 495

Glu Leu Leu Arg Lys Glu Glu Gly Val Thr Val Thr Arg Glu Glu Phe
            500                 505                 510

Leu Gln Ala Val Arg Glu Leu Asn Pro Tyr Val Asn Gly Ala Ala Arg
        515                 520                 525
```

```
Gln Ala Ile Val Phe Glu Tyr Thr Asp Trp Thr Glu Pro Asp Asn Pro
            530                 535                 540

Asn Ser Asn Arg Asp Ala Leu Asp Lys Met Val Gly Asp Tyr His Phe
545                 550                 555                 560

Thr Cys Asn Val Asn Glu Phe Ala Gln Arg Tyr Ala Glu Glu Gly Asn
                565                 570                 575

Asn Val Tyr Met Tyr Leu Tyr Thr His Arg Ser Lys Gly Asn Pro Trp
            580                 585                 590

Pro Arg Trp Thr Gly Val Met His Gly Asp Glu Ile Asn Tyr Val Phe
            595                 600                 605

Gly Glu Pro Leu Asn Pro Thr Leu Gly Tyr Thr Glu Asp Glu Lys Asp
            610                 615                 620

Phe Ser Arg Lys Ile Met Arg Tyr Trp Ser Asn Phe Ala Lys Thr Gly
625                 630                 635                 640

Asn Pro Asn Pro Asn Thr Ala Ser Ser Glu Phe Pro Glu Trp Pro Lys
                645                 650                 655

His Thr Ala His Gly Arg His Tyr Leu Glu Leu Gly Leu Asn Thr Ser
            660                 665                 670

Phe Val Gly Arg Gly Pro Arg Leu Arg Gln Cys Ala Phe Trp Lys Lys
            675                 680                 685

Tyr Leu Pro Gln Leu Val Ala Ala Thr Ser Asn Leu Pro Gly Pro Ala
            690                 695                 700

Pro Pro Ser Glu Pro Cys Glu Ser Ser Ala Phe Phe Tyr Arg Pro Asp
705                 710                 715                 720

Leu Ile Val Leu Leu Val Ser Leu Leu Thr Ala Val Arg Phe Ile
                725                 730                 735

Gln

<210> SEQ ID NO 162
<211> LENGTH: 676
<212> TYPE: PRT
<213> ORGANISM: Schizaphis graminum

<400> SEQUENCE: 162

Met Asp Gln Trp Leu Leu Trp Phe Gly Tyr Leu Val Ala Ser Thr Tyr
1               5                   10                  15

Gly Leu Ser Leu Arg His Ala Arg His Gln Ser Val Gly Thr Pro Thr
                20                  25                  30

Ala Glu Glu Ile Leu Glu Pro Gln Ile Leu Ile Glu Asp Thr Asp His
            35                  40                  45

Val Phe Arg Gln Arg Ala Ser Asp Met Phe Ala Gln Glu Pro Glu Tyr
        50                  55                  60

Thr Glu Lys Arg Asn Leu Asn His Arg Arg Ser Glu Phe Ser Gly
65                  70                  75              80

Asn Gln Asp Thr Asp Phe Ala Ser Ser Gly Thr Tyr Ser Ala Tyr
                85                  90                  95

Thr Ser Asp Asp Pro Leu Ile Ile His Thr Asn Lys Gly Lys Ile Arg
            100                 105                 110

Gly Ile Thr Gln Thr Ala Thr Thr Gly Lys Leu Val Asp Ala Trp Leu
        115                 120                 125

Gly Ile Pro Tyr Ala Lys Lys Pro Ile Gly Asp Leu Arg Phe Arg His
    130                 135                 140

Pro Arg Pro Ile Asp Arg Trp Asp Thr Thr Pro Glu Thr Ile Leu
145                 150                 155                 160
```

-continued

```
Asn Cys Thr Thr Pro Pro Asn Thr Cys Val Gln Ile Phe Asp Thr Leu
                165                 170                 175

Phe Gly Asp Phe Pro Gly Ala Thr Met Trp Asn Pro Asn Ser Pro Val
            180                 185                 190

Ser Glu Asp Cys Leu Tyr Ile Asn Val Val Pro Lys Pro Arg Pro
        195                 200                 205

Gln Asn Ala Ala Val Met Val Trp Ile Phe Gly Gly Gly Phe Tyr Ser
    210                 215                 220

Gly Ser Ala Thr Leu Asp Ile Tyr Asp Pro Lys Ile Leu Val Ser Glu
225                 230                 235                 240

Glu Asn Val Ile Leu Val Ser Met Gln Tyr Arg Val Ala Ser Leu Gly
                245                 250                 255

Phe Leu Tyr Phe Asp Thr Glu Asp Val Pro Gly Asn Ala Gly Leu Phe
                260                 265                 270

Asp Gln Leu Met Ala Leu Gln Trp Val His Glu Asn Ile Lys Leu Phe
            275                 280                 285

Gly Gly Asn Pro Asn Asn Val Thr Leu Phe Gly Glu Ser Ala Gly Ala
    290                 295                 300

Val Ser Val Ser Leu His Leu Leu Ser Pro Leu Ser Arg Asn Leu Phe
305                 310                 315                 320

Asn Gln Ala Ile Met Glu Ser Gly Ser Ser Thr Ala Pro Trp Ala Ile
                325                 330                 335

Leu Ser Arg Glu Glu Ser Phe Asn Arg Gly Leu Lys Leu Ala Lys Ala
                340                 345                 350

Met Gly Cys Pro Asp Asp Arg Asn Thr Ile His Lys Thr Val Glu Cys
            355                 360                 365

Leu Arg Lys Ala Asn Ser Ser Val Met Val Lys Glu Trp Asp His
    370                 375                 380

Val Ala Ile Cys Phe Phe Pro Phe Val Pro Val Val Asp Gly Ala Phe
385                 390                 395                 400

Leu Asp Asp His Pro Gln Lys Ser Leu Ser Thr Asn Asn Phe Lys Lys
                405                 410                 415

Thr Asn Ile Leu Met Gly Ser Asn Ser Glu Glu Gly Tyr Tyr Ser Ile
                420                 425                 430

Phe Tyr Tyr Leu Thr Glu Leu Phe Lys Lys Glu Glu Asn Val Met Val
            435                 440                 445

Ser Arg Glu Asn Phe Ile Lys Ala Ile Gly Gln Leu Asn Pro Asn Ala
    450                 455                 460

Asp Ala Ala Val Lys Ser Ala Ile Glu Phe Glu Tyr Thr Asp Trp Phe
465                 470                 475                 480

Ser Pro Asn Asp Pro Glu Lys Asn Arg Asn Ala Leu Asp Lys Met Val
                485                 490                 495

Gly Asp Tyr Gln Phe Thr Cys Asn Val Asn Glu Phe Ala His Lys Tyr
            500                 505                 510

Ala Leu Thr Gly Asn Asn Val Tyr Met Tyr Tyr Phe Lys His Arg Ser
    515                 520                 525

Leu Asn Asn Pro Trp Pro Lys Trp Thr Gly Val Met His Gly Asp Glu
530                 535                 540

Ile Ser Tyr Val Phe Gly Asp Pro Leu Asn Pro Asn Lys Arg Tyr Glu
545                 550                 555                 560

Ile Glu Glu Ile Glu Leu Ser Lys Lys Met Met Arg Tyr Trp Thr Asn
                565                 570                 575

Phe Ala Lys Thr Gly Asn Pro Ser Lys Thr Leu Glu Gly Ser Trp Val
            580                 585                 590
```

```
Thr Pro Lys Trp Pro Val His Thr Ala Tyr Gly Lys Glu Phe Leu Thr
            595                 600                 605

Leu Asp Thr Asn Asn Thr Ser Ile Gly Val Gly Pro Arg Leu Glu Gln
            610                 615                 620

Cys Ala Phe Trp Lys Asn Tyr Val Pro Asp Leu Thr Ala Ile Ser Lys
625                 630                 635                 640

Ser Met Lys Ser Asp Lys Asn Cys Thr Thr Ile Ser Gly Gly Thr Lys
            645                 650                 655

Thr Asn Val Ile Glu Leu Ser Val Trp Thr Ile Val Met Thr Thr Ala
            660                 665                 670

Val Leu Met Leu
            675

<210> SEQ ID NO 163
<211> LENGTH: 645
<212> TYPE: PRT
<213> ORGANISM: Anopheles gambiae

<400> SEQUENCE: 163

Met Ala Ser Ala Tyr Tyr His Gln Ser Ala Val Gly Val Gly Asn Val
1               5                   10                  15

Leu Val Leu Leu Leu Gly Ala Thr Val Ile Cys Pro Ala Tyr Ala Ile
            20                  25                  30

Ile Asp Arg Leu Val Val Gln Thr Ser Ser Gly Pro Ile Arg Gly Arg
            35                  40                  45

Ser Thr Met Val Gln Gly Arg Glu Val His Val Phe Asn Gly Val Pro
        50                  55                  60

Phe Ala Lys Pro Pro Val Asp Ser Leu Arg Phe Lys Lys Pro Val Pro
65                  70                  75                  80

Ala Glu Pro Trp His Gly Val Leu Asp Ala Thr Arg Leu Pro Pro Ser
            85                  90                  95

Cys Ile Gln Glu Arg Tyr Glu Tyr Phe Pro Gly Phe Ala Gly Glu Glu
            100                 105                 110

Met Trp Asn Pro Asn Thr Asn Val Ser Glu Asp Cys Leu Tyr Leu Asn
            115                 120                 125

Ile Trp Val Pro Thr Lys Thr Arg Leu Arg His Gly Arg Gly Leu Asn
130                 135                 140

Phe Gly Ser Asn Asp Tyr Phe Gln Asp Asp Asp Phe Gln Arg Gln
145                 150                 155                 160

His Gln Ser Lys Gly Gly Leu Ala Met Leu Val Trp Ile Tyr Gly Gly
            165                 170                 175

Gly Phe Met Ser Gly Thr Ser Thr Leu Asp Ile Tyr Asn Ala Glu Ile
            180                 185                 190

Leu Ala Ala Val Gly Asn Val Ile Val Ala Ser Met Gln Tyr Arg Val
            195                 200                 205

Gly Ala Phe Gly Phe Leu Tyr Leu Ala Pro Tyr Ile Asn Gly Tyr Glu
        210                 215                 220

Glu Asp Ala Pro Gly Asn Met Gly Met Trp Asp Gln Ala Leu Ala Ile
225                 230                 235                 240

Arg Trp Leu Lys Glu Asn Ala Lys Ala Phe Gly Gly Asp Pro Asp Leu
            245                 250                 255

Ile Thr Leu Phe Gly Glu Ser Ala Gly Gly Ser Ser Val Ser Leu His
            260                 265                 270

Leu Leu Ser Pro Val Thr Arg Gly Leu Ser Lys Arg Gly Ile Leu Gln
            275                 280                 285
```

```
Ser Gly Thr Leu Asn Ala Pro Trp Ser His Met Thr Ala Glu Lys Ala
    290                 295                 300

Leu Gln Ile Ala Glu Gly Leu Ile Asp Asp Cys Asn Cys Asn Leu Thr
305                 310                 315                 320

Met Leu Lys Glu Ser Pro Ser Thr Val Met Gln Cys Met Arg Asn Val
                325                 330                 335

Asp Ala Lys Thr Ile Ser Val Gln Gln Trp Asn Ser Tyr Ser Gly Ile
            340                 345                 350

Leu Gly Phe Pro Ser Ala Pro Thr Ile Asp Gly Val Phe Met Thr Ala
                355                 360                 365

Asp Pro Met Thr Met Leu Arg Glu Ala Asn Leu Glu Gly Ile Asp Ile
            370                 375                 380

Leu Val Gly Ser Asn Arg Asp Glu Gly Thr Tyr Phe Leu Leu Tyr Asp
385                 390                 395                 400

Phe Ile Asp Tyr Phe Glu Lys Asp Ala Ala Thr Ser Leu Pro Arg Asp
                405                 410                 415

Lys Phe Leu Glu Ile Met Asn Thr Ile Phe Asn Lys Ala Ser Glu Pro
            420                 425                 430

Glu Arg Glu Ala Ile Ile Phe Gln Tyr Thr Gly Trp Glu Ser Gly Asn
                435                 440                 445

Asp Gly Tyr Gln Asn Gln His Gln Val Gly Arg Ala Val Gly Asp His
450                 455                 460

Phe Phe Ile Cys Pro Thr Asn Glu Phe Ala Leu Gly Leu Thr Glu Arg
465                 470                 475                 480

Gly Ala Ser Val His Tyr Tyr Tyr Phe Thr His Arg Thr Ser Thr Ser
                485                 490                 495

Leu Trp Gly Glu Trp Met Gly Val Leu His Gly Asp Glu Val Glu Tyr
                500                 505                 510

Ile Phe Gly Gln Pro Met Asn Ala Ser Leu Gln Tyr Arg Gln Arg Glu
            515                 520                 525

Arg Asp Leu Ser Arg Arg Met Val Leu Ser Val Ser Glu Phe Ala Arg
530                 535                 540

Thr Gly Asn Pro Ala Leu Glu Gly Glu His Trp Pro Leu Tyr Thr Arg
545                 550                 555                 560

Glu Asn Pro Ile Tyr Phe Ile Phe Asn Ala Glu Gly Glu Asp Asp Leu
                565                 570                 575

Arg Gly Glu Lys Tyr Gly Arg Gly Pro Met Ala Thr Ser Cys Ala Phe
            580                 585                 590

Trp Asn Asp Phe Leu Pro Arg Leu Arg Ala Trp Ser Val Pro Leu Lys
            595                 600                 605

Asp Pro Cys Lys Leu Asp Asp His Thr Ser Ile Ala Ser Thr Ala Arg
            610                 615                 620

Ala Ala Pro Thr Val Ala Leu Leu Ile Ala Leu Ser Leu Ala Val Ala
625                 630                 635                 640

Arg Leu Val Ala Ala
            645

<210> SEQ ID NO 164
<211> LENGTH: 664
<212> TYPE: PRT
<213> ORGANISM: Anopheles stephensi

<400> SEQUENCE: 164

Met Phe Val Asn Gln Arg Thr Arg Arg Pro Tyr Met Ser Val Phe Val
1               5                   10                  15
```

Leu Val Leu Gly Ala Ala Val Ile Cys Pro Ala Tyr Gly Ile Ile Asp
              20                  25                  30
Arg Leu Val Val Gln Thr Ser Ser Gly Pro Ile Arg Gly Arg Ser Thr
          35                  40                  45
Met Val Gln Gly Arg Glu Val His Val Phe Asn Gly Val Pro Phe Ala
50                  55                  60
Lys Pro Pro Val Asp Ser Leu Arg Phe Lys Lys Pro Val Pro Ala Glu
65                  70                  75                  80
Pro Trp His Gly Val Leu Asp Ala Thr Arg Leu Pro Pro Ser Cys Ile
              85                  90                  95
Gln Glu Arg Tyr Glu Tyr Phe Pro Gly Phe Ala Gly Glu Glu Met Trp
          100                 105                 110
Asn Pro Asn Thr Asn Val Ser Glu Asp Cys Leu Tyr Leu Asn Ile Trp
          115                 120                 125
Val Pro Thr Lys Thr Arg Leu Arg His Gly Arg Gly Leu Asn Phe Gly
          130                 135                 140
Ser Asn Asp Tyr Phe Gln Asp Asp Asp Phe Gln Arg Gln His Gln
145                 150                 155                 160
Ser Lys Gly Gly Leu Ala Met Leu Val Trp Ile Tyr Gly Gly Gly Phe
              165                 170                 175
Met Ser Gly Thr Ser Thr Leu Asp Ile Tyr Asn Ala Glu Ile Leu Ala
          180                 185                 190
Ala Val Gly Asn Val Ile Val Ala Ser Met Gln Tyr Arg Val Gly Ala
          195                 200                 205
Phe Gly Phe Leu Tyr Leu Ala Pro Tyr Ile Asn Gly Tyr Glu Glu Asp
          210                 215                 220
Ala Pro Gly Asn Met Gly Met Trp Asp Gln Ala Leu Ala Ile Arg Trp
225                 230                 235                 240
Leu Lys Glu Asn Ala Lys Ala Phe Gly Gly Asp Pro Asp Leu Ile Thr
              245                 250                 255
Leu Phe Gly Glu Ser Ala Gly Gly Ser Ser Val Ser Leu His Leu Leu
          260                 265                 270
Ser Pro Val Thr Arg Gly Leu Ser Lys Arg Gly Ile Leu Gln Ser Gly
          275                 280                 285
Thr Leu Asn Ala Pro Trp Ser His Met Thr Ala Glu Lys Ala Leu Gln
          290                 295                 300
Ile Ala Glu Gly Leu Ile Asp Asp Cys Asn Cys Asn Leu Thr Met Leu
305                 310                 315                 320
Lys Glu Ser Pro Ser Thr Val Met Gln Cys Met Arg Asn Val Asp Ala
              325                 330                 335
Lys Thr Ile Ser Val Gln Gln Trp Asn Ser Tyr Ser Gly Ile Leu Gly
          340                 345                 350
Phe Pro Ser Ala Pro Thr Ile Asp Gly Val Phe Met Thr Ala Asp Pro
          355                 360                 365
Met Thr Met Leu Arg Glu Ala Asn Leu Glu Gly Ile Asp Ile Leu Val
          370                 375                 380
Gly Ser Asn Arg Asp Glu Gly Thr Tyr Phe Leu Leu Tyr Asp Phe Ile
385                 390                 395                 400
Asp Tyr Phe Glu Lys Asp Ala Ala Thr Ser Leu Pro Arg Asp Lys Phe
              405                 410                 415
Leu Glu Ile Met Asn Thr Ile Phe Asn Lys Ala Ser Glu Pro Glu Arg
          420                 425                 430
Glu Ala Ile Ile Phe Gln Tyr Thr Gly Trp Glu Ser Gly Asn Asp Gly

```
                435                 440                 445
Tyr Gln Asn Gln His Gln Val Gly Arg Ala Val Gly Asp His Phe Phe
    450                 455                 460
Ile Cys Pro Thr Asn Glu Phe Ala Leu Gly Leu Thr Glu Arg Gly Ala
465                 470                 475                 480
Ser Val His Tyr Tyr Tyr Phe Thr His Arg Thr Ser Thr Ser Leu Trp
                485                 490                 495
Gly Glu Trp Met Gly Val Leu His Gly Asp Glu Val Glu Tyr Ile Phe
                500                 505                 510
Gly Gln Pro Met Asn Ala Ser Leu Gln Tyr Arg Gln Arg Glu Arg Asp
            515                 520                 525
Leu Ser Arg Arg Met Val Leu Ser Val Ser Glu Phe Ala Arg Thr Gly
        530                 535                 540
Asn Pro Ala Leu Glu Gly Glu His Trp Pro Leu Tyr Thr Arg Glu Asn
545                 550                 555                 560
Pro Ile Phe Phe Ile Phe Asn Ala Glu Gly Asp Asp Leu Arg Gly
                565                 570                 575
Glu Lys Tyr Gly Arg Gly Pro Met Ala Thr Ser Cys Ala Phe Trp Asn
            580                 585                 590
Asp Phe Leu Pro Arg Leu Arg Ala Trp Ser Val Pro Ser Lys Ser Pro
        595                 600                 605
Cys Asn Leu Leu Glu Gln Met Ser Ile Ala Ser Val Ser Ser Thr Met
    610                 615                 620
Pro Ile Val Val Met Val Val Leu Val Leu Ile Pro Leu Cys Ala Trp
625                 630                 635                 640
Trp Trp Ala Ile Lys Lys Asn Lys Thr Pro Pro His Pro Gln Val Ile
                645                 650                 655
Leu Glu Thr Arg Ala Phe Met His
                660

<210> SEQ ID NO 165
<211> LENGTH: 637
<212> TYPE: PRT
<213> ORGANISM: Aedes aegypti

<400> SEQUENCE: 165

Met Lys Met Ser Ala Val Val Arg Leu Cys Cys Asn Met Ile Ser Leu
1               5                   10                  15
Leu Leu Cys Ile Thr Val Ile Ser Pro Val Tyr Gly Ile Phe Asp Arg
            20                  25                  30
Leu Val Val Gln Thr Ser Ser Gly Pro Ile Arg Gly Arg Ser Thr Met
        35                  40                  45
Val Leu Gly Arg Glu Val His Val Phe Asn Gly Val Pro Phe Ala Lys
    50                  55                  60
Pro Pro Val Asp Gly Leu Arg Phe Arg Lys Pro Val Pro Ala Glu Pro
65                  70                  75                  80
Trp His Gly Val Leu Asp Ala Thr Arg Leu Pro Pro Ser Cys Ile Gln
                85                  90                  95
Glu Arg Tyr Glu Tyr Phe Pro Gly Phe Ala Gly Glu Met Trp Asn
            100                 105                 110
Pro Asn Thr Asn Val Ser Glu Asp Cys Leu Tyr Leu Asn Ile Trp Val
        115                 120                 125
Pro Thr Lys Thr Arg Leu Arg His Gly Arg Gly Leu Asn Phe Gly Asn
    130                 135                 140
Asn Asp Tyr Phe Gln Asp Asp Asp Asp Phe Gln Arg Gln His Gln Ser
```

```
            145                 150                 155                 160
Lys Gly Gly Leu Ala Met Leu Val Trp Ile Tyr Gly Gly Phe Met
                165                 170                 175
Ser Gly Thr Ser Thr Leu Asp Val Tyr Asn Ala Glu Met Leu Ala Ala
                    180                 185                 190
Val Gly Asn Val Ile Val Ala Ser Met Gln Tyr Arg Val Gly Ser Phe
                195                 200                 205
Gly Phe Phe Tyr Leu Ala Pro Tyr Leu Asn Asp Asp Ala Pro Gly
            210                 215                 220
Asn Val Gly Leu Trp Asp Gln Ala Leu Ala Ile Arg Trp Leu Lys Glu
225                 230                 235                 240
Asn Ala Lys Ala Phe Gly Gly Asp Pro Asp Leu Ile Thr Leu Phe Gly
                    245                 250                 255
Glu Ser Ala Gly Gly Ser Ser Val Ser Leu His Leu Leu Ser Pro Val
                260                 265                 270
Thr Arg Gly Leu Ser Arg Arg Gly Ile Leu Gln Ser Gly Thr Leu Asn
            275                 280                 285
Ala Pro Trp Ser His Met Ser Ala Glu Lys Ala Leu Ser Val Ala Glu
            290                 295                 300
Ala Leu Ile Asp Asp Cys Asn Cys Asn Val Thr Leu Leu Lys Asp Asn
305                 310                 315                 320
Pro Asn Tyr Val Met Asn Cys Met Arg Asn Val Asp Ala Lys Thr Ile
                    325                 330                 335
Ser Val Gln Gln Trp Asn Ser Tyr Ser Gly Ile Leu Gly Phe Pro Ser
                340                 345                 350
Ala Pro Thr Ile Asp Gly Val Phe Met Thr Ala Asp Pro Met Thr Met
                355                 360                 365
Leu Arg Glu Ala Asn Leu Glu Gly Val Glu Ile Leu Val Gly Ser Asn
            370                 375                 380
Arg Asp Glu Gly Thr Tyr Phe Leu Leu Tyr Asp Phe Ile Asp Tyr Phe
385                 390                 395                 400
Glu Lys Asp Ala Ala Thr Ser Leu Pro Arg Asp Lys Phe Leu Glu Ile
                    405                 410                 415
Met Asn Thr Ile Phe Ser Lys Ala Ser Glu Pro Glu Arg Glu Ala Ile
                420                 425                 430
Ile Phe Gln Tyr Thr Gly Trp Glu Ser Gly Asn Asp Gly Tyr Gln Asn
            435                 440                 445
Gln Gln Gln Val Gly Arg Ser Val Gly Asp His Phe Phe Ile Cys Pro
            450                 455                 460
Thr Asn Glu Phe Ala Leu Gly Leu Ala Glu Arg Gly Ala Ser Val Tyr
465                 470                 475                 480
Tyr Tyr Tyr Phe Thr His Arg Thr Ser Thr Ser Leu Trp Gly Glu Trp
                    485                 490                 495
Met Gly Val Leu His Gly Asp Glu Val Glu Tyr Ile Phe Gly Gln Pro
                500                 505                 510
Met Asn Val Ser Met Gln Tyr Arg Gln Arg Glu Arg Asp Leu Ser Arg
                515                 520                 525
Arg Met Val Leu Ser Val Ser Glu Phe Ala Arg Ser Gly Asn Pro Ala
            530                 535                 540
Leu Glu Gly Glu His Trp Pro Val Tyr Thr Lys Glu Asn Pro Ile Tyr
545                 550                 555                 560
Phe Ile Phe Asn Ala Glu Gly Glu Asp Asp Leu Arg Gly Glu Lys Tyr
                    565                 570                 575
```

```
Gly Arg Gly Pro Met Ala Thr Ala Cys Ala Phe Trp Asn Asp Phe Leu
                580                 585                 590

Pro Arg Leu Arg Ala Trp Ser Val Pro Pro Lys Ser Ser Cys Asn Ile
            595                 600                 605

Leu Glu Gln Thr Ser Ala Ala Thr Ile Leu Tyr Val Asp Ile Lys Ile
        610                 615                 620

Val Thr Val Leu Met Val Phe Ile Leu Val Arg Leu Tyr
625                 630                 635

<210> SEQ ID NO 166
<211> LENGTH: 649
<212> TYPE: PRT
<213> ORGANISM: Drosophila melanogaster

<400> SEQUENCE: 166

Met Ala Ile Ser Cys Arg Gln Ser Arg Val Leu Pro Met Ser Leu Pro
1               5                   10                  15

Leu Pro Leu Thr Ile Pro Leu Pro Leu Val Leu Val Leu Ser Leu His
            20                  25                  30

Leu Ser Gly Val Cys Gly Val Ile Asp Arg Leu Val Val Gln Thr Ser
        35                  40                  45

Ser Gly Pro Val Arg Gly Arg Ser Val Thr Val Gln Gly Arg Glu Val
    50                  55                  60

His Val Tyr Thr Gly Ile Pro Tyr Ala Lys Pro Val Glu Asp Leu
65                  70                  75                  80

Arg Phe Arg Lys Pro Val Pro Ala Glu Pro Trp His Gly Val Leu Asp
                85                  90                  95

Ala Thr Arg Leu Ser Ala Thr Cys Val Gln Glu Arg Tyr Glu Tyr Phe
            100                 105                 110

Pro Gly Phe Ser Gly Glu Glu Ile Trp Asn Pro Asn Thr Asn Val Ser
        115                 120                 125

Glu Asp Cys Leu Tyr Ile Asn Val Trp Ala Pro Ala Lys Ala Arg Leu
    130                 135                 140

Arg His Gly Arg Gly Ala Asn Gly Gly Glu His Pro Asn Gly Lys Gln
145                 150                 155                 160

Ala Asp Thr Asp His Leu Ile His Asn Gly Asn Pro Gln Asn Thr Thr
                165                 170                 175

Asn Gly Leu Pro Ile Leu Ile Trp Ile Tyr Gly Gly Phe Met Thr
            180                 185                 190

Gly Ser Ala Thr Leu Asp Ile Tyr Asn Ala Asp Ile Met Ala Ala Val
        195                 200                 205

Gly Asn Val Ile Val Ala Ser Phe Gln Tyr Arg Val Gly Ala Phe Gly
    210                 215                 220

Phe Leu His Leu Ala Pro Glu Met Pro Ser Glu Phe Ala Glu Glu Ala
225                 230                 235                 240

Pro Gly Asn Val Gly Leu Trp Asp Gln Ala Leu Ala Ile Arg Trp Leu
                245                 250                 255

Lys Asp Asn Ala His Ala Phe Gly Gly Asn Pro Glu Trp Met Thr Leu
            260                 265                 270

Phe Gly Glu Ser Ala Gly Ser Ser Val Asn Ala Gln Leu Met Ser
        275                 280                 285

Pro Val Thr Arg Gly Leu Val Lys Arg Gly Met Met Gln Ser Gly Thr
    290                 295                 300

Met Asn Ala Pro Trp Ser His Met Thr Ser Glu Lys Ala Val Glu Ile
305                 310                 315                 320
```

```
Gly Lys Ala Leu Ile Asn Asp Cys Asn Cys Asn Ala Ser Met Leu Lys
            325                 330                 335

Thr Asn Pro Ala His Val Met Ser Cys Met Arg Ser Val Asp Ala Lys
            340                 345                 350

Thr Ile Ser Val Gln Gln Trp Asn Ser Tyr Ser Gly Ile Leu Ser Phe
            355                 360                 365

Pro Ser Ala Pro Thr Ile Asp Gly Ala Phe Leu Pro Ala Asp Pro Met
370                 375                 380

Thr Leu Met Lys Thr Ala Asp Leu Lys Asp Tyr Asp Ile Leu Met Gly
385                 390                 395                 400

Asn Val Arg Asp Glu Gly Thr Tyr Phe Leu Leu Tyr Asp Phe Ile Asp
                405                 410                 415

Tyr Phe Asp Lys Asp Asp Ala Thr Ala Leu Pro Arg Asp Lys Tyr Leu
            420                 425                 430

Glu Ile Met Asn Asn Ile Phe Gly Lys Ala Thr Gln Ala Glu Arg Glu
            435                 440                 445

Ala Ile Ile Phe Gln Tyr Thr Ser Trp Glu Gly Asn Pro Gly Tyr Gln
            450                 455                 460

Asn Gln Gln Gln Ile Gly Arg Ala Val Gly Asp His Phe Phe Thr Cys
465                 470                 475                 480

Pro Thr Asn Glu Tyr Ala Gln Ala Leu Ala Glu Arg Gly Ala Ser Val
                485                 490                 495

His Tyr Tyr Tyr Phe Thr His Arg Thr Ser Thr Ser Leu Trp Gly Glu
            500                 505                 510

Trp Met Gly Val Leu His Gly Asp Glu Ile Glu Tyr Phe Phe Gly Gln
            515                 520                 525

Pro Leu Asn Asn Ser Leu Gln Tyr Arg Pro Val Glu Arg Glu Leu Gly
530                 535                 540

Lys Arg Met Leu Ser Ala Val Ile Glu Phe Ala Lys Thr Gly Asn Pro
545                 550                 555                 560

Ala Gln Asp Gly Glu Glu Trp Pro Asn Phe Ser Lys Glu Asp Pro Val
                565                 570                 575

Tyr Tyr Ile Phe Ser Thr Asp Asp Lys Ile Glu Lys Leu Ala Arg Gly
            580                 585                 590

Pro Leu Ala Ala Arg Cys Ser Phe Trp Asn Asp Tyr Leu Pro Lys Val
            595                 600                 605

Arg Ser Trp Ala Gly Thr Cys Asp Gly Asp Ser Gly Ser Ala Ser Ile
            610                 615                 620

Ser Pro Arg Leu Gln Leu Leu Gly Ile Ala Ala Leu Ile Tyr Ile Cys
625                 630                 635                 640

Ala Ala Leu Arg Thr Lys Arg Val Phe
                645

<210> SEQ ID NO 167
<211> LENGTH: 708
<212> TYPE: PRT
<213> ORGANISM: Lucilia cuprina

<400> SEQUENCE: 167

Met Ala Arg Phe Ile Thr Thr Ser Ser Pro Thr Leu Thr Thr Ser
1               5                   10                  15

Thr Ala Ala Thr Ala Pro Ser Ser Trp Ser Ser Asn Ala Thr Ser
            20                  25                  30

Thr Ala Ser Ile Ser Ser His Ser Arg Thr Ser Arg Lys Ser Arg
            35                  40                  45
```

```
Tyr Thr Ser Ser Asn Leu Leu Asn Ala Phe Ala Ser Leu Thr Ser Arg
 50                  55                  60

Ser Ser Leu Ser Leu Ser Ser Thr Ser Ser Asn Asp Leu Tyr Arg Gly
 65                  70                  75                  80

Phe Leu Thr Thr Leu Val Ile Leu Leu Arg Met Ser Ser Val Ala Tyr
                 85                  90                  95

Gly Ile Thr Asp Arg Leu Ile Val Gln Thr Thr Ser Gly Pro Val Arg
             100                 105                 110

Gly Arg Ala Val Thr Val Gln Gly Arg Glu Val His Val Phe Thr Gly
         115                 120                 125

Ile Pro Tyr Ala Lys Pro Pro Val Asp Asp Leu Arg Phe Arg Lys Pro
     130                 135                 140

Val Pro Ala Glu Pro Trp His Gly Val Leu Asp Ala Thr Arg Leu Pro
145                 150                 155                 160

Ala Thr Cys Val Gln Glu Arg Tyr Glu Tyr Phe Pro Gly Phe Ser Gly
                 165                 170                 175

Glu Glu Ile Trp Asn Pro Asn Thr Asn Val Ser Glu Asp Cys Leu Tyr
             180                 185                 190

Met Asn Ile Trp Ala Pro Ala Lys Ala Arg Leu Arg His Gly Arg Gly
         195                 200                 205

Ala Asn Gly Gly Glu His Ser Ser Lys Thr Asp Pro Asp His Leu Ile
     210                 215                 220

His Ser Ala Thr Pro Gln Asn Thr Thr Asn Gly Leu Pro Ile Leu Ile
225                 230                 235                 240

Trp Ile Tyr Gly Gly Gly Phe Met Thr Gly Ser Ala Thr Leu Asp Ile
                 245                 250                 255

Tyr Asn Ala Asp Ile Met Ser Ala Val Gly Asn Val Ile Val Ala Ser
             260                 265                 270

Phe Gln Tyr Arg Val Gly Ala Phe Gly Phe Leu His Leu Ser Pro Val
         275                 280                 285

Met Pro Gly Phe Glu Glu Glu Ala Pro Gly Asn Val Gly Leu Trp Asp
     290                 295                 300

Gln Ala Leu Ala Leu Arg Trp Leu Lys Glu Asn Ala Arg Ala Phe Gly
305                 310                 315                 320

Gly Asn Pro Glu Trp Met Thr Leu Phe Gly Glu Ser Ala Gly Ser Ser
                 325                 330                 335

Ser Val Asn Ala Gln Leu Val Ser Pro Val Thr Arg Gly Leu Val Lys
             340                 345                 350

Arg Gly Met Met Gln Ser Gly Thr Met Asn Ala Pro Trp Ser His Met
         355                 360                 365

Thr Ser Glu Lys Ala Val Glu Ile Gly Lys Ala Leu Ile Asn Asp Cys
     370                 375                 380

Asn Cys Asn Ala Ser Leu Leu Pro Ala Asn Pro Gln Ser Val Met Ala
385                 390                 395                 400

Cys Met Arg Ala Val Asp Ala Lys Thr Ile Ser Val Gln Gln Trp Asn
                 405                 410                 415

Ser Tyr Ser Gly Ile Leu Ser Phe Pro Ser Ala Pro Thr Ile Asp Gly
             420                 425                 430

Ala Phe Leu Pro Ala Asp Pro Met Thr Leu Met Lys Thr Ala Asp Met
         435                 440                 445

Ser Gly Tyr Asp Ile Met Ile Gly Asn Val Lys Asp Glu Gly Thr Tyr
     450                 455                 460

Phe Leu Leu Tyr Asp Phe Ile Asp Tyr Phe Asp Lys Asp Glu Ala Thr
465                 470                 475                 480
```

```
Ser Leu Pro Arg Asp Lys Tyr Leu Glu Ile Met Asn Asn Ile Phe Asn
                485                 490                 495

Lys Ala Thr Gln Ala Glu Arg Glu Ala Ile Ile Phe Gln Tyr Thr Ser
            500                 505                 510

Trp Glu Gly Asn Pro Gly Tyr Gln Asn Gln Gln Ile Gly Arg Ala
        515                 520                 525

Val Gly Asp His Phe Phe Thr Cys Pro Thr Asn Glu Tyr Ala Gln Ala
    530                 535                 540

Leu Ala Glu Arg Gly Ala Gln Val His Tyr Tyr Phe Thr His Arg
545                 550                 555                 560

Thr Ser Thr Ser Leu Trp Gly Glu Trp Met Gly Val Leu His Gly Asp
                565                 570                 575

Glu Ile Glu Tyr Phe Phe Gly Gln Pro Leu Asn Thr Ser Leu Gln Tyr
                580                 585                 590

Arg Ala Val Glu Arg Glu Leu Gly Lys Arg Met Leu Asn Ser Val Ile
                595                 600                 605

Glu Phe Ala Lys Thr Gly Asn Pro Ala Val Asp Gly Glu Trp Pro
        610                 615                 620

Asn Phe Ser Lys Glu Asp Pro Val Tyr Tyr Val Phe Ser Thr Asp Glu
625                 630                 635                 640

Lys Thr Glu Lys Leu Gln Arg Gly Pro Leu Ala Lys Arg Cys Ser Phe
                645                 650                 655

Trp Asn Asp Tyr Leu Pro Lys Val Arg Ser Trp Val Gly Ser Glu Cys
                660                 665                 670

Glu Asn Asn Ser Ala Glu Ser Ala Ala Val Ser Ile Ile Tyr Glu Lys
                675                 680                 685

Gln Gln Asn Leu Leu Lys Trp Val Ile Met Leu Thr Ile Met Val Thr
    690                 695                 700

Cys Ile Phe Gln
705

<210> SEQ ID NO 168
<211> LENGTH: 692
<212> TYPE: PRT
<213> ORGANISM: Musca domestica

<400> SEQUENCE: 168

Met Ala Arg Ser Val Arg Thr Pro Ile Ser Pro Ser Ser Ser Ser Ser
1               5                   10                  15

Ser Ser Arg Ser Ser Trp Ser Ser Pro Ser Ser Phe Tyr Ser Leu
            20                  25                  30

Leu Ser Ser Phe Lys Ala Ser Leu Thr Arg Pro Ser Ser Ser Ser Ser
            35                  40                  45

Val Ala His His Leu Ala Ala Arg Asn Asn Asp Ile Cys Arg Gly Leu
    50                  55                  60

Phe Ala Thr Leu Val Ile Leu Leu Arg Met Ser Ala Leu Thr Ser Ala
65                  70                  75                  80

Met Thr Asp His Leu Thr Val Gln Thr Thr Ser Gly Pro Val Arg Gly
                85                  90                  95

Arg Ser Val Thr Val Gln Gly Arg Asp Val His Val Phe Thr Gly Ile
            100                 105                 110

Pro Tyr Ala Lys Pro Pro Val Asp Asp Leu Arg Phe Arg Lys Pro Val
            115                 120                 125

Pro Ala Glu Pro Trp His Gly Val Leu Asp Ala Thr Arg Leu Pro Ala
        130                 135                 140
```

-continued

Thr Cys Val Gln Glu Arg Tyr Glu Tyr Phe Pro Gly Phe Ser Gly Glu
145                 150                 155                 160

Glu Ile Trp Asn Pro Asn Thr Asn Val Ser Glu Asp Cys Leu Phe Met
                165                 170                 175

Asn Ile Trp Ala Pro Ala Lys Ala Arg Leu Arg His Gly Arg Gly Thr
            180                 185                 190

Asn Gly Gly Glu His Ser Ser Lys Thr Asp Gln Asp His Leu Ile His
        195                 200                 205

Ser Ala Thr Pro Gln Asn Thr Thr Asn Gly Leu Pro Ile Leu Ile Trp
210                 215                 220

Ile Tyr Gly Gly Gly Phe Met Thr Gly Ser Ala Thr Leu Asp Ile Tyr
225                 230                 235                 240

Asn Ala Glu Ile Met Ser Ala Val Gly Asn Val Ile Val Ala Ser Phe
                245                 250                 255

Gln Tyr Arg Val Gly Ala Phe Gly Phe Leu His Leu Ser Pro Val Met
            260                 265                 270

Pro Gly Phe Glu Glu Ala Pro Gly Asn Val Gly Leu Trp Asp Gln
        275                 280                 285

Ala Leu Ala Leu Arg Trp Leu Lys Glu Asn Ala Arg Ala Phe Gly Gly
290                 295                 300

Asn Pro Glu Trp Met Thr Leu Phe Gly Glu Ser Ala Gly Ser Ser Ser
305                 310                 315                 320

Val Asn Ala Gln Leu Met Ser Pro Val Thr Arg Gly Leu Val Lys Arg
                325                 330                 335

Gly Met Met Gln Ser Gly Thr Met Asn Ala Pro Trp Ser His Met Thr
            340                 345                 350

Ser Glu Lys Ala Val Glu Ile Gly Lys Ala Leu Val Asn Asp Cys Asn
        355                 360                 365

Cys Asn Ala Ser Leu Leu Pro Glu Asn Pro Gln Ala Val Met Ala Cys
370                 375                 380

Met Arg Gln Val Asp Ala Lys Thr Ile Ser Val Gln Gln Trp Asn Ser
385                 390                 395                 400

Tyr Ser Gly Ile Leu Ser Phe Pro Ser Ala Pro Thr Ile Asp Gly Ala
                405                 410                 415

Phe Leu Pro Ala Asp Pro Met Thr Leu Leu Lys Thr Ala Asp Leu Ser
            420                 425                 430

Gly Tyr Asp Ile Leu Ile Gly Asn Val Lys Asp Glu Gly Thr Tyr Phe
        435                 440                 445

Leu Leu Tyr Asp Phe Ile Asp Tyr Phe Asp Lys Asp Ala Thr Ser
450                 455                 460

Leu Pro Arg Asp Lys Tyr Leu Glu Ile Met Asn Asn Ile Phe Gln Lys
465                 470                 475                 480

Ala Ser Gln Ala Glu Arg Glu Ala Ile Ile Phe Gln Tyr Thr Ser Trp
                485                 490                 495

Glu Gly Asn Pro Gly Tyr Gln Asn Gln Gln Ile Gly Arg Ala Val
            500                 505                 510

Gly Asp His Phe Phe Thr Cys Pro Thr Asn Glu Tyr Ala Gln Ala Leu
        515                 520                 525

Ala Glu Arg Gly Ala Ser Val His Tyr Tyr Phe Thr His Arg Thr
530                 535                 540

Ser Thr Ser Leu Trp Gly Glu Trp Met Gly Val Leu His Gly Asp Glu
545                 550                 555                 560

Ile Glu Tyr Phe Phe Gly Gln Pro Leu Asn Asn Ser Leu Gln Tyr Arg

```
                  565                 570                 575
Pro Val Glu Arg Glu Leu Gly Lys Arg Met Leu Asn Ser Val Ile Glu
                580                 585                 590

Phe Ala Lys Ser Gly Asn Pro Ala Val Asp Gly Glu Trp Pro Asn
            595                 600                 605

Phe Ser Lys Glu Asp Pro Val Tyr Tyr Val Phe Ser Thr Asp Glu Lys
        610                 615                 620

Ile Glu Lys Leu Gln Arg Gly Pro Leu Ala Lys Arg Cys Ser Phe Trp
625                 630                 635                 640

Asn Asp Tyr Leu Pro Lys Val Arg Ser Trp Ile Gly Ser Glu Cys Glu
                645                 650                 655

Asn Lys Ser Ser Thr Ser Ala Ser Ala Ala Ile Tyr Glu Met Lys Met
            660                 665                 670

Gln Gln Leu Thr Leu Leu Ala Val Ala Ile Ile Leu Thr Met Val Asn
        675                 680                 685

Ser Ile Phe Gln
    690

<210> SEQ ID NO 169
<211> LENGTH: 635
<212> TYPE: PRT
<213> ORGANISM: Culex pipiens

<400> SEQUENCE: 169

Met Ser Ser Ile Ser Met Val Val Gly Ala Val Leu Leu Cys Ser
1               5                   10                  15

Ala Val Ile Ser Pro Val Tyr Gly Ala Phe Asp Arg Leu Val Val Arg
            20                  25                  30

Thr Ser Ser Gly Pro Ile Arg Gly Arg Ser Thr Met Val Gln Gly Arg
        35                  40                  45

Glu Val His Val Phe Asn Gly Val Pro Phe Ala Lys Pro Pro Val Asp
    50                  55                  60

Gly Leu Arg Phe Gln Lys Pro Val Pro Ala Glu Pro Trp His Gly Val
65                  70                  75                  80

Leu Asp Ala Thr Arg Leu Pro Pro Ser Cys Ile Gln Glu Arg Tyr Glu
                85                  90                  95

Tyr Phe Pro Gly Phe Ala Gly Glu Glu Met Trp Asn Pro Asn Thr Asn
            100                 105                 110

Val Ser Glu Asp Cys Leu Tyr Leu Asn Ile Trp Val Pro Thr Lys Thr
        115                 120                 125

Arg Leu Arg His Gly Arg Gly Leu Asn Phe Gly Asn Asn Asp Tyr Phe
    130                 135                 140

Gln Asp Asp Glu Asp Phe Gln Arg Gln His Gln Ser Lys Gly Gly Leu
145                 150                 155                 160

Ala Met Leu Val Trp Ile Cys Gly Gly Phe Met Ser Gly Thr Ser
                165                 170                 175

Thr Leu Asp Val Tyr Asn Ala Glu Ile Leu Ala Ala Val Gly Asn Val
            180                 185                 190

Ile Val Ala Ser Met Gln Tyr Arg Val Gly Ala Phe Gly Phe Phe Tyr
        195                 200                 205

Leu Ser Pro Tyr Leu Asn Gly Arg Glu Glu Ala Pro Gly Asn Val
    210                 215                 220

Gly Leu Trp Asp Gln Ala Leu Ala Ile Arg Trp Leu Lys Glu Asn Ala
225                 230                 235                 240

Lys Ala Phe Gly Gly Asp Pro Asp Leu Ile Thr Leu Phe Gly Glu Ser
```

245                 250                 255
Ala Gly Gly Ser Ser Val Ser Leu His Leu Ser Pro Ala Thr Arg
            260                 265                 270

Gly Leu Ser His Arg Gly Ile Leu Gln Ser Gly Thr Leu Asn Ala Pro
            275                 280                 285

Trp Ser His Met Thr Ala Glu Lys Ala Leu Ser Val Ala Glu Ser Leu
            290                 295                 300

Ile Asp Asp Cys Asn Cys Asn Val Thr Leu Leu Lys Asp Ser Pro Ser
305                 310                 315                 320

Ser Val Met His Cys Met Arg Asn Val Asp Ala Lys Thr Ile Ser Val
                325                 330                 335

Gln Gln Trp Asn Ser Tyr Ser Gly Ile Leu Gly Phe Pro Ser Ala Pro
            340                 345                 350

Thr Ile Asp Gly Val Phe Met Thr Ala Asp Pro Met Thr Met Leu Arg
            355                 360                 365

Glu Ala Asn Leu Glu Gly Ile Asp Ile Leu Val Gly Ser Asn Arg Asp
            370                 375                 380

Glu Gly Thr Tyr Phe Leu Leu Tyr Asp Phe Ile Asp Tyr Phe Glu Lys
385                 390                 395                 400

Asp Ala Ala Thr Ser Leu Pro Arg Asp Lys Phe Leu Glu Ile Met Asn
                405                 410                 415

Thr Ile Phe Ser Lys Ala Ser Glu Pro Glu Arg Glu Ala Ile Ile Phe
            420                 425                 430

Gln Tyr Thr Gly Trp Glu Ser Gly Asn Asp Gly Tyr Gln Asn Gln Gln
            435                 440                 445

Gln Val Gly Arg Ala Val Gly Asp His Phe Phe Ile Cys Pro Thr Asn
            450                 455                 460

Glu Phe Ala Leu Gly Leu Thr Glu Gln Gly Ala Ser Val His Tyr Tyr
465                 470                 475                 480

Tyr Phe Thr His Arg Thr Ser Thr Ser Leu Trp Gly Glu Trp Met Gly
                485                 490                 495

Val Leu His Gly Asp Glu Val Leu Tyr Ile Phe Gly Gln Pro Met Asn
            500                 505                 510

Ala Thr Leu Gln Tyr Arg Gln Arg Glu Arg Asp Leu Ser Arg Arg Met
            515                 520                 525

Val Leu Ser Val Ser Glu Phe Ala Arg Ser Gly Asn Pro Ala Leu Glu
            530                 535                 540

Gly Glu His Trp Pro Leu Tyr Thr Lys Glu Asn Pro Ile Tyr Phe Ile
545                 550                 555                 560

Phe Asn Ala Glu Gly Glu Asp Asp Leu Arg Gly Glu Lys Tyr Gly Arg
                565                 570                 575

Gly Pro Met Ala Thr Ser Cys Ala Phe Trp Asn Asp Phe Leu Pro Arg
            580                 585                 590

Leu Arg Ala Trp Ser Ile Pro Pro Lys Ser Ser Cys Asn Leu Leu Glu
            595                 600                 605

Pro Thr Ser Gly Ala Pro Val Arg Tyr Val Asp Ile Lys Val Leu Thr
            610                 615                 620

Val Leu Thr Val Leu Ile Val Leu Arg Leu Phe
625                 630                 635

<210> SEQ ID NO 170
<211> LENGTH: 91
<212> TYPE: PRT
<213> ORGANISM: Anopheles gambiae

<400> SEQUENCE: 170

Thr Glu Pro Asp Asn Pro Asn Ser Asn Arg Asp Ala Leu Asp Lys Met
1               5                   10                  15

Val Gly Asp Tyr His Phe Thr Cys Asn Val Asn Glu Phe Ala Gln Arg
            20                  25                  30

Tyr Ala Glu Glu Gly Asn Asn Val Tyr Met Tyr Leu Tyr Thr His Arg
        35                  40                  45

Ser Lys Gly Asn Pro Trp Pro Arg Trp Thr Gly Val Met His Gly Asp
    50                  55                  60

Glu Ile Asn Tyr Val Phe Gly Glu Pro Leu Asn Pro Thr Leu Gly Tyr
65                  70                  75                  80

Thr Glu Asp Glu Lys Asp Phe Ser Arg Lys Ile
                85                  90

<210> SEQ ID NO 171
<211> LENGTH: 2109
<212> TYPE: DNA
<213> ORGANISM: Culex pipiens

<400> SEQUENCE: 171
atggagatcc gaggcctaat aacccgatta ctgggtccat gtcacctgcg acatctgata      60
ctgtgcagtt tggggctgta ctccatcctc gtgaagtcgg tccattgccg gcatcatgac     120
atcggtagtt cggtggcaca ccagctagga tcgaaatact cacaatcatc ctcgttatcg     180
tcatcctcgc aatcgtcatc gtcgttagct gaagaggcca cgctgaataa agattcagat     240 gcattttta caccatatat aggtcacgga gattctgttc gaattgtaga tgccgaatta     300
ggtacattag agcgcgagca catccatagc actacgaccc ggcggcgtgg cctgacgcgg     360
agggagtcca gctccgatgc caccgactcg gacccactgg tcataacgac ggacaagggc     420
aaaatccgtg gaacgacact ggaagcgcct agtggaaaga aggtggacgc atggatgggc     480
attccgtacg cgcagccccc gctgggtccg ctccggtttc gacatccgcg accggccgaa     540
agatggaccg tgtgctgaa cgcgaccaaa ccgcccaact cctgcgtcca gatcgtggac     600
accgtgttcg gtgacttccc gggggccacc atgtggaacc cgaacacacc gctctcggag     660
gactgtctgt acatcaacgt ggtcgtgcca cggcccaggc ccaagaatgc cgccgtcatg     720
ctgtggatct tcggggggtgg cttctactcc gggactgcca cgctggacgt gtacgaccat     780
cggacgctgg cctcggagga gaacgtgatc gtagtttcgc tgcagtaccg tgtcgcaagt     840
cttgggtttc tcttcctcgg cacaccggag gcacccggta acgcgggcct gttgatcag     900 aacctggcac tgagatgggt ccgcgacaac atccaccggt tcggcggtga cccctcgcgg     960
gtcacactgt tcggcgagag cgccggagcg gtctcggttt cgctgcacct gctgtcggcg    1020
ctctcgcggg acctgttcca gcgggccatc ctccagagtg gctccccgac ggccccgtgg    1080
gcgctggttt cgcgcgaaga agctacgctt agagctcttc gtctggccga ggccgtcaac    1140
tgtccgcacg atgcgaccaa gctgagcgat gccgtcgaat gcctgcgaac caaggatccg    1200
aacgagctgg tcgacaacga gtggggcacg ctggggatct gcgagtttcc gttcgttccg    1260
gttgtggacg gagccttcct cgatgagaca ccgcagcgtt cgttggccag cgggcgcttc    1320
aagaaaacgg acatcctgac cggcagcaac accgaggagg ttactactt tatcattac    1380 tatctaaccg agctgctcag gaaagaggaa ggggtcacgg taacacgcga ggagttccta    1440
caggccgtcc gggagttgaa tccgtacgtg aacggtgccg cccggcaggc catcgtgttc    1500
gagtacacgg actggattga accggacaac ccgaacagca ccgtgacgc gctggacaag    1560

-continued

```
atggtcgggg attatcactt cacctgcaac gtgaacgaat tcgcccagcg gtacgccgag   1620
gagggcaaca acgtgttcat gtacctgtac acgcacagaa gcaaaggaaa tccctggccg   1680
aggtggaccg gcgtgatgca cggcgacgag atcaactacg tgtttggcga accgctgaac   1740
tcggccctcg gctaccagga cgacgagaag gactttagcc ggaaaattat gcgatactgg   1800
tccaactttg ccaagactgg caatcccaac ccgagtacgc cgagcgtgga cctgcccgaa   1860
tggcccaagc acaccgccca cggacgacac tatctggagc tgggactgaa cacgaccttc   1920
gtgggacggg gcccacgatt gcggcagtgc gcttctctgga agaaatattt gccgcaacta   1980
gtagcagcta cctctaacct ccaagtaact cccgcgccta gcgtaccttg cgaaagcagc   2040
tcaacatctt atcgatccac tctacttcta atagtcacac tactttagt aacgcggttc   2100 aagattaa                                                             2109
```

<210> SEQ ID NO 172
<211> LENGTH: 623
<212> TYPE: PRT
<213> ORGANISM: Anopheles gambiae

<400> SEQUENCE: 172

```
Ala Phe Phe Thr Pro Tyr Ile Gly His Gly Glu Ser Val Arg Ile Ile
1               5                   10                  15

Asp Ala Glu Leu Gly Thr Leu Glu His Val His Ser Gly Ala Thr Pro
            20                  25                  30

Arg Arg Arg Gly Leu Thr Arg Arg Glu Ser Asn Ser Asp Ala Asn Asp
        35                  40                  45

Asn Asp Pro Leu Val Val Asn Thr Asp Lys Gly Arg Ile Arg Gly Ile
    50                  55                  60

Thr Val Asp Ala Pro Ser Gly Lys Lys Val Asp Val Trp Leu Gly Ile
65                  70                  75                  80

Pro Tyr Ala Gln Pro Pro Val Gly Pro Leu Arg Phe Arg His Pro Arg
                85                  90                  95

Pro Ala Glu Lys Trp Thr Gly Val Leu Asn Thr Thr Thr Pro Pro Asn
            100                 105                 110

Ser Cys Val Gln Ile Val Asp Thr Val Phe Gly Asp Phe Pro Gly Ala
        115                 120                 125

Thr Met Trp Asn Pro Asn Thr Pro Leu Ser Glu Asp Cys Leu Tyr Ile
    130                 135                 140

Asn Val Val Ala Pro Arg Pro Arg Pro Lys Asn Ala Ala Val Met Leu
145                 150                 155                 160

Trp Ile Phe Gly Gly Gly Phe Tyr Ser Gly Thr Ala Thr Leu Asp Val
                165                 170                 175

Tyr Asp His Arg Ala Leu Ala Ser Glu Glu Asn Val Ile Val Val Ser
            180                 185                 190

Leu Gln Tyr Arg Val Ala Ser Leu Gly Phe Leu Phe Leu Gly Thr Pro
        195                 200                 205

Glu Ala Pro Gly Asn Ala Gly Leu Phe Asp Gln Asn Leu Ala Leu Arg
    210                 215                 220

Trp Val Arg Asp Asn Ile His Arg Phe Gly Gly Asp Pro Ser Arg Val
225                 230                 235                 240

Thr Leu Phe Gly Glu Ser Ala Gly Ala Val Ser Val Ser Leu His Leu
                245                 250                 255

Leu Ser Ala Leu Ser Arg Asp Leu Phe Gln Arg Ala Ile Leu Gln Ser
            260                 265                 270

Gly Ser Pro Thr Ala Pro Trp Ala Leu Val Ser Arg Glu Glu Ala Thr
```

```
                275                 280                 285
Leu Arg Ala Leu Arg Leu Ala Glu Ala Val Gly Cys Pro His Glu Pro
290                 295                 300
Ser Lys Leu Ser Asp Ala Val Glu Cys Leu Arg Gly Lys Asp Pro His
305                 310                 315                 320
Val Leu Val Asn Asn Glu Trp Gly Thr Leu Gly Ile Cys Glu Phe Pro
                325                 330                 335
Phe Val Pro Val Val Asp Gly Ala Phe Leu Asp Glu Thr Pro Gln Arg
                340                 345                 350
Ser Leu Ala Ser Gly Arg Phe Lys Lys Thr Glu Ile Leu Thr Gly Ser
                355                 360                 365
Asn Thr Glu Glu Gly Tyr Tyr Phe Ile Ile Tyr Tyr Leu Thr Glu Leu
370                 375                 380
Leu Arg Lys Glu Glu Gly Val Thr Val Thr Arg Glu Glu Phe Leu Gln
385                 390                 395                 400
Ala Val Arg Glu Leu Asn Pro Tyr Val Asn Gly Ala Ala Arg Gln Ala
                405                 410                 415
Ile Val Phe Glu Tyr Thr Asp Trp Thr Glu Pro Asp Asn Pro Asn Ser
                420                 425                 430
Asn Arg Asp Ala Leu Asp Lys Met Val Gly Asp Tyr His Phe Thr Cys
                435                 440                 445
Asn Val Asn Glu Phe Ala Gln Arg Tyr Ala Glu Gly Asn Asn Val
450                 455                 460
Tyr Met Tyr Leu Tyr Thr His Arg Ser Lys Gly Asn Pro Trp Pro Arg
465                 470                 475                 480
Trp Thr Gly Val Met His Gly Asp Glu Ile Asn Tyr Val Phe Gly Glu
                485                 490                 495
Pro Leu Asn Pro Thr Leu Gly Tyr Thr Glu Asp Glu Lys Asp Phe Ser
                500                 505                 510
Arg Lys Ile Met Arg Tyr Trp Ser Asn Phe Ala Lys Thr Gly Asn Pro
                515                 520                 525
Asn Pro Asn Thr Ala Ser Ser Glu Phe Pro Glu Trp Pro Lys His Thr
                530                 535                 540
Ala His Gly Arg His Tyr Leu Glu Leu Gly Leu Asn Thr Ser Phe Val
545                 550                 555                 560
Gly Arg Gly Pro Arg Leu Arg Gln Cys Ala Phe Trp Lys Lys Tyr Leu
                565                 570                 575
Pro Gln Leu Val Ala Ala Thr Ser Asn Leu Pro Gly Pro Ala Pro Pro
                580                 585                 590
Ser Glu Pro Cys Glu Ser Ser Ala Phe Phe Tyr Arg Pro Asp Leu Ile
                595                 600                 605
Val Leu Leu Val Ser Leu Leu Thr Ala Thr Val Arg Phe Ile Gln
610                 615                 620
```

<210> SEQ ID NO 173
<211> LENGTH: 2534
<212> TYPE: DNA
<213> ORGANISM: Anopheles gambiae

<400> SEQUENCE: 173

```
gaatgcgcat tgttgcgata gattgaattt ccttggttgt tgttgttgtt ggttttcttt      60
tgacatgttt gtgtgttgtt ttttctttct ctctctctct ctctgtggtt ccaacatttc     120
agacgcattt tttacaccat ataggtcac ggtgagtcc gtacgaatta tagatgccga      180
gttgggcacg ctcgagcatg tccacagtgg agcaacgccg cggcgacgcg gtctgacgag     240
```

```
gcgcgagtcc aactcgggta agtacgcgat tggaagtggg gggacgttta ccctgccgtg    300
tactacaatg cactttaccc ccacgcacac gcaccggcag acgcgaacga caacgatccg    360
ctggtggtca acacggataa ggggcgcatc cgcggcatta cggtcgatgc gcccagcggc    420
aagaaggtgg acgtgtggct cggcattccc tacgcccagc cgccggtcgg gccgttacgg    480
ttccgtcatc cgcggccggc cgaaaagtgg accggcgtgc tgaacacgac cacaccgccc    540
aacagctgcg tgcagatcgt ggacaccgtg ttcggcgact cccgggcgc gaccatgtgg     600 aacccgaaca cgcccctgtc cgaggactgt ctgtacatta cgtggtggc accgcgaccc     660 cggcccaaga atgcggccgt catgctgtgg atcttcggcg gcggcttcta ctccggcacc    720
gccaccctgg acgtgtacga ccaccgggcg cttgcgtcgg aggagaacgt gatcgtggtg    780
tcgctgcagt accgcgtggc cagtctgggc ttcctgtttc tcggcacccc ggaagcgccg    840
ggcaatgcgg gactgttcga tcagaacctt gcgctacggt aggtgtcttt gcatgggtga    900
atgagggtat agtattctaa cgaggtgctc ttcttcccat cacttcttgg gagtcagctg    960
ggtgcgggac aacattcacc ggttcggtgg tgatccgtcg cgtgtgacac tgttcggcga   1020
gagtgccggt gccgtctcgg tgtcgctgca tctgctgtcc gccctgtccc gcgatctgtt   1080
ccagcgggcc atcctgcaga gcggctcgcc gacggcaccg tgggcattgg tatcgcgcga   1140
ggaagccacg ctaaggtacg tgccagctgc tgctttcccc aaaccaccaa cccgcgacag   1200
ctcacacaac cctcttttcc ttcgctcttt tctcgctcca gagcactgcg gttggccgag   1260
gcggtcggct gcccgcacga accgagcaag ctgagcgatg cggtcgagtg tctgcgcggc   1320
aaggatccgc acgtgctggt caacaacgag tggggcacgc tcggcatttg cgagttcccg   1380
ttcgtgccgg tggtcgacgg tgcgttcctg gacgagacgc cgcagcgttc gctcgccagc   1440
gggcgcttca agaagacgga gatcctcacc ggcagcaaca cggaggaggg ctactacttc   1500
atcatctact acctgaccga gctgctgcgc aaggaggagg gcgtgaccgt gacgcgcgag   1560
gagttcctgc aggcggtgcg cgagctcaac ccgtacgtga acggggcggc ccggcaggcg   1620
atcgtgttcg agtacaccga ctggaccgag ccggacaacc cgaacagcaa ccgggacgcg   1680
ctggacaaga tggtgggcga ctatcacttc acctgcaacg tgaacgagtt cgcgcagcgg   1740
tacgccgagg agggcaacaa cgtctacatg tatctgtaca cgcaccgcag caaaggcaac   1800
ccgtggccgc gctggacggg cgtgatgcac ggcgacgaga tcaactacgt gttcggcgaa   1860
ccgctcaacc ccaccctcgg ctacaccgag gacgagaaag actttagccg gaagatcatg   1920
cgatactggt ctaactttgc caaaaccggg taagtgtgtg tgtgtgtgtg tgtcaaacag   1980
cagagtgtcg atcgctctaa cgccttctct cttcaacagc aatccaaatc ccaacacggc   2040
cagcagcgaa ttccccgagt ggcccaagca caccgcccac ggacggcact atctggagct   2100
gggcctcaac acgtccttcg tcggtcgggg cccacggttg aggcagtgtg ccttctggaa   2160
gaagtacctt ccccagctag ttgcagctac ctgtaagtct cgtgcagcgc ttgaaatcct   2220
ctcccgcatc ctcaacaggg tccaggttgc aataacaaat gtatctctct ctctctcacg   2280 tctctttttcc ccaaaacagc gaacctacca gggccagcac cgcccagtga accgtgcgaa   2340
agcagcgcat ttttttaccg acctgatctg atcgtgctgc tggtgtcgct gcttacggcg   2400
accgtcagat tcatacaata attactaccc catccatggc ctagttcttt taagctttaa   2460
gatagtgagg aacaaatttt tcctaaccaa tttcccaacc cccttagag cagaaccgag    2520 ggagagatag gact                                                     2534
```

```
<210> SEQ ID NO 174
<211> LENGTH: 623
<212> TYPE: PRT
<213> ORGANISM: Anopheles gambiae

<400> SEQUENCE: 174

Ala Phe Phe Thr Pro Tyr Ile Gly His Gly Glu Ser Ala Arg Ile Ile
1               5                   10                  15

Asp Ala Glu Leu Gly Thr Leu Glu His Val His Ser Gly Ala Thr Pro
            20                  25                  30

Arg Arg Arg Gly Leu Thr Arg Arg Glu Ser Asn Ser Asp Ala Asn Asp
        35                  40                  45

Asn Asp Pro Leu Val Val Asn Thr Asp Lys Gly Arg Ile Arg Gly Ile
    50                  55                  60

Thr Val Asp Ala Pro Ser Gly Lys Lys Val Asp Val Trp Leu Gly Ile
65                  70                  75                  80

Pro Tyr Ala Gln Pro Pro Val Gly Pro Leu Arg Phe Arg His Pro Arg
            85                  90                  95

Pro Ala Glu Lys Trp Thr Gly Val Leu Asn Thr Thr Pro Pro Asn
        100                 105                 110

Ser Cys Val Gln Ile Val Asp Thr Val Phe Gly Asp Phe Pro Gly Ala
    115                 120                 125

Thr Met Trp Asn Pro Asn Thr Pro Leu Ser Glu Asp Cys Leu Tyr Ile
130                 135                 140

Asn Val Val Ala Pro Arg Pro Arg Pro Lys Asn Ala Ala Val Met Leu
145                 150                 155                 160

Trp Ile Phe Gly Gly Ser Phe Tyr Ser Gly Thr Ala Thr Leu Asp Val
            165                 170                 175

Tyr Asp His Arg Ala Leu Ala Ser Glu Glu Asn Val Ile Val Val Ser
        180                 185                 190

Leu Gln Tyr Arg Val Ala Ser Leu Gly Phe Leu Phe Leu Gly Thr Pro
    195                 200                 205

Glu Ala Pro Gly Asn Ala Gly Leu Phe Asp Gln Asn Leu Ala Leu Arg
210                 215                 220

Trp Val Arg Asp Asn Ile His Arg Phe Gly Gly Asp Pro Ser Arg Val
225                 230                 235                 240

Thr Leu Phe Gly Glu Ser Ala Gly Ala Val Ser Val Ser Leu His Leu
            245                 250                 255

Leu Ser Ala Leu Ser Arg Asp Leu Phe Gln Arg Ala Ile Leu Gln Ser
        260                 265                 270

Gly Ser Pro Thr Ala Pro Trp Ala Leu Val Ser Arg Glu Glu Ala Thr
    275                 280                 285

Leu Arg Ala Leu Arg Leu Ala Glu Ala Val Gly Cys Pro His Glu Pro
290                 295                 300

Ser Lys Leu Ser Asp Ala Val Glu Cys Leu Arg Gly Lys Asp Pro His
305                 310                 315                 320

Val Leu Val Asn Asn Glu Trp Gly Thr Leu Gly Ile Cys Glu Phe Pro
            325                 330                 335

Phe Val Pro Val Val Asp Gly Ala Phe Leu Asp Glu Thr Pro Gln Arg
        340                 345                 350

Ser Leu Ala Ser Gly Arg Phe Lys Lys Thr Ile Leu Thr Gly Ser
    355                 360                 365

Asn Thr Glu Glu Gly Tyr Tyr Phe Ile Ile Tyr Tyr Leu Thr Glu Leu
370                 375                 380

Leu Arg Lys Glu Glu Gly Val Thr Val Thr Arg Glu Glu Phe Leu Gln
```

```
                385                 390                 395                 400
Ala Val Arg Glu Leu Asn Pro Tyr Val Asn Gly Ala Ala Arg Gln Ala
                    405                 410                 415
Ile Val Phe Glu Tyr Thr Asp Trp Thr Glu Pro Asp Asn Pro Asn Ser
                    420                 425                 430
Asn Arg Asp Ala Leu Asp Lys Met Val Gly Asp Tyr His Phe Thr Cys
                    435                 440                 445
Asn Val Asn Glu Phe Ala Gln Arg Tyr Ala Glu Gly Asn Asn Val
        450                 455                 460
Tyr Met Tyr Leu Tyr Thr His Arg Ser Lys Gly Asn Pro Trp Pro Arg
465                 470                 475                 480
Trp Thr Gly Val Met His Gly Asp Glu Ile Asn Tyr Val Phe Gly Glu
                    485                 490                 495
Pro Leu Asn Pro Thr Leu Gly Tyr Thr Glu Asp Glu Lys Asp Phe Ser
                500                 505                 510
Arg Lys Ile Met Arg Tyr Trp Ser Asn Phe Ala Lys Thr Gly Asn Pro
                515                 520                 525
Asn Pro Asn Thr Ala Ser Ser Glu Phe Pro Glu Trp Pro Lys His Thr
                530                 535                 540
Ala His Gly Arg His Tyr Leu Glu Leu Gly Leu Asn Thr Ser Phe Val
545                 550                 555                 560
Gly Arg Gly Pro Arg Leu Arg Gln Cys Ala Phe Trp Lys Lys Tyr Leu
                    565                 570                 575
Pro Gln Leu Val Ala Ala Thr Ser Asn Leu Pro Gly Pro Ala Pro Pro
                580                 585                 590
Ser Glu Pro Cys Glu Ser Ser Ala Phe Phe Tyr Arg Pro Asp Leu Ile
                595                 600                 605
Val Leu Leu Val Ser Leu Leu Thr Ala Thr Val Arg Phe Ile Gln
                610                 615                 620

<210> SEQ ID NO 175
<211> LENGTH: 194
<212> TYPE: DNA
<213> ORGANISM: Anopheles gambiae

<400> SEQUENCE: 175
ccgggcgcga ccatgtggaa cccgaacacg ccctgtccg aggactgtct gtacattaac      60
gtggtggcac cgcgaccccg gcccaagaat gcggccgtca tgctgtggat cttcggcggc     120
ggcttctact ccggcaccgc caccctggac gtgtacgacc accgggcgct tgcgtcggag     180
gagaacgtga tcgt                                                      194

<210> SEQ ID NO 176
<211> LENGTH: 194
<212> TYPE: DNA
<213> ORGANISM: Anopheles gambiae

<400> SEQUENCE: 176
ccgggcgcga ccatgtggaa cccgaacacg ccctgtccg aggactgtct gtacattaac      60
gtggtggcac cgcggccccg gcccaagaat gcggccgtca tgctgtggat cttcggcggc    120
agcttctact ccggcaccgc caccctggac gtgtacgacc accgggcgct tgcgtcggag    180
gagaacgtga tcgt                                                      194

<210> SEQ ID NO 177
<211> LENGTH: 194
<212> TYPE: DNA
```

<210> SEQ ID NO 177
<211> LENGTH: 194
<212> TYPE: DNA
<213> ORGANISM: Culex pipiens

<400> SEQUENCE: 177

```
ccgggggcca ccatgtggaa cccgaacaca ccgctctcgg aggactgtct gtacatcaac    60
gtggtcgtgc cacggcccag gcccaagaat gccgccgtca tgctgtggat cttcggggt    120
ggcttctact ccgggactgc cacgctggac gtgtacgacc atcggacgct ggcctcggag   180
gagaacgtga tcgt                                                      194
```

<210> SEQ ID NO 178
<211> LENGTH: 194
<212> TYPE: DNA
<213> ORGANISM: Culex pipiens

<400> SEQUENCE: 178

```
ccgggcgcga ccatgtggaa cccgaacaca ccctctcgg aggactgtct gtacatcaac     60
gtggtcgtgc caaggccgag gcccaagaat gccgctgtca tgctgtggat ctttgggggt   120
agcttctact ccgggactgc cacgttggac gtgtacgatc atcggacgct ggcctcggag   180
gagaacgtga tcgt                                                      194
```

<210> SEQ ID NO 179
<211> LENGTH: 194
<212> TYPE: DNA
<213> ORGANISM: Anopheles albimanus

<400> SEQUENCE: 179

```
ccggggggcga ctatgtggaa cccaaatacg ccactctcgg aggactgcct gtacatcaac   60
gtggtggcgc cgaggccacg gcccaagaat gctgccgtca tgctgtggat cttcggcggt  120
ggcttctact ccggtacggc cacactggac gtgtacgatc accgggcgct cgcctcggaa  180
gagaacgtta tcgt                                                      194
```

<210> SEQ ID NO 180
<211> LENGTH: 194
<212> TYPE: DNA
<213> ORGANISM: Anopheles albimanus

<400> SEQUENCE: 180

```
ccggggggcga ctatgtggaa cccaaatacg ccactctcgg aggactgcct gtacatcaac   60
gtggtggcgc cgaggccacg gcccaagaat gctgccgtca tgctgtggat cttcggcggt  120
agcttctact ccggtacggc cacactggac gtgtacgatc accgggcgct cgcctcggaa  180
gagaacgtta tcgt                                                      194
```

<210> SEQ ID NO 181
<211> LENGTH: 586
<212> TYPE: PRT
<213> ORGANISM: Torpedo californica P04058
<220> FEATURE:
<221> NAME/KEY: mat_peptide
<222> LOCATION: (22)..(586)

<400> SEQUENCE: 181

```
Met Asn Leu Leu Val Thr Ser Ser Leu Gly Val Leu Leu His Leu Val
    -20              -15                 -10

Val Leu Cys Gln Ala Asp Asp His Ser Glu Leu Leu Val Asn Thr Lys
-5              -1  1               5                  10

Ser Gly Lys Val Met Gly Thr Arg Val Pro Val Leu Ser Ser His Ile
            15                  20                  25
```

```
Ser Ala Phe Leu Gly Ile Pro Phe Ala Glu Pro Pro Val Gly Asn Met
         30                  35                  40

Arg Phe Arg Arg Pro Glu Pro Lys Lys Pro Trp Ser Gly Val Trp Asn
 45                  50                  55

Ala Ser Thr Tyr Pro Asn Asn Cys Gln Gln Tyr Val Asp Glu Gln Phe
 60                  65                  70                  75

Pro Gly Phe Ser Gly Ser Glu Met Trp Asn Pro Asn Arg Glu Met Ser
             80                  85                  90

Glu Asp Cys Leu Tyr Leu Asn Ile Trp Val Pro Ser Pro Arg Pro Lys
             95                 100                 105

Ser Thr Thr Val Met Val Trp Ile Tyr Gly Gly Gly Phe Tyr Ser Gly
         110                 115                 120

Ser Ser Thr Leu Asp Val Tyr Asn Gly Lys Tyr Leu Ala Tyr Thr Glu
         125                 130                 135

Glu Val Val Leu Val Ser Leu Ser Tyr Arg Val Gly Ala Phe Gly Phe
140                 145                 150                 155

Leu Ala Leu His Gly Ser Gln Glu Ala Pro Gly Asn Val Gly Leu Leu
                 160                 165                 170

Asp Gln Arg Met Ala Leu Gln Trp Val His Asp Asn Ile Gln Phe Phe
             175                 180                 185

Gly Gly Asp Pro Lys Thr Val Thr Ile Phe Gly Glu Ser Ala Gly Gly
             190                 195                 200

Ala Ser Val Gly Met His Ile Leu Ser Pro Gly Ser Arg Asp Leu Phe
         205                 210                 215

Arg Arg Ala Ile Leu Gln Ser Gly Ser Pro Asn Cys Pro Trp Ala Ser
220                 225                 230                 235

Val Ser Val Ala Glu Gly Arg Arg Arg Ala Val Glu Leu Gly Arg Asn
                 240                 245                 250

Leu Asn Cys Asn Leu Asn Ser Asp Glu Glu Leu Ile His Cys Leu Arg
             255                 260                 265

Glu Lys Lys Pro Gln Glu Leu Ile Asp Val Glu Trp Asn Val Leu Pro
             270                 275                 280

Phe Asp Ser Ile Phe Arg Phe Ser Phe Val Pro Val Ile Asp Gly Glu
285                 290                 295

Phe Phe Pro Thr Ser Leu Glu Ser Met Leu Asn Ser Gly Asn Phe Lys
300                 305                 310                 315

Lys Thr Gln Ile Leu Leu Gly Val Asn Lys Asp Glu Gly Ser Phe Phe
                 320                 325                 330

Leu Leu Tyr Gly Ala Pro Gly Phe Ser Lys Asp Ser Glu Ser Lys Ile
                 335                 340                 345

Ser Arg Glu Asp Phe Met Ser Gly Val Lys Leu Ser Val Pro His Ala
         350                 355                 360

Asn Asp Leu Gly Leu Asp Ala Val Thr Leu Gln Tyr Thr Asp Trp Met
         365                 370                 375

Asp Asp Asn Asn Gly Ile Lys Asn Arg Asp Gly Leu Asp Asp Ile Val
380                 385                 390                 395

Gly Asp His Asn Val Ile Cys Pro Leu Met His Phe Val Asn Lys Tyr
                 400                 405                 410

Thr Lys Phe Gly Asn Gly Thr Tyr Leu Tyr Phe Phe Asn His Arg Ala
             415                 420                 425

Ser Asn Leu Val Trp Pro Glu Trp Met Gly Val Ile His Gly Tyr Glu
         430                 435                 440

Ile Glu Phe Val Phe Gly Leu Pro Leu Val Lys Glu Leu Asn Tyr Thr
445                 450                 455
```

```
Ala Glu Glu Glu Ala Leu Ser Arg Arg Ile Met His Tyr Trp Ala Thr
460                 465                 470                 475

Phe Ala Lys Thr Gly Asn Pro Asn Glu Pro His Ser Gln Glu Ser Lys
            480                 485                 490

Trp Pro Leu Phe Thr Thr Lys Glu Gln Lys Phe Ile Asp Leu Asn Thr
            495                 500                 505

Glu Pro Met Lys Val His Gln Arg Leu Arg Val Gln Met Cys Val Phe
        510                 515                 520

Trp Asn Gln Phe Leu Pro Lys Leu Leu Asn Ala Thr Ala Cys Asp Gly
        525                 530                 535

Glu Leu Ser Ser Ser Gly Thr Ser Ser Ser Lys Gly Ile Ile Phe Tyr
540                 545                 550                 555

Val Leu Phe Ser Ile Leu Tyr Leu Ile Phe
                560                 565

<210> SEQ ID NO 182
<211> LENGTH: 676
<212> TYPE: PRT
<213> ORGANISM: Schizaphis graminum

<400> SEQUENCE: 182

Met Asp Gln Trp Leu Leu Trp Phe Gly Tyr Leu Val Ala Ser Thr Tyr
1               5                   10                  15

Gly Leu Ser Leu Arg His Ala Arg His Gln Ser Val Gly Thr Pro Thr
            20                  25                  30

Ala Glu Glu Ile Leu Glu Pro Gln Ile Leu Ile Glu Asp Thr Asp His
        35                  40                  45

Val Phe Arg Gln Arg Ala Ser Asp Met Phe Ala Gln Glu Pro Glu Tyr
    50                  55                  60

Thr Glu Lys Arg Asn Leu Asn His Arg Arg Ser Glu Phe Ser Gly
65                  70                  75                  80

Asn Gln Asp Thr Asp Phe Ala Ser Ser Gly Glu Thr Tyr Ser Ala Tyr
                85                  90                  95

Thr Ser Asp Asp Pro Leu Ile Ile His Thr Asn Lys Gly Lys Ile Arg
            100                 105                 110

Gly Ile Thr Gln Thr Ala Thr Thr Gly Lys Leu Val Asp Ala Trp Leu
        115                 120                 125

Gly Ile Pro Tyr Ala Lys Lys Pro Ile Gly Asp Leu Arg Phe Arg His
    130                 135                 140

Pro Arg Pro Ile Asp Arg Trp Asp Thr Thr Pro Glu Thr Ile Leu
145                 150                 155                 160

Asn Cys Thr Thr Pro Pro Asn Thr Cys Val Gln Ile Phe Asp Thr Leu
                165                 170                 175

Phe Gly Asp Phe Pro Gly Ala Thr Met Trp Asn Pro Asn Ser Pro Val
            180                 185                 190

Ser Glu Asp Cys Leu Tyr Ile Asn Val Val Pro Lys Pro Arg Pro
        195                 200                 205

Gln Asn Ala Ala Val Met Val Trp Ile Phe Gly Gly Gly Phe Tyr Ser
    210                 215                 220

Gly Ser Ala Thr Leu Asp Ile Tyr Asp Pro Lys Ile Leu Val Ser Glu
225                 230                 235                 240

Glu Asn Val Ile Leu Val Ser Met Gln Tyr Arg Val Ala Ser Leu Gly
                245                 250                 255

Phe Leu Tyr Phe Asp Thr Glu Asp Val Pro Gly Asn Ala Gly Leu Phe
            260                 265                 270
```

```
Asp Gln Leu Met Ala Leu Gln Trp Val His Glu Asn Ile Lys Leu Phe
        275                 280                 285
Gly Gly Asn Pro Asn Asn Val Thr Leu Phe Gly Glu Ser Ala Gly Ala
    290                 295                 300
Val Ser Val Ser Leu His Leu Leu Ser Pro Leu Ser Arg Asn Leu Phe
305                 310                 315                 320
Asn Gln Ala Ile Met Glu Ser Gly Ser Ser Thr Ala Pro Trp Ala Ile
                325                 330                 335
Leu Ser Arg Glu Glu Ser Phe Asn Arg Gly Leu Lys Leu Ala Lys Ala
            340                 345                 350
Met Gly Cys Pro Asp Asp Arg Asn Thr Ile His Lys Thr Val Glu Cys
        355                 360                 365
Leu Arg Lys Ala Asn Ser Ser Val Met Val Lys Glu Trp Asp His
    370                 375                 380
Val Ala Ile Cys Phe Phe Pro Phe Val Pro Val Val Asp Gly Ala Phe
385                 390                 395                 400
Leu Asp Asp His Pro Gln Lys Ser Leu Ser Thr Asn Phe Lys Lys
                405                 410                 415
Thr Asn Ile Leu Met Gly Ser Asn Ser Glu Gly Tyr Tyr Ser Ile
                420                 425                 430
Phe Tyr Tyr Leu Thr Glu Leu Phe Lys Lys Glu Glu Asn Val Met Val
        435                 440                 445
Ser Arg Glu Asn Phe Ile Lys Ala Ile Gly Gln Leu Asn Pro Asn Ala
    450                 455                 460
Asp Ala Ala Val Lys Ser Ala Ile Glu Phe Glu Tyr Thr Asp Trp Phe
465                 470                 475                 480
Ser Pro Asn Asp Pro Glu Lys Asn Arg Asn Ala Leu Asp Lys Met Val
                485                 490                 495
Gly Asp Tyr Gln Phe Thr Cys Asn Val Asn Glu Phe Ala His Lys Tyr
            500                 505                 510
Ala Leu Thr Gly Asn Asn Val Tyr Met Tyr Tyr Phe Lys His Arg Ser
        515                 520                 525
Leu Asn Asn Pro Trp Pro Lys Trp Thr Gly Val Met His Gly Asp Glu
    530                 535                 540
Ile Ser Tyr Val Phe Gly Asp Pro Leu Asn Pro Asn Lys Arg Tyr Glu
545                 550                 555                 560
Ile Glu Glu Ile Glu Leu Ser Lys Lys Met Met Arg Tyr Trp Thr Asn
                565                 570                 575
Phe Ala Lys Thr Gly Asn Pro Ser Lys Thr Leu Glu Gly Ser Trp Val
            580                 585                 590
Thr Pro Lys Trp Pro Val His Thr Ala Tyr Gly Lys Glu Phe Leu Thr
        595                 600                 605
Leu Asp Thr Asn Asn Thr Ser Ile Gly Val Gly Pro Arg Leu Glu Gln
    610                 615                 620
Cys Ala Phe Trp Lys Asn Tyr Val Pro Asp Leu Thr Ala Ile Ser Lys
625                 630                 635                 640
Ser Met Lys Ser Asp Lys Asn Cys Thr Thr Ile Ser Gly Gly Thr Lys
                645                 650                 655
Thr Asn Val Ile Glu Leu Ser Val Trp Thr Ile Val Met Thr Thr Ala
                660                 665                 670
Val Leu Met Leu
            675
```

```
<210> SEQ ID NO 183
<211> LENGTH: 6
<212> TYPE: PRT
<213> ORGANISM: Artificial Sequence
<220> FEATURE:
<223> OTHER INFORMATION: Peptide motif

<400> SEQUENCE: 183

Phe Gly Glu Ser Ala Gly
1               5
```